(12) United States Patent
Ghazal et al.

(10) Patent No.: US 6,692,954 B1
(45) Date of Patent: Feb. 17, 2004

(54) GENERATION OF HUMAN CYTOMEGALOVIRUS YEAST ARTIFICIAL CHROMOSOME RECOMBINANTS

(75) Inventors: Peter Ghazal, Edinburgh (GB); Huang Huang, Chicago, IL (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 09/705,400

(22) Filed: Nov. 3, 2000

(51) Int. Cl.$^7$ .............................................. C12N 15/79
(52) U.S. Cl. ................ 435/320.1; 435/69.1; 435/235.1; 435/255.1; 536/23.1; 536/23.72
(58) Field of Search ............................. 435/69.1, 235.1, 435/255.1, 320.1; 536/23.1, 23.72

(56) References Cited

U.S. PATENT DOCUMENTS

| | | |
|---|---|---|
| 3,959,466 A | 5/1976 | Plotkin |
| 5,552,143 A | 9/1996 | Plotkin et al. |
| 5,591,439 A | 1/1997 | Plotkin et al. |
| 5,721,354 A | 2/1998 | Spaete et al. ............ 536/23.72 |
| 5,925,751 A | 7/1999 | Spaete et al. ............ 536/23.72 |
| 6,040,170 A | 3/2000 | Spaete et al. ............ 436/252.3 |
| 6,277,621 B1 | 8/2001 | Horsburgh et al. ....... 435/235.1 |
| 6,291,236 B1 | 9/2001 | Spaete et al. ............ 435/320.1 |

FOREIGN PATENT DOCUMENTS

| | | |
|---|---|---|
| WO | WO 95/03400 | 2/1995 |
| WO | WO 99/43842 | 2/1999 |
| WO | WO 99/06582 | 11/1999 |

OTHER PUBLICATIONS

Ketner, PNAS 1994, 91: 6186–6190.*
Borst (Journal of Virology 1999 73 (10) pp. 8320–8329.*
Mocarski J Gen Virol. 1987 pp. 2223–2230.*
Demmler, G.J., 1994 Congenital cytomegalovirus infection, *Semin. Pediatr. Neurol.* 1(1):36–42.
Daniel, Y., et al., 1995, Congenital cytomegalovirus infection,*Eur. J. Obstet. Gynecol. Reprod. Biol.*, 63(1):7–16.
Alford and Britt, "The Human Herpesviruses", Eds. Roizman, B., R. J. Whitley and C. Lopez, Raven Press, New York, 1993, pp 227–55.
Pritchett, R. F., 1980, DNA nucleotide sequence heterogeneity betweeen the Towne and AD169 strains of cytomegalovirus, *J. Virol.* 36(1):152–61.
Lehner, R. et al., 1991, Comparative sequence analysis of human cytomegalovirus strains, *J. Clin. Microbiol.* 29(11):2494–502.
Fries, B. C., 1994, Frequencvy distribution of cytomegalovirus envelope glycoprotein genotypes in bone marrow transplant recipients, *J. Infect. Dis.* 169(4):769–74.
Condie, R. M. et al., 1984, Prevention of cytomegalovirus infection in bone marrow transplant recipients by prophylaxis with an intravenous, hyperimmune cytomegalovirus globuin, *Birth Defects*, 20:327–344.

Perrillo, R. P. et al., 1987, Immune globulin and hepatitis B immune globulin, *Arch. Intern Med.*, 144:81–85.
Snydman, D. R., et al. 1987, Use of cytomegalovirus immune globulin to prevent cytomegalovirus disease in renal–transplant recipients, *N. Engl. J. Med.*, 317:1049–1054.
P Plotkin, S. A., et al., 1984, Towne–Vaccine–Induced Prevention of Cytomegalovirus Disease After Renal Transplants, *Lancet*, 1:528–30.
Plotkin, S. A. et al., 1976, Clinical Trial of Immunization of theTowne 125 Strain of Human Cytomegalovirus, *J. Infect. Dis.*, 134:470–75.
Glazer, J. P. et al., 1979, Live Cytomegalovirus Vaccination of Renal Transplant Candidates: A Preliminary Trial, *Ann. Intern. Med.*, 91:676–83.
Cranage, M. P. et al., 1968, Identification of the Human Cytomegalovirus Glycoprotein B Gene and Induction of Neutroalizing Antibodies via its Expression in RecombinantVaccinia Virus, *EMBO J.*, 5:3057–3063.
Johnson, D. C. et l., 1988, Abundant Expresson of Herpes Simplex VirusGlycoprotein gB using an Adenovirus Vector, *Virol.*, 164:1–14.
Dewar, R. L. et al., 1988, Synthesis and Processing of Human Immunodeficiency Virus Type 1 Envelope Proteins Encoded by a Recombinant Human Adenovirus, *J. Virol.*, 63:129–136.
Davis, A. R. et al., 1985, Expression of Hepatitis B Surface Antigen with a Recombinant Adenovirus, *Proc. Natl. Acad. Sci., U.S.A.*, 82:7560–7564.
Morin, J. E. et al., 1987, Recombinant Adenovirus Induces Antibody response to Hepatitis B Virus Surface Antigen in Hamsters, *Proc. Natl. Acad. Sci., U.S.A.*, 84:4626–4630.
Takajuji, E. T. et al., 1970, Simultaneous Administration of Live, Enteric–CoatedAdenovirus Types 4,7, and 21 Vaccines: Safety andImmungenicity,*J. Infect. Dis.*, 140:48–53.
Collis, P. B. et al., 1973, Adenovirus Vaccines in Military Recruit Populations: A Cost–Benefit Analysis, *J. Inf. Dis.*, 128:74–750.
Messerle, M., et al. 1997, Cloning and mutagenesis of a herpesvirus genome as an infectious bacterial artificial chromosome. *Proc. Natl. Acad. Sci. U.S.A.*, 94: 14759–14763.
Schlessinger, D. 1990, Yeast artificial chromosomes: tools for mapping and analysis of complex genomes, *Trends In Genetics* 6:248–253.
Choi, T. K. et al., 1993, Transgenic mice containing a human heavy chain immunoglobulin gene fragment cloned in a yeast artificial chromosome. *Nature Gen.* 4:117–123.

(List continued on next page.)

Primary Examiner—James Housel
Assistant Examiner—Myron G. Hill
(74) Attorney, Agent, or Firm—Bowditch & Dewey, LLP

(57) ABSTRACT

The present invention relates to a recombinant DNA construct comprising a YAC vector and at least a portion of the HCMV genome. The vector is useful as a basic research tool with which to study CMV biology, or as a vaccine with which to immunize a mammalian host against infection by CMV.

11 Claims, 13 Drawing Sheets

OTHER PUBLICATIONS

Ramsay, M. 1994, Yeast artificial chromosome cloning. *Mol. Biotech.* 1:181–201.

Nemani M. et al., 1994, A YAC contig in 6p23 based on sequence tagged sites,*Genomics* 53: 388–396.

Derossi, D. et al., 1994, The Third Helix of the Antennapedia Homeodomain Translocates through Biological Membranes, *The Journal of Biological Chemistry*269: 10444–10450.

McVoy, M. A. et al., 1993, Human Cytomegalovirus DNA Replicates after EarlyCircularization by Concatemer Formation, and Inversion Occurs within theConcatemer,*J. Virol.* 68:1040–1051.

Lukac, D. M., et al., 1994, Transcriptional Activation by the Human Cytomegalovirus Immediate–Early Proteins: Requirements for Simple Promoter Structures and Interactions with Multiple Components of the Transcription Complex.

Furnari, B. A., et al., 1993, Human Cytomegalovirus Immediate–Early Gene 2 Protein Interacts with Itself and with Several Novel Cellular Proteins,*J. Virol.* 67 (8):4981–4991.

Hagemeier, C., et al., 1992, The Human Cytomegalovirus 80–Kilodalton but Not the 72–Kilodalton Immediate–Early Protein Transactivates Heterologous Promoters in a TATA Box–Dependent Mechanism and Interacts Directly with TFIID. *J. Virol.* 66 (7): 4452–4456.

Jupp, R., et al., 1993, Human Cytomegalovirus IE86 Protein Interacts with Promoter–Bound TATA–Binding Protein via a Specific Region Distinct from the Autorepression Domain *J. Virol.* 67 (12): 7539–7546.

Angulo, A. et al., 2000, Identification of a Boundary Domain adjacent to the Potent HumanCytomegalovirus Enhancer that Represses Transcription of the Divergent UL127 Promoter *J. Virol.* 14: 2826–2839.

Garcia–Ramirez, J. J., et al 2001 Jan., Dominance of Virus over Host Factors in Cross–species Activation of Human Cytomegalovirus Early Gene Expression,*J Virol,* 75(1): 26–35.

Tamachiro, J. C. et al., 1986, Terminal structure and heterogencity in human cytomegalovirus strain AD169, JVirol. 59: 591–604.

Kemble G., et al., 1989, A host cell protein binds to a highly conserved sequence element (pac–2) within the cytomegalovirus A sequence, *J. Virol.* 63: 4715–4728.

Ibanez C. E., et al., 1991, Human Cytomegalovirus Productivity Infects Primary Differential Macrophages*J. of Virology*65: 6581–6588.

Smith, D. R. et al. 1999, Amplification of large artificial chromosomes,*Proc. Natl. Acad. Sci.* 87: 8242–8246.

"Human herpesvirus 5, genome" Accession: NC_001347 http://www.ncbi.nlm.nih.gov/cgi–bin/Entrez/framik?db–genome&gi–10043.

"Human adenovirus A, complete genome" Accession: NC_001460 http://www.ncbi.nlm.nih.gov/cgi–bin/Entrez/framik?db–genome&gi–10190.

"Simian immunodeficiency virus, complete genome" Accession: NC_001549 http://www.ncbi.nlm.nih.gov/cgi–bin/Entrez/framik?db–genome&gi–10371.

"Human immunodeficiency virus 1, complete genome" Accession: NC_001802 http://www.ncbi.nlm.nih.gov/cgi–bin/Entrez/framik?db–genome&gi–12171.

"Mouse cytomegalovirus 1, complete genome" Accession: NC_004065 http://www.ncbi.nlm.nih.gov/cgi–bin/Entrez/framik?db–genome&gi–16530.

Brune, W., et al., "Rapid identification of essential and nonessential herpesvirus genes by direct transposon mutagenesis," *Nature Biotechnology,* 17:360–364, (Apr. 1999).

Mahoney, T.J., et al. "Construction and Manipulation of an Infectious Clone of the Bovine Herpesvirus 1 Genome Maintained as a Bacterial Artificial Chromosome," *J. of Virology,* 76(13):6660–6668 (Jul. 2002).

McGregor, A. and Schleiss, M.R., "Recent Advances in Herpesvirus Genetics Using Bacterial Artificial Chromosomes," *Mol. Gen. and Metab.*, 72:8–14 (2001).

McGregor, A. and Schleiss, M.R., "Molecular Cloning of the Guinea Pig Cytomegalovirus (GPCMV) Genome as an Infectious Bacterial Artificial Chromosome (BAC) in *Escherichia coli*," *Mol. Gen. and Metab.*, 72:15–26 (2001).

Monaco, A.P. and Larin, Z., "YACs, BACs, PACs, and MACs: artificial chromosomes as research tools," *TIBTECH,* 12:280–286 (Jul. 1994).

Smith, G.A. and Enquist, L.W., "A self–recombining bacterial artificial chromosome and its application for analysis of herpesvirus pathogenesis," *Proc. Natl. Acad. Sci. USA,* 97(9):4873–4878 (Apr. 2000).

Wagner, M., et al., "Systematic Excision of Vector Sequences from the BAC–Cloned Herpesvirus Genome during Reconstitution," *J. of Virology,* 73(8):7056–7060 (Aug. 1999).

Yu, D., et al., "Construction of a Self–Excisable Bacterial Artificial Chromosome Containing the Human Cytomegalovirus Genome and Mutagenesis of the Diploid TRL/IRL13 Gene," *J. of Virology,* 76(5):2316–2328 (Mar. 2002).

Horsburgh, B.C., et al., "Allele replacement: an application that permits rapid manipulation of herpes simplex virus type 1 genomes," *Gene Therapy* 6(5):922–930, May 1999.

Kemble, G., et al., "Defined Large–Scale Alteration of the Human Cytomegalovirus Genome Constructed by Contransfection of Overlapping Cosmids," *Journal of Virology* 70(3):2044–2048, Mar. 1996.

\* cited by examiner

A

B

SEQUENCE LISTING

<160> NUMBER OF SEQ ID NOS: 64

<210> SEQ ID NO 1
<211> LENGTH: 22
<212> TYPE: DNA
<213> ORGANISM: Human cytomegalovirus

<400> SEQUENCE: 1
acgtcgcttt tattcgccgt cg                                       22

<210> SEQ ID NO 2
<211> LENGTH: 23
<212> TYPE: DNA
<213> ORGANISM: Human cytomegalovirus

<400> SEQUENCE: 2
acacacgcaa ctccaagttt cac                                      23

<210> SEQ ID NO 3
<211> LENGTH: 16
<212> TYPE: DNA
<213> ORGANISM: Human cytomegalovirus

<400> SEQUENCE: 3
atcaggatcg cgacag                                              16

<210> SEQ ID NO 4
<211> LENGTH: 16
<212> TYPE: DNA
<213> ORGANISM: Human cytomegalovirus

<400> SEQUENCE: 4
cgttatccgt tcctcg                                              16

<210> SEQ ID NO 5
<211> LENGTH: 16
<212> TYPE: DNA
<213> ORGANISM: Human cytomegalovirus

<400> SEQUENCE: 5
acgaggtaat caacgt                                              16

<210> SEQ ID NO 6
<211> LENGTH: 16
<212> TYPE: DNA
<213> ORGANISM: Human cytomegalovirus

<400> SEQUENCE: 6
atgttaagcc ttagtc                                              16

<210> SEQ ID NO 7
<211> LENGTH: 16
<212> TYPE: DNA
<213> ORGANISM: Human cytomegalovirus

<400> SEQUENCE: 7
gacacctcta tgttac                                              16

<210> SEQ ID NO 8
<211> LENGTH: 16
<212> TYPE: DNA
<213> ORGANISM: Human cytomegalovirus

```
<400> SEQUENCE: 8
cgtatatgta cgtcat                                                    16

<210> SEQ ID NO 9
<211> LENGTH: 16
<212> TYPE: DNA
<213> ORGANISM: Human cytomegalovirus

<400> SEQUENCE: 9
tagacagtat accctc                                                    16

<210> SEQ ID NO 10
<211> LENGTH: 15
<212> TYPE: DNA
<213> ORGANISM: Human cytomegalovirus

<400> SEQUENCE: 10
agtaccacat tttgc                                                     15

<210> SEQ ID NO 11
<211> LENGTH: 16
<212> TYPE: DNA
<213> ORGANISM: Human cytomegalovirus

<400> SEQUENCE: 11
acatggattc gtgcac                                                    16

<210> SEQ ID NO 12
<211> LENGTH: 16
<212> TYPE: DNA
<213> ORGANISM: Human cytomegalovirus

<400> SEQUENCE: 12
atcgatctgg agcact                                                    16

<210> SEQ ID NO 13
<211> LENGTH: 16
<212> TYPE: DNA
<213> ORGANISM: Human cytomegalovirus

<400> SEQUENCE: 13
gtgaagccga tacgag                                                    16

<210> SEQ ID NO 14
<211> LENGTH: 16
<212> TYPE: DNA
<213> ORGANISM: Human cytomegalovirus

<400> SEQUENCE: 14
aggagaccac ggtttg                                                    16

<210> SEQ ID NO 15
<211> LENGTH: 20
<212> TYPE: DNA
<213> ORGANISM: Human cytomegalovirus

<400> SEQUENCE: 15
ggtccgcaac ttctgatcca                                                20

<210> SEQ ID NO 16
<211> LENGTH: 20
<212> TYPE: DNA
```

```
<213> ORGANISM: Human cytomegalovirus

<400> SEQUENCE: 16
cagatcagtc cacaggttct                                               20

<210> SEQ ID NO 17
<211> LENGTH: 16
<212> TYPE: DNA
<213> ORGANISM: Human cytomegalovirus

<400> SEQUENCE: 17
gctaccttgt gcagtc                                                   16

<210> SEQ ID NO 18
<211> LENGTH: 16
<212> TYPE: DNA
<213> ORGANISM: Human cytomegalovirus

<400> SEQUENCE: 18
gtcctacgtt gctact                                                   16

<210> SEQ ID NO 19
<211> LENGTH: 16
<212> TYPE: DNA
<213> ORGANISM: Human cytomegalovirus

<400> SEQUENCE: 19
acgcaggtga atatcc                                                   16

<210> SEQ ID NO 20
<211> LENGTH: 16
<212> TYPE: DNA
<213> ORGANISM: Human cytomegalovirus

<400> SEQUENCE: 20
aggttatcgt caagcg                                                   16

<210> SEQ ID NO 21
<211> LENGTH: 20
<212> TYPE: DNA
<213> ORGANISM: Human cytomegalovirus

<400> SEQUENCE: 21
caccatctta gggacgtctc                                               20

<210> SEQ ID NO 22
<211> LENGTH: 20
<212> TYPE: DNA
<213> ORGANISM: Human cytomegalovirus

<400> SEQUENCE: 22
gcatgctcaa gacatgctga                                               20

<210> SEQ ID NO 23
<211> LENGTH: 16
<212> TYPE: DNA
<213> ORGANISM: Human cytomegalovirus

<400> SEQUENCE: 23
gatggtggaa atcgga                                                   16

<210> SEQ ID NO 24
<211> LENGTH: 16
```

```
<212> TYPE: DNA
<213> ORGANISM: Human cytomegalovirus

<400> SEQUENCE: 24
acctgtcggt tgaagc                                                    16

<210> SEQ ID NO 25
<211> LENGTH: 16
<212> TYPE: DNA
<213> ORGANISM: Human cytomegalovirus

<400> SEQUENCE: 25
tcgtcgacgc atctgt                                                    16

<210> SEQ ID NO 26
<211> LENGTH: 16
<212> TYPE: DNA
<213> ORGANISM: Human cytomegalovirus

<400> SEQUENCE: 26
atatcgcacc gattgc                                                    16

<210> SEQ ID NO 27
<211> LENGTH: 20
<212> TYPE: DNA
<213> ORGANISM: Human cytomegalovirus

<400> SEQUENCE: 27
gttggcgttg agcacgtcta                                                20

<210> SEQ ID NO 28
<211> LENGTH: 20
<212> TYPE: DNA
<213> ORGANISM: Human cytomegalovirus

<400> SEQUENCE: 28
agccgacaac ctgctgcact                                                20

<210> SEQ ID NO 29
<211> LENGTH: 16
<212> TYPE: DNA
<213> ORGANISM: Human cytomegalovirus

<400> SEQUENCE: 29
taagtggaag tggccg                                                    16

<210> SEQ ID NO 30
<211> LENGTH: 16
<212> TYPE: DNA
<213> ORGANISM: Human cytomegalovirus

<400> SEQUENCE: 30
gacgacgatg acctca                                                    16

<210> SEQ ID NO 31
<211> LENGTH: 16
<212> TYPE: DNA
<213> ORGANISM: Human cytomegalovirus

<400> SEQUENCE: 31
cagcaatgtt agcgag                                                    16

<210> SEQ ID NO 32
```

```
<211> LENGTH: 16
<212> TYPE: DNA
<213> ORGANISM: Human cytomegalovirus

<400> SEQUENCE: 32
tcacgcgact gtcata                                                    16

<210> SEQ ID NO 33
<211> LENGTH: 16
<212> TYPE: DNA
<213> ORGANISM: Human cytomegalovirus

<400> SEQUENCE: 33
gtgaagcgat tgcaca                                                    16

<210> SEQ ID NO 34
<211> LENGTH: 16
<212> TYPE: DNA
<213> ORGANISM: Human cytomegalovirus

<400> SEQUENCE: 34
tcaggtgcga ttgacg                                                    16

<210> SEQ ID NO 35
<211> LENGTH: 16
<212> TYPE: DNA
<213> ORGANISM: Human cytomegalovirus

<400> SEQUENCE: 35
cgttatccgt tcctcg                                                    16

<210> SEQ ID NO 36
<211> LENGTH: 16
<212> TYPE: DNA
<213> ORGANISM: Human cytomegalovirus

<400> SEQUENCE: 36
cttgcggaat tgacat                                                    16

<210> SEQ ID NO 37
<211> LENGTH: 16
<212> TYPE: DNA
<213> ORGANISM: Human cytomegalovirus

<400> SEQUENCE: 37
tatcgttcgg acggga                                                    16

<210> SEQ ID NO 38
<211> LENGTH: 16
<212> TYPE: DNA
<213> ORGANISM: Human cytomegalovirus

<400> SEQUENCE: 38
ttggatcaga ctcacg                                                    16

<210> SEQ ID NO 39
<211> LENGTH: 16
<212> TYPE: DNA
<213> ORGANISM: Human cytomegalovirus

<400> SEQUENCE: 39
aatcaccgtc attccc                                                    16
```

-continued

```
<210> SEQ ID NO 40
<211> LENGTH: 16
<212> TYPE: DNA
<213> ORGANISM: Human cytomegalovirus

<400> SEQUENCE: 40
ctcctcagct tgttgt                                                    16

<210> SEQ ID NO 41
<211> LENGTH: 16
<212> TYPE: DNA
<213> ORGANISM: Human cytomegalovirus

<400> SEQUENCE: 41
ctagcacgat aaggcg                                                    16

<210> SEQ ID NO 42
<211> LENGTH: 16
<212> TYPE: DNA
<213> ORGANISM: Human cytomegalovirus

<400> SEQUENCE: 42
tgacatgtgg cgtaca                                                    16

<210> SEQ ID NO 43
<211> LENGTH: 16
<212> TYPE: DNA
<213> ORGANISM: Human cytomegalovirus

<400> SEQUENCE: 43
agttggacta cgaaga                                                    16

<210> SEQ ID NO 44
<211> LENGTH: 16
<212> TYPE: DNA
<213> ORGANISM: Human cytomegalovirus

<400> SEQUENCE: 44
ctgtatgtag aagacg                                                    16

<210> SEQ ID NO 45
<211> LENGTH: 16
<212> TYPE: DNA
<213> ORGANISM: Human cytomegalovirus

<400> SEQUENCE: 45
tccataacca ccgtgg                                                    16

<210> SEQ ID NO 46
<211> LENGTH: 16
<212> TYPE: DNA
<213> ORGANISM: Human cytomegalovirus

<400> SEQUENCE: 46
gctgtcgcac tttctg                                                    16

<210> SEQ ID NO 47
<211> LENGTH: 34
<212> TYPE: DNA
<213> ORGANISM: Human cytomegalovirus

<400> SEQUENCE: 47
gacacgtcgt tacagatatc gccttcctac gagg                                34
```

<210> SEQ ID NO 48
<211> LENGTH: 34
<212> TYPE: DNA
<213> ORGANISM: Human cytomegalovirus

<400> SEQUENCE: 48
cctcgtagga aggcgatatc tgtaacgacg tgtc                34

<210> SEQ ID NO 49
<211> LENGTH: 22
<212> TYPE: DNA
<213> ORGANISM: Human cytomegalovirus

<400> SEQUENCE: 49
tcgccctgga tatcgacccg ct                22

<210> SEQ ID NO 50
<211> LENGTH: 23
<212> TYPE: DNA
<213> ORGANISM: Artificial Sequence;
<220> FEATURE:
<221> NAME/KEY: misc_feature
<223> OTHER INFORMATION: Description of Artificial Sequence: 5' primer
      complementary to the 5' region of the luciferase gene.

<400> SEQUENCE: 50
ctttatgttt ttggcgtctt cca                23

<210> SEQ ID NO 51
<211> LENGTH: 19
<212> TYPE: DNA
<213> ORGANISM: Human cytomegalovirus

<400> SEQUENCE: 51
gtagccggag acggcggtt                19

<210> SEQ ID NO 52
<211> LENGTH: 16
<212> TYPE: DNA
<213> ORGANISM: Human cytomegalovirus

<400> SEQUENCE: 52
atgaggatcg cgacag                16

<210> SEQ ID NO 53
<211> LENGTH: 16
<212> TYPE: DNA
<213> ORGANISM: Human cytomegalovirus

<400> SEQUENCE: 53
cgttatccgt tcctcg                16

<210> SEQ ID NO 54
<211> LENGTH: 16
<212> TYPE: DNA
<213> ORGANISM: Human cytomegalovirus

<400> SEQUENCE: 54
agatggattc gtgcac                16

<210> SEQ ID NO 55
<211> LENGTH: 16
<212> TYPE: DNA
<213> ORGANISM: Human cytomegalovirus

<400> SEQUENCE: 55
atcgatctgg agcact    16

<210> SEQ ID NO 56
<211> LENGTH: 20
<212> TYPE: DNA
<213> ORGANISM: Human cytomegalovirus

<400> SEQUENCE: 56
ggtccgcaac ttctgatcca    20

<210> SEQ ID NO 57
<211> LENGTH: 20
<212> TYPE: DNA
<213> ORGANISM: Human cytomegalovirus

<400> SEQUENCE: 57
cagatcagtc cacaggttct    20

<210> SEQ ID NO 58
<211> LENGTH: 16
<212> TYPE: DNA
<213> ORGANISM: Human cytomegalovirus

<400> SEQUENCE: 58
acgcaggtga atatcc    16

<210> SEQ ID NO 59
<211> LENGTH: 16
<212> TYPE: DNA
<213> ORGANISM: Human cytomegalovirus

<400> SEQUENCE: 59
aggttatcgt caagcg    16

<210> SEQ ID NO 60
<211> LENGTH: 16
<212> TYPE: DNA
<213> ORGANISM: Human cytomegalovirus

<400> SEQUENCE: 60
gatggtggaa atcgga    16

<210> SEQ ID NO 61
<211> LENGTH: 16
<212> TYPE: DNA
<213> ORGANISM: Human cytomegalovirus

<400> SEQUENCE: 61
atatcgcacc gattgc    16

<210> SEQ ID NO 62
<211> LENGTH: 20
<212> TYPE: DNA
<213> ORGANISM: Human cytomegalovirus

<400> SEQUENCE: 62
gttggcgttg agcacgtcta    20

<210> SEQ ID NO 63
<211> LENGTH: 20
<212> TYPE: DNA

<213> ORGANISM: Human cytomegalovirus

<400> SEQUENCE: 63
agccgacaac ctgctgcact                                                20

<210> SEQ ID NO 64
<211> LENGTH: 229354
<212> TYPE: DNA
<213> ORGANISM: Human cytomegalovirus
<220> FEATURE:
<221> NAME/KEY: misc_feature
<223> OTHER INFORMATION: Human cytomegalovirus strain AD169
      (GenBank X17403.1)

<400> SEQUENCE: 64

```
gggccgcgtg gtgggtcctc gaggggcggg gggtgtttt tagcgggggg gtgaaacttg      60
gagttgcgtg tgtggacggc gactagttgc gtgtggtgcg gaggacggcg acggcgaata    120
aaagcgacgt gcggcgcgca cggcgaaaag aagacgcgtg tctgtgtctg tgtgattccc    180
cggggaaaag aggaagttcc cggggacacg cagcatgggt ccctggggac acacgaaaag    240
caacgcccgg gggcgaggga cgacggccct ggggaccgcg ggggaaataa cggccgcgag    300
gccacacact cgttcctgcg aagccgcaca ccccgaggcc gcgcacaccg ccgacacacc    360
ccgccaccac accccgccgg cacacccgcc acacgcccgc gacacaccog gcacgacaca    420
cccggcacac gcccgcgaca caccctgaca caccctgcca acacaccccc gacacaccca    480
acacacgccc gcgacacacc cggcacacac ccacccggcc gcgccccgac acacccaaaa    540
cacgccggt gcggggccgc gtggtgggtc ctcgagggag tgttgagggc cgtaagcgtg    600
ttgtgtccga cgctgcctgc gcactgccgg tgcgtgtcgt cccacggtat ttgttgtcgg    660
caccgggctt cgggacggtg tttcggcgcg ctgccggtgc gttccacggt ccttgcctgt    720
gtcgtttcgg cgctgcgctt gtcggggtt tcgagcgtt ctggccgccg gcgatgccgg    780
ggtgttgcgg agacgggggg tgtgcgggac ggtgttgggg ccggggacgg gggttgcgct    840
ggggccgggg ctgttcgcgc gcgtaggggg aggttacgtt ggggacgggg acagtttgcg    900
gcgcggacca gggaacccac ctcacctatt taacctccac ccactacaac acacacatgc    960
cgcacaatca tgccagccac agacacaaac agcacccaca ccacgccgct tcacccagac   1020
gcccaacaca cgttacccct acaccacagc aacacacaac cgcatgtcca aacctcggac   1080
aaacacgccg acgaagaaca ccgcacacag atggagctcg acgccgcaga ctacgctgct   1140
tgcgcacagg cccgccaaca cctctacgat caaacacaac ccctactact cgcataccccc   1200
aacaccaacc cacaggacag cgctcatttt cccacagaga atcaacatca actcacgcat   1260
ccacttcaca acattggcga gggcgcagca ctcggctacc ccgtccccccg cgcggaaatc   1320
cgccgcggcg gtggcgactg ggccgacagc gcaagcgact ttgacgccga ctgctggtgc   1380
atgtggggac gcttcggaac catgggccgc caacctgtcg tcaccttact gttggcgcgc   1440
caacgcgacg gcctcgctga ctggaacgtc gtacgctgcc gcggcacagg cttcgcgca   1500
cacgattccg aggacggcgt ctctgtctgg cgtcagcacc tggtttttt actcggaggc   1560
cacggccgcc gtgtacagtt agaacgtcca tccgcgggag aagcccaagc tcgaggcctc   1620
ttgccacgca tccggatcac ccccatctcc acatctccac gtcggaaacc gccgcacccc   1680
gccacatcca ccgcatcgca ccacccacat gcttcgcctc ggtcagatca cacgcttttt   1740
cctgtcccat ctacaccctc agccacggtt cacaatcccc gaaactacgc cgtccaactt   1800
cacgccgaaa cgacccgcac atggcgctgg gcacaacgcg gtgaacgtgg cgcgtggatg   1860
```

```
ccggccgaga catttacgtg tccaaaggat aaacgtccct ggtagacggg gtaggggat    1920 ctaccagccc agggatcgcg tctttcgccg ccacgctgct tcaccgatat ccaataaacc   1980
catcccctcg ccacgacgtc tccgcgtatc tttgtagcct caagaatccg tccccacgtc   2040
cacccatccc gagcactcca cacgccataa caaaccacgg acacgacaaa tgcatgcaaa   2100
cttctcattt attgtgtcta ctactctgtg ttgctacagg gagtgaagag ggtgaaggca   2160
aagaaaaaaa aaaggaacaa aataatagat tagcagaagg aataatccgt gcgaccgagc   2220
ttgtgcttct tttcttataa ggaggcaaat atactaggga aaacataaga ataggaagaa   2280
accgaggttt gggagaaaag ctgagataaa atagcgcatt ttccatacag aggttgttgt   2340
ttttgtggat cctaagaggt ttcaagtgcg aatctcaaag ttctcacgag aatattgtct   2400
tcaagtatcg acaactgtgg tccaagattt tttttggtc tttttaggtt ctgcgaggga    2460
catcacgatg gatcgttgcg atgaagtcac gcgtacgcct ctggtgtggc gcggtgtcgt   2520
gacaggagag tgtgttttca gtgcagagct gtcttgattc ctatatccga gtatctgttt   2580
tctcgtaagg acggtaatct tctttggtgt aagtacatct aaaagctgca aactatattt   2640
taagggctgt ctctaggtgt actttgatgc tggagttttt cgctgtgttg atgtgaataa   2700
atctactact actattatat gcagaaagag tgattatgcc gagacaagat tgcattggct   2760
gaactgtttc aaaaacgcct acactctact tatccgtaaa cctaaggtaa tactatgtgt   2820
aagttgtttt tttttctttt tgtagtaaaa tggtgatacg tgcaattaaa actgtattcc   2880
atgtttccat cctttcattt caactttaaa ggcggctttg agagcgaaga agtgcgagga   2940
taaaaatgga tgactccttc gtgtccaggg agtcgactac tgcaacgctg attgattaaa   3000
agatggtctc cgatgatgat gttgttattg atcgaatcat ggtgcagaac ggcgacggag   3060
aggagcgtgt ccgccgccgg gaaggtggtc tctttctctt ttcttttttc aagaaatctt   3120
ccatgtgttt atcgtagtga tcgaaatcga ctgatctcgg gttcttttg ttggtttctt    3180 ttcggttaat catgtattgt tttctttttt tacagaaaga tacttttttt catgagcaat   3240
tcctcgcccg gcgccggcat gccgaggtgg ggccactgcg atcagcggca tgccgacgcc   3300
gacccgggga tcttggattc accgttttct ctcttctctc tctacataca gaccgggtgg   3360
caggagcggt aaggaatcat cgtcgtcttt cattcttcga tgattatggt aatactaaat   3420
cttatctagg agcatataca tctaagattg gagtactagt agtcgtttgt ggtttctatt   3480 ttttttata tttatctatg acagtttttc tgttttcgt tttgataata atataataaa      3540
aactcatgga cgtgaaatct ggcttggttg tggtgatttc attctcatta ttgttgtttt   3600 cttccgtct tgcggatgaa gatgttgcga tgcggttgtt gttggtgttg ctatacaccg     3660
agagagatga tcttttttgtt cttctggttc atttcctatg attgtttggc tgctgaccga   3720
cgcgtcagga tgtgcaggc atgcggggaa tcaggaccgg acacgggata atttcatcta    3780
cctatacgga gatcgcggtc ctcgccatga ggatcgcgac aggcgcgtcg agggggcagg   3840
aacacccttg cggattgaca ttcttggtgg tgtttcgttg ttgtcggtag ttgttgttga   3900
cgatgaggat aaataaaaat gaccttgttt ttgttctgtt ttctcttgtt gggaatcgtc   3960
gactttgaat tcttcgagtt atcggaaagc tgaggtaccc aaatgtctgt agcttttttc   4020 tttttacccct cttgtttatc atctgcgatt cgtggtaggt aggagaggga aatgataatc   4080
cgagattaag gaaaggagaa gataaaaaat aaaaaaaat aataaaacag aagccgaccg    4140
gccgccgacc cgttccccag gaccagccta cgaggaacgg ataacgcggt ggcgacggca   4200
```

| | | | | |
|---|---|---|---|---|
| gcggtggtgg | cgctgggggt | ggcggcagtg | gtactgctga | tggtagtcgg gacgaggag 4260 |
| aggcgatgca | tacatacacg | cgtgcatgct | gcatgggtgg | atggtacggc cgggagacgc 4320 |
| ggaagagaaa | ctcacataaa | aaggtgacaa | aaagagcggt | tgaaaaaaga aaacaagatt 4380 |
| cgaccagaca | gaagagaagg | accggggctt | ggcgacccct | ccacgactgc tgttgtcatc 4440 |
| tcggctcctc | cgtcttctcc | cggccacggg | cggctaagtc | accgccgttc tccccatccg 4500 |
| tccgagcgcc | gaccgaccag | ccggccgatt | cgcccgccgg | ggcttctgga gaacgccggg 4560 |
| gcagcagcga | tctggggaag | ctgctaaacc | cctgcgtttt | tatatggtag ctctgccgag 4620 |
| cgcgggctga | cgcgttgggt | aagcggaaag | acgtgtgtga | cgaaaagggg tcccatggta 4680 |
| tttcacgtga | cgatgaggag | atacggtttg | gagcacatac | ggtttagaaa aagggagttg 4740 |
| tcgtgacaag | ggctgaggga | cctctgtctc | catgtgtgta | taaaaagcaa ggcacgttca 4800 |
| taatgtaaaa | aagaacacgt | tgtaaacaag | ctattgctgt | atcattcggc tgactatgct 4860 |
| tcattcggac | tgattttctt | ttcctaacgg | cgtaacttaa | agtgattaac gtatgatatt 4920 |
| tgttccccag | agttatacta | tagtcatcat | cctaaaattc | agatataaat gaacacatgt 4980 |
| cgtatgggat | tattaagaaa | ccgaaactct | ccacagttca | ccatcttctt cgtcattcaa 5040 |
| ccgatgaccc | actccgtaca | acgaatcagt | ctgctgcgtc | atattgcaaa gcacaagcga 5100 |
| cgtatgcgaa | caacttgaaa | cacaggctgt | tgtattgacg | accgttgtac cattattagt 5160 |
| caccaccgtt | atcccatgtt | tcccacccga | tggaaaaccg | tcttctatca tcaactgtgg 5220 |
| taagatttcg | accctgcgag | gtattcagtt | tcctcatatc | cataacctgg attttatcat 5280 |
| taaaccccaa | tattaaacac | ttttttagta | ccccccaccc | accaaaaaat gtgactggac 5340 |
| cggttcctag | cagctctggg | agccatgttc | aggttgaacc | acagctacag cgaaaccgag 5400 |
| tccagtgacc | ggtaaccacg | tccagcccct | gcgtatgtac | cagtccaagc acgtccggtc 5460 |
| attgttctac | acaggaaatc | taactaggtc | aacgcaattt | tattccaccg ttacgcagaa 5520 |
| tactaacaaa | aaaacacaca | aatttaacga | attcacgta | gtttattaca tgaaaactgt 5580 |
| aagaacacca | attcactaag | cgatacaaca | tttagctgac | ttccaagtgc cacacatcac 5640 |
| cactgtattc | atccatgttt | tcaccgaacc | aacgagacag | atcgaagaag ccagaatctc 5700 |
| ccgactttaa | attacataaa | tccaacgtat | tatgaccaca | gctcgacaca caaatagttg 5760 |
| cgttactatt | cacagtagca | ttacctatac | ccgtaacgtt | gcacaaccac tgatcaccat 5820 |
| tgttaccaaa | aacggttttc | cacttagttg | tcaacggatc | tttcctatgc gtaatggtaa 5880 |
| aattactacc | agtcgtcgct | tttagctcat | tacgagtatt | atccgcatcc acatatatca 5940 |
| acgtcatagc | taggcacgct | ataagtaccc | cccccccaca | atggaatgtt gccaaaccgg 6000 |
| ttctttcccg | ttatagccat | agcgttccca | ggcaaaagca | aacgccaaac ctaatgcagt 6060 |
| gaaaagcgct | tgcagccaga | accagcttat | gtaccagcca | caatcacatc cggttattgt 6120 |
| ttccacagga | atcctacca | ggcaaagccc | cgcttgtttt | gttcctatct tgtttagcaa 6180 |
| ttcgtaaact | gtcagcctag | cgacgtccgt | ttagatcaaa | agtcacgtat atagcgacgc 6240 |
| tgtttccatc | cgtttccccg | tcccgccgtt | tccgaacaac | ccacccgggt tcagacaacc 6300 |
| gaccaccaac | agaaatatac | acacagacca | ctgggagttc | agttaaagat tcatcaggt 6360 |
| ttattttggc | tgctgctagt | cttttgcttc | ttagaaaaaa | aatacccata tagagaaata 6420 |
| atgatagttt | gacaacacat | atggcaggga | tttcttcttc | atcaataaga tatgcaattc 6480 |
| ccccagggag | agactttcaa | caattgaatt | tacaaaaaca | aaattacatc aggagaaaga 6540 |
| gaggatacat | taataaatat | attatatctg | gtgtatatac | tgaatgctgc tggttcataa 6600 |

```
ggtaacgatg ctactttttt taattccaag atggttttc tttgttagtc ttttgttgac      6660
ttgctggttc ctaaaagttc gcaaaaacga ttgtgtgaag attttatgac gttggttgac      6720
tagttcatga gattctgctg tacgtgtgat ggttattcgc tggttcgttc taagatgagt      6780
atcgtactgt gtctgcgatg gtcgtctctt actggcattc tctcggctgc ctcttgcttt      6840
catgattgaa aaggaaaaaa ggactccgag ggcgcggtca tctttactt ttcggttttc      6900 tcgttggcgg gtcagaggta gtcagatcat gagactgtcg tggtcgatga aactgtgtct      6960
gctcaagtga cgtccatttc ttgtacgag aaaaagtca tcgggataaa taaggctata      7020
caaggcgttg tcaagcgtgc ggctctaaac aaattaagcg atacaaaatt acagtaatac      7080
gaataataaa ttacccccct cccctgtgg tcccccgaga cgagagccac ccatcgtgta      7140
ctctcgcacc acccacgacc acagagggag acgggacgaa gagacgacgc acagcgccat      7200
ctcctcctgg aggccggcga cgttaactgc tacagctgcg gcggcgaaga cagctgcgat      7260
ttgtcggccg acatgccgat ggtatgggcg gcggcggcaa tggccgcggc agcggggagg      7320
agaggagaga gaagaggagc ggggcgtccg aaggcgagga tggcatggtc tcgccggagc      7380
gcccggcttt tatggaacac tcgcgtccgg ttgggtatca cccacaggaa gatgagtcac      7440
aacttccaaa ccatcttgag acccgagtaa cggtttacag gtcgcacgcc agtcagctaa      7500
aaacagcgga cagtcccacg ctgtttctgt tgtggctctc tccagtttcc tcatcaccgt      7560
cccggtctcc gtcgtcatcg gaagaatacc acccgctctc atgcggcagt cgatcggcct      7620
cgacgaacga gacgcggcga cgcctctcca cggccgactg gttgtggtgg tgaaagaaga      7680
gcaccagcaa tccaggagg agcaacaagc cctcacatgt ccaggaggtc ggggagaggg      7740
cctgtcggag atggccgtga ggcatcacgt acggcagctg aggagaaacg gagaagaaag      7800
gaaaattacc gtcaggggcc ggggttctta ttagagaaac agcacgtagg tcaggatcca      7860
gatgctaatg gcaatcatga tgacgatgat catgcaggcc aagacgcggc gcaccaatgc      7920
cgaatccaat agccgccgtg cctccggttg gtggccggcg gcatctagag acatgatttg      7980 gggggaccg gcggcgcaaa aagacaggga gatggacagt gtcacggtgt tttgttataa      8040
ttaggacatg gggaccggaa gccgagacag agtactacag ggtgttgaag ggtaacgtga      8100
gggagatcat gtcatgggcg ggctgaagac cgtgcgggga ggattgacgt gtgcggtgct      8160
tgtgaaacac ggtgttttaa tatgtatccg cgtgtaatgc acgcggtgtg ctttctggca      8220
ctcagcttgg taagctatgt ggccgtctgc gccgaaacca aagtcgccac caactgtctc      8280
gtgaaatcag aagatacca tttgacgtgc aagtgcagtc cgaataacac atcatctaat      8340
accggcaatg gcagcaagtg ccacgcgatg tgcaaatgcc ggatcacaga acccattacc      8400
atgctaggcg catactcggc ctggggcgcg ggctcgttcg tggctacgct gatagtcctg      8460
ctggtggtct tctttgtaat ttacgcgcgc gaggaggaga aaacaacac gggcaccgag      8520 gtagatcaat gtctggccta tcggagcctg acacgcaaaa agctggaaca acacgcggct      8580
aaaaagcaga acatctacga acggattcca taccgaccct ccagacagaa agataactcc      8640
ccgttgatcg aaccgacggg cacagacgac gaagaggacg aggacgacaa cgtctgataa      8700
ggaaggcgag aacgtgtttt gcaccatgca gacctacagc accccctca cgcttgtcat      8760 agtcacgtcg ctgttttgt tcacaactca gggaagttca tcgaacgccg tcgaaccaac      8820 caaaaaccc ctaaagctcg ccaactaccg tgccacctgc gaggaccgta cacgcacgct      8880
ggttaccagg cttaacacta gccatcacag cgtagtctgg cagcgttatg atatctacag      8940
```

-continued

```
cagatacatg cgtcgtatgc cgccactttg tatcattaca gacgcctata aagaaaccac   9000
gcgtcagggc ggtgcggcgt tcgcgtgcac gcgccaaaat ctgacgctgt acaatctcac   9060
ggttaaagat acgggagtct acctcctgca ggatcagtat accggcgatg tcgaggcttt   9120
ctacctcatc atccacccac gtagcttctg ccgagccttg gaaacgcgtc gatgctttta   9180
tccgggacca gggagagttg tggttacgga ttcccaagag gcagaccggg caattatctc   9240
ggatttaaaa cgccagtggt ccggcctctc actccattgc gcctgggttt cgggaatgat   9300
gatctttgtt ggcgcgctgg tcatctgctt cctgcgatcg caacgaatcg gggaacagga   9360
cgctgaacat ctgcggacgg acctagatac ggaacctttg ttgttgacgg tggacgggga   9420
tttacagtaa aagatgcgtg tcgcctgccg aagacctcac catctcacgt acaggcatac   9480
ggcgtataca atcataatat tctatattct gcatagagtt acatgcaaca gtactactac   9540
caatactgca tccatcacat cacccaacac tgcttctacc acctttgtga ccagcgtatt   9600
ttctactccg aataacaaca catcaacgac gccacacaca tctgtcacct cacaagcgtc   9660
aaccattggc aacatcacca acgttacctc cgacttgagt actttcacaa ccgtatattc   9720
tacattcaat acatcatatg ctaatatatc caatacggct gccactacag aattgatttc   9780
aacaaatacc aacactatat tatcttttac caacgtaaca gcaaacgcta catcatctta   9840
taacacaaca atcaccgtaa ctatcacgtc agatgaaact tcgcacaacg tatccactaa   9900
tactgcactt ataagcacgc catggcttac aaattgcagc gccacaacgt acaccacgta   9960
caaccgtact aactcttcca acgcttgtca cacagagaca acaatcatac gtttcaaaga  10020
aactaataca acaggaatag aagggagtaa tgtcaccata aaaggtaatt ctacgtggga  10080
ttgtctttca gtcgcctgga tacgacatta caatcgatcc acacacggac atcatctagg  10140
tcatcgtaag aacgcacata cccaatcttg gtattggtta cgcatcctta cctctcatac  10200
tgtatgtcat tctcaacatg aaagaccttc actgtaccat gacttatgtc gttcgtgcaa  10260
caacacagaa ctacatctgt acgatctaaa tatcaccaat tccggcaggt acagcagacg  10320
ttgttttaaa gaaaattact tcacaggaca tcacgaagat gaaaatttct acctattagt  10380
aacaccaaaa aatcatactg aagctattaa tgctactttc gtttgcccta gatacaacac  10440
cgatatcgaa aatgaagata gagagaaagg aagtcaacat actaacaata cacatccacca  10500
caaacgtaat ctctatcata gctcgcaaag aagccgcacc gtatggacca tcgtgttggt  10560
ttgtatggcc tgcatagttc tgttttttgc acgacgagcc tttaacaaaa agtaccatat  10620
gttgcaagac accgtcagtg aatcagaatt cattgttcga tatcacacag aacatgaaga  10680
ttgagctacg tttccgggca gacatcttat gaagctgaac aataaactaa acattctgt  10740
aaggctcagc gttcaaagga atattaatgc ccattgagcg agaactaata ttgcaatgga  10800
ctggcgattt acggttatgt ggacgatact aaatatccgcg ttatcagaaa gctgcaatca  10860
aacctgttcc tgtcaatgtc cctgtagtac taccgttaac tattccacta gtactgagac  10920
agccacatca acatacagta caacagttat cagcaataaa agcacttcag aatctataaa  10980
ttgctctact gcaactgcac cagcaaccac cgtttctaca aaaccgtcga aacaaccac  11040
acagatatcc acaacgacaa atacaaacgt tgagactacc acatgtacca acaccaccac  11100
gaccgttact tgtgatggtt tcaattatac agtccataaa agatgcgacc gcagttacga  11160
ggtaatcaac gtaacaggat acgttggtgg caacataact ctaaaaaatg caatcagact  11220
gagaaatggc acaatgtaga ctggattcat tatgagtacc ccacgcataa aatgtgcgaa  11280
ttaggcaact atcaccaaac aacaccacgg cacgacatat gttttgactg caacgacacc  11340
```

```
tccctaacta tctacaactt aaccacaaga aacgctggaa aatataccag gcatcaccgt   11400
gataacggtc aagaagaaaa ttactacgta acggtgttaa ttggagacac aacgttatcc   11460
actcttggca catgccctgt aagatataaa gaatctagga acactgaaaa caccattgga   11520
agtaacatca taaaaaccat tgagaaagct aacattcccc tgggaattca tgctgtatgg   11580
gcaggcgtag tggtatcagt ggcgcttata gcgttgtaca tgggtagcca tcgcattccc   11640
aaaaaaccgc attacaccaa acttcccaaa tatgatccag atgaattttg gactaaggct   11700
taacatgcac atcaataaac ttttttaac caataacatg tctctgtttt tttttgttaa   11760
caacctatga tataaagcgg tatattcaat cattactaaa caaaaaaaca tgggcatgca   11820
atgcaacact aaattgttat tgccagtcgc actaataccg gttgtaatca tcctaattgg   11880
tactctagtg cccatacttt tacatgaaca aaaaaggcg ttttactggc gactttttct   11940
gcaaagtcaa catgtagaag cacccattac agtaacgcag ggagacacag tctacctaga   12000
tgctagcaat aatccctgta attattccag cttttggtac cacggtaatt gcgaactttg   12060
tggatggaac ggatatctac gcaatgttac acattactac acaaacacat cgtgttcccc   12120
gcaattcatg tgcataaacg aaactaaagg tctgcagtta tataatgtaa cattaaacga   12180
ttcaggtgct tatactgaac acgtttacga atgtgatctt tcatgtaaca ttactactta   12240
taacgaatat gaaatactca attacttcga taactgtaac tacaccataa atagcaccaa   12300
gcatattatc accgtggtgt cttcacgtca ttctaaacaa acaaattccc acgtatccac   12360
tcacgctggt tgggcagccg ccgtggtgac ggtaattatg atctacgttt tgatccactt   12420
taacgttccg gcaactctga gacacaaact acgaactaga aacaacgtaa atcgcatagc   12480
gtgattacaa agtatcgaca ctaatttatc caagataaaa tttgattact ccgtgcggtt   12540
ctcaaaaact gtaaggtccc gcttttctac tccatcatga aggatcgcaa tagaatactg   12600
ctatgtatca tctttatttg catcatgtgc ctcatttgta tttactttaa acgtcgttgt   12660
gttcttactc cgtctccaga caaagcggat ctgcgagtgg aatttccctc gttaccccg    12720 tgtatcggca tacaatgtgc tgcatgagaa cacgcgtgac acatagcgta cccctggacg   12780
gtacagttta tgataacgtc attcagggga agtatacatt actatcgacg tgttatcaca   12840
gaacacacag attttctgcg tgttttataa aagagcgtct cgaagcagct tgagccacac   12900
tacggtccag atgacgagcg taatcaaaaa tatgccgcgc agtagtcgaa agccgtactg   12960
agcgtgcgag gcgggtaggg tgccgaacga cggatatgcg tcgttgtcat cttcgactat   13020
aaggatcgcg accgagtctt cggccatggt aaacgtcacc ctgtgtggct ggtatgtagc   13080
gtatccggtt tggaattgtt ctgctccagc tcggggata gtgaggaatt ctcaagggat    13140
acgggaccca atgactggat aagagaaggg ttttcccg taagatgatc ctcgtatcac     13200
atgaggtctg gatatgtata aatgaagagt gaaataggca cagggaatca gatgccagcc   13260
tcgtgatgca gccgctggtt ctctcggcga agaaattgtc gtctctgttg gcttgcaaat   13320
acatcccacc ttaagcgatg agtccataaa gcaccgttgt ccgggtacgg tgaaagtgac   13380
tcggattgta gcacgtccct ttttttgtt tttgtatcgc ttatcgccac tgacagtgca    13440
atattttgat cgtgaggctg agtatggtta tgatgcttag aacgtggaga ttattaccaa   13500
tggtactact tgccgcgtac tgttattgtg ttttgggac ttgttcaatc ggcacgacga    13560
ctgctcccgt ggaatggaag tctcccgacc gtcagattcc taagaatatt acttgcgcta   13620
actactcagg gaccatcaac ggcaacgtta catttcgagg tcttcagaac aaaacggaag   13680
```

```
acttttttgca ctggttgtta gggtggggtc ataagtccat ctgttcgttc ttcccgaaac    13740
tccagggcaa ctataacgaa caacattaca gatatgaagt agcgaacctg acgtataact    13800
gcacctataa ccgcttgacg ttgctaaatc tgacgacgga aaacagcgga aagtactatt    13860
ttaaaaggga agatgcgaat ttcaccttttt attactcttg ttacaacctg accgtgtcct    13920
aaagaacgca cgtgaagttc cacagagccg cgtggctgta gctattgtgt ttacgttgct    13980
tttgaaatgt taagcgtccc tacggcgcta acatgtttct aggctactct gactgtgtag    14040
atcccggcct tgctgtgtat cgtgtatcta gatcacgctt aaagctcgtg ttgtcttttg    14100
tgtggttggt cggtttgcgt ctccatgatt gtgccgcgtt cgagtcctgc tgttacgaca    14160
tcaccgaggc ggagagtaac aaggctatat caagggacaa agcagcattc acctccagcg    14220
tgagcacccg tacaccgtcc ctggcgatcg cgcctcctcc tgatcgatcg atgctgttgt    14280
cgcgggagga agaactcgtt ccgtggagtc gtctcatcat cactaagcag ttctacgag    14340 gcctgatttt ccacaccacc tgggtcaccg gcttcgtctt actaggactt ttgacgcttt    14400
tcgccagcct gtttcgcgta ccgcaatcca tctgtcgttt ctgcatagac cgtctccggg    14460
acatcgcccg tcctctgaaa taccgctatc aacgtctcgt cgctaccgtg tagctagtta    14520
gccagctgtg tatagtttgt tgtgttttgc ttttgcatat ttgttttcag tcagagagtc    14580
tgaaacgggg tgggagggac ttttacgggt aatgcatgct aagatgaacg ggtgggctgg    14640
ggtgcgcttg gtaactcact gtttgaatac gcgctcacgc acatatgtag cactcaacat    14700
gttagctttt gcccgcacgc cccggggcgt gccgagctgc cttttttaata aagtctgggt    14760 ttccagatac gcgctggttc tgattttgat ggtttgtgcc tctgaaagct ctacgagctg    14820
ggccgtgaca tccaatcgac tgcctaactg tagcacgata actacaacag cgggtcaaga    14880
cgctgaattg cacggtccgg caccgttaag ctgtaatgtg acccagtggg gacgttacga    14940
gaatggaagc acaccgtat tatggtgcac tttatgggga tcacgcacgc gagtctcatt    15000
aggacaccgt gtagcgtttg gctgttcttg gaaaacattt tttatttata acgtttctga    15060
aagtagtggt ggcacttatt atcaaaaagg ttacaactgc accgacaaac atataacact    15120
atcttgtttc aacctaacgg tggttcctcg agcggttcaa agcacaacca ccgtaatgac    15180
acccacggtg gttacaaact ccacattcag tgtgtcactt gttgcgtcga gactgacgac    15240
aaattccagc gcgtttagac acgctagtta tcaacggcaa cagcgtgtcg gaaacgggac    15300
gttatccaag aacataacta acttggcatt cacctacggc agctggggcg tcgcgatgct    15360
gctgttcgcc gccgtgatgg tgctcgttga tttgggtttg cctcaatcgg cttggcgacg    15420
ctggcgaagc cacgtggacg atgaagaacg tggtttgtta atgtaggaaa taaaaggcac    15480
tgtttgagca tgactgtttc caaaccgtaa cgtggtaaat aaatcatggc ttccgacgtg    15540
agctcccatc ttctaacggt tacacaatcc cgttggacaa tacatcatat gtacaataaa    15600
ctgttgattt tggcgttgtt taccccccgtg attctggaat ccatcatcta cgtgtctggg    15660
ccacagggag ggaacgttac cctggtatcc aacttcactt caaacatcag cgcacggtgg    15720
tttcgctggg acggcaacga tagtcatctc atttgctttt acaaacgtgg agagggtctt    15780
tctacgccct atgtgggttt aagcctaagt tgtgcggcta accagatcac tatcttcaac    15840
ctcacgttaa acgactccgg tcgttacgga gcagaaggtt ttacgagaag cggcgaaaat    15900
gaaacgttcc tgtggtataa tttgaccgtg aaaccgaaac ctttggaaac tactacagct    15960
agtaacgtaa caaccatcgt cacgacgaca ccaacggtga tcggcacgaa aagtaacgtt    16020
acggggaacg ccagtttagc accacaacta cgtgccgtcg ctggattctt aaatcagacg    16080
```

```
cctcgggaaa acaacacgca cctggccttg gtaggtgtta tcgtatttat agctctaata    16140
gttgtttgta ttatgggatg gtggaagttg ttatgtagta aaccaaagtt atagtgatgt    16200 gcttttatc agggagaagg ttttgtgcca acaatgacta ccctgggct atatgcatcg      16260 gaaaattata acggaaatta tgaacttacg gaagccgcca atacagcacg tacaaatagc    16320
agtgactggg taacgttagg aaccagtgcg tcgctgttga aagcacgga gactgcggtt     16380 aaccctagca acgcgactac ggttactcca caacctgtgg aatacccagc tggggaagta    16440
caatatcaaa gaacgaaaac acattattct tggatgctaa ttattgccat aattctcatc    16500
attttattta tcatctgtct gcgagcacct caaaaagtct acgatcgctg aaagacaat     16560 aaacagtacg gacaagtatt tatgacggac acggagctgt gatgaactac aatgtataga    16620
tacacgtggc tgctttggtg gataacaata ttgcttcgta tacaacagtt ctatcaatgg    16680
tggaaaccag atacaacgtc atgcattcag aaaacgggat atgaaggtca aaacctcagt    16740
ctgcctccta gtaatgcatt atcatctaaa gactatactt tttcatggta taaagattca    16800
cttaaagccc ttaacatgtt atgttattat actgaaaaac ttgaagaaat agatagcaag    16860
ccagatacta tacgacgatg ttttttgaat catacattgt ttcttattaa tttaacaagt    16920
cactatagcg ggatttacta cttcgattct ctatacacat atggttgggt attacggaca    16980
cctctatgtt acaatgtcac tgtatattcc atatatcaaa cacacatcca cacaactata    17040
ttgctctatc cgcctacgtc cacatataat tcattaacta tatcatcatt tacctcaacc    17100
aacttaacac ataccgcggt ccactatgcc gccggtaacg ttgaagcaca acacgatact    17160
gccaccccac ataccatgtg gatcataccc ttagttatcg ttacaacaat tatcgtttta    17220
atttgtttca aatttcccca gaaagcttgg aataaattca cacaataccg atacaacagt    17280
atgctcaccg ccgcttaaag aatcaccgtc gagaaaacta aaacgtaaaa agaatggcca    17340
tgtacgttta ttttttcagct cactgtttga ataccgtaaa cataatgacg tacatatacg    17400
tgattataca acaggtgttt gtgttatgcg gcgactgatt aaccatatcg tgaaccatga    17460
tcttttccga tggtccgtca tgaccgcaat gatatttac aggtattccg aaacctgtat     17520
ggaggtcact gtcagagtag gtgatccagt taccctcggt agtggacatg gttatcatcc    17580
aggacaaaaa gtacactggt ataaccagtc atgcgtcggc attagcaacg gcgaaaatac    17640
gcatcctatc tgcacctacg accctcctaa acctggtaga cgaaagacaa tgaaaaccac    17700
tccgttacca tcaccactgt tgtacgagtg tcacaattcc acattaagca ttcttcatgt    17760
aaacgtctca gatcccaaaa actattgcag gcgaaaatgt ccaccaaacg gtaactgtga    17820
atttcccaca tgttttacgt tatcactgat ttccagaacg acaaccacca gaaacccgg     17880 acaaaaaact acgttgtcgc gattaaaaac cacgccaaat aaacatacgc agcacaaaag    17940
atccacgcga agaacgtcac ctagagatta caatgtaacg ggtctgccga aaggctttgc    18000
ggactcgttt accggtaacg tagaggcaca tagagccaaa gatgccgcac acagcgcatg    18060
gatcctcatt gtcatcatca ttatcatagt cgtcatttta ttttcttca agattcctca     18120 aagactcaga gagaaatggg acaccagagg ataccttac aaaggaaccg acggcctgcc     18180
cactacggac tacttatcgt gagcggacgg atatctccgg tttcaaaccc actgtttgaa    18240
tatagggaca gtccctacgg aacctgagaa catgtggaaa tcacctgtgg tagaatgctg    18300
ctcaggtaca ttacctttca tcgtgaaaag gtactttacc tagcgatcgc atgcttcttt    18360
ggtatctaca tcagtttcca cgacgcatgc attctggtac ctgctaaagt aggtactaac    18420
```

```
gtcacattga acgcggtaca tgtgcatgac ggtgactatg tgtactggtc ttttggtgga    18480
ggtggagcta atagattaat gtgtcgctat acaccaaggc tagacgaaat tcacaaaaac    18540
accaatcgaa gtttttcatg tcttacaaat cacagtctcc ttctcatcaa tgtaacggaa    18600
gaatatactg attactatcg caccatgacc acattcgtac atcagtccca taattggcac    18660
aaccacggca acaaatggac tttagacaca tgttattatg tatacgttac ccaaaacgga    18720
acacttccca ctaccaccac caaaaaaccc actacgacca cgagaacgac aactaccacc    18780
acaacaaaga aaacaaccac cacgagcacg caaacgacca ccactaccac caagaagacg    18840
acgacaagca ctacccatca tcgacactcc aatcccaaag aatccaccac ccctaaaacc    18900
cacgtagaac ttcacgtcgg tttaggagcc acagcagcgg aaacaccgtt acaaccaagc    18960
ccacagtacc aacacgtggc tacacacgcc ctctgggttt tagcggtcgt aatcgttatt    19020
atcatcatta tcattttcta ctttcgaata ccgcaaaagc tgtggctgct ctggcagcat    19080
gacaagcacg gcatcgtgct catccctcaa accgatctgt gagcaagtcg cgtaggaaat    19140
gattgcatga aatcactgtg aaacgccaac tccgtgccag ctggcgcggc ggacaggcct    19200
ttgacgtatt tgaagccagg cgcgctctcg ataccgaaag gatccgaggg ggctttccaa    19260
agccgacgtc cctgattccc ttcataaagc tgttgaccgg ccctagaaag accaagagca    19320
tgctgtgggc ccactgcggt cgcttcttgc gttatcatct gctcccgctg ctgctgtgta    19380
gactgccatt cttactcctt ttccagcggc cgcagtgggc ccacggcttg acattgtcg     19440 aggaggacga gtggctacgg gagatacaag gagcgacgta ccagctgtcc atagtgcgcc    19500
aagccatgca gcacgccgga ttccaagtca gagcagcgtc ggtcatgacg cggcgaaacg    19560
ccgttgacct ggaccgaccg ccgctttggt cgggatcgct cccgcatttg cccgtctacg    19620
atgtgcgttc cccgcggccg ttgagaccgc cgtcatcaca gcatcacgcc gtatcacccg    19680
aactgccgtc gcgagacggg atacgttggc agtaccaaga gctgcagtat ctggtggaag    19740
aacaacggcg gcgaaatcag tcgcgcaatg cgattccgag accctcgttc ccccctccgg    19800
atccaccatc gcagccggca gaggatgcac gagacgcgga cgcagaacgt accgaatcac    19860
cacatagtgc agaaagcacc gtcaggcacg acgcgagtga gaacgcagtg cggcgacggc    19920
acgaaagacg gcgctataac gctctgacgg tccgcagccg ggactcgctg ctcctgacgc    19980
gaatacgctt ctccaaccaa cggtgtttcg gacgcgggcg tctgagacat cccgcgggaa    20040
gcggtcccaa caccggcgga ccgcgacccg gcggtgcggg actccgtcaa ctacgccaac    20100
aactgacggt ccgctggcag ctgttccgcc tacggtgcca cggttggaca cagcaggtct    20160
ctagccagat cagaacccgc tgggaggaaa gcaacgtcgt gagccagacg gccacgcgag    20220
tacgtacgtg gttcgtggaa agaaccacgt tttggcgtcg cacgtgggtt ccgagacaga    20280
acccggcggc cgaagcgcaa gaactggccg tcataccgcc ggcacccacg gtgctccggc    20340
agaacgagga accacgtcaa cagcttacgg gagaggagac aagaaattca acgcacactc    20400
aacgtgaaga agtggaggac gtttcgagag agggcgcgag agaagggaat gatgggagcc    20460
gagcaagtgg aaacgacgag agaaggaata atgcgggaag atatgatgat gatcatgagg    20520
ttcaagagcc gcaggtcact tatccagcgg gacaaggaga actgaatagg aggtcacagg    20580
aggagaacga ggaaggtgga ccgtgtgaat cgccgccaat gacgacaaat acgctgaccg    20640
tggcctgtcc gccccgagaa cccccgcatc gtgccctgtt tcgtctatgc ttaggactgt    20700
gggtctcgag ctacctggtt cgacggccca tgacgattta gaatacaccg agccattcct    20760
ttatttcccc ccatccccgg tcgcttatgc gtgttaaaca ctaccaataa agataatctg    20820
```

```
ccaatcgcac cttatatata atatgtggtc gcgtgtggtc tttttaagga gctctgaaac   20880
acagacaggt atgggcggtg gtcggctgcc gccgctgtgg ctgccgctac tgatcgcctg   20940
gagcgagtgg ggcaactgct gcctcgatgc gcctccggtg gtgcgttcgc cctgtctgca   21000
gccggtgcgc gaccgcaacc gcgagcggaa cccgggctca ccgcagttgc tgccttacgg   21060
cgaccgtctg gaggtggcct gcatcttccc cgcgcacgac tggccagagg tctctatccg   21120
agtccacctc tgctactggc ccgagatcgt gcgttcgctg gtggtggacg cacgcagcgg   21180
tcaggtgtta cacaacgacg ccagctgtta catcgccggc gggcgctggc gcttcgagga   21240
cggcggcgcg cgcagcggc tgagcctctc gtttcggctc atcaccgaga ccgcgggcac   21300
ctacacctgc gtgctgggca acgagaccca cagcctggcg accagacca cggcgctggt   21360
ggccgacgtg cacgacctgc gccactcgga ccgctcctgc gacctggctt cggatcgcg   21420
ctcacagacg cggtacctgt ggacgcccga tccctccagg ttgcgcagta taaactgcgg   21480
ttgggagggt gaacggcacc gcgtagtcca ctacatcccc ggcacctcgg gtttgctgcc   21540
ctcgtgcgag gaggacgagc gcgaactgtg cgtgcccttc atcagccaga gcattgcgga   21600
caacaactgc agccgccggc atcgagttga cggcgctagg cggcgctatc atctacggag   21660
ggattactgg ctgacggatc cgaagatcgg gttgctggcc gcgggatcgg tggccctgac   21720
ctccctctgc cacctgctgt gctactggtg ttccgaatcg taccggcgtc tgaacaccga   21780
ggaggaaagc gaggcggcgg aggaaactgc gcgggagaa gcctctgcgg tagcggcggc   21840
ggccgtctct gaggaagagc agcggcggga gtaaacgagg agagccatga agcggatgat   21900
tcgcagtcac ggcaggaaaa cggaatgtca gatgacgagc gccggcgagc gacgcgctcc   21960
gccgtcggtg cgcccatctg cggcagcggt acccgacgcg gcacggcgcc aacgaacgcc   22020
gcgactccga cgtcggtccc atcgcccaca gtagcggtac cagacgcggt tcggcgaatg   22080
aaacgtccgc ctgtacgcgg accgatcacc agaaggcgga cattgggctg tggttcatgt   22140
ttctggtttt tggactgtgt tcgtggttgg cgatgcggta tcgcgcacaa taaattttga   22200
atcgatgtca aggaacgcgt gttttgtatt ttattgggaa tattggcggg gataaacctg   22260
tttcggatgt ttaccttaa tcttaccggg gacctcgttg tcctctcctc cttcttcctc   22320
ggacaccggg ctccatgctg acgtaggtac cgactggggt caaaagcctg ggtacttatg   22380
aggagcgcgc acaaaggacc gttaggcgcc ggcatggagc gtcgccgagg tacggtaccg   22440
ctgggatggg tgttttttgt tctttgctta tctgcctctt cctcgtgtgc tgttgacctg   22500
ggtagcaagt cctccaactc gacctgccgc ttgaatgtga cggagttggc ctcgatccat   22560
cctggggaaa cgtggacgtt acacgggatg tgtatttcta tctgctacta cgagaatgtg   22620
accgaggacg agatcatcgg cgtggcttt acttggcagc ataacgagtc tgtggttgac   22680
ctgtggttgt accagaacga cacggtgatc cgcaatttca gcgacatcac cactaacatc   22740
ttgcaagacg gactgaaaat gcgaaccgtc cctgtgacta aactgtacac cagccgcatg   22800
gtcactaatc ttaccgtggg ccgctatgac tgtttacgct gcgagaacgg tacgacgaaa   22860
ataatcgagc gcctctacgt ccgattgggc tcgctatatc cgagaccgcc cggatccggg   22920
ctcgccaaac acccctccgt aagcgccgac gaggaactgt ccgcgacctt ggcgagagac   22980
atcgtgttgg tctcagccat cactctgttc ttcttcttgt tggccctacg gatcccccag   23040
cgactgtgtc agcggctgcg cattcgcctg ccgcatcgat accagcggtt acgcaccgag   23100
gactgaacgg ataaccgcaa aggccacgtg caacgttcac gctgctataa gaaggccatg   23160
```

```
tcccccgtgg acgggtctct ttgacacgag cgcggcacgc cgttgccacg agcatggatc   23220
acgcgctctt cacacacttc gtcggccgac cccgtcactg tcggttggaa atgttgattc   23280
tggacgaaca ggtgtctaag agatcctggg acaccacgg ttaccacagg cgccgcaaac    23340
atctacctcg acgtcgcgct ccgtgcggcc cccagaggcc cgccgagatt cccaaaagaa   23400
gaaaaaaggc ggccgtcctt ctattttggc acgatttgtg ctggctgttt cgacgacttt   23460
tctttcctcg ggaggactca gagccactga tgtcggatcc ggcacggtct cccgaagagg   23520
aggagtaaac aacacacggc taagaggata catcatcaaa aagataggg ggggtcaaaa    23580 cgcggactga aagtatataa cgccgatcat gtccgaggaa ctgttaataa aacgccatga   23640
tgacaatgtg gtgtctgacg ttgtttgtgc tgtggatgtt gagagtggtg ggaatgcacg   23700
tgttgcgtta cgggtacacg gggatttttcg atgatacatc gcatatgacg ttgaccgttg   23760
tgggattttt tgacgggcaa cacttttta cctatcacgt taattccagc gataaagcgt   23820
caagtcgggc caacggtacc atttcttgga tggctaacgt ctcggcggcc taccccacct   23880
acctggacgg ggaaagagcc aaggtgacc ttattttta ccaaaccgag caaaacctgt    23940
tagagctgga aattgcgttg ggttaccggt cacagagcgt gctgacgtgg acgcacgagt   24000
gtaataccac ggaaaacggt agttttgtag ccggttacga gggatttggg tgggacgggg   24060
aaactttaat ggagctcaag gataacctga cactatggac gggccccaat tacgaaatta   24120
gttggttgaa gcaaaacaaa acgtacatcg acggtaaaat taaaaacatc agcgagggg    24180 atactacaat acaaaggaac tatctcaagg gtaattgcac tcaatggtcc gtcatttata   24240
gcgggtttca accccccgtc acccaccag tggtaaaggg cggtgtccga aaccagaatg    24300
acaacagagc tgaagcattc tgtacatctt acgggttctt tccaggggaa attaatatta   24360
cttttattca ttacggtgat aaggtgcccg aggatagcga gcctcaatgc aatccgctac   24420 ttcccaccctt ggatgggact ttccatcagg gatgttacgt agccatcttt tgcaatcaaa   24480
actacacctg ccgcgttaca cacggtaatt ggacggtgga aatccccatc agcgttacct   24540
cacctgacga cagttcctcg gggagtcc ctgatcaccc gacagctaac aaacgctata    24600
acaccatgac catcagcagt gtcctcctag ccctgctttt atgcgctttg ctattcgcgt   24660
tcctgcacta ctttaccacc ttgaaacaat acctacgtaa cctggccttt gcgtggcgct   24720
atcgcaaggt ccggtcgtca tgaccagcaa cgccctgtat gagctgtttc gacgtaggtt   24780
accgcgtgcc cccgtcaaca cggtcatgtt tctcacgcga cgcactcgtg atgggttctg   24840
cggtcggttg acgtccatcg ccacgaattc ccactacact atgttcgtgt tagatcacgg   24900
gtccgtgcgc atcgagcgac cgagtcagtc agaagtggga tgcgccagtt taatggaaac   24960
gctgaagcgg attcggttac gaaattcgtg gtagcgtca aagacgagc tagatgtgag     25020 tcgcggggac gcgtgacaca aaacgcgttc aggattaacg taggttttcg aaataaccta   25080
cgtccgtgag tgacgcggtt tcgtgttgaa acccgcgccg gttctcacgg tggtttatga   25140
tgaaaccggc gttggggatc tacgcggtt cctcattcaa cctgcgaaaa gaggaagttg    25200
cggtaaaacc acgtcaataa agacgtcaat gacacctcaa tgttgcgttg gaacggtctt   25260
tatatataca aacgccgtta tgttcagtgt ccggcaagat gctcgggata cgggctatgc   25320
tggtgatgct ggattactac tggatacagt tgataacaaa caatgacact cgaagcaaca   25380
ataccgatac catctttgta tctctcctta ccggggccaa cggagttact cgcacagcca   25440 tcggggtct gcattcaaac tacaccaact taaccgaggc attcagattc actccagcaa    25500
acacaacaac taactcttcc acggagggta attggagcgt gactaaccta acggagagtt   25560
```

```
gcatcaaccg cggtgagtcc tatctaacta ccatctggct tctgaactgc gctgacaaca    25620
atacttattg gtactctgga aatgcctata accatacaat tgacacttgt aaaaatacag    25680
tttcgggata tctcttcttc ggcatgtgcc agctatggaa agattgggtt actaatgctt    25740
ctcacgacac tgtcagaatt cagtcgttgg gaaatgaaat acgctgcatg ctgctcccta    25800
gacagtatac cctcaacgcc acggtggaat ggtacaacaa atctgaaggt gacgtaccag    25860
aagaatttat ggactatgtt atcctgaccc ccttggcagt gcttacatgc ggactgcagg    25920
aagcttatat actcgacaag ggtcgtagat acatgtattt gttttccgtg tcctgcgcgg    25980
gaatcacagg taccgtatct attatactcg tctccctatc gctgctcatc ctcatctgtt    26040
actatcgctg tggccggctt ctgatatgcc cacgcggctt tgaactcttg ccagaattca    26100
ctgaggaaga ggaggaaaaa gaaaaattgt taacgtacaa ggacattgaa gtccaggtgc    26160
ctatccgcac gcgcggcctg ctcgtcccct tggatccggga gagcaaaatg tgggtactac    26220
cacccccgct gcctccacga cctccccact aatagaatt cccgccgtct cctccgccgt    26280
cgcctgggcc catgcacatg gtggtctgca tgccagcatg acggactttg aactttgagc    26340
cccaagcggt acggactaca tattttccat aaatctacac tgaacttgag cacaaaaata    26400
ctgacaatgg actgaatata cagactttta tatgatcctt gtacagatgt aaataaaatg    26460
tttttattta aaactggtcc caatgttctt cgggaatcat ggggtgggga cggggacgc     26520 ggtaaggagc aaaaccgggt acatgggggg gaacatcgtc cagcagtagc accagcggat    26580
tgggtagggg ttgctgcgga ggtcggtcga tgacgatgtc gatctccatc ggcagatccg    26640
gcaacatctc ttcgtctccc tcaccgacca gcactcggcg ctgttctgga tgtatatgat    26700
tttggaaaag cctccgacga gctcgcggcg cgtagaaagc caagcggcgc aagggccggc    26760
gagcccgaaa gtccatgcgc acagatggca tgagtccttg agtgacggtg gtgagctggg    26820
gaacagggct acctcccatc gcgacggtga cagtggatcc atgagagagg cgccgcacgc    26880
tgcatggcta aataccgtga atccctgac gtcgtctttc gtcccgaacg cgtcatgttg    26940
ggggcgaggc gtaaaccgtc gaggttgaaa aaccgcgtat ctgcgacccg tccggactac    27000
gttgtttttc agaagcggcc acatgacctc gagatgtcgt cacccaaggt atttaacggc    27060
acacagccag acgcgttcgt cagcagcgac gccgacaaga cctcagcatg gctcggaggc    27120
tatggatctt gagcttacta gccgtgacct tgacggtggc tttggcggca ccttctcaga    27180
aatcgaagcg caggtaaacg gaatctgggg aattcaacac aggtaagaaa tacaaaaaat    27240
aacgtgattg tgaacgcggt tatcgtgttt ttgcagcgtg acggtggaac aacccagtac    27300
cagcgctgat ggtagtaata ccaccccccag caagaacgta actctcagtc agggggggtc    27360
caccaccgac ggagacgaag attactccgg ggagtatgac gttttgatta cagacggaga    27420 tgcagcgaa catcagcaac cacaaaagac tgatgaacac aaagaaaatc aagccaaaga    27480
aaatgaaaag aagattcagt aacagcagac cccaagggtt aacgattatg ttgactacct    27540
tgttttttat taaaaagctg taaggttttg ctctaaaaac accccgcctc cggtctttt     27600 tcttttgtat tcggcacgcg aaacacggtt tcttcccata gcctgtctaa ctagccttcc    27660
cgtgagagtt tatgaacatg tatctcacca gaatgctagt ttgtagaggc tatgcgggat    27720
gctgcggcgg cgcgaccttc cctctccacc cagccccgtc aaaacacacg cgactcgagc    27780
ggttcgtatg aaaaataaaa aacagctttt tatttacagg aacggggaaa aaaaaggcac    27840
acggtccgtg ggagacgcgg gttcacgcgt cgtcaaaaag ttggtggtcc actccgtaag    27900
```

```
gacaggtagg cttatttagc ttccgcatgc tcctggttcc gtaataaatg ccgttttcgt   27960
ggcagcgtgt catgccgcga gtcacaaact ccatcaaact gtcggccacg atgcaaacgt   28020
gctgattgtt ggcagcaaag acgcgcatac agtcgtccac gaagaggttg atcacgtcgt   28080
aggggctcac caaccagcct aaaggttcca cgtggttact gccgaccatg accctccagt   28140
cgttaatctc gctccagtcg tacagccgaa tcgtggagac gcgaatgacg ctgtaatcac   28200
ccatgaccat gagtcggccg cgatacgtag cacgccactg cgcgaacgcg tggatgtgca   28260
tgcagccggc cagcgctcta agcgaggcgg tgtgcgcag ctcctctggg acggtgatga    28320
agttgcagcg tcgcaaaccg atgttgagaa attcagtgat gctctcggcc acaaaggtca   28380
acgagtcaga gtagatgtgg tcggtccaca ggtacatggc gcccgaggcg cccaggtaca   28440
gttcagacgg cacgttgtga tcgcccttgt gtttaagaaa gttgtaggtg cagatgctgc   28500
cgacgaaacg cagcggctcg gggcagcaga ggtagctggc cagacgctgt gcatcccgtc   28560
cttcgtcgcg caccaagcgc cagcgacgcc ggataacgag gcagcggtct ttgggccaga   28620
ccagggccac gcgttgcccg ggtttccacg gtcgcgacgt cttaggaggc ctccagcggt   28680
cgagcagatt gagaaaacag tccttgatta ccgacatcgc ggtcgcgcgt cggtggacaa   28740
aaagaaatcg ggccgatccg gaaaaaaaaa acgacggcaa acaccgccg tgctcgagcg     28800 aagggtggcg gagggccaga agaggcggcc ttgacgcgt tggcagcgaa aaaattggca     28860
cgcgagtcaa acgggaagta gcgtcggtgt tttatgcccc aagcagcgtc gtcgtcactc   28920
gtggcgtcac agtcaacggt gctgacgtcc tttggggcag tcgggcacgc gatcgtagat   28980
gccgttgtgg ccgctgaaac gtcggttttc aaacagcagg ttaagtccca gacacatgaa   29040
cgtgttgaga ttatctccca cccggatgta gcggtcgtcg cgcacgtcgc aggcgtagac   29100
ggccccggta taggcgacga cgatggggat aaggtcgacg ggccagcgca agtgaggaaa   29160
gggcgcgttc tcgcccttga ggctgacggt tccaggccg agaacgcgca ttccgaaagc     29220
ggttttgatg ttgcgcagca agtgaccgcc ttccacgctg ttttcgaaac acctgaggtt   29280
gcatagacgc agttccgttc ccggcgggta cgtcaacggc atgaactgcc cgtggtggcg   29340
gatgatgaat cgcgccatgg tatccaaacc gaggctccag gcgcgcaaca gcgggcgaaa   29400
gtagcgctta accaacgacg aggtcaggta gcgcatgcag tgcagggtct cgacggcgcg   29460
cagcccgacg cgcgcaaact ccatgaggtt gcgggccagg tagtagacgg cggtgtcctc   29520
gcgtacatag caaaaaacat agccctcgtc cgagatgagg cacacagcgg tcttcttctg   29580
ctgatccggc gacaacacgc cctcgttcac gaagcgaccc acgaaggcca ggcgcgtctg   29640
gcaacacagg tagtgactcc aagccttcac gtcctccggt ttgaagtcct cgtccgtctc   29700
gatctcctgc agcactaggt tccagcccgg cggccagacc acgggcaaca cctggcctgc   29760
gttgatgcgc acgtaagctt ccagacagcc caggccgaac tcggccgtga gcgccaggct   29820
agccagatcg ctcatgtgac gcgccgagtc agtgggcgag cccgggggcc cgtcgcacac   29880
cacgctccgt cttcttgtcc tcaccgcggc cagcgtggcg aggacacttt ccgcgcccga   29940
ggctgtatct tcggtttgcc cgccggagcc ggccctcact atataacgtc ccgcccgggt   30000
ctcctccatg tatgcaggta agcaactgag ccgaacgcac ctcagcagac gagaggatgt   30060
cgtcgcggcg tcgcagctcg tcacgtcgct ctggcgaacc ctcgacggtg atttatatcc   30120
cctcgagcaa cgaggacacg ccggcggatg aggaggcgga ggacagcgtt ttcacgagca   30180
cgcgggcgcg cagcgccacg gaagatctgg atcgcatgga ggccggtttg tcgccctaca   30240
gcgtctcctc ggacgctccg tcgtccttcg agctcgtgcg cgagaccggc ggcaccggcg   30300
```

-continued

```
ccgccaagaa accgagcgaa aagaaacgat cgtcgtcgcg tcggcaaccg cagatcgcag    30360
cgggcgcgcc tcggggctcg ccggcgacac ccaaggccgg caagtcgcct aaagtctcgc    30420
gaccgcctag tgtgccctcg ctgcccgaga acggcgccgc cggcggtggc gacgataaca    30480
gcagcagcgg cggtagcagc agtcgcacca ccagtaacag tagcagaagt accagtcccg    30540
tggcgccagg tgagccgtcc gctgccgagg gcgatgagtt ttccttctgc gacagcgaca    30600
tcgaagactt tgagcgcgaa tgttaccggg tcagcgtggc cgacaatctg ggcttcgagc    30660
ccagcgtggt cgcgccgcag cacgtcgagt atctcaaatt cgtgctgcaa gactttgacg    30720
tgcagcacct ccgccgcctc aacgaatgca tacccatgcc ggccttcgcg ctcaccagcc    30780
tcgtcgaccc cgtcttaaac aacgtagcgc ctggcgagcg cgatctcacg cgtcggataa    30840
tcacgcacgc ggtgatcatc aactattact acgtggcgca aaagaaagcg cgccacatgg    30900
tggaggccat acgaccacc gtgcggggcg acacggtacg ccgggtagcc gcgcaggtca     30960
acaaccagag ccgttcgggg cgtgcggccg cgctagcgct tcattttctc acgtcacgaa    31020
aaggagtgac ggacggccag tacgccacgt ctctgcggcg gctggacgaa gagctgcggc    31080
atcgcggcac gcccgaatcg ccgcggctca ccgaggttta ccagacgcta cgcgattaca    31140
acgtgctctt ctataccgcc cactacacct cgcgcggcgc gctctacctc tatcggcaaa    31200
acctgcagcg gctcaacgag aaccaccggg gcatgctccg gctgctttcg gtcgaagaga    31260
tatgcgaaga gcacacgctc aacgatctgg cgttcctagt aggcgtcgag cttatgatca    31320
cgcactttca acgcaccatt cgcgtgctgc gctgctatct ccagcaccag ctgcagagca    31380
tctcggagct gtgttacctc atctatgtac aactgccgtc gttgcgcgaa gactacgcgc    31440
agcttagtga cgtgatctac tgggccgtca gtcaaaacta cgactacgcg ctctacgcga    31500
gcacgccggc gttgtttgac tttttacgcg tcgtgcgtca gcaggacgcc ttcatttgca    31560
ccgactacgt gtactgcgcc ctgcgtctgc tggcctgtcc cgacagacct attatcggtg    31620
acaccggcgg cagcagtagc tcccaacgcc tcgtaggcga gtttatggtg cgcgatccgc    31680
tgttgcgcga cccgcgcgcc acccacctgc gccagaaact catcacccgc gacatatgcg    31740
tggcgcggtt gcaagcgcag ccctcgagtc gacacattcc ggtcgaacac acgggtgtct    31800
cctccgtcac cctgctcaaa atctttagcc aagtcccccc cgacgaacgc gaagaagaca    31860
cgttacgcga gatggctctt aaagcgttta tggaagcgaa cggtaatcac cccgaacaaa    31920
tctgccgatc cccaccaccc ccgctgccac cgcgcgacta cctcaacgc gacgagcggg     31980 accgtcaccg tcgcgaccgc cgcgacagcg gggaatactg ttgctgatgg tgggacgaaa    32040
cagcagggcg gaacagtttta tgatagaaag tcacaggaaa gtatgtgttg ttttttttt    32100 aatgtaccaa gaataaaaag tgcgtctacg accaaagcgg tgtgtggacg ctcgtcctct    32160
ctgtcttctc cgggttttt tttcacgtgt ttttccttc ctattttgtt acggcaacag      32220
cgctgatggc acgttgccgg cttcgaacat cgcgtcggtg atttcttgct tgcccggcgt    32280
cacacggtga cgtagcagca cgcggctcac gtagcaggcc gactcgcgga tgacctggcc    32340
gtcggcgtcg cgtcgcaggc ccgagcggtt gccgtgacgc agtctgccct gcgcagcgcg    32400
ctccacgtct tcaaagtagc tgtgtagcag gccgcgctcc agcagctgcg gcagcgagtc    32460
ggcggcgcgc actacaaagt tctcacggct gatctcgtag cacagcacgc tgccgtcggc    32520
cgccacgccg gccacgctgc ggtcccaact gaaaaggttg gcgagtccga tggtgccgat    32580
gacgcgcaac tgaccctggg tcaccaccag cagcttccag tattctacgt cgcgcggggt    32640
```

-continued

```
gaggatggtc tcctccacgt cgcagacaaa caacgtgtag ccgcgcggat agggcagatc    32700
caggtggcga ccgcgctggc ggcgcataaa atcgtctaaa ttcaaaccgc cgtcgggtgc    32760
gcgcctactc gtcatcgccg cgccttgtcg gtcgatgacc ccacggtgct tataacgcgc    32820
cgccgcggct tcatgtggcg tgacctccga cctcgtgagg ccgaaaacgg cgtacatgaa    32880
gacgctcaaa cttttgaatg tgggcccggt agcgcaccga gggcccgggg gcggcgacga    32940
cggcgggccc gagttccagc ggggccttgc ggcggcagcg gttggcgtgg ttgctcagct    33000
cggcgtccga gagcgccgag ctgaactgcg gcagccgcgt gcgatcctgc ggcgcgtccc    33060
cgtgtcgcag cgagtgccag agcaggcgct ggacgcgcgc cgtctcgggc gtcggcggcg    33120
cgcgacagcc ccgcgcagc ttgaaaacgt gcaggcacag cagctcgcgc ttgatgcgca    33180
gcgacacgct gcggtagtcg ggaatccgct gcaccagctc gagaaagtcg cagaaggtct    33240
ccacgaacgt gtcctcggtg aagcgaatgc gcttcagatc gtggacgtgt ttgcgaaacc    33300
gcgacagttc tcgacgttgc acggggttct gagcgagtcc cttgcgcagc agcgcagcct    33360
cgcctttaaa cagcctgatg agccgctgca cgtccccgct caacatacgt atacacgccg    33420
tgtactcgtg acgtatactg gcgcgcagca gccgaatgat acgcagggcc agcacggcgt    33480
tagaggccag gtacatggcg tagccgcgac gcgggttggc acaggcccag cccgcgggga    33540
gcagaaagta gtcgtcgatc agcgtctgcg accagtcggc gaagcccagg tcacgtgata    33600
cgctgtcctg gacgcgggcc acgtcgccgg ccgtgaggtg gcggatcgcc ggcaggtgaa    33660
acgcgcccag gtgtcggttg cgctccagcc tcagctcggt gtgctccaaa cgggaatggt    33720
gggacgccac cgcggagggc gacaaagagg agtggtcatt gccgtcgtgg ttaccgtcgt    33780
ggttaccgcc gttgtcgcgc ccgtcgccgc actcgcaaaa ggccgcgtag aggtccttca    33840
atgccgcttc ggctcgcgcc ataaacgtgg cgtggaaaaa aacggcggcg cggtgcgtcc    33900
ggtacttgac gggcaacccg cggcacaggg ccgccggcag gcagcggccg atgagttcgc    33960
gctcctcggg ctccagaaac aggcacaggg tgccgtccag gcgcaggtac agctcctcgg    34020
tcatcgagca tagctgccgc aagtaatggg tgcgcgtccc aaaggtcttg taatcgagca    34080
acgtgcacac cacgtattgc cccgtggcca cggccagagc gatgcgtttg gcggcacgac    34140
tgatctctgg caagtactgc gcctcgtgca ccagacggcg gaaagcgccg gcgttgagcc    34200
agcgaaaatg ctgcggatcg ggcggcaagg gcacgcctcg aagcgcggcc cagacagcga    34260
ggtccgactc gagcgtcaga ccgcggatgt cgtacttgcc gtgcgccgta gcgcaggctg    34320
aatggaccag acagctgcgg cgaatgtaca ccatggcgtg cttgggatgt ttgggcgccg    34380
gcgtttcttt ttctgaccg ccggcggccg ccagatcctc gggcgtgcga cacaacaggc    34440
cggcgcgcac agcctcctgt cgattacgaa tcggcgtcag gtaggcgcgc aggaactggt    34500
gacaaaactc ctcatcatca cgacagtcgt cgagatactc gtacgtggtg agcggatcgc    34560
gaaataggcg ctcgtcaccg tcgtcatggt cttctttagc ctgctcctcc ggctgctggg    34620
ttggcagtgg aggcggcggc tgatccacgg ggttcatgac tgagaggaag aagaaggtgg    34680
cggcgaagcg acgcggagcg acggcggtaa agccagacac cggctatata gctagtcatc    34740
acagtctcct ccttcacgac gccccgtgcc cgctcacgct atccagcacg ctacggcccg    34800
aaaacacgta ctcgctgacg tcgtacgcgg gcgatgtatg gctgctcacc ggtttcgcgg    34860
cgacggttgc gctcgagtcc aacggcgaga agcaaaaacg ccgtgggcaa cgaaaccaga    34920
aggagccctg acggataaaa ccgcgcagcg tctcggccaa cttaaccagc atcgtaccgt    34980
acagcagtac gtgaatgccg ccatgcgcgt ccataaatac ggctttgttc acgggttcca    35040
```

-continued

```
tccatccgat gactacaaaa tgggcctgtt ctagcacgcc gatcacgaaa ttgttggcct    35100
cgtcggcctc ggccacgttc cacgagccga aagtgaaagt acaagcgggc gagccgccca    35160
ggcggatctt gctaccggcg tggagctgac atacgcgcag cagattggcg cggtcgtgca    35220
gtatctggga gagttcgtac atgcccgcaa aggtgtgctt aaaccacgcg ccctctacga    35280
tctcatccac gtagtcgcgc tcaaagaagc tgtacacggc aaagaggccg ttctcaaaaa    35340
actcgccgaa cgagagcccc agcacgtaca ccttgtcctc gccgggcagg tacgcaaagg    35400
cgtgcccgtg cccggagacc cagatctcgg gcgccgtgtt tgcgtccggc acgcattcgt    35460
acacactgac gaggccgata aagtacaagc ggccagcctg gcgcaggcac gagaagcgcc    35520
ggtaggtctt gtgatcgcgc accacccaa agtactgagt gtcgcccagc atgatgccgt     35580
gcagcggcgg ccagcacagc gggagccaac gacccgccgt ggcgcgcacg tagcgctgca    35640
ggtgaacccc gctcgcacgc tcgcgcggct tcgggcgctt gtgggtccag gcatcacgca    35700
gaccgcgcca gatgctgctg aacttgggct gcccgcgcag atagagcgac gagagcgagt    35760
caaagtagcc cacgacgagc ctgtcgggag acacaagagc gcgaaaatca aacctagagc    35820
gacgacggtg aaaaaaccga ccagaagcgc gtgtctcaaa cacgctactt tcggttataa    35880
aaacaccgtc gccctatttc tgggcgcgtg tacactgatg actcacctac gcttttttgaa   35940 cggcagtctc agctcgggat tggcctcgta cagcgagctg cggtccacgg ggccgatgct    36000
ctcgtagcga aagtcgtcga tgagcagcgc cagccccacg cgcacgaagc ccctgaggtc    36060
gcgcgccagc cgcaccaact tatcctgccc caccagcgcc gcgtacacgg tgcccgtgtc    36120
gccgcagaga atccgcacgc ggtgaaagaa ggtcttgtcc tcggcgccct caatttcgcc    36180
cagcggcatg acgggctcgc gcgtgtacaa cgaacgttga aagcggcgca gcatcgaggc    36240
cgagagcccc agatcgcgcg ccgtgcgcag cactagggaa tgcttctcgg gccagatgag    36300
ggtcagttgc gcctcgcggt gcgcctctac gtaggcgcaa cgagcggcgg tgtcctcgca    36360
ggccagcaac tcgcggaaag ccagcagcga acgtaggtag cggccgcgag cggaggcgcg    36420
cgagcggcgg cacagctcgg cccgatggtc gggatgcacc aagggcacgt taggttgcag    36480
acgcgcgcag atggattcgt gcaccgggtc gcagcggatc atgcccttgg caaaaaatcc    36540
ggccagatcc gaggccaact cgtacaggca gtcctcttgc gcgtcgtagg cgaacacggc    36600
gccgtacgcg tccacgaaca cctggtaccg gcaggtggcg tgcgagaccg tgccaatgag    36660
atgcagagct cggaattcgc cgaaaaagtc gttctggcag tgctccagat cgatctcggt    36720
cagcgagtgc ggcgaatgct cgcccccgac cacgtagatg cactgcgagg gccagcccag    36780
cgacacgcac gagccctcga agcgccgcaa gtaacgccgc aggccctcat agtcgcgtcg    36840
cacgcacagg tcggccaagt cgcgcgtgca aaagacctcg ggtaccaagc agcgtttgcg    36900
acgcggccga cgcgcgtgcc caggcagagg aggaaggcgc gacggcggcg acgacgagga    36960
ggaagacgcc gtggccgccg agcagcccctt gcgacggccg gacatgccgg cagtccgcga   37020
cgatccacag gagacaaaaa agcagaagca gcagtagcct cggcgacccg ctccacccgg   37080
tcctccacac gctcagccgc gactgaacgc cggggcgcgc cgctacttgg gtttttatag   37140
ccatctgccc cccgtctcgg gcacccggga gcgatctacg gagacctgac agcagttggg   37200
caacacaaga tagggaaata caaagacact tttaataaaa aacgagacta ctttgtgtgt    37260
gtgctccgta aactgtttat tctcccctc cgcttcgctc tggatgggct ccgggtccgt     37320
caacacgcga ctcgcgcggc aaaaggcacg ctgttgacgg cgcgagagcc cgtcgtgata    37380
```

-continued

```
gtccatcatg ccccggagat cgtgcacaaa gcagctgtcg ccgcgcagaa accgacgcag   37440
cgtctccacg tgctgcagct gccggcgcgt atcaggagcc gtcatcgctg atgtcgtcat   37500
cgccctgaca ggcgcgtaga tggcttcgcg agatcatgcg cgttttcaac cgccgtgaca   37560
catcaggtcc atcttgagct ggcgccgggc ctcgcgcagg tgttgcacgc gttgtgagcg   37620
ggaggcgagt tcggcttctt gctcgaactc ctgctgctca ctgtccgaga gggtgcgata   37680
aaaggcggca aagtcctcca agtcggctac atgcgccctg ggtctgacgc tccaaagcgt   37740
acgcagtctg atgaagcgga cccatcgagc gtcacggcac gccgtcttga acgcggggcc   37800
cgggaagagg ttcttctccc cggcgcgctc gggccggcga ggccgacgcg gtttatatac   37860
accgtctcgg acggcgggac gccgagcccg cgccgcggcc gctcatccgg agacggcgga   37920
aaccgcgacg ccggaggaaa cggggaccgg caacgacggc ggtggcggcg accagattat   37980
gggggacaaa cccacgcttg tgaccctgtt gaccgtcgcc gtgtcgtcgc cgccaccgtc   38040
gtcgccgctg ccgctcgtca gcttcacgga gctgttgtta ccgccgccgt ccgtcgccgc   38100
cgctgcggtg gcgcgacag cgacgagcga ggtgggcgag aaaaccgcgg agcaagaggt   38160
agcggctgcg gatccggaga ccgggaatga gagaagagaa aacagggaga acgaaggagg   38220
ggagacgagg acgacaggca ccaccgcggt caaaaggtcg cacgacggta tccctcgcca   38280
actggcagag cgcctgcggc tgtgccgcca catggacccc gagcaggact atcgtctgcc   38340
ggcgcaggac gtggtgacct cgtggatcga agcgctacgc gacgcggacc gcgacaacta   38400
cggtcgctgc gtgcgccacg ccaagattca ccgttcggcc tcgcacctga cggcctacga   38460
gtcgtacttg gtgtccatca ccgagcagta caacacggcc tcgaacgtga cggagaaagc   38520
ttcgtacgtg cagggctgca tctttctctc gtttcccgtc atttacaaca acacgcaggg   38580
ctgcggctac aagtacgact ggtccaacgt ggtgacgccc aaggcggcgt acgccgagct   38640
cttctttctg ctctgctcca ccagcgagag ctccgtggtg ctgcaaccgc tcatcaccaa   38700
gggcgggctc tgctcgtcca tggcggttta cgacgaggaa accatgcggc agtcgcaggc   38760
ggtgcagatc ggttttctgc acacacaact ggtcatggtg cccttcgtgc cgcacgcctg   38820
cccgcattac gccgtgcctt tcacgacgcc gggaaagccg ggctgcggcg gtgctccgag   38880
cggcgttgcg gggttggagg aggcggcgcc ctttggacgg gtcagcgtca cgcggcatgg   38940
cgcgacgctg ctatgtcgcg tggaccatct gacctggatc agtaagcgcg taaccacgta   39000
cggacacaaa aaaattacgc gctacctcgc gcagttccgc ggcacgatgg acgacgacga   39060
ggcagcgcta cccggcgagg acgaagcgtg gatcgcgtcc aaaaacgtgc agtacgaatt   39120
catgggtctc atttttcaccg tcaacgtgga ttcactatgc gtggacgcgg aacagcgcca   39180
actgctgggc accgtggcca cctccttctg tcaccgcgtc tcggacaaga tcacggcgcg   39240
caacatgccg cgcgcttttt ccttctacct gctgacgagc gcgcagcgcg ggtacgacct   39300
gcgattcagc cgcaacccgt cactcttttt tagcggcgac gcgctcaact gtccgcttct   39360
caatgagccc aacgtgtttt cgctcacggt gcacgcgcct tacgatatcc acttcggggt   39420
gcaaccgcgg cagacggtgg agttggactt gcgctacgtg cagatcacag accggtgttt   39480
cttggtggcc aacttgccac acgaggacgc ctttacacg gggctcagcg tgtggcgcgg   39540
cggcgagccg ctcaaagtca cgctgtggac gcgcacgcgt tccatcgtga tcccgcaggg   39600 caccccatc gccacgttgt atcaaattac cgagggcgac ggtaacgtgt actcgtacaa   39660
ccaccacacg gtgtttcggc agatgcacgc cgccggaaca accacgttct ttctgggcga   39720
catgcaattg cccgcggaca actttctcac gtctccccat ccctgaccct ccgtccgtcc   39780
```

-continued

```
tcctttcccg acacgtcact atccgatggt ttcattaaaa agtacgtctg cgtgtgtgtt   39840
tcttaactat tcctccgtgt tcttaatctt ctcgatcttt tggaggatgt tctgcacggc   39900
gtccgacggc gttttggcgc ccccccatgcc ggcagaaccc ggttgcggcc ccgtaccgct   39960 cttctgggc gacgataggt cgaaagccac cgttttcatg cccgtcgtgc tcttgacggg   40020
ggaacctacg gcggcggtcc ccgtcgagcg gcgtgattgc aaagccgcgc tcgccccgg   40080 tttcaggatg gaggggagg ccacaggcgg cgcattcgat acgctgcttt tggccgtaga   40140
cgacggtggg taaacggtgg ttaccgcggg atacgtcggc gtggtcgagg cggcccggct   40200
gctgccggac aggcgacccg gcgcgctacc gctcacgggg accgagggcg gtcgacctac   40260
caccgccttg ccgcccaaag taggtttcaa ggaaggaaca ccgacgcggc tgccccggcc   40320
tttcaccgga gacgggggg cactcttggc cggggacgga gaggctgacg aaagcatgga   40380
cagcggcgat gtggcggggg acacgacatc atcctccgtg ggcgacaaaa cggacgccga   40440
ggctgacggc tgtcgagccg aagaagcgga agaggttccc gcgccagaag tcacgttcct   40500
tgatgacgtc gttttagacg aagccggttg aggttgcaac agcgtggcgg gtaccgtcga   40560
cggcgtgccc gacacctgtt tctctagcct tccctgaacc ggcgtcgacg tcaccgtctg   40620
cgctcgggcg gacgcgtgcg gcgtcgcgac tcgcttgccc agcaccggtt tctggctcgt   40680
ggatgtcgtc gtcattggag acgataactt agctttacgt attctggacg cgtcgactg    40740 ctcgggcgtc tgactgggag gcgaaatgac gtcgttgttg taatcggacg acggtgttgt   40800
gtgtcccagg ctgacgacgg agccggtgtc cgaggagtcg tcgtcttcct cctcgctgtc   40860
ttcgaccggt gactctgcag tttggtccct taaagcccaa acctcatcag cggcgtcccg   40920
agacgctgtt tgtgtcaccg cggcgcgtgg agtcgacggc ctccgagggg tggtggacac   40980
ggtgttttga gaagccgtgg aagtcgtagg catcctgaag ggattgtaag ccaggtgagg   41040
attcttgagg gcccacgcgc gttcgcgcgg ccagttggcg gggttcatat ccccgggcaa   41100
cggcgccgtc ggagcccagg gcgagttacc gttgaccggg gttgggtac ccgcgaaggt   41160 aggtgtcggg gccggagcgg gggccgtgga aggattgaca ggcgtcggcg tgaggatggc   41220
agcgccggcg ccagcaggaa cgttaactcc ggcgccgaac gtcaacgtcg gttgctcgaa   41280
cttgtacgcg gtggtgacgg gcggtttggc gctcgtctcg gtatccgtga tgtccaccag   41340
cgtgtcggtg aaacgcggat cttgacggtt gggggatag ccatccgagc tgtcggaatc    41400
ctcgtcgccc gagaaaagat cccctctggt ctccgtgagc ggcctcacgt cccacgcgct   41460
gtcccgacgg accctccccg ggctggcctt ggtcacctgc ggggagacga gactgaaagc   41520
cgcgtgacgc tgttgttgtt gcgggatgtt caagggaccc ctggtcggtt tctgactgcc   41580
cgaggataac aggccgctga aaatgctgga aacaccgcca ccactagcgg cgcccttgcc   41640
gctagttccc ggtttcttga tgggcgtaaa gatgttttc tcgtcatcat catcgtcgtc   41700
gtcctcatcg gcactggagc caaagagcct ccgggaggcg ctcggtttac gtgccggggg   41760
cggtggttgc tgctgacgtt gctgcaggtt ctgctgcctc tcctcccaag ccttcagctg   41820
ctgtttctca cgctgcacca cctcgtcgtc cacccgtttc tgccgctcgc gacgcttttc   41880
ctcttcgtcg taatagccga cggccgccga acgggcagcg tgggcttcgg cggccggtgc   41940
cagagaacca tgggcctcga agcggaacgg tttgtgtccc ttccagggac tggcgatcca   42000
gctccagccg tccagcggct gcgtggggac atgtttcttg ggtaccgacg agaaggccga   42060
accgccgccg agcgagagga gattggcgtc atcgtcaaac tccaacgacg gcgagcgcgc   42120
```

```
gcccaaaaac gtgtgcgccg actgtgggaa gctgtccacg tagatatcaa agtcctcgat    42180
gagcagctcc aacagcgtgt cggccgagtc gccgttttcc acggcgtgct tgaggatatt    42240
gcgacagtag ttggaatcaa aggaaaggca catgcgcagc tccttgacca gcagcttgca    42300
gcgctcctga atgcgcgcca gacatttgcg ctccagctcc tcccaagacc tgcgcacgtt    42360
catgatgaga cggcccgtgt acacgagctt gttgacggcg ttgaccagcg ccgtgttggc    42420
gtgccggtcc aggttaaggt cgagcggttt cacgcagaac atgttacggc gcacaccctc    42480
caggttttct tcaatgcgct gcacctccgt atccttgagg tgcacaaagg cgatgggttc    42540
cgtctggccg atggctgtga ccagcgtctc gcgcaccgac atcttggcca gaatgaccgc    42600
gcttacgagc gcgcgttcca cgatctcggc atcgtggcgc acgtccgtat cgaattcggt    42660
acggtctagc acagccaggt ggtcacgcgc cttaccacga tcaccgaacg ggtaagtgta    42720
gccgcgacgc gccacggcca cgcaacgcac ctcgaactcc tcgagcactg aggagaggtc    42780
ggggttgtga aaacgcagct cgcggtagta tcccaaccaa agcatgagct cgttgaacag    42840
caccgtacgc cggtgcaggc gttttttcgcc acatttttttc aggatcttgg ggtgtgcctc    42900
gagatccacg tcgggctttt gcgtgagatg gcgcagaaag ttgaccaggg ctaccacatc    42960
gcgccgctgt agaccgataa actgcaaact catgctggct tttctccaga acccggaagc    43020
gtcgtcgccc cggactgcgc ccgcggtctg ctattcgccc acgatggaca ccatcatcca    43080
caactcggtg agcgccccac ctagagggag gggggtagt ttaatagcgg aggcggatac    43140
gcggttttct tttaagcgcc gctgacttgt ttcttctgtt ttttcgcccc gtgtgctgtt    43200
ccgcccagac ccgcaacaac actcctccgc acatcaatga cacttgcaac atgacagggc    43260
cgctattcgc cattcgaacc accgaagccg tactcaaaac attcatcatc ttcgtgggcg    43320
gtccacttaa cgccatagtg ttgatcacgc agctgctcac gaatcgcgtg cttggctatt    43380
cgacgcccac catttacatg accaacctct actctactaa ttttctcacg cttactgtgc    43440
taccctttat cgtactcagc aaccagtggc tgttgccggc cggcgtggcc tcgtgtaaat    43500
ttctatcggt gatctactac tcaagctgca cagtgggctt tgccaccgta gctctgatcg    43560
ccgccgatcg ttatcgcgtc cttcataaac gaacatacgc acgccaatca taccgttcaa    43620
cctatatgat tttgctattg acatggctcg ctggactaat ttttttccgtg cccgcagctg    43680 tttacaccac ggtggtgatg catcacgatg ccaacgatac caataatact aatgggcacg    43740
ccacctgtgt actgtacttc gtagctgaag aagtgcacac agtgctgctt tcgtggaaag    43800
tgctgctgac gatggtatgg ggtgccgcac ccgtgataat gatgacgtgg ttctacgcat    43860
tcttctactc aaccgtacag cgcacgtcac agaaacaaag gagtcgtacc ttaacctttg    43920
ttagcgtgct actcatctcc ttcgtggcgc tacaaactcc ctacgtctct ctcatgatct    43980
tcaacagtta tgccacaacc gcctggccca tgcagtgtga acacctcaca ctgcgacgca    44040
ccattggcac gctggcgcgt gtggtgcccc acctacactg cctcattaat cccatcctgt    44100
acgcgctgct gggtcatgat ttctgcaac gcatgcggca gtgtttccgc ggtcagttgc    44160
tggaccgccg cgctttcctg agatcgcagc agaatcagcg agctacagcg agacaaatc    44220 tagcggctgg caacaattca caatcagtgg ctacgtcatt agacaccaat agcaaaaact    44280
acaatcagca cgccaaacgc agcgtgtctt caattttccc cagcggtacg tggaaaggcg    44340
gccagaaaac cgcgtccaac gacacatcca caaaaatccc ccatcgactc tcacaatcgc    44400
atcataacct cagcggggta tgagctttcc tgttacttta ttcagaaagc accagaaccc    44460
gtcgccattt cccctcatat acggtacacg tcccctgat ctgtcatcac ggtacacaga    44520
```

```
tttcgcccga ctgcggacgc cgacggccaa tcgcgtggcg taggagtggc gccccggctt   44580
cattataacg ccacgtcgga gcccctgcgc gccacaacgc cgtccggcgc aacttctgtc   44640
tcggcacggt acgataaaaa caacgtcccc cgtcgacgtt gttttctccg agcggtgatc   44700
gttcccgtcc ctctcctccc tccgcggccc ccacggcggc ggcctgctcg cacggaccta   44760
tactattacc gccccaccgc cgtcgtcgtc atgaacttca tcatcaccac ccgagacttc   44820
tccaacgacg attcagtcct gcgagccgcc gagatgcgtg acaacgtggc aggctcgatt   44880
tccaaagcgt acaagggcac ggtacgcgcc gaaggcaaga agaagctgct gctgaagcac   44940
ttgcccgtgc cgcccggcgg ctgctcgcgc cgcaacagca acctcttcgt tttctgcacc   45000
gagcgcgact accgcaagtt ccaccagggc atcgcacagc tcaagcgcgc gccggccgaa   45060
ctggaccccc acgagatcca gcaagtcacg gccagtatcc gctgccgcct gcagcccagt   45120
ctccgcgagc cgcccacgcc ggccgacgag ctgcagacgg ctgtgtcgcg cgtgtgcgcg   45180
ctcttcaacc agctggtttt cacggcccag ctgcgccact actgcgagca ccaggacaag   45240
gtggtgagct acgcgcgcga cgagctgact aaacgctgcg gcgaaaaatc ggcgctgggc   45300
gtggaagtgc atcaactggt agccctgctg ccacacgagc gccaccgcga actgtgccac   45360
gtcctcatcg gcttgttgca ccagacgccg cacatgtggg cgcgctccat ccgtctcatc   45420
ggacacctgc gccactacct gcagaacagc ttcctacacc tgttgatgaa ctcaggtttg   45480
gatatcgcac aagttttcga cggctgttac cacagcgagg cctaccgcat gctcttccag   45540
atcggtcata cggactcggt gtcggcggcc ctggaactct cacacggcgc ggcggccggg   45600
ccgcccgagg ccgatgaaaa caacgacgag ggagaggagg acgacgacga gctccgtcac   45660
agcgacccgg cgccgcttca cgagtccaag aagccccgca acgcccgtcg tccccgcaca   45720
cgcgtgccgc ctcacgagca aaagcccgaa gaaaacgagg aggaagaaga ggagctgttt   45780
ccctcctgca aggcaaccgc agcattcctg cgggcagaac cctccgtctc caacgacgac   45840
ggcaacggcg gcgaacgctg cgacacgcta gcgaccgccc tgcggcatcg cgccgacgaa   45900
gaagacggac ctctagccag ccagaccgct gtgcgggtcg ccgcgacccc ctcaccttca   45960
gtcaccccag cccttacccc cgtcacgtcc cccataaccc cgttgtgtat ttaacgtcac   46020
tggagaacaa taaagcgttg atttctcaag ttccgctctg gttttggttt cgttttcaaa   46080
gggagcccca tcatggccca aggatcgcga gccccatcgg gcccgccact gcccgttctc   46140
cccgtggacg actggctcaa cttcgggtt gatctatttg gggacgagca ccggcgcctg   46200
ctgctcgaaa tgttgaccca gggctgctcc aactttgtgg ggctgctcaa ctttggcgtg   46260
cccagccccg tatacgcgct ggaggccctg gtggacttcc aggtgcgcaa cgcttttatg   46320
aaggtaaagc ccgtggccca ggagattatc cgtatctgca tactcgctaa ccactaccgc   46380
aacagccgcg acgtgttgcg ggacctgcgc acgcagctcg acgtgctgta ctcggatccg   46440
cttaagacgc ggctgcttag agggctcatc cggctctgcc gcgctgcgca aaccggcgtc   46500
aagcccgagg acatcagcgt gcacctaggc gccgacgatg tgacattcgg cgtgctaaaa   46560
cgagcgctgg tccggctgca ccgggtacgc gacgcgctgg ggctgcgcgc gtctcccgag   46620
gccgaggcgc gctatccgcg cctcaccacc tacaacctgc tgttccaccc accgcccttc   46680
accacggtcg aggcggtgga tctgtgcgcc gagaacctgt ccgacgtaac acaacgtcgt   46740
aaccgaccgt tgcgctgcct cacctccatc aaacgcccgg gctcacgcac cctggaggac   46800
gcgctaaacg acatgtatct gttgttgacg ctgcgacact tgcagctgcg acacgcgctg   46860
```

```
gagctacaaa tgatgcagga ctgggtggtg gaacgctgca accggctttg cgacgcgctt    46920
tacttttgtt acacgcaagc ccccgagacg cggcagactt tcgtcacgct ggtgcgtggg    46980
ctggaacttg cgcggcaaca cagcagtccg gccttccagc cgatgctgta caatctgttg    47040
cagctactga cgcaactgca cgaggccaac gtgtacctct gcccgggata tttacatttc    47100
agcgcgtaca agctgctgaa aaagatccaa tcggtctcgg acgcccgcga gcgcggcgag    47160
ttcggggacg aggacgaaga gcaggagaac gacggcgagc cgcgcgaggc ccagctcgat    47220
ctcgaagcca tcccacggc gcgcgagggc gagctctttt tcttctccaa gaacctgtac    47280
ggcaacggtg aggttttccg cgtgccagaa cagcccagcc gctacctgcg ccgacgtatg    47340
ttcgtggaac ggcccgaaac cctgcagatc ttttataact tccacgaagg caagatcacc    47400
accgagacgt atcacctcca gcgcatctat agcatgatga tcgagggcgc ctctcggcag    47460
acgggcctga cacccaagcg cttcatggaa ctcctcgaca gagcgcctct gggccaggag    47520
tcggaacccg agatcacaga acatcgcgat ttatttgccg atgttttttcg ccgtcctgtg    47580 accgacgcg cttcttcgtc gtccgcgtct tcgtcgtcgt cctcagcatc tccgaattct    47640
gtttcgctgc cgtctgccag gtcgtcatcc acacgaacca ccacgcccgc gtccacgtac    47700
acctcggccg ggacttcttc taccacaggt ctccttgctct cttcttcctt gtcggggtcg    47760
cacggcatta gctccgcgga cctggagcag ccgccccggc aacgacgccg catggtcagc    47820
gtgaccctct tttcgcccta ctcggtagcc tacagccacc accgacgtca ccgaaggcga    47880
cgcagcccgc caccgcacc ccgagggccg gcccacacac gcttccaggg acccgacagc    47940
atgccgagca ctagctacgg cagcgacgtc gaagacccgc gggacgatct ggccgaaaac    48000
ctacggcatc tctgaaagcg gttttttcctc tttttctacg tgtctgtctc aagatgagac    48060
gtcgatatca ataaaaatac cgtcgacgtg gtttttttaa cagtgtggtt ttctttattg    48120
actagcgaag tacacagttt acgagtagaa aagacaggga aaggttatat aaaatgctgt    48180
attatataca aaaacatgca cataaacaaa cgggaccatc gtgctcatca tcccctcctt    48240
gatcagttgt tcatgtaaac gtgtggcggg gtgaggggcg gcatgccgtt ggcggcgccg    48300
ggaataatgt gccgtcgacc gacgtcgcac accttgaaac gccgtcggcg cacgcagcgg    48360
tcgcaggacg ggatatccca gaggaagccc atgtaggtct cggggtcctc gtcgtgaaag    48420
cggtaggaga gttcaaagtg gtgcaacgag cccgtccgag ctcgcagctt ctggcgaaca    48480
ccctccacgt catcggtgca cagcgacagt gctgggctgt cacacagggc ctgaagctcc    48540
tgcggccaca ggtgcgtggc caggggcgag tccgtcgtca ccagtttgac gcagtgcatc    48600
aggttctcgg tgatggcgtc gtacaggcga ctctcagcct cctcgtgcgt catcacgttt    48660
cgaggcagcg acagctcgtc gtcgtcatcc tcgtcaaaca tgatcatggg gtcagggg tt    48720 tttttgggat gttgacaggt gggtgtcttt tccagacgca cgatggcctc acgccggccg    48780
ctgaaacggt ggtttcggtg tcccttcttt cccatgacgc aggtgaacat aaccacgtcc    48840
tcggccaaac ggtagacggc gtccatggcg gggtcgtagc cgtagacgac gccgaaagtg    48900
tccaccaaga cgtactggcg tacgaggaac tctttgcgtt ctggcacctc gtggcccagc    48960
gcgcccaaca actggtggta acaggtgatg cgcggcacgg tacggatcat gagctccatg    49020
gtctggatgc tgccgcccgc gcggacgacg ctgaaggatg tttccttgaa cttcataacc    49080
tctgtgttgt gggtccagaa ggcgaaatgg gtgtcgggac actcatcgaa agggtcgtcg    49140
atggtgtagg aagcgtagcc tcgcttggtc acctcggcca acaggctctc cacgtcaccg    49200
cggtagagca tgacggcgtt ccagtagtcg tcgtactgca ccatgggccg ctggtagtcg    49260
```

```
cgcatagtgt ggaagtggtc gcggtgacga aagccgttcc gcagaaagtc cttcatggtg    49320
ggtgccagct cgtagacgca gtcgcgcagg tcatcgtagc agtagatgcc gccgcgctgc    49380
ccgatgagca cgatgagttg gtagcgcata aagcccggac cctcgacgaa gccaaagggg    49440
tgcaggtact cctgacagca gacgtaagca cctggtagag aatagaaaaa atccacgcac    49500
gttgaaaaca cctggaaaga acgtgcccga gcgaacgtcc tctttccagg tgtcttcaac    49560
gacgtggggc ttaccttgcg aacagacggt gcccatcttg cccacgaagg gccccagggc    49620
gctgcgcgaa cggagctgga tgaagcagcg ttcgggccag gccacgtgca gccgggtgcc    49680
gcattcctgc tccagaaagt cgttgagacc gttaaagtcc ccggctcgga tggcgatgca    49740
gccgtaggcc atcagcgtgt cccgtaggtc gtccatgacg gactcctcta ccttcgctcg    49800
ccgacgctgc gcttctccag ccaccgctgc ggtcgacaga ctcctccgtc cgccttcgga    49860
gaactacggc gcggcggcac ggcctttata gacactatca gcgttgacgt cagacgatcc    49920
gatgaacgtc gttttttgtg ctggaacttc cctcgtcccg acaaatgtag cggaaatctt    49980
caagcaaatc gcgacgaagt ccgatgagga ggatgcaaaa gaggctgagc aacgcgatgc    50040
tgcccgccgc cacagtacat atgctcaaca acgcccagtg tcccaaggcg cgacttttgg    50100
ctcggaggag agccgaacgg cggtttctcc acatgacgga caacgtggtc cagtacgtcc    50160
atcctttgca ttccggtgtc cagacgggaa gcgttgtcat gttatttccc gtaactgtca    50220
cgttatgttt tgttttgttt ctcgtgagct taacggtcct cttgagaaat cgcgggcaca    50280
tgtcttgtag aaagatataa tcactttccg cgtatttcgt cagtgttgac atcacggtgg    50340
tagtgttttc tgaagaagta gcgttgtcag tgacgtttgt ttcttcccaa cgtacgtatg    50400
attcgaacgg actcgtgtgc gctattgccc gcaacacgta gctgtggccg gtgaagttga    50460
gcgtcagttg tcccacggtc acgttcgtgt cattcctaaa acatgctact ctccgtgaa    50520 cttccgtgac gtttatctca cgactctcgt tcaagacacg caggggaaac cagccttcca    50580
ggtgatactg aaaaccaaat ttaagcatga cgctgtgcca tttccgtcgt gattgattaa    50640
acgttacatt caagggcagt ctggcttcgg tcccgagaca ggggccgttg tagatttgcg    50700
tgtgattgcg tgtgcagttt aggtggcagt tcatgctcgt ggtgttggaa gtgcgattaa    50760
cgtccgtacc gtggtacgta catcggaccg aaacaccgtg tcccgtgctc caaagcagcg    50820
tcaacaacag ccacacagaa acctacgtgg agacgcacg ggacttttta ttgacggaga    50880
ctcacgtttc taccctcccc tttcccgtag gtaaaaaccc acgtttatca cacacgttgt    50940
ttttacctga aacccgcgca gcccgtggac gcgacaaaaa accgcggcac tagaaagaaa    51000
atgaaacaag tatgtttatt aagcagcatg tggggctaat agggggggata actgaggtat    51060 agcaactatg aaaaaatact acaaaaaaaa aagctgaaca tggtcatcta gcagcaaagt    51120
tctccttcta gaccacgacc accatctgta ccacgtcgcc ctccccggcc gtgtacacga    51180
catccttcac cacgaccggc ggcagcggcg gcgacgagga caactcgctc tcgacggagg    51240
ccgggacgac agaggacggg ggggtggtgg cggcggagga cgaagggtg gcggcggcag    51300 cgggatcttc ttccgacacg ggcaacggca ggctcggcgg cgcggacagc acccgttgcg    51360
ccggggcgtg agaaggctga gccccggtgg cctggatgtg ggccaacgaa ttggctcgca    51420
gcgagtcgcg atccacgaag gtcataggaa ttttcccttc gcggatccgc cgctcagatt    51480
ccaggatggc gcgcacgtag ctgttcaccg acttggcaaa agtgcgcggc ccctccgtat    51540
tcttgtcgcg acgcgcttcc agcacctgct tttcgtagtc cagctggtgg aagaccatca    51600
```

```
ccaggtcgtc catagtgtgc gcgtgctgac ggacgtggga gcgcacctcc accgggaaca   51660
aagcgttcca atactccagc acgatagcac cgtgccagaa ctgcgccatg ctgggcgcca   51720
ggaaaaacag gataccggag tcgtaggcga acacgtccca cttgggcgtc atgaacaaca   51780
ccagctgacg cgtgggccgc accgaagctt cctcccaggc ctcgatgacc ccgaacatga   51840
tgagctcctg gtccaacggg gggcagtgtc gctccagcca actgatcttg ctcaggttca   51900
tctgcagaaa ctcgtacgaa gggtcgcaga tgcacacgta gagacccgag tcgtgccgca   51960
gcctggctcc gcgcttcatc agtttcctca ccgcgtagcg aagcgccacc ttgcccaacg   52020
ccgacgcctg gatcagtccc cccacgtcca tctgcgtctg tcgccactcg gcctcgtcca   52080
gcaggctcat gatagcggca gtgctatgcg tggtcgtagt catcctttct atccttctct   52140
atgaatagca gcaatagcgg taaagtccct tcttatacta tcccggagtc tgtggttttt   52200
ttgtttaccc ctgcttactg gtgagactgc tgggggccgt tgtgctgcag catccgagct   52260
cgttgccgcc gttgccacag gaaccggtgt ctccgcaggg cctttttgag ggcttcgcag   52320
gcttctcgcg caagtcctga gaggccctcg gcgtcgatgg ggttcacctc gggcgtccga   52380
gcctcgtttt cttcttcttc atcctccctt tcctcctccg tgtcctcccg ctctgtgtcc   52440
tccgttacgc tctcctcccc ggcctcggcc aagagcgcgg ccaccaagtc cacgaccgc    52500
tcggtctccg agttctcacc gtcaattacg ccatgttggc ggcgtaaccg gtgccgagaa   52560
cgccgggtga gcgcacatgc ttttttcttt cttaaccaag gcgggagagg atcttcaagg   52620
cgttttcgct ggatccagcg gtagctaaag taccaaaagg ccagcaggcc cacgctacct   52680
aacagattca cgtagactgg agacataatt aaagaaagaa gtgaaacccg cgtgtgggtc   52740
tcacgtcgtc ttgaaacacc gtcttatata catgaagatg ccggacatga cgcgcccaag   52800
acacgtgggg ttttccccctt aggcgacccg gtttcttaag atgtttttca tcttcgcacg   52860
cgatgtacta catcaaaggg tcggctgacc gaccgcattg acgcacagtt ccgagtacg    52920
cgcgtctcgg agcacctgac ggtgagccac ccaactcacg cggatagggg acaacactga   52980
cgtgaggggc gattcacgtc actgacggga ataagacggg tgagggattt ccaccttttt   53040
cttaagtgtg actctcttta cggtaaatcg cacctgtgac ctcttaaccc ctcctccctg   53100
gtacccgata accgtgaaaa acacacacca cacgtcacga caccgatcga ttttctttat   53160
tcttagtgtg atgataggta agggcactcg tgaggatgtg caattatcat tatcaagcct   53220
ttttcaaggc gtagtgatga tcgttgggca gaacccccag gctcctagcg atctgggaat   53280
agaaggagga gaacgagccc agggccagaa tgcccacagt gtacatggcc caggtctcca   53340
gaccgaacgt ggcgggtcgc agcttcagat ggtaggccac ccgctccgag agttgtgaat   53400
gctcgttcag gcaacaggac tgcaggtggg tgagcccaaa agcgctttcg tttacgccgc   53460
gcacgtgcac cgtctgggcc gggcaatcct ggtgttgcgc gcgaaagtgg tcctgacagg   53520
aaattccgtc tacgtggcgg cgcgtgttgt tacccacttc gatcaacaac gtgttatcgg   53580
caggatgatg cgagaacgcg acgacggtgt tgttggaggt ctggcggcaa cagtacacgt   53640
cgagcgtcat gagggccatg tcgccttggt ggtacacggc gtacgcccaa ccctggaaca   53700
cgagcggaca taacgaccg tgagcggacg tcacggcggc ggttgttacc gtcgtctcgg    53760
caggagaaca caataaactc ctgatcctca tacacaggag tccaaccgtc agaattaaag   53820
tccgcggagc cataaccgcg caagtgaagc cgatacgagt gttgctgaat ttgttcattc   53880
tgccgactgt tgctcacgag cgttcggagg cggtgccaca ggctgttggc cattaaaaag   53940
tcctggcccg aatgacgaca agacagagcc cgaggcgaag aaaaaggcgc ccgtcatgaa   54000
```

-continued

```
gacgtaggca ggggaattcc catattttta tggcttcttt taaaagtctg tatccgactc  54060
catccggcgc ttttcccaaa ccgtggtctc ctcgtcgtcc gactcggtac ccaggaggtg  54120
gtaagtcttt tgccgcacgt agaaagcttt caacgtggag caaaagatga aataaagac   54180
cccgaaaacg aaacaaacca cgccgatcat gccgatgcag acgttcatgt cgacgtagcc  54240
ggcggtgctg ttggcggtgc ggcaaaagag tgtcatgtcg tgcgtgcaca aaaacaaca   54300
cacaccacag gccaggtcgt agcgtagtta ttattccgta gcagcaatga tggtacagtc  54360
aagcacatgc tctatccccg ttaccccgat gatgcttgcg tccccgttgt tatattggca  54420
ctgtcccggt taatcaccac ggtgaacacc acggccaaga aaatgatccc taatatagcg  54480
accactaaga gagcaaaagt ccatttccag ccgttgtcaa agtacgcccc cgtggtggga  54540
tgcatggtgg cgggcatttc catcatgtcc atgtcgaacg tgtgtcgcgg cgacggcgaa  54600
ctaaccaggc aggaacttgt cgcagcacag gaaggtcttc tccaaacctt taatattgag  54660
atgtccaaag taaccaacgc gtaacaggtc gcagtaggtg aagaaccaac cgtttggcca  54720
gctgagacgc agcaccgtgc cgctgacgcg acgaaccagc ttctgcaggt ccttgcgagc  54780
gtcggaggtg acagagcagc ggaaggtctc gttaaccagc tcgacagcca gcgcgtcctc  54840
cagcgtgcgt tccttcatct cgtcgttgat gctctgacgg cgccgccgga tttcgtcgaa  54900
acgggccgcg gaggcggcga ccgacgcgga ggtcgtccga acgccctctg tgacgctgcc  54960
gtccggccag tcaagaaagc taaggctggc gctgcgccgc ctaaagtgtc cgatccgcgc  55020
gggacgtcgc tgagggacgg tggctggtct gctggggcgg gtacggccgc gggtgtccgc  55080
ggacacgtta gttatacacg gaattgagtc acgtggcacg ttgccagctg aaaccgccgt  55140
cgtctccgcc ggcgttttct ccatcacggg accgcgccgt gcgcgcgttc ccaggcacgc  55200
ggcccgcgct ctagccgcac ttttgcttct tggtgttagg gacgaactcg aacgttacag  55260
aatcctcgct gtcgctctcc tctttcgcgt cgttgaagta attgccggag ttgcgatcca  55320
aaccgccgcc tcctcctcct ccgccgccgc ccgatccacc tttggacgtc aggtagctgg  55380
tgatcttgtg ctgctcgtat ttttccttgg aggaaagacc gtggtcgtga tcaccgccgc  55440
cgccaccgct gctcattttc cgcgtaccgg aaccaccgcc gccaccgcgg tcgtgcttct  55500
tgccgccacc gccgccacct cctcccagac cgccgagacc catgggctcg ttcatgagat  55560
cgttatccag acccgggccg tcgtcatgca gaccgccggc attggccagc gaagagaggc  55620
tgccgccacc accgccgccg ccacgcgact tgccgctgtt cccgacgtaa tttttgtcga  55680
agggatcgcc acgctggaaa ggttcctcgg tgagaaaatt ctccacggcg aacagaccgt  55740
tgcggctggc cacgtacaac agcgtgtcgt gctccgtaac tatacgcaac gtgcacggca  55800
gtttggtgac ggcgcaattg agcagcgtct ggtagaagtt cttcagctgc acgttgatac  55860
gcatgttttt cacgccgtgg aaactgacgc ggttattggc tgtgaattcc agctcgctgc  55920
cgttggtcag gataaacttg atggccggtg gaccggcgtg caccagaatc tgcacggtgc  55980
ccgtagggca gggcgctttt ttaacgttac gcttgacgcg ggtatgcggc ccgatccact  56040
taagcaggtc ggccaccacg ccgaaatcta gatccacgtg cacggccgaa ttctcgcttt  56100
cgcgcacaat gtcttggccg tgcacgcagg ccgagctgaa ctccatattg aaatcgggcg  56160
cgcacatgga gatcttggcc gacaggtccg agatgtcctg cacgtagaac ttggtcaggt  56220
ccttgctgga agtcaggtac atgaaattac ccagcagcgg cgtggaattg ttaatggtct  56280
tgggctgaaa cgacttgtca gtgatgtaga ggcatgagct gttaaaagtg attttgaca   56340
```

```
cgcagtgact gcgtaccgtt tgcaagataa gcgacggcgt gggcaagaag gtaaccgtgg   56400
tgttctcctt gagcgcacgg atcacagatc gcagctgctg gatagccgtc ttgtacggct   56460
tcagccgcag cgccagcgtc ggcggctccg agaggcgcgt cttgcgatcc atcccggaca   56520
gcgtgcaagt ctcgactaag gagcgggcgc gagcgagcga aagttttata gagagcacac   56580
acgacgaccg ggaacgctgc gaagacgccc ggcgtctaat aatacagccg cgccgagcca   56640
gcgggccccc gactaagagg cacagtactt atatactccg accttaaagc gccagtggta   56700
ccacttgagc atcctggcca gaagcacgtc gggcgtcatc cccgagtcat agtagaaaac   56760
cagggccacg cactggtcca caaacacgct caggttcacg gccgccattt ccacgtcgtt   56820
ttggatcgcc ggtgccgcct ggaacagaca ctgcgtcgcc ttgccctcct cctggtgctg   56880
ctccaaccac gcgtaattca ccacgggcac gcgcagcggc ctccgcacca cggtggggaa   56940
gtaacactca cggttgggcg ggcacaatga ccacaccgtc tcctcctcga acacggtgcc   57000
gcgcgaagcc cacactgacg gcgtcacgcc ccacagatgc gccacctcgt cgtcgggacc   57060
caccgccaga aactgacagt tgcgcaatcc gaactcgagc atgtcggcgc gcagcgcttc   57120
ccagcgcgcg ctggcgatgg agagccgcgg caaccgatac aattcgaaaa tgaatttgcc   57180
ctcttgatag atggtgcgtt cgaaccactc gcagcgcggc aaacccgact tgcacaaatc   57240
gacgctagcg cgcaccgcgg caaagtacat gtgctcaaag atgcgctcga tcaagtccca   57300
agaggcaaag tacgtgaacc ctaaccgcat gagcgccgtg tgcaagccag ccacgccgat   57360
gtgcagcgga cgcagttttt ccagcgcgct ctctacccac cattcggacg ccgacattag   57420
cgcgtccaag cgcgcgttgc cccaaaccac cgcctcggtc accaactcgc gcagcacgct   57480
caaatcaaag taacgtcgcg tgttccccaa aaccacgtcg ggtagatgca gcttctgctc   57540
gtcgctacgc gcaaacacgc agcgagccac gttcaccgtc agccgctgca ccggcatgtc   57600
acactcgcca aagtggcacg acgccatatc gggactcaag cacggcggca ggcacacgct   57660
gtcggccata atcgagtact tgactacgtg atggacaaag accaccgagg cacggcccct   57720
gagcgcgcac agcaacatct ttttcagaaa atcgtccgtg ttcacgacca ccttgggcca   57780
cgattgctcg cagcgcgaat actctttctc gaaagccgac tcctgaccca ggtccgagag   57840
ccgccgggag acaggccgcc caaacagcga gtagcgctgc tcacgcgcac ggtagcgctt   57900
cattaacacg ctaggcacgt tgaaagcgta gcaaaccccc gtcaactccg acgtgctttc   57960
tttgagaata aagttaatca cgcggatagc ggccacgtcc cacatgtcca caaacacacg   58020
taccacgggt cgatgcacct ccttctcgcg tatcaaatcg cagtatcccc ccaggcaacg   58080
aatcacgctg ttcacatcgg cgttaagtcg cgttacgttc accgacacag aaacgccgca   58140
actcaaggta ctcatccact tgcacatggc cgcccaactg gcgtcacgcg agaaagggtc   58200
ggccgagatc agaaagtcgt actgcggcac gcgatcgaaa cccacggtag acatggtgaa   58260
ggtggacagc gacagctgcc catcgcgaca gcgcttcaac accgattcca cacctcgcc   58320 ctcgaaacgc gcatccagat ggaaacgata gatgcgcgag tgcctactgt tctcgatagc   58380
ggccgtcaac gccacggcga tgcgcaaaaa cacgccgccc gggctctcgt cctgtccgtg   58440
cagttggcga cacaccttat ccaaacacaa aatggccgcg tacaagcccc agcaaccggc   58500
caattccaca aaacgcgccg tctcctcggc cagcttgggt agatcctcca tgtgacgcag   58560
cacaaaacgg cgcaccgact catcgcacag ctccgaagcg taacacagtg gcgtgcggct   58620
ttcacgcgcc cagttggctt tgaaataaaa gcgacccaac agcaggtcgc aacgcggcga   58680
gtgacgaatc agacagggac cgtggcgcat aatgagctga aatagcctga aactgcccaa   58740
```

```
accggcactg tgccgcgaca cggtgtccat ctcgcgccac agcgcgttcc tgtcggacgg   58800
cagctcccgc gccggctcct gtacgccgca aaagcgaaac ttgccccagt agccgtgaca   58860
atgacacttt ttgcccatca acatgcgcgt agcttgtatc ggcggcgata ctttgcagag   58920
cgaagcgccg aaatcgtcct cctcctcgac actgtccagc tccatcctgg tcgcgccggc   58980
cggattaaag gtgctcagac cgctactcac gcgtccaccg cgactgggca cggcgggacc   59040
gctgtcacgc gtcaacgaca gcacagacgg cgtgccgtcg ggagacggcg actcgggacg   59100
ccaactgacg acgccgccac cactcgtaaa acccgctaca catgctacac cgctcgatac   59160
gttggtattt ccagcggacg cttccttgtc accccgggc agcggcccct cctcgagctc    59220
gctgtcatct cccccgatag tatcagcggc gacctctgcc gacgattcct ccgtctcggt   59280
ttccgcgctg cggcttggaa tcctacctgg ccggcaccga tgtgcgggca ccaggacac    59340 ccgctgttcc tcgtccgcgt cagccggatt cataagttta cgaggaaaat aacaaagaaa   59400
tcaggtagat ttcaataaag tgagtctaga tggcgccgac aactacggtt tataaagtct   59460
gtgtgcgatg tgttttttc ttctgtgtct cctccccgta tgctgtcagc gccgctcaga    59520
cgaattctcg aaagtctccc aattcgacgc taaagttgtc caaacggacg acggacagtt   59580
tgagttcttt gtgtaccagg aacgaggtgt gaatgtcgtc agccaggcac cagcccagct   59640
tttgtatgac cccggtacac agagggatct ggcgcgggcg cgtgatgcga cggttgacaa   59700
agctacagcg ctcgcgggcg aactttccgc gtgcaacgtc gaccaaggtc tgccagtgtg   59760
cgatgctgga ggtgagcacg tagatgccgg gacgtgtttc gggcccgtca tagtcataga   59820
cgatgattaa atacacgtat tgcagccgtc cccgggtctc ttcccacgtc aggtacatgt   59880
ctttcggtat catcaacgcg aacacctccg ttttgagcgt gttgtaaagg tagccgcgca   59940
tgacgcaggt gagcaacgag gtgatgccca gcgagacggt cttgacgcag cccagcgtct   60000
cgaggcggcg gtgcagcaga tgcgggccca ggtccagcca ctgcagcgcg gcgcgcgcgg   60060
ccgaggccgt gtacacgctt tcgagcaggc agcgcgtgct ggccgagacg ttggaggcgc   60120
gaatgcctaa caggtaaagg ctaatgtaga ggtgtcgcgg cgagtcgcaa cccgtctcca   60180
tgcggatgag cagcgcgccc ggctgcgcct cgaactctac caggccctcg ggcacgaaga   60240
aacgcgccgt gagcgcctgg tgatcggcgt ggtagagata gcgaaccgat atagtattta   60300
cctcgcgttt ggctttgagc gccgtcacta gttcattgtc ctcgtcggcc gggtcgcgcg   60360
gccgtttggc caccgcgcgc gcgtccatga tggcgaggcg cacggtagat ttcaaaaagt   60420
tgatagagca gctgcgggca cgggccacga acaaagcgga ggcgttaaat accgtgagcc   60480
aattggagat cggcgcggtg gatgcccagg acgtgaccgc gagcgccgtg cgcgccttcg   60540
tgggtgcgtt gccgagctcg ggctaccact ttggcttcgt gcgtcagaac gtggtctttt   60600
acctcctaag ccacgccacg gtacagacgc gcgcgaccc gctgtacgcc gccgagcagt    60660
tgcacgaaca gctggaccgc ttcctgcgac accagcacga cggcggcgga gacgaggacc   60720
ggttgccgtt ctaccacaac ggggccacgc tgacggcttt ccagaagctg ttgcagaccc   60780
tgcgcgagat ccagaccgta atagccgaac agagcggcgg caccgcggcg gcggcggact   60840
tgatcgccag taacaacgcg tcgaccgagc gccgcggcaa gaaggggcggt tcgagttccg   60900 ggggccagca gccgctggtc cgccgggtga tcacgcagct ggaaacggct gccacggagg   60960
cgcggcccta cgtcaattgt cgcgccgtgg ccgaactcct ggacctgacc taccagcggc   61020
tcatctactg ggcctgcacg ctcatgccct acgtgttgtt tcggcgcgac accgacaccg   61080
```

```
aactggacac ggtgcttctg atgcattttt tttacacaca ctaccgttcg gttaacggcg   61140
atttggccgt ggagtttcaa aactacgtca agaacagcgt gcggcacatg agctctttcg   61200
tcagttccga tatcgacggc gaccagaagc ccggtgccga acacatgcgt gacgtcagct   61260
acaagctgtt cgtgggtaat ctgcaagcgc gtgacgccag cggcctcatg tttcccatca   61320
ttagcacgcg catctccacc gtgaaccttt acctgtcgcc cgaacgtatg ttttttccacc   61380 cgggtctgat ctcgcgtctg ttgagtgagg aagtttcgcc gcgcgccaac ctagacgctt   61440
acgcgcgcgt gtgcgatcgc gtgctggaag accacttgca tacgccgcga cgcgtgcaac   61500
ggctactaga tctgacgcag atggtaatgc gactggtgga actgggtttc aatcacgata   61560
cctgcgcggc ctacgcacaa atggcgctga tccagccggc cagtcagaag agctcgctct   61620
ttgtcagcga gattcgcgag aaactcatac agatcatcta caatttttac acgttttca   61680 tgtgcctcta tgtgtacagc cccacgttcc tgttcgacca ccggcggcgg ttgattttgg   61740
agcagcatcg atccacgttg atcggctcca aggaggaact acagcacgtc tggagcaacg   61800
tgacactgaa cgtcaatacg cactttgcgg ttcagtacac ggaagaagac tttgaggcac   61860
atacgaaggg tgccacggag gcggacgcg agtacctgta tcgggacctg cacagcaagt   61920
ggggcgtgca cctgtttacc ttgcgtccgt ctcgcggcgc ggccggcgcg gcctcgcctt   61980
tgcctccgct tgacggcgtc acacgctccg acatcttacg cgaatgcgcg ctcgttaatc   62040
tgaacgaagg ccgcgtcaac tacgcctccc tgctagcctt cagccatcat cccgagttcc   62100
ccagcatctt cgcgcagttg gtggtggtaa ctgagttctc ggagatcttt ggtatcccgc   62160
agggcctgtt tcaagccgtg ggttcgccgc gtcttttcgc actcattcag ctgtgccgtg   62220
tattgttgcc cgagcaggtg acgctgtacc agaacctggt ctccatctac aacctgacca   62280
ccttcgtcaa gcacatcgac gccgcggttt ttaagacggt acgcgattgc gtcttcgaca   62340
tcgccacgac tctcgagcac ctcagcggtg tacccgtcac gcccaatgtg gacctgctgg   62400
ccgagctcat ggcgcgctcc gtagcgcata acctgtacac caccgtcaac ccgctgatcg   62460
aggacgtgat gcgcagcagc gccggcagtc tgagaaacta tctgcgacat acgcgactct   62520
gtttcggtct ggcgcgtggc cgggcgcgcc tctcggagga cggcgtgacg gtgtacgtgg   62580
aggtacaagg tcaatacgga ctacgcgtac ccaccacgcg tttcgtagaa cagttgcgcg   62640
agctggttcg ccgcgatcgg ctgttggccg agaatctgcg cggcttgaac gagcgcctgc   62700
tgagtgttcg cgtgcgcgta cgtcagatca gcagcgacac agaggaagta agccgacacg   62760
ccaagggtca ccgcacggtg gcccagatga gcaaggcgct caaaaagacg gcctccaaaa   62820
tcaaagtgtt ggaaacacgc gtgacattgg cgctcgagca ggcgcaacgt tccaatggcg   62880
ccgtcgttac cgcggtgcaa cgcgcgctag ccgtctttga cgtactaagt cgcgagaact   62940
tggaacgccg cggcgcacag ctctgtctga cggaagcgac gagcctactg caccgacatc   63000
gcgcgctagc gccgatgacc tggcccgcgg gcacgggcgt tgcggcggcg gccgaagcgg   63060
atcgcgcctt acgcgagttc ttggaggcgc cctgggaatc ggcgccccaa ccgccgcgac   63120
tccgcatgac gcccgacacc gatcacgaag aatcaacggc aggcgcgacg tccgtaccgg   63180
aggtcctggg tgcgcgctac gaacccgcac acctggccgc gagcgaccta ttaaactggt   63240
acatcgtccc cgtaagccag gcgcagcagg acatcttgtc ttcgatcgac cgcccgccg   63300 gctcgacatc ggtgtccctg ccgccggcct cgccatgaaa gtcacacagg ccagctgcca   63360
ccagggcgac atcgctcgct ttggagcgcg agcgggcaat caatgcgtct gcaacggcat   63420
catgttccta cacgccttgc acctgggtgg aacgagcgcc gtcctgcaga ccgaggcgct   63480
```

```
ggacgccatc atggaagagg gcgcgcgtct ggacgcgcgg ctagagcgcg agttgcaaaa   63540
gaagctgccc gccggcgggc ggctgccggt ctacagactg ggcgacgaag tgccgcgccg   63600
cctggagtcg cggttcggcc ggaccgtgca cgcgctctcg cggcccttca acggcaccac   63660
cgagacgtgc gacctggacg gctacatgtg tccgggcatc ttcgactttc tgcggtacgc   63720
gcacgccaaa ccgcgtccca cctacgtact cgtcaccgtc aactcgttgg cgcgcgccgt   63780
ggtcttcacc gaggaccaca tgttggtctt tgatccgcac agctccgcgg aatgtcacaa   63840
cgccgccgtg tatcactgcg agggtctcca tcaggtgctg atggtgctca cgggcttcgg   63900
cgtgcagctg tcgcccgctt tctactatga ggccttttt ctctacatgc tggatgtggc   63960
gaccgtacca gaggctgaga tcgccgcgcg tttggtctcc acctatcgcg accgcgatat   64020
cgacctcacc ggcgtcgtcc gagaaagcgc ggacacggca gcgacaacga ccaccgccgc   64080
accttcctta cctccgctgc ccgaccccat cgtcgaccg ggttgccctc ctggcgtggc   64140
gcccagcatt cccgtctacg atccctcgtc ctcacccaaa aaaacacccg agaaacgccg   64200
caaggacctc agcggtagca aacacggagg caaaaagaaa cccccgtcca cgacgtccaa   64260
aacactggcc accgcctcct cctcccctc agcgatagcg gcggcctctt cttcgtccgc   64320
ggtaccaccg tcctacagct gcggcgaagg ggccctgccg gccctgggcc gctaccaaca   64380
gctggtcgac gaggtagagc aggagttgaa ggctctgacg ctgccgccgt tgcctgccaa   64440
caccagcgcc tggacgttgc acgcggcggg taccgaaagc ggcgctaacg cggcaacggc   64500
cacggcgccg tccttcgacg aagctttcct caccgatcgt ctccagcagc tcatcatcca   64560
tgccgtcaat cagcgctcgt gtctgcgtcg ccctgcggt ccgcaatcgg cggcgcagca   64620
ggcggtacgc gcctatctgg gcctatccaa gaaactggat gcctttctgc tcaactggct   64680
gcaccacggc ctggatctgc agcgcatgca cgactacctg agccacaaga ccaccaaagg   64740
cacgtactcg acgctggatc gcgcactgct ggagaaaatg caagtcgtct tcgatcccta   64800
cggacgtcag cacggcccgg cgctcatcgc ctgggtggag gagatgctgc gctacgtgga   64860
aagcaagccc actaacgaac tgtctcaacg actgcaacgt ttcgtaacca agcgaccgat   64920
gcccgttagc gacagcttcg tctgcctgcg acccgtagac tttcagcgtc tgacgcaggt   64980
catcgaacag cgacgtcggg tgttgcaacg tcaacgcgag gaataccacg gcgtttacga   65040
gcacttggcc ggcctcatca ccagcatcga cattcacgac ctagacgcca gcgatctgaa   65100
ccgacgcgaa attctgaaag cgctgcagcc gttggacgac aacgccaagc aggaactctt   65160
tcgcctgggc aacgccaaaa tgctagagtt gcagatggac ctggaccgtc tgagcacgca   65220
gctgctgacg cgcgtgcaca atcacatcct taacggcttt ttgccggtag aggacctgaa   65280
gcagatggaa cgcgtcgtcg agcaggtact gagactcttt tacgacctgc gcgacctgaa   65340
actgtgtgac ggcagctacg aagagggatt cgtcgtcata cgcgaacaac tgagctacct   65400
catgacgggc actgtgcgcg acaacgtacc gctactgcaa gagatcctgc agctgcgaca   65460
cgcgtaccag caagccacgc agcaaaacga gggtcgcctc acgcagatcc acgacctgct   65520
tcatgtcatc gagacgctgg tgcgcgaccc gggcagccgc ggctcggcgc tgacactggc   65580
cttggtacag gagcagctag ctcagctgga agcgctaggc ggcctgcagc tacccgaagt   65640
gcagcagcgc ctacagaacg cgcaactcgc gctaagccgc ctctacgaag aggaagagga   65700
aacgcagcgt ttcctcgacg gactctcgta cgacgatccg cccaacgaac agaccatcaa   65760
gcgacaccca caattacgcg agatgttacg tcgcgacgaa cagacgcgtc tgcgactcat   65820
```

```
caacgccgta ctgagcatgt tccacacatt agtgatgcga ctggcgcgcg acgagtcgcc   65880
gcgaccgacg ttttttgacg ccgtcagttt gttgttgcag caactgccac ccgactcgca   65940
cgaacgtgag gatctgcgtg ccgccaacgc cacgtacgcg cagatggtca agaaactgga   66000
gcagatcgag aaagccggta ccggcgcatc cgaaaaacgt ttccaagcgt tacgggagtt   66060
ggtttacttt ttccgtaatc atgaatattt ctttcaacat atggtcggac gactgggcgt   66120
cggacctcag gtaacggaac tctacgagcg atatcaacac gagatggaag aacagcacct   66180
ggaacggcta aacgtgaat ggcaagaaga ggccggcaag ctcacggtaa cttctgtgga   66240
ggacgtgcag cgtgtcttgg cccgggcacc gagccatcgt gtcatgcatc aaatgcaaca   66300
aacgttaacc accaagatgc aagactttt agacaaggag aaacgtaaac aggaagaaca   66360
gcaacggcag ctactggacg gctaccaaaa aaaggtgcag caggatttgc aacgcgtggt   66420
ggacgccgtt aagggcgaga tgctctccac catcccgcac caaccactgg aggccacact   66480
cgagctgctc ttgggcctag atcaacgcgc ccaaccgcta ctagacaagt tcaaccagga   66540
cttgctgtcg gcgctgcagc agctgagcaa aaaactagac gggcgaatca acgagtgtct   66600
gcacggcgtg ctgacgggtg atgtagagcg gcgctgtcac ccgcaccgag aagcggctat   66660
gcaaacccaa gcctcgctaa accacttgga ccaaattttg ggtccgcaac ttctgatcca   66720
tgagacgcag caggccctgc aacacgccgt ccatcaagcg cagttcatcg agaagtgtca   66780 acgggcgat ccaactacag ccatcacggg cagcgagttc gagggcgact ttgcacgcta   66840
ccgcagcagt caacagaaga tggaggaaca attacaagag actagacaac agatgaccga   66900
gactagcgag cggctagatc gctcgctgcg ccaggatccc gggagcagct ccgtcacgcg   66960
tgtacccgag aaacccttca agggtcagga gctggcgggt cggatcacgc ccccgcccgc   67020
cgacttccag cagcccgttt tcaaaacgct gctagatcag caggccgacg cggcccggaa   67080
agcgctcagc gacgaggccg atctgctgaa tcagaaagta cagacgcagt tgcgacaacg   67140
cgacgagcag ctgagcacgg cgcagaacct gtggactgat ctggtcacgc gccacaaaat   67200
gagcggcgga ctgacgtga ccaccccga cgccaaggcg ctgatggaaa agccgctgga   67260
gacacttcgc gagctgttgg gcaaagccac gcaacaactg ccgtacctgt cggcggaacg   67320
cacagtgcgc tggatgctgg cctttctgga ggaagccctt gcgcaaatca ccgcggaccc   67380
tacgcacccg catcacggaa gcaggaccca ctaccggaac ctgcaacagc aagctgtcga   67440
gagcgccgtg acgctagcgc atcaaatcga acaaaacgcg gcctgtgaaa atttattgc   67500 acagcatcaa gaggcgactg ccaacggcgc gtccacgccg cgggtcgaca tggtccaggc   67560
ggtggaagcg gtctggcagc gactggaacc cggacgcgta gccggcggcg ccgcgcgtca   67620
tcaaaaagtg caggaactgt tgcagcgctt gggtcagacg ctaggcgacc tagaactgca   67680
ggaaacgttg gcgacggaat actttgcgct gttacacgga atccagacct tcagctacgg   67740
gctggacttt cggtcgcagt tggaaaagat ccgcgatctg cggactcgtt ttgcggaact   67800
ggccaagcga cgcggcacgc gtctctccaa cgagggagtc ctgcccaacc ccggaaaacc   67860
gcaggcgacg acttcactgg gcgcctttac acgcgggttg aacgcgctgg aacgacacgt   67920
ccagctgggt caccagtatc tgctcaacaa gctcaacggc tcatcgctag tctataggct   67980
ggaagacatt cctagcgtgc ttccggcaac acacgagacc gaccccgcgc tgataatgcg   68040
cgaccgcctg cgtcgcctat gcttcgcgcg tcaccacgac accttccttg aagtggtaga   68100
cgtcttcggc atgcggcaaa tcgtcacgca ggccggcgaa cccattcacc tggtcaccga   68160
ttatggcaac gtagccttta agtacttggc gctgcgagac gatggtcggc ccctggcatg   68220
```

-continued

```
gcggcgccgc tgtagcggcg gaggactcaa gaacgtcgtc accacacgtt ataaagccat    68280
cacggtagcc gtggccgtct gtcagacatt gcgcactttc tggccacaga tctcgcagta    68340
cgacctacga ccctacctca cgcagcatca gagccacacg caccccgcgg agactcacac    68400
gttgcataac cttaagctct tttgttatct ggtgagcacc gcctggcacc agcgcatcga    68460
cacgcagcag gagctgacgg ccgccgatcg cgtaggcagc ggcgagggtg gtgacgtagg    68520
ggaacagaga ccgggccgcg gtaccgtgct gcgcctgagt ctgcaagagt tttgtgtact    68580
catagcggct ctgtaccccg agtacatcta caccgtcctc aaatacccgg tgcagatgtc    68640
actaccctcc ctcacagctc acctacatca ggatgtgata cacgcggtag tcaataacac    68700
acacaaaatg ccccccgacc acctccccga acaggtcaag gccttctgta tcaccccac     68760 ccaatggccc gccatgcagc tcaataaact gttttgggaa aataaactgg tacagcaact    68820
gtgccaggta ggcccgcaaa aaagcacacc gcccttaggc aagctatggc tctacgccat    68880
ggccacgctg gtcttttccac aagacatgct gcagtgtctg tggctagaac tgaaacccca    68940
gtacgccgag acatacgcct cggtgtccga attggtacag acgttgtttc agattttcac    69000
gcaacaatgc gaaatggtga ccgaggggta cacgcaaccg cagctcccca ccggagagcc    69060
ggtgcttcag atgatccgcg tgccacgtca ggacacaacc accacagaca caaacacgac    69120
cacggagccg ggactttttag atgttttttat tcaaacagaa accgccctag actacgcgct    69180
gggctcctgg cttttcggca tacccgtgtg tctcggcgtg catgtagccg acctgctgaa    69240
aggccaacgt atactagtag cgcgccacct cgaatacacg tcgcgagacc gcgacttcct    69300
ccgcatccaa cgctcccggg atctcaatct cagtcaactg ctccaggaca cgtggaccga    69360
aacgccgctg gagcactgct ggctacaagc ccaaatcaga cggctacgcg attacctgcg    69420
tttccccacc cgcttagagt ttattcccct agtcatttac aacgcacagg accacaccgt    69480
cgtacgcgtg ctgcgaccgc cctccacgtt cgaacaggac cacagtcggc tggtgttgga    69540
cgaggccttc cccaccttcc cgctgtatga ccaagatgat aactcatccg cggacaaacat    69600 cgctgcgtct ggcgccgctc caacaccgcc ggtacctttc aaccgcgtgc cagtcaatat    69660
tcagtttctg cgtgaaaacc cgccacccat cgcgcgagtt cagcagccgc cgcgccgaca    69720
tcgtcatcga gcggccgcgg ccgcagacga cgacggacag atagatcacg tacaagacga    69780
tacatcaagg acagccgact ctgcattagt ctctaccgcc tttggcgggt ccgtctttca    69840
agaaaaccga ttgggagaaa caccactatg ccagatgaaa cttgtggccg tggcgcccgg    69900
cgccgccagc accagtttcg cctcgccgcc tatcacggtg cttacgcaga acgtcctcag    69960
tgctctagaa atactgcggc tagtgcgatt ggacctgcga caactggcgc aatccgtaca    70020
ggacactatt caacacatgc ggtttctcta tcttttgtaa ccgacactga cagtagcggg    70080
taataaaaac aataggattt ttatcgtttt tttatgttac aaaacaacgt atcactttca    70140
cggtgattta tcttgctat tcctttcccc cttgggctgt cagcgccggg tgcgcgacac      70200
ggctaccatg cgcaacaggt ccagcttaaa ggcgcacttg tcattaaaca ggctggacat    70260
gcgcgtgtac ttgctcagca tggtggccaa caccgggtgg gtggcctctg atatctcggt    70320
cggcagctcc aaaacgacgt taacgacgtg acggtgtttt tcgtcccgct tgttggccac    70380
cgtgggtccc ggcgcggtgt tagacatggg gcaggccgtg gggggaggac gaagaggaag    70440
ccgctgctaa accgccgcgc gcctgctgca caatgtggcc gccgacgtgg caggcggtct    70500
gtttaaccag cgcgcagccc cgacacagcg gggcgccgtc ctcgctttcc aaacagctgt    70560
```

```
cgcggtactc gcccgtctga cagcgcgcgc acagcaggcc gtgcccgtgc gaagtgaggc   70620
gcaggagacg cgggaccgtc acgtcgcgta ccaccacagt ggagtcgcag gtgcgtgccg   70680
cgcagggcag aatgacgtcg aaagccagcc ggtgatcgta cacggcacaa gccgcgttga   70740
ggcccagcac ggctttccag cccacgcgta cgcagcgctg tccaaagagc gtctcggaga   70800
cgagctcgta gacgcgctgc cgcaccaccc gctgactgcc gcagagcgag cagtgcacga   70860
gctcggcgtg cgtgttgaag atgacgctct tttcttgacg gtcccgataa tagaacatcg   70920
agttgagcgg aaagttttgc tggcagtgta gcttttcctt acccaggttg aggcagtgtc   70980
cgcactgccg acagaccacg gccaccagcg agcgcgcgtc cagatggcgc tcgcacttga   71040
gtcgacacag acaccagagc ggcaggtcga tgacgctgcc gatgaggccg ccgcgcagcg   71100
cggcgctgag tgcaaagagg acgatcttgg tgggctctac gtgacgcgcc tgctgtccgg   71160
cgcccgcgtg tcctaccgcc gcagctgccg ccgtcgagcc tcctccgcgc gtctcgtcgt   71220
gcagacccag tgcccgcaac ggcaccaggt atcgcggaca cgtgtcgcaa aacgtctgca   71280
ccgcttgtcg ggccagtacg tagagcgggt ttccgcaggg taccttcccg gcgtaccggc   71340
gcaaggctgc gatgaggccc cgcaactgcg gcgaccgcgg ctgccgttgg tgacaccact   71400
ggttacggtg gtatacggcc aaatcagcgc gggcgtcgaa gcgcttggcg cgtagtaatg   71460
ctaggcacgg cgagctggtg gggtgaagca cgggcagccc aaggtccacc ccgaaaagga   71520
aacggtgaag gtcacctagc agcgaggcgg tgacaccgtc caacaacgcg tgcagccgct   71580
cgggcgggta gagccgcaga cggcgcagca ggtagtcggt gtcgtagcgt tcgaaacgca   71640
gaaaggccat cgtgcggacg gccacggtgt gcagacagtc catgctgtag acgtaagcga   71700
gaaacacaaa gtagggcttg gtcataacca tacgctgaaa gagcgccgtc accgcctccc   71760
gctcggcttg ccgacacacc agccattcgc gcaggaagcg ttggtagaga cggtcgccca   71820
gctcgcgatt cagaaagcgc ttatccgtca cgaagagatg aaggacgcaa gaacgtggca   71880
cgtgatgcac cagctgctgc tggaggaccg ccgacgtctg cgccgcaaac tgcgccggtg   71940
gctgcgacgt ttctaccgcc gcttcctccg gctgcagcgc accgcggccg atcaccagct   72000
gcacatggaa atggtcctcg tgaacgcaga ggggcgcgaa gagacggcgc agagcctggt   72060
ggaactcatc agtcgcggtg tgcggagcgt gtcggagacg acgactggcc atgaccgcgc   72120
cacagcagag ccagcaccag cagaagagcc agcaccagcg ggcccagagt cgcaaagcgc   72180
gcgggcagcc acgcccagat ctgcggtcgc gatggcccgg agcgcgctcg ccaccacgat   72240
gacggtgccc aacgataacc agtccgctcc aaggacggcg cgcacggcgg agacggcgga   72300
tgacggtgat gggtcgacac ccctcgccga cgactcacgt gctcctccag aggccgacgg   72360
gcggaccctc cgacgtcctg gcccgccgct gccgctgccg ccttcccttc tcccgccaga   72420
gccagcaact cctcctcctc ttcatcagcg tctccctcgc ttgcgcatcc gcatcgtccc   72480
atacaggcct cacaacgaca cagccgccac gaccccgccg ccatgggtgg cggcggcggc   72540
cgaggcccgg cagcggcgcc gccagcggcg accatggtgg gagagcaact cggatgacga   72600
ggaggaggag ggggagatgc ggtccgagag gaccgctttc ccgccgttcg cgtaagcgcg   72660
gccgacatgc gggcgcgcca cagggacgga ccgctgccgc tgtgactgct tacggtgacg   72720
tggttccgga ccgccaacga cgtcgacgcg gctttcttgg cgtacagctc gcgcagcaga   72780
ttctcgtact cgccctcgtt ttcgggtccg aaggcgatga gctcgatgtt gaagaccgac   72840
gccgaattgg atttgcgcac cacgcacttc gtcagcactc cgtaggccga gggcttgatc   72900
tcctcgatgt ccttgagcgt gacgatgagc gactcgttca ccttaagcac attgaactca   72960
```

-continued

```
cctacgtggc gcgccggcga aacgagcttg acgggcgctc gtacaaaaca gcagagggag    73020
acggcgcagc cagtgttttt aaagataaaa caaggcacgt ggtctgtgcg gctctcccag    73080
tagctgagta gatactcgac acaatagacc gtgtctgtct tgagcatggc gtcgcacacc    73140
gagtaattgg ggttttttaca gatgaggccg gcatcggtga cgcgcagctc gctgggaccc    73200
aacttgagga tacgccgcgt ggcctgcacc agatcctgat ggagaacctt gttcatctcc    73260
atcgcaccga cgccaccgcc gatttattta cccggcgccg actcgtcttt tcctccagg    73320 attccgttaa tgtccatgag cttgctgacg atcgccgtta atagttgcgt cttctcacgg    73380
aggatctctc cgtgactgca ggtcgcgcag tcgccgtgca cgtacttgag gaaggcggcg    73440
tacttctgac ccgcgttcac gaaatttaag cgcgcgtcca gagagggcag caacagatcg    73500
tagacgcgcg gcagcatcgg ctcgaactgt aatagcagat cgtcgtcaag atcgggtagc    73560
gcgtgtccgt cttcaccgtc ctcgtcgtca ccacctcccc cctcgagccc accgctcgta    73620
ccagccgcgg gctccgcgtc ctcgtcgatc accagcggtc gcgtcggcac cggagaatcc    73680
acgtcatcct gcacgtcgtt ttcctcctct ccgtcgtcat cgtccagaaa cggcacccgc    73740
tgcttagccc aggacattct ttttttccgcg tcctcaatca gcggcgccga tcgccatgaa    73800
tccgagtacc cacgtgagca gtaacggccc aacgactccc cctcacgggc cccacaccac    73860
gtttcttccc ccgaccagcc cggccccgtc caccagctcc gtcgccgccg ctaccttgtg    73920
cagtccgcaa cgacaggccg tttcgcgtta cagcggctgg agcaccgagt acacccagtg    73980
gcactcggac ttgacaactg agctgctatg gcacgcgcac ccgcgtcaag tacctatgga    74040
cgaagcgctg gccgccgcgg cggccgcctc ataccaggta aatcctcaac ccccgccaa    74100 ccgttaccgt cattacgaat tccagacgct cagcctcggc acctcggagg tagacgaact    74160
gctcaactgt tgtgcggaag aaaccacgtg cggcggcacg caatccaccg tactcaccaa    74220
tgcgaccaac accactagct gcggcggagc cgtcgccggc agtagcaacg taggacccgc    74280
cggcgcttcg gccgcctgcg acctagatgc agaactggcc ggcctcgaaa cctcggcggc    74340
cgactttgaa caactgcggc gactgtgcgc gccgctggcc atcgacacgc gctgtaacct    74400
atgcgccatc atcagcatct gcctcaaaca ggactgcgac cagagctggc tcctcgagta    74460
cagcttgctg tgcttcaaat gcagttacgc gccccgtgcg gcgctcagca cgctcatcat    74520
catgtccgag tttacgcatc tgctgcagca gcactttttcc gatctgcgca tcgacgacct    74580
gttccgacac cacgttctca cggtcttcga tttccacctg cacttttttca tcaatcgttg    74640 ctttgaaaaa caagtgggcg acgcggttga taacgagaat gtcaccctga accatctggc    74700
cgtggtgcgg gccatggtca tgggtgaaga cacggtgcct tacaacaagc ctcggcgcca    74760
cccgcaacag aagcaaaaaa acaacccctta tcacgtcgaa gtgccgcaag aactgatcga    74820
caactttcta gaacacagct cacctagccg cgaccgcttc gtgcagctgc ttttctatat    74880
gtgggccggc accggcgtca tgagcaccac gccactcacg gaactcacgc acactaagtt    74940
cgcgcgacta gacgcgttat ccacggcctc ggaaagagaa gacgcaagga tgatgataga    75000
agaagaggag gatgaagaag gaggagaaaa aggaggagac gatccgggcc gtcacaacgg    75060
cggtggcacc agcgggggt tcagcgagag cacgctaaaa aaaacgtgg gtcccattta    75120 cctatgtccc gtaccgctt tttttaccaa gaaccaaacc agtaccgtgt gtctgctgtg    75180
cgaactcatg gcctgctcct attacgataa cgtcgtcctg cgcgagctgt accgccgcgt    75240
cgtctcgtat tgtcagaaca atgtgaagat ggtggaccgc attcagctgg tattggccga    75300
```

-continued

```
tctgttgcgc gaatgcacgt cgccgctcgg cgcggcacac gaggacgtgg cgcgctgtgg   75360
actcgaagca cccacctcgc ccggaggcga ctcggactac cacggcctga gcggcgtcga   75420
cggcgcactg gcgcgacccg acccggtatt ttgccacgtc ctgcgtcagg caggcgtcac   75480
gggcatctac aagcactttt tctgcgaccc gcagtgcgcc ggcaacatcc gcgtcaccaa   75540
cgaggccgtg ctcttcggac gcctgcaccc ccaccacgtc caggaggtga aactggccat   75600
ctgtcacgac aattactata taagtcgact tccgcgacgt gtgtggctct gcatcacact   75660
cttcaaggcc tttcagatta caaaacgcac ctacaaaggc aaagtgcacc tggcggactt   75720
tatgcgcgat ttcacgcagc tgttggagag ttgcgacatc aagctggtgg accccacgta   75780
cgtgatagac aagtatgtct agcgtgagcg gcgtgcgcac gccgcgcgaa cgacgctcgg   75840
ccttgcgctc cctgctccgc aagcgccgcc aacgcgagct ggccagcaaa gtggcgtcga   75900
cggtgaacgg cgctacgtcg gccaacaacc acggcgaacc gccgtcgccg ccgacgcgc    75960
gcccgcgcct cacgctgcac gacctgcacg acatcttccg cgagcacccc gaactggagc   76020
tcaagtacct taacatgatg aagatggcca tcacgggcaa agagtccatc tgcttaccct   76080
tcaatttcca ctcgcaccgg cagcacacct gcctcgacat ctcgccgtac ggcaacgagc   76140
aggtctcgcg catcgcctgc acctcgtgcg aggacaaccg catcctgccc accgcctccg   76200
acgccatggt ggccttcatc aatcagacgt ccaacatcat gaaaaataga aacttttatt   76260
acgggttctg taagagcagc gagctactca agctctccac caaccagccg cccatcttcc   76320
aaatttatta cctgctgcac gccgccaacc acgacatcgt gcccttatg cacgccgagg    76380
acggccggtt gcacatgcac gtcatcttcg aaaacccga cgtgcacatc ccctgcgact   76440
gcatcacgca gatgctcacg gcggcgcgcg aagactacag cgtcacgctc aacatcgtgc   76500
gcgaccacgt cgttatcagc gtgctgtgtc acgccgtctc ggccagcagc gtcaagatcg   76560
acgtgactat tttgcaacgc aagattgacg agatggacat tcccaacgac gtgagcgagt   76620
cctttgagcg ctacaaagag ctcattcagg agctgtgtca gtccagcggc aacaacctat   76680
acgaggaggc cacgtcgtcc tacgcgatac ggtctccctt aaccgcgtcg ccgttgcacg   76740
tagtttccac caacggctgc ggcccctcct cctcgtccca gtccacgccg cctcatctcc   76800
acccgccgtc gcaggcgacg cagcccccacc actactctca ccaccagtct cagtctcagc   76860
agcatcatca ccgtccccag tcaccaccgc cgccgctgtt tctcaacagc attcgtgcgc   76920
cttgacactg tacggcagaa aagccggctc caagtgcaag cgccgcggca gcaccatgtg   76980
caaaaacttg tccttgcgcg cggtttcgcc gccgggaaag acgggcgaca gcacgttagt   77040
tacagccttg agaacctgct caaagtactt gtcggcgtga atgggcacgc cgtgctcgcg   77100
cacgtagctc ggatcttcgg ctacctcgta gttgcacacg gccgacggtg gtttccgcgc   77160
cctcttcttt gccggctctc ctcctctcct gttgctctcc tctacccgc cgccgtcagc    77220
gtcgtcgtcc gtgccatcaa tcgcgtccga ccgggaaacc acgccggcgg ttacagaatc   77280
accgttgtcg gaggaaccct gcggcgccgt ccggacaccg ggcgccgtca gaacgtaaaa   77340
gacccgatcc ccgaccgagg gtagctcctc agaacgggcc gccaatcgct taatgacggc   77400
aatgtgcggc aggttagatt gacggtacag cgagatgtcc ttagagagca ccgacgaaag   77460
caccaggtcc tcgacacgca cacggtgcag gtacagatcg tcgcgggcct gcaccaagcg   77520
gcgtaagata cgccagaaac cgcgtggcac gccgtacttc ttgacttcat cgagtgagag   77580
gcgcgacagg cgcacggctg cttccgagac ctcgcgatcc tcaaagagca gcgagaggac   77640
gtcacgcgtg acgcccttga cgaactcgca ggccgtcttg cgcaccagat ccacgccctt   77700
```

-continued

```
catgctcaga cccgaggcgc cctccacttt gccgatgtaa cgtttcttgc agatcatcat    77760
aagagagacg aagacctttt caaactccag cttgacgggc tccacaaaaa gacaggccgt    77820
cacgtagtgc gccaggctgg gcccacgcgc caccagagcc tgcggcgtca ggccacgaaa    77880
gcggacaaac acgctgtccg tgtccccgta gatgacccgc gcctccaccc gccgttcgtt    77940
cgagccccct gacgatgttt cgagcccctc cggtaacgcg ctgctctcct ccgaatcccc    78000
ctcccgcgtt cccactacat agtcttcctg attaaaaaaa ttgtgcaaaa aacacggctc    78060
tgaaaagttg tctttgatga accgcgccgt gcgctctagc atgtcgcgac cgatgcgcgt    78120
gatgctggcg gcgatgggca gacacggcat cataccgttg accacgccgg taaaaccgta    78180
gaaagcgttg cacgttactt tgagcgccat ctgttccttg tcgagcagca tacggcgcac    78240
agggtcttga cactcgcgca tgcattcgcg cacggcacgc cgctgcgaaa cccacttgtt    78300
gagcagttcc gagagcaccg agacgcgcac cgaagcacgc acaaagcggt gggtcacgcc    78360
gttctctagc gtgacgctgt atacgtcggc ggggtccaca gggtactcgc cacccggcac    78420
cagcagggtg gagtagcaga ggttgtgggc catgatgatg aagggtaga ggctggcaaa    78480 gtcgaacacg gccacggggt cgttgtagta acccacctcg ggctcaaaca ccgtggcgcc    78540
ctggtacgaa accgccgcag taccgccggc gccgtgattg tcgttggaaa cgccgacgcc    78600
gccactactg ccggagccga cgctgaaaac gccgacgctg ctactactgt tactgccgga    78660
gccgggtgaa acgccgtcct gactggacgg cgcagattgc aagggcggcg acatctgaaa    78720
catagccgcc acagaacccg cgtcgccggg cacagcggcg gtagagatga tagcagcgtt    78780
aggtgacaca gcaacgctat tcgtttcggg caccgtcgta cctttgctgt agtggttggg    78840
caggataaaa tcgcggcagg cgcactcgtc cagcagcgag gtgtagatac ggatctgctg    78900
tccgtcaaag atgacacgcc gcaacggaat tttagccagc cgcgcgatgg ccccggcctc    78960
gtagtgaaaa ttaatggtgt tgaacagatc gcgcaccaat acgcgtcct gcagacagta    79020 acggcctacc tgggcgcggc cctcggcatt agccacgaaa caacgcggga tgtccttgta    79080
agacaggtca tccttgcgtt gccgcaggta aagctcggcc atagtgttga gcttatagtt    79140
gggcgagtta gtcttggcca tgcatacagg gtacatgtcg ataaccaccg aacccgcaat    79200
atacaccttg gtggcggccg tgctggccgg attgttgtga gaagccgagg gaaaagcggc    79260
ggcgtactgc cgcttaaaac ccacggcggg gctgtgtaaa aagaaacggc cgccctgcgc    79320
cgtaggcaac ttgcagaagc gctgcgagtc caccttatac aggtactcga gacgcgtgag    79380
gatgtacttc aagtcaaaag agttgatgtt gtaaccggtc acaaaggccg gcgcgtaccg    79440
ttgaaagaaa agcataaagc ccagcagcag ctcgtattcg gaagggaact cgtagacgtc    79500
cacgtctggg cccacctgcc cgcaggtgcc gatcgtaaag agatgaagac ccgagtgccc    79560
aaagatcaca ccctccgaag tgcagccccg accatcgttc ccgtttggga tccctgatc    79620 cacggcggtg tttccccccg tctcgtagca cacgcacgag atctgaatga caatgtcatc    79680
ggacttctcg gcgcagggaa aaccaccctc gccgctcatg cactcgatat cgaaggacag    79740
gcatcgatag cgcggccacg agctgtcgtc gggcacagcc accaggtcag agacatcgca    79800
gtctacctcg atatcacaag tcgacgcgcg accctgctgc cgccagtcgt aacgattcac    79860
ggagcaccag ccgaacgtgg tgatccgccg atcgatgacc aaacgcgtca gcggatccac    79920
acggacctcg tacacgggaa aaccctgctc cagcagatac tcgccgattt ttctggccat    79980
ggtccagttg ctgatagaca cacactgcaa atcgggcacg ggtcgcgtcc cgtacccata    80040
```

```
gatggaggtc ttggtggccg gcgtgacaga cacggcgtat ggcgtccgcg gttcgggcac      80100
tagttcgccc acgctggcaa tgacctcacg cagcctatcg gtgtcgctgt actcacagta     80160
aaagtagctg cgctgcccga aaacgttgac gcagatactg tagccgtgtt ctgtggcccc     80220
gaagaaacgc aacacgttcc ccgaaggcac cagatgctga cgatagcgcg gcgacacgtt     80280
ttcgggcgag tcgaagaaga gcacggcgtc cgtctgatcg taggtgtgaa aacgaatagg     80340
tcccaccacg cgacccacca gggtctcgcg ccaaggacac ggccaaacca tgtcatgact     80400
caacaaatgt ttaatctctc gatagaacat gagaggcagc cgtcccgtct tatgcttgat     80460
caaccccgtc tgaccgtcga acatgacacc tcgcggcacg atctgcaaaa actgtttctg     80520
tggcggccgc ttgcccgagc cctgcgcgga gccgggctgc gaacgctgac gccggccacc     80580
cgcgaccgca ccgccggtca cgccgccgct cagatacggg ttgaaaaaca tagcggaccg     80640
tgagaggctg acagcttacg aagcaaaatc acaaagaaaa tacacatgca gcacctagat     80700
atccagttta accccgtata tcacaagtct ctgtgtcaat atttttttgtc tagttttttt    80760
ttcctcctgg ttcagacgtt ctcttcttcg tcggagtctt tcaagtgtct gtagccgttt     80820
ttgcgatgtc gcagccggtc tagcaggtta ggcttctgtc ccttgtcctg cgtgccagtc     80880
tgtccgtcca aagaatctgt accgttctgc tgcgctcgct gctctgcgtc cagacgggcc     80940
agggccagaa gcatctggta agcctgctcg ttggtgtaag gcggagccgc cgtggatgca     81000
tcagacgacg gtggtcccgg tcctttgcga ccagaattat aaacactttc ctcgtaggaa     81060
ggcggagcct gtaacgacgt gtcttttggtg ctgcccgacg tcacggtggt cccgtcggcg     81120
gacaccagat agggaaagag gttctgcagc ggctgcgtgc acagacgccg ctgtcgagta     81180
tagatcaaat aagtgataat gactacggct atggccacga ggatgatggt gaaggctccg     81240
aagggttttt tgaggaaggt ggcaacgcct tcgaccacgg aggccaccgc gccacccacg     81300
gccccaatgg ctacgccaac ggcctttccc gcggcgccca ggccgctcat gaggtcgtcc     81360
agacccttga ggtagggcgg tagcgggtcg actaccttgt cctccacgta ctttacccgc     81420
tgcttgtacg agttgaattc gcgcatgatc tcttcgaggt caaaaacgtt gctggaacgc     81480
agctcttttct gcgagtaaag ttccagtacc ctgaagtcgg tattttccag cgggtcgata    81540
tccagggcga tcatgctgtc gacggtggag atactgctga ggtcaatcat gcgtttgaag     81600
aggtagtcca cgtactcgta ggccgagttc ccggcgatga agatcttgag gctgggaagc     81660
tgacattcct cagtgcggtg gttgcccaac aggatttcgt tgtcctcgcc cagttgaccg     81720
tactgcacgt acgagctgtt ggcgaaatta agatgacca cgggtcgtga gtagcagcgt      81780
cctggcgatt ccttcacgtt catatcacgc agcaccttga cgctggtttg gttgatggtc     81840
acgcagctgg ccaggcccaa gacatcaccc atgaaacgcg cggcaatcgg tttgttgtaa     81900
atggccgaga gaatgctgac cggggttgatc ttgctgagtt ccttgaagac ctctagggtg    81960
cgccgttgat ccacacacca ggcttctgcg atttgcgcca gcgcccggtt gatgtaaccg     82020
cgcaacgtgt cataggtgaa ctgcagctgg gcgtagacca gattgtgcac cgattccatg     82080
ctggacaaat gagttgtatt attgtcactc gtacttcttc tggtcctatg agtgatattc     82140
agactggatc gattggccaa acgttccaat tccaccaaag atttttgctt gatgccttgc     82200
cagaacacca ccagaccgcc gctggtttcg aagacggaca cgtttccgta tttttcatat     82260
gtttgattgt atgaagtatt gaaaatctgc tgtaacttat ttatagcctc atcacgtacg     82320
cagtccagcg cggagtcgga catgttcact tcttgtttct tagacagaaa agttgcagtc     82380
attttggcag aagaaaagtg gtacgagtct tcggcttcgg aacggatagt acgttccgag     82440
```

```
gcttcccaga aggtgagctg gcaggtgaca ttcttctcgt cctgtatatc ccaagagatc   82500
accgagtcgg cacgttcgag aaaagccacc aacctatggg tttctggcgc agcgttgggt   82560
cttccaaagt cggaaacgat ggtgtagttc gggaaaatga aaaacttgtc ggcgttttct   82620
ccaaagtagc tggcattgcg attggttccg ttgtagaaag gagaaatgta aaccacatca   82680
cccgtggaag ttgcaaaaaa atgataagga tacttggagc gcgcagtagt gatggtcagc   82740
atacagttca gattacaggt ctcacgatag agccaggtgc tgccgcggct gtgccactga   82800
tccttgaccg tcacgtaacg ggtactgtgg gtgttggaat aatcgtcggg aattaattgc   82860
atggttttgt tttcataact gtccctatga tatgccacga aaccgtgcc tcctataacg    82920 cggctgtagg aactgtagca ttgagcaaac ttgttgatgt gatgaatctc ccacatagga   82980
ggcgccacgt attccgtatt gctgcccagc agataagtgg tgtagatgta agcgtagcta   83040
cgacgaaacg tcaaaacctt ttggtagacc cgtaccttaa aggtgtgcgc cacgatgttg   83100
cgcttgtaga ccaccatgat gccctcatcc aagtcttcat tgataggctt catcgaggtg   83160
cagatgatat tacgttcaaa gcgaataaga tccgtaccct gggccataga acacacgcga   83220 tagggtact tggtagtgtt gactcccacc acatctccgt acttgagggt agtgttgtag    83280
atagtctcgt tggctctatg actgacggct tcagaagacg ttacgtgttg agaatagact   83340
gaccgggttt gagcagacgt cgtacgagaa gtatggcttc cattgtgagt agaagaagtt   83400
gcatgggaag tactagaaga ggaaaccgca gcacccagac agacgataca caggttaacg   83460
cagactacca ggcaccagat cctggattcc atgttcgtcg cgggccaaat ccagcagcga   83520
tgaggcgcgt cgtggtctct tgcgtgtcgc gcggaccctc cgggaaacac ccgcagtcga   83580
ggaggaggga tacggacttg gcagccaagg tcggtccggc tccctgaaga caccgagac    83640 ggccgcggcg gccgtcaggg tggagggctt ggccacggga gctgttggca cgtcgccact   83700
ctcatccggt ctggacagat gcctgtagag gaggagatat agatctttgg acttataaag   83760
acttccttcg tgacgaagca gcagcggcca ctctttgtta tacgtgagaa tcacatctct   83820
gtccgggtgc agttcgtcgc gcaggcacgc gatcgagagt tgtttcccga aagtttcatt   83880
atatagtgcg acggagagca cgagctcccg cacgtgcatc cacatctcct tctgcagcac   83940
gtttaggtcc tgacagtccg aaaaattgaa aaaacccata tacttcacca ccatccactc   84000
actgggatac acggtacctt ccgcgcattt gaccaaatcg tccttgacgt ggggtagtac   84060
gcccgcgttg tcgcaggcat aggccatgtc cacattgtga gagaggggat aacgatcggt   84120
gcagtgggtg aagaggggcc cgttacacaa ctcgtagatc tgctgaccca gtagcgggag   84180
ggattccaca ggcagactct tgtggatcag gttattgacc acatacaggt gctcatcgta   84240
ggtgaactga tcacccacgt ccaccacgtc ttggtcctgg tggtattggc tgcggtacag   84300
aaacccattc atgagcttag agataaagtc cagacacaag ggccccacta gattgacatc   84360
gatgagcttg ctagtcagac gctcctgcgt tttgatgcaa cggatcacct tgccatagcc   84420
cacctccgag accttctgca ggtaggcgcg tttgcgcacg ttcacctcgc gagtgacgtt   84480
gtggatgcgg gagcgcgcgt ccaccaagtc gagagcctcg tgttcgtcgc agttgcgcac   84540
ccgtaagccg ttctcgctgc cgtcgccgtc ctgcccattc accctccccc ctaccacttt   84600
cttgcctcct ccacgagccc ggccgccgcc accgttattc ctctgactgt gagtactgct   84660
gttgctgctg ttgctggccg tcatcaaagt cgtaccgtc cccgacatcg cctcccgtcc    84720
acgcaggtga atagcctcgc cctcggggcc gtcgcccccc gtgccatctg gcagcggacg   84780
```

-continued

| | | | | | |
|---|---|---|---|---|---|
| tcgaatctcc | tcgagaatat | gcttgatttt | ggtgtacatc | tcgttgcttt | cgtggagctt 84840 |
| gttgaacacc | gggttgtcct | cgaaagcttg | aatgctgagg | gatgtgatga | ggtcgatgat 84900 |
| cctgttgggg | gcggcaaaga | ccgacccac | gaacatgcgc | tcctcccgt | ccaacgcctt 84960 |
| ttccccgagc | acgaagatgt | cctccacgtc | ctccccgtac | agatggcgac | tgatgccgtt 85020 |
| catgagcgcc | cggcacagct | ggtgatacac | atttagctgc | tggatggtga | tgcccacccg 85080 |
| cttgacgata | acctccgagg | tacgggacca | gtaggtaaaa | tccgacaagg | aatatattcg 85140 |
| ttccggtata | tccgtaaaca | ggttgtactc | cctcagcgcc | tcctccgcct | cctggatgta 85200 |
| gctgtggtag | gccgatgaag | aagagaatag | gcttttgagg | gccgaaagga | ctccagccaa 85260 |
| gtgggggatg | cgcgttgtca | ggtccagcag | gtcctgctcc | accgtctgga | tattcacatc 85320 |
| ggactggctt | gacggacggt | ggaccgctat | atggttgcac | agcaagccct | gcagccgctt 85380 |
| gttcagcgag | cggccctgat | tcgggatgat | ggtcagctcc | tcgtagcatt | gggcgcatgt 85440 |
| cgtcccttcg | acgtacactt | cctgacgcgc | caccggcgag | atgccgcata | ggcgacggag 85500 |
| gagctccagc | aactgcgcgc | agacctccag | gccggcctcc | ggcgccagga | tcccgtacac 85560 |
| gtagttcatt | ttgcacagga | agcgctcgat | gtcgttgagt | gtggccagac | tgacgctgaa 85620 |
| acggacgttg | tccgtaaact | ggagctccac | ggtgtgatgg | cgatcgcagc | gatccaaacg 85680 |
| gaggacggta | cggtagaagg | ccgcccggtc | cggctggcgc | gagtaggcca | tcagcgcccg 85740 |
| atccagcaaa | gccgtatcct | cgtgcagcgc | cttcagcagc | atctccaggt | agagcgtcag 85800 |
| caacgaactc | tgcgtacgat | tctgcgccac | cacctccggg | tagatcttcc | ggtacagata 85860 |
| cactatagcc | gccgcgtttc | tcttgaacgg | cgtggactcc | gccagtaaca | cgttcggatc 85920 |
| gcagtacttt | agacactcca | gctccatggc | gtattcgttg | catttcgaac | acactacgca 85980 |
| tagtttctgt | aacaaattca | tctccatgac | tcgactcgct | cacgtacgag | acgctgtcgt 86040 |
| ccggtctggc | gccggccaga | gacatggagt | cggtgcacaa | ataactcgcg | ggccgctcgc 86100 |
| tatgccgact | gacgttgacg | ttaatatata | acgacgtcgt | cgacgacgcg | ggttctgctc 86160 |
| ccgaagctgt | tgccgccgct | tgcggcgcaa | cctcctccac | caccgccgcc | gcggctcct 86220 |
| ccgcctcggg | cgacgggggc | tcggagatga | ccggctgtgt | ctgacactcc | tcccctttcct 86280 |
| caggcggccc | gggcgccgac | gcgaatgtcg | gagtttgcca | gcgcggcggc | ggtctctgtc 86340 |
| tctggtgccg | cggcgctaac | cttcggggct | gttgctgctg | ttgatgatgc | gacgccgtct 86400 |
| gtcgccgctg | ttgcggcggt | agctgatacg | gtgtcgcctg | gtgctgctgt | gtcggtggct 86460 |
| gctgttgctg | ctgttgttgc | ggtctgaaaa | gcggccacgg | gggctgcgac | tgttgttgct 86520 |
| gttgttgcga | tgctcgtggc | tgcggcggcc | gttgtcgcgg | cgtttgctgg | cggttacaac 86580 |
| cggctgcgtt | tggccggcaa | taaccccgctg | ccccgccgc | ccccgctgct | cccgccgacg 86640 |
| ccgccagcct | cgtcttcgcc | ggcgttcacg | agaaagcagc | cacctcccgt | ctcgccgggc 86700 |
| acgccgaagc | aaatggagtt | gcccgcgacg | gactcgccga | aagaagacc | gccaccccg 86760 |
| acgccggacg | ccgcgccgac | gccactgggc | gcgaagagcg | ccgacaggtc | gtgcacctcc 86820 |
| cccccggcgg | cgtccgttaa | tcgctgggcg | tcggcgtcca | gcacgcgtcg | caagttctcc 86880 |
| agcgaaaagt | cctccacgcc | ctgctcctgc | aacgcggcaa | acttgtccat | cagcgacgcg 86940 |
| gccagcgcct | cgcagccatc | cacgaagaag | agcacatcgt | cggacgcggg | gatctcctcg 87000 |
| cgcacgctca | gaatctcgta | cacggccatc | acttcggggt | cgcaatccaa | gttctcggcc 87060 |
| tccagcgcca | gcatgacgcg | gtttttata | agatccgcgt | caaaaagcac | gttctcgcgg 87120 |
| cgcgagcgtt | tgatgagcac | gtcggccaga | cgcgtagcca | agaggtagcg | ctggcgcatg 87180 |

-continued

```
aaacgataat cttggccgct catagagctc acgttaaggc tgcgttccac accgttgccc    87240
gaaaagtagc cgatctgccc aaactgatag atctccttgc tgttgttgat acccgcatat    87300
ttttccacgc tcacgggcac ggtcaccaag gaacgatgct caaaaacgct ccgtaccaac    87360
gattcacgcg ccacagtggc ggccatgggc gccggcacgc ctgcggtctt caagcccttg    87420
acatgcaacg caaattcggc gggcgacgag aaccgcggac tagcacctaa cacgtgagga    87480
aactgcgcgt ggttctgcgt cgttaagcgc gtcgtcaacc cgtgcagcga gccgatgtag    87540
tctttgaagc cataatagca gaggaatttg ttatggaaac ggctttccac gtaactcagc    87600
acacagtctg gcgccacatc cagcagatcg tgctcctgat agtcagccgt cacagccacc    87660
agaaatttga cgaaagcatt gaactcgccc atgtcaccta tgggcacatt cttgggcaac    87720
gcgttggaac agaccttctg ccaaaactgt aagcagggga gaccacattc aggaaagagt    87780
cgctcgtgat gtcgatacag cagaaatccc aagcagccct tagccggatt acgacgcgga    87840
acgtgatcgc ggcgaaaaaa cacgctaccc gcgttgccct tgcccgcgcg gtagatgggt    87900 cggttttttca cccgcaccat gatcaacgtg ggtaccgaca gccgcgagag cttgatctcc    87960
atgggcacca cggcgtacgt gccctgcgcg tacagcctaa agtccagcag gcggtcgtga    88020
tccgaattct tggacgactt gatctgcttg gtgaagagaa agcccttgcg cgacgacgtg    88080
gtggagaacg cgccgtgaat ggattgaaaa tgctgcgtca tccatttgga taccaagttg    88140
gtggtcaacg gattgtccac aatgtatgag gtagcgctaa taagcgccac gttctggatc    88200
acgtaaaaga cggatctgaa ataggcgtag gctagcagcg gctggaaggc cacggcgtag    88260
ggattcagat ccaggttgaa ggcctgcgtg gcgcccgcca cctcgtcgcg gctgctcttg    88320
aggcgcacct ccgaaacgaa acccagggcc tcgtcgtcca caaacttgtt gagcgccgaa    88380
aagacggcca caaagtcgct tttgccgtgc gcgctaaagg tatcctcgcc cgtcacgggg    88440
tcgatgagcc gcatcttgcg gcagtaatcc aagatgcgat tgagccgata ggtacggtcc    88500
acgctagcgc ccaacatgcg accgccgcgc cccatcattc ccccggaatc cccaccaccc    88560
ccaccaccac gaccgccacc cagaccgtcg ctcgggcccc cgctcacgtc tcgtccacca    88620
cccccgccag caccgccgcc cggaacccg tcgtcacctt tgccgtccaa acccccgtcc    88680
ttggcgtcga cgttgtaacg ccgaccgaag ctgcccaaaa tatccacgtc gttgagaaaa    88740
cgcgactgca cggtgatcac gcagggctcc ttcttgggct gcttgggcac cacgggcaag    88800
cgggtgcgca cccgcacgaa ggccgtctga taacacgtgt ggcaacaagt accccacag    88860 gcctcgcaca gccccgcggc gcagcccacc aggtgattcg tgagcgtcga cgaacccgac    88920
aagcccgtgt tgtacaccga gacacgattc agataccaga cgaagcccga aactagctgc    88980
ggacacgtgc cacacaccaa cgccaaatgc tgcggcccat agcgttcgtc cttgagcggc    89040
gcgccctgaa acttgagcac cttgcgcgcg tcgttgtaga cgtcttcgca ggccgccgac    89100
aacccgttgg tgaactgaat agccttgagc aacgtctcct gactggccgt accgccggcg    89160
ctgggatgcc gcgccgacga ctggagatac accagcctgt gctggtagag caccgaatta    89220
gcgctgaaga ccaaggcggc cacgtgcgtc gagagatgca acttgagctc ggtcagcgcg    89280
cggatcagat cgcggtgatc ggttgcgttg gtcactaaag gccactcgga aaagagcata    89340
gattcggcag gttggtaagc cgaatcgaaa ataccgagg caaaactgaa ggccaactcg    89400
caaaccaccg cgtcactcag catcagatga tccttttcca gactgctgag tcgctggctc    89460 atgtaccca agtagcgctt atgtggcgcc agcttcaccg actgctgact gtcgtgcaca    89520
```

```
aactgccgca acgccgcctc gatcagcaca cgcggctccg agaagcgcag cgattgacac   89580
catgacgtgt acacgtagta gaaaagcgtc tcgcttacgg ccggcacgta gagccctcgc   89640
gcctccacaa aagcgctgcg cgcatccagc gagacctcgt cggcttcggc gtcaagctgc   89700
aacgaattaa agagcgtagg cgggtacaac ggcacgcgca ccgcctcgcc gccgtgcagt   89760
cgcaccgtgg tcgcctcctc cacgcatgga atcagctgac cggcaaagag aaactccttc   89820
aagccgttgc ccaccaccac gtgcacagtc gtctcggacg cctgacagcc caccgccgcg   89880
cacaacgccg ccagatcggt aggcacgcga tccgcctcgg gcatgtaagc ctccaacgcg   89940
tacttctggc gggcgtcctc gcacagccga tgcacgtctc cgtgatcctc ggtaaaagcc   90000
acgatgcctt gcgtatgatg aaagtagagc gcaaaaggac agaaggacgt gactttcgtg   90060
agcaccccgc cgtcgtaaca aagcacaggc gtgcgcacag agacgccgaa atccgcctcc   90120
accgtgagcc ccgccaacaa aggagcgatc accacgctcg aggaacggtc gcatagcgag   90180
agagtggcca gaatctcctg cgtttctgcg ttcaacctgc tgaagtagag aaaagccgcg   90240
ggccccaccg gcgctagcgc ggttagttcc tcgtggctca tggtggatga acggaagaca   90300
atggctacgc cgccactgag tgaattttat accaaggaaa agttcagcac gtcatgtttg   90360
acgcacgacg tctgagacac caccgtggcc accactgcgg tctggctgcg gttgcggacc   90420
accaaaggcg acaaccgcaa cgatcccagc aattcgtaag aaaagctaac cgctacggtc   90480
aggtagcctc tcgcagccag accgctagcc gacgcacccg cccgcgaaaa tagcgtgatg   90540
ttcgggacgg ctttgcgtca ccgccaacta acgtcggtag tcgagcacgt cgtttatcct   90600
cagcacaccg tccgatcaca atccgttttc ccactcagtc gcacaagcag cacataaaaa   90660
ccccacacag ggcacgtgaa aacaccgtcc ctagaaaacg gcgttttctg tcctaccgtc   90720
acccgtatac acaggcaaat cccaatcccg atccccgaaa acaccgtacg gtgtttgtga   90780
cctccaaaat cacatcagct aacaaaccgt gaaaagtcac gtttcacgaa cacggtgttt   90840
ttaaatcaca aagaaccgcc tgacggttta caagcagaaa caccgcacca cggtggtaca   90900
agcgcgatga atctggtctc gcaacctcaa tcgccgctat caccaccgat tttcgctgcg   90960
ctccgccgac aaaacgccgt acaagctaca caccccaaaa acccgcgcgc ctacgggcgc   91020
caaacctgtg tgttatctca acgtcacaac acgacacaaa ccgcgtaacg tggtttcccg   91080
aacacgtacg cggcacagac ccccgacacg tactcgaaga ccttacagtt tacgagtcaa   91140
taaaacagga aaagatccga actttaaaat tgtgtgtttt tattttccca tccccctctt   91200
tttaccaaaa aacacatttt tcgtcttgta aaaagtaact ttcgcccatt gccatgaaac   91260
accgtgatgg ggaacggtgt tgtgtgtcga ctgacgtcac tacggcgatc agtatcgacg   91320
tcgtgtatac ataacggtgc ccggtgtttt tattcggggc gttgtcgcgt cttgatgtaa   91380
tgtaacctga aaccgccgtg cccaagaatg cggaagccag cgtgtaatca taacggggtt   91440
ttgggtacaa tctgacgaca tctggcggcg agcgtacacc atcgaatgtg gcgatcgccg   91500
gctctacgtc acaatgacgc aaaaacacac tgtaaaccc gcgtagacag ctttcctggt    91560
caacgagcgc catctggtgt cggcataaga acaggcatca accccgtggc cggcgaggcg   91620
gtgagcactt ttgttggtca cgtgaccatc agcgcaggaa gcgaggcccg tagaaccgcc   91680
caagaggcgg tgccagatgc caacgtcata atcacaaggt gatttgttac gtcacgcgcg   91740
cgcacgcacg cgcgcggtag aatacagcga tccctagtga agccacaccc attacgtgta   91800
gccatatccg cttacgtata cagccacacc cctaggtacg ccaccttatc taccaatcac   91860
agaaacggat atacaatgac ccctccctag actccacccc ttgtacggaa atttcagata   91920
```

```
ggtggaaccc gttagggttc caccgtcctc ggtgtacgta caggcttctc cgtctaccgg    91980
aaatatacac ctgctgacgt agacgctact cccggatacg cgtcataagc tactggaccc    92040
taggggggag tgtctacagg gctacgtgca cgcccccta cctagggtat ccgcccctt     92100 cctctgtttt ggcctagtaa acttaacgcc gccgcttctc acgtgacccc tgacaagcct    92160
acgtcacact cgcgtgacca cacccactcc ggatatacgt catcctgtgg aattccggac    92220
atacggtgac gtagcgagcg tagcgagcta cgtcacgtat gcgtgcgtca tctccggcgg    92280
aaatcatctc tgatgacgta gcgagcgaag cgagctacgt catcagtccg ttttacgtat    92340
accggatgct aggcgacgcc ccgtaggggc ggagcctagc ttccacccct aggatgcata    92400
ccctatatag cataattctt ctaacgaaac gttctacgaa aacggactgg cggaacggga    92460
accaccgtaa cccccccccc tcaccccccc ccttctcctc cggaaccggg gggggcaaat    92520
ttttaccaaa tttgggcaac catgatttcc aatgggacgg cgtttccgtg cgcatgcgca    92580
gtcggggcga gttttttggtt gtcagggcgt tgccacgcgg attatgggat ggtgactcga    92640
gtgcgcatgc gccggggatg ccgcatggaa aacctatata taaggagggg tgaaccaggg    92700
gccccggggc gcatgcgcgg gccagggccc gcgggagggt cgccctgcgc atgcgccggt    92760
aaaattccac tgtgtgtgtc gtgcgcatgc gccagtattt ttccactaga ggcggtcagt    92820
gcgcatgcgt cggtaaaatt ccactagatg tgcgccgtgc gcatgcgccg gtattttcc     92880 actgggcggc gcacctagg gagcgcgagc ccgtgccgg gcatgggccg cggcggtgga      92940
aaattaccgc tccgcccacc taggcgggc atctgaaaac ctataaaacc cggcgtgccc      93000
gccgcccccc ggcgcagtcc gcggcagggt tccggccgtg ctgcggtccg cacgctgcgc    93060
ccgctcccgc ctgcctcccg ccctacccc caccctcccc ggccgaggcc cggcgccggt     93120
ccgtccgcgg gccgtccca ccgccctgga gcaccatccg gggccgtggg ccgggcaccg     93180
ggcgcggccc gctccggacc tcggccgggg gtccctcccc tccccccgct cgaccccccc    93240
atccgacggc ccgccggc tgggacccc gcaccgggt cccggttccc gtccgtggcc        93300
cggggggacc cgagcgggg cttcccaccc ccaccccgct cctccccggg ctccggcccg    93360
ggatccctcg ctgctcccgg cgacctccgc cggcttcccg gtccaccgc cgcggaatgg    93420 acgggacccg gggtccgcgc ccttcccctc cccccacggg gggctgggtc gcggaccccg    93480
gttcctaggc tcgttccgcg gtgggcgacc ggggatcccc cacccagctc cccttcccgg    93540
cccgccttgc tggcttttgg gcccctgcgg gctttttttt tccggctggg ggtcgcggcg    93600
gtcggccgac gacgacggta ggtgggccgg gtgacggtg gtgggacgg gcgacgcccc     93660 ggctcgacgg caatcggtcc cggaaggttg ggggctgggg gccggtcag gagctccggg    93720 agcggggtcg accgcgacgg cttccgggtc tcgcggcggc tccctctcgg cggctccggt    93780
tgggctcccc tcccccctct cgagggtccg gccgccagtc gtgaccgggg gtccctcggc    93840
ctagccgccg gctctcggtc cgccttatcc tgggcgttgg cctgtcccgt gacgctcccc    93900
tcccccgctg ctccccaaaa aaactccgcc cgaaccgtcg cggcttgctg gccctgggcg    93960
tggtccccca ctccctccc ccatcggcc gcccagccgg ggtcggcgcc tcggacccca     94020
ccaggctgtg gcgtgtgtgc tggccgatgc ggcggcgagg ttgggtgtgg ccggaagcgc    94080
tcggggtcga cggtgggccg ccatgacacc tcaattgtcg tcagtacgcc cctccacaat    94140
caccgtcccc acacgatggg cccggcaggt cacccaacgt tggttcaggc ccagtcggt     94200 tttttccccg gcacgaacgc acgtcccgt gggctccacg cgttttccac cctttcctgg    94260
```

```
agggaccacg
aggggtccgg aacaccgtga atccacgggg agggtccccgg cacggggccga         94320
accgtcccac ccggcgtgtc gactcgtccg agacccggga agggaacagg ccccacctttt  94380
ttttcccttc tccgatttttg ccgtggaaaa cccgtgaacc gatacgggtg cagacggccg  94440
aaaaaaatcg agacgacaat atgacggcag ggcgcgatct tctcccccat ccgacaaaac  94500
cgtgtccctt aaaattcccc acctttctct gttcaaatgg ccccgaaact gtaaaacacc  94560
gtttgaccgc accccaaccg cgccatcttt ggtgaccttc tcgacggttc tctcgctcgt  94620
catgccgttc tgagctccga catggcggac gagagaaaat ggcgtcgaga gcctaggagc  94680
gttttttgctc caggcgggta aaaaaatagc acgataactt ttctgtgctt tttttttgaga  94740
cgttttagaa gagctttttt ctgctcagag cgaaaaaatg atagccctga aaatctcgac  94800
gagtctggcc gagcggcgcc atcttggagg aggggcgagt cgcgggcacc gcctcggtac  94860
cccctggccg aggcgagtcc gcggtcgccg cctgttccgt gatgctacct agagggcgct  94920
gtcgaggcga ctcttcctgt tttcgccctg agggctaacg gtcgctgacg tcaaaccatc  94980
tcgtgctcgc tgagtcacat ccggttgttg acaagcgatg gaggaccgca cccaaagtgc  95040
gccctctagt catcgcgcct gaccccttttt ataaactgct cgaagaaaag aacaccttat  95100
gtgaaaaaat acagaatgat gacaagttca tccaacacaa ccgctcaaca acgccatatc  95160
tatcagtgtc caaaaactat cttctatcct ttgaaactat aaatgctgcc tatatacata  95220
tttagtatcc aagactctta ccacgtagac gaaaagaagt gatacaatga tcttgacgtg  95280
tatcgtctat atcgtgctag atatattcag ataagacgcg caaaccatag atttctcatc  95340
agtatcatga aagacctata gctctatata cgaacctagt cattttagga cagccgccgg  95400
agaagccgac gagggatcgg gcgggtgcag ccagaaccctc acgcccgatc ccgcctccgg  95460
taggcgattt gcatctgttt ggtaaaaagc tcataagtct gtatgtgacc tatatatatt  95520
atacgctatg tacaccgaac tgtcgctgtt gtataagaag aaaaaactct ccatatttat  95580
atcgtctgaa tttttgcttg atagacacgt gtttggaact ctgtccccccc acgttttcac  95640
tgtgtataac aaaaatatgt gtttctcaaa agatcttgag gtgtttgaaa acgggggaaa  95700
cctgcgtttg ggtgctctaa gccccggact gggacgtagc cggcgtccgg cacctatatt  95760
tttctattttt tttttacaaa atatatgatg aaccaagaat aaaactctag ctctcgtcta  95820
ttttttaatat gctctactta gaaccttttt aatgacagaa tgaactccat gttatacgct  95880
ctttatatag tttctctgca ctaaccttta aaaccgtatc cttccctgtt gtacaaatca  95940
tcttttgata cacaatgatg acctgatatc cctccatata tatgatcgga tattattccg  96000
ttagacttgt cctcctttttt ttttcctcatc tcctgtatct ggagatatat gttgaccacc  96060
accgccatga ccaccaaaaa gctagccgtc acgactagaa atgtgtagga ttcggacttt  96120
ccgttcgaga agaaaaagag accgcgtctc tggacgctct ttttgtcagt ctgaatcgac  96180
ccgggatacg taagagagcg gccctacatc ggggggcgct cgagaccgac gacgttccat  96240
ctgaccagaa aaaaaaaggc acccctcggt ggcgacctct caccatcgtt tgcccgtccg  96300
cccgtccttc gtagccatca tcatctcagg ctctatcggt accatcgttg tcatctgaaa  96360
aaaaaactgc ctcaccccacc tgcgtaaaaa caccatcttt ccggaggtgc ggtaagacgg  96420
gcaaatacgg tcgtgccgag gcaaaaaaaa cgcaccatcg acaccacacc ctcatgagca  96480
ccacctgtcg gtgttggtcg tcctccatcg ttctctacga acatctcgac gcccgggtga  96540
cggacgacgg caagacgtcc cggagaagac ggtgttctct cgggcggtac gctctctgga  96600
tctataatat ctatagtagc taaacgagac tgtgagtacg acgaaccaca tcatctttttt  96660
```

```
tttatgttgc ttctttagaa aatgacttat gtcgacgaca ctcggcatca gccatctcgt    96720
gaaacacgct cgcttttcgt ctctccaagg aacactgggt ccgctgaaag ggaccgtgta    96780
ccgaccaaag caaaaaacac acacgtagta acatgatcaa ccacgtctga atgacacgaa    96840
aacacaatcg tataacgctc tattcatgga acgaacttgg aataaaaaaa ccatcgcagg    96900
ccagaggcta agccgaaacc gtccggggaa gcgggcgcga gttttccgac ttagcctttg    96960
gtgctcgttg agcctctttt ttttttctga ttctctgaag aatcaccgtc acagccctat    97020
gacgcgaaat caattgctag aacataaacg ttctcaacag gtatgaaatg aacaaactag    97080
atgatgctat aaccttatat tgtgtgtata tagataggtg tgaaatttgt aggataaaaa    97140
gtgtcgttgt atgatgcaca acgatcgtga aactggagac tgtagctctc taccgaatgc    97200
aaatacacaa atgacatcga ttcccgtccc cacataaaga aatgtgcttt actgtgaaag    97260
aatgaagaag attcttgttc ctcgtacgac ggggccctcg ctcgtcgtgc ctcttccccc    97320
ctccgggaga ggggacgtcg gggccctccg tcgcaccggg ccgaagccag tgaaatgttt    97380
actacactgt catcagaata tatgatgtat attatttcct ccaaactcct caccatagcc    97440
accaattcgc atcacttaag aaagtagtag caaccgcggc ggcggcgacc ggccggtcgt    97500
cgtctcctcg tcctcaaatg ttgtacatgt gcagaaaaat gtgtaaatac gtgttattta    97560
tcccatgcgt cttgtacata gatatatgtt tttatatacg ctatttatac tttatatatc    97620
cttttgcata accatagaca gtcaaggatt ttaatgattt gctcatccgc cttttgagcca    97680 tcgcttagga gttagttcct ctatgttctc ggcccacctt ttcgactaca gtagcaaacc    97740
cttgtactac caccccgata aaaccacat catcatcgtc accacgacct ggaaacgaca    97800
cacgttcccc cccaatcttg ggcatgtgta tatataaaaa gaatgggagg gagaggacgt    97860
ggggctcgag aagaaataaa cgccaagctc gattcgaacc aaaaaaccac atgtgtattg    97920
tgctttgttt tttttttttac ggtgggggaa aaggaggggg ccgtcattaa cggaaaccgt    97980
gtatggggtc cggacacgaa cagtacacag cttatgggga aaaagctcca cagagagaaa    98040
aaacaccaag ctcaggcacg cgtacatcat tattatcatc atcggatatc tcaccacggg    98100
tcatagtagt accaaggagt gtgtaacacc atttttttctt ttctttgtaa cgggataagg    98160
gacagcaatc atcacgcaca acacccttca ctctcttttt agtcatccat atcatcgctg    98220
taacacagca tgtcctcgta atcgggcgtc tggcagcgca ttaccaccga gtcgtcttct    98280
tgcggtaccg gtggtggtgg tggtggcggc ggcggctgct gctgctgggt tgccgtcgta    98340
ctgtgattac cgttggcgga ctgcaccggg atgatgggct gcttgtgggg aacctggggt    98400
ggactgccgc cgtgagaagg cgacggcgtc atcaagttaa gctcaccacg gtgactccgg    98460
acaccggcga ggggcgccgg gggactggga gggaccgcgg tcgtcttgta gacgacggtg    98520
tccccgtgtc gatccgtggc tcgtaccaga tcttgactgc tagcgtcgtc actgtcttcg    98580
tcctcttcca gctcgccctc agagtagtgc tgctgtggtt gcgacggtgg ctgggcggga    98640
ggagcggcgg cgatcattgg agagggatgt cgatgactcc cttctctgtc cttttatcg     98700 taggctgtca gcgttgctgg gtccgtcctg cttccatat ttgcgtattg ctcatcggtg    98760
ggatgaattt ggtctcctcc ccgctgttgt ccgccggcag tggcgtggtt gctggcggtt    98820
gtcgttgtcg taccggcaaa gacggtgaga tccaatagcg actgctcgtc gaagggacag    98880
tacgctatca tgaaacgata gggtgccaac gcgcgttgga tgcgcagttc gcacatctcg    98940
ttctgacact cgtggcactg cagggcgcct aggatcaggt ccgagacagc gccgcagcgg    99000
```

```
taggtaccca tggcgttgtt agtatcgaac tggtcaaaaa attggggcgt accggtgact   99060
tgcaacgcgc gacggcgtag cgagacggcc acgcgcgaga aagagcacac ataggccatg   99120
gcgcggtgca tggttgcga gaaggtctcg ggcggacgct tctgcagatc gcagacgtcg   99180
tcgcgtagcc aggcgctcat ttgaccgggc ttcttgacta gccgtttgag cgtgctgcaa   99240
tggtcgcccc agccgtcctg gtggtccagg atgcagccca ggtccaggtt gttgagtttg   99300
ttgaagagta gctgacgcat gccgcccacc gtctccagat agggatcgtg cgggttgacg   99360
ggtagcccgt gcaggtggtg gtacttcatg tagctgagcg tttcgtcgat gatggccagc   99420
aacgtgtgca agttgggagc gttgtacacg gcgaagatct tttccaccac cagcttgcgc   99480
agcaacggtt cctccagcca atcgaactgt tgacgaatgt gcaacaggta gtcggtgtgc   99540
atgagctcgt cgtgtgacag caggatgcga ccgcgcggct gatgatcttg cgggaaggcg   99600
gtggggacct tgagatcggc ggggtagggt gccagacgta gactctcggc cgtgtagcgc   99660
tgaaggtcgt aaacgggcga ggtagaactc ggtgaggtac ccgacgaggc ggcgccgcgc   99720
tgcagacgcg ctctttttt cttttcgatc aaacggctga gttgctgtag ttcgtcctcg   99780
tccatggcgt ccagttcgtc gtcaataagc gccagcatct gttgttgttg cggtccggcg   99840
gacgatccgt gatgattatt ggctgaggag gggtgagaag aaccgaaagt cgtaggacaa   99900
ctgggaactc ggcgacgaag atgcgtcgaa tcgccgccgt gatggtgcgg ttcgccgtca   99960
tcgttgtcgt aagacttacc gtagtggggg ttaaggggca ccgaggcgga cgcggccacg   100020
cgtcgcttga aagaggagga cgccctatgt ccgccacgga agcccgcggt gcccatgatg   100080
atgtgtccgc cggtgccccc gagtgcgtgg cgggaggagg gtggaagggg aggaggatag   100140
tggtccggat cgccttcggt atcatcgtct ttgctgtagc ggggtcgtcg tgcggggacg   100200
cagggtcggt gatgatgcga ggcggcgccg acggtatctt ccgcgagatg gtgttcgctg   100260
gcggctgctc cgttccgtgt cgacggcgag gttggacttc gctcgcgtcg gaacttccgt   100320
ggcacgggtt cgtaatccag acagaagcgc cgtgcgcgac gggcgcggcg ttcgcgctcg   100380 ctcaggggaag ataacgacgg agcgtcgtga cggccgcgtg agtgcagctc catggccgcc   100440
gtcgctagga aggtcacgtt cggcacgct gatgtatata tagatgagac cgctgccggg   100500
gggcgggtca ccgcgccgt ggaaagtgag gctcagacgg cggtcgccgg cggcacgggc   100560
gcgtcgggcg gtctgatttt gatggaaatg tggacgtttt tggcgttgga gtgacacttt   100620
ttggtgaaac agcggctcca gaggctggcc cagagcgcgt agctgtgctc ggtgcgcagg   100680
tcgatgaaca cctgcacggt ctcttgcggg ttgcggtgcg tgtagttgag acagcgaaaa   100740
tcccgcgtgc gcgcgccgtc gcgccgcttg acggccacgc agcaggcgcc gtggggctga   100800
aagaggagga cgtgggcgc ggtaaactgc tcgctgacgt gcggttcgta gtgttgcgtg   100860
aggtgctcga gcagcggcgg ccacacgcgg gtgacgacga gccgctgcaa gtccgtgtcg   100920
gaaatcgcag cggcagtggc gccgtcgcca ccgtacaggt gataggcgag cacctcggtg   100980
agaccgcggc gtcgataacg cgtcacgtta agcgagcgcg tctcgataaa gttggcttcg   101040
gtcgaggggc agattttgtc gcgtacgctg agaatgacgc gtggcggcgg cgacagggggc   101100 aacgcgggca ggtcgtgcgg cggtgtgg tgaagcaggt tacgcagatc cagttgggcg   101160
cgcacaaagc ctagcgggtg ttcgcggtag gcgtcgggca cgatgaacag cggcaacaga   101220
cggcgatgca tgaaatagcc gtcgtcttgg tccattttat acatgtaggg cagacgtaca   101280
gagcgtccat ggtggtagat gcctgtgtct aggctgctct cggatgcga gatggggtcc   101340 agcagcgtgt gcagttcggc gtcgagacag acggcgtgat tgagcacctg cgccacggcg   101400
```

```
cgtaaaacgc tgggtgtac  ggcgacggtg caggcgggga acggcgtgat gatgcgcagc  101460
cccagtttgc ccttgcagcg gcagtaaggg ggtgacgtgt caacggagga cgttgttttt  101520
tggaaaacgc cgttatccgg gacgttattt ttatcctctt tcccgtcttc gtcttcctct  101580
gtgtcgcgct cgtcccggta atcgagatag tcgtcgtcat cgaaaggcgc gccggccgcg  101640
tccacgggca cgctgttggg tgggcacgcg cttttgaaga aatagaccgg gtgccggtcg  101700
gggtgcgtgt agccaaagag gctcgcccat acggtcatcc agacgcgtcg tagtccgcga  101760
catagctcaa agacggtgtg tcgcgccaga ccggagacgc cgtcgcgcag ccgtaaatca  101820
aagtcggcca caaaattgaa gacgggcaga cgttcgttga agacttcgtg tcgcgtgtag  101880
tagaactgtg tctcggggct ggtgctggcc acgtcgtcgt cgtgtagcca cacggtctcg  101940
gtcagggcct cgtccgagaa acggctgtcg ggtacgtgac ggagcaggtc acgcggaaag  102000
aggctgcgat gccaggtttc ggaggccacg cgcagaaga  cgtgctggtc attgggcagg  102060
tgtacgcggt agacgggcag cggtcgctcc agcagcggtg ccagcgcggg ctcgggtagc  102120
aggtagcgac gttgcgagta acgcgttagc gtgccggtgg tgtaagtctg ggctgtgcgt  102180
agcgaggcgc atagacgtaa caagccggac agggagcgtt ccagcgggga gaagacagac  102240
tcggaaagcg tgttgatgcg ttcgagctgg cgcgccagct gcgtggaggt gccgaagaag  102300
cccgccaggt gcgtgccgtc gatgcggccg ccgtagccgg ccagcccaa  gccgtgcggg  102360 ctggtcgccg agtggggga  ttcgtcgaga cgcagtaggc gcgtctccac gtagtcgtgt  102420
agaaagttgt cgagcgagaa gtattttgc  atgacgtcca gcagctcggt ggaaagccgg  102480
cggcccagaa aacccggttc gcgcgtgcac tgcgcttcgg gcgccgcgtc agcgtcgtaa  102540
gccaccacgc gccggtactc gagcaaccgc gcgcgtgcca gcgccgtgcg gtaggccagg  102600
tagacgtagt gcacgcagac cgtgtcgggc agacgcgcac gttcgcggaa cgcgttgatc  102660
tgcgtgtcca cctgctctag ctcggtgtag tcgcggcggt tgcgcgcgac ggcgtacgcc  102720
acgaaagcgg acacgcgctg acggaagggc gagcccagta gcagacgcgc gaactcgccc  102780
atggaggcgt gcgtggggat gatggtgccc aggtcgcgcg tgcagaagct gcgcacgtac  102840
tcctccacgg tggagatggt gctgtactgg ccctcgaata ggtagtaggc catggtcagc  102900
agcacctggc cctcggtgtg cccgaagacg ctgatgaacc acgagggcga ggtggggcag  102960
aggaagacct ggttgagatg acgtagcacg gccgcgtggt gaaagtacac caggtgcttg  103020
aattcgcgca cctcgccgcc gtgttcgggc gagagcacgg gcgtgcggaa aagatgccgg  103080
tagagcggtt gcgtctcggc ctcgtccaga ctggcgatga gcgccgagag ggggatgggc  103140
tggcgcgcgg ccaggtagcg cgagagctgc agcgtttcgt tgttcacggc gaagacgggc  103200
gccacccgcc gcgagtccga gcacttttgc gtctgtaggc agaagtaaac acgtcgcgag  103260
acctggtgtt tgaccagcag ggggaagacg cagtggtccg tcggtgtctg cgagagtacg  103320
ttggcgacta tatgagcaga atcatactct gttgcgaaca gaacgagcgt catcgtcgcg  103380
ccggcacgat gcagctggcc cagcgcctgt gcgagctgct gatgtgccgt cgcaaagccg  103440
cgcctgtggc cgattacgtg ctgctgcagc ctagcgagga cgtggagctg cgcgagctgc  103500
aggcgtttct ggacgagaac tttaagcagc tggagatcac cccggccgac ctgcgaacct  103560
tttctcgcga cacggacgtg gtgaaccacc tgctgaagct gctgccgctc tataggcaat  103620
gccagagcaa gtgcgcgttc ctcaagggct atctctcgga gggctgtttg cctcacacgc  103680
ggccggcggc cgaggtggag tgcaagaaat cgcagcgtat cctagaggcc ctggacattc  103740
```

```
tcatcctcaa actggtggtg ggcgagtttg ccatgtccga ggccgacagc ctggagatgt   103800
tgctggacaa gttctccacg gatcaggcct cgctggtgga ggtgcagcgc gttatgggcc   103860
tggtggacat ggactgcgag aaaagcgcgt acatgctcga ggccggcgcg gctgcgacgg   103920
ttgcgccact gacgccaccg gcggtcgttc agggggaaag cggcgtccgc gaggacgggg   103980
aaacggttgc cgccgtgtcg gccttttgcct gtccctcggt ttcggactcg ctgatccccg   104040
aggaaacggg ggtcacgcgt cctatgatga gtttggctca cattaacacc gtctcctgtc   104100
ctaccgttat gaggttcgac cagcggctgc tggaagaggg cgacgaggag gatgaagtga   104160
ccgtgatgtc gccgtcaccc gagcccgtgc aacagcagcc gccggtcgag cccgtgcagc   104220
agcagcccca gggacgcggg tctcaccgtc ggcgctacaa ggagtcggcg ccgcaagaga   104280
cgctgcctac gaatcacgaa cgcgagattt tggatctcat gcgacacagc cccgacgtgc   104340
ctcgggaggc ggtgatgtca ccgaccatgg tcaccatacc tcctccccag atacccttttg   104400 tgggttccgc gcgtgaactc aggggcgtga agaaaaagaa acccacggcg gcggccttgc   104460
tgtcctccgc gtgaacagcc tggcacgttt tggaaaacgt acgtgatcac ggacacgacg   104520
agtacggggt ttctcataga cgtactttat taggtcaggg atgacgggga ggtttcgggc   104580
cgacgtcaaa ataacgtca ttcgtgttga cagggctttc tgcgtcggag ctctttttcat   104640 cttcttctgt ctcgtcgacg tcatcgtcta ccggcgaggg tgtccgttgc agcaacgcgt   104700
gctcgggcgt gtgggtgaaa ccgatgtcgg gggtgggcgg cacgatcatc tgtcctaggg   104760
ggtgactgcc caccggcaga taggtaaagc ggtgggtggt aaaaaccgct ttggctacgg   104820
tggtgtgtgg ggagatgcag acggtggtgt gcgaagtgtt gaccaccgtc acgccggccg   104880
cggtacccgg gagccagatg gtgggtcgga tgatgagatc cgattgacta aactggcgca   104940
cgcccactat gagggcgcag ataccgggcg cgtgcacgta ggccgcgtca aaatagacgg   105000
tttgcgtgtg acccggaccg atcaccagcg tctgacgggt acgtaacgaa agaaacggt   105060 gttcgttggg cggcggcaag ttcatgagct gccagggttc tggtacaaaa caggggaaaa   105120
cgccgatatc gccttcgatg gtgcccggaa agatggactg aaaagtgtcg ttgaggttga   105180
cgacatccaa ctgcgggact tgcagcctgg attccagcag ctcgggcatg caaacgaatt   105240
gcgcgtccga gcatttgtaa aaggtaatgc cgaaaaaacc ttcggggata tagaggctga   105300
cgcccagcga ggtgggcact ttgcgctcgc gtgatagcca aatgatgtgt ttattgtaaa   105360
aggccagctg cgtgtggcat tgtttgacga tgaaactgga aggcatccac ttgtaaggaa   105420 cttttgagcgg tgacggtaat ggcgacgacg cttcatcctc tcccggatgc tgctcttttgt   105480 cgtatttctc ctcggtcgat tggggcagcg taaatgtggt ttgaaaatcg ctatcgctag   105540
cgaaacgcac gcagtaacgc atgttgacgg atttctcggc taggatgatg gagcctgatg   105600
acgatgcgga ctcttccttc attattaacg taggggtctc ccagaatcgc tgaaaacggg   105660
agcgcggcag ccgcgacagt accagttgag agtcgattcg gtcggtcaac atcgtaagca   105720
tcgtggcggt ggtgtgatgg agtggaacac actagtatta ggtcttttag ttttatcggt   105780
agtggcagag agttctggta caattcatc cacgtcaacc tctgcaacta catcaaagtc   105840
ttctgctagc gtatcaacta ccaaactaac aacagttgca acaacttctg caacaactac   105900
gacgactacg accttatcga caactagcac taaactcagt tctaccaccc acgatcctaa   105960
tgtgatgaga cgacatgcga acgatgattt ttacaaggcg cattgcacat cgcatatgta   106020
tgagctctca ctgtccagct ttgcggcctg gtggactatg cttaatgctc taattctcat   106080
gggagctttt tgtattgtac tacgacattg ctgcttccag aactttactg caaccaccac   106140
```

```
caaaggctat tgagggtgga cagatttaca gcccggcggt gttccggcgg ggtaaggttt   106200
acatacgtgg gtgaccggag gctaaagtta cgaatctcat ctagaaacag cagcgagtct   106260
agatagtccc acagggatc tataaatgtt ctctgaaacc ccattgatgg tgacgtaggt    106320
gtagttttgt tactatcgga agctgttttg ttttccacga acatggtttc gttgtaatat   106380
aaggagctca tgtcgagagt accgtaaata gtgtacggcg tttcgttacg gattagtacg   106440
tgcgtgtttt tcataaattc tgacacggcg gttcggttgc ggcttggttc acaaaaagga   106500
ttttgccggt aacgtagagt ggtatacacc cacgttgcta ggtcccttaa ctgtgtggcc   106560
ataatggact tcataaagct gctatcagga cgataagcaa ttgtagacgt ggaaacccgc   106620
cttgcggcgg tagtaatact ataagtcacg ttagtagtga cgttgagagc ggcagacgtt   106680
gtataggaaa agtatggcgt agtagtactc tgagttttct tagctttttt ttcgaattgt   106740
tccttaacgg gcgcttgttt acgttttagt tttcgcatag tgtttttttaa cttggtgccg   106800 ttaatatact tggggacgcg aaatagattc cggctcatgg cgttaaccag gtagaaactg   106860
tgtgtacagt tgcgttgtgc gtaacgtaaa agcagggcgg ttaaacctag aaaataaatc   106920
gtttgactat ctacgttaac cttagtcgga cccacgtaca atttggtgtt ccaacgcggt   106980
acattgaaaa acatggggtt gaacgtggtg aaattaccgc aaccttgttc gccagtatca   107040
ttacgtttgg aaacgtttag catttcggaa agacaagtca tggaaggcac agtaccacaa   107100
ggtgggggtc tgaatgttat cgttttagcc gtatgattgt actgtgagta aacgtatttt   107160
gcgggttttc taagctgggt actataaaaa tcaaaccaca gataggttat actataattc   107220
tgaatggggc ccgctaaaat gtagtattgt ggaaactctg tcatgttcat agtgagattt   107280
ttaaccggtt gtttacttac attgtatttt gtagaaatag tcgtttctag ttgtctcaaa   107340
atttctaact taagctgatc taatttatat ttgcctatct tagacagtac caagcccctc   107400
caaggacgat tataaagcgc ttttgacata actttacagt ttatgaaaga acaagcaag    107460 aaagatatag atattagaaa caccatctta gggacgtctc tcaccatcat ctcttttctc   107520
cccatgacag aggaggagac cccgcaccgt ccgtctgcct tgtggtttgg cttgcctgcg   107580
tgtactcact gctgattctg gtcgttttgc tgctcatcta ccgttgttgc atcggcttcc   107640
aagacgacct agtctcccgc accttggctg tgtaccaagc ttgtatccag ggcccgatat   107700
gtaaccagac ccataacagt acctcgtaaa taaagacgca cagacctcac gcatatagta   107760
ccatcacacc gtgtggcgtg tactttatta caacgagcaa gagtgcccct aagtattggg   107820
gcccgtaccg ttttagaaga ttttgtgtga atgtctttaa cttttctgtc ccttttctca    107880
taaactgtca ggttctacag tcagcatgtc ttgagcatgc ggtagagcag atagatgccg   107940
atgatggccg atagcgcgta gacggacatc atgaggagac gactgtcggt ggcgtccacg   108000
acgacgtcag ttacttctag gaccgtaccg tttttcaaaa gcatgaggta gtgagttcgc   108060
ggagatgaga ccaccacttc gttgtaggga tccagggcga aaaggacgtc gtccgagtcg   108120
tgcatgtaca tgatgttgat gacgccttgc gtgtcgtcgt attctagcag ggcgctttgg   108180
caaaaggcgc agttttctag tgaaatgttg agcgccgctg tgatgctgtg tgtggtgtgc   108240
atgttgcgcg ttagttcgca tttagtttga ctgtccgttt gggtgatgat gaggctctgg   108300
cctacgacgg tggtggagac agggtaggag ataccttga  tcaggtactg gtttgttacg   108360
acataactga cgtgttcgga gacggttagc gcggagaagg attcgccgag cggcagacaa   108420
aacaggtcgg ggaaggtttc cagcgtgctt ggttgcatgg tagataggat ggagagggcg   108480
```

```
gcgggaacgg tagcaggaac ggtggcatcg gggaagagac gcgtgaggcg ttcgagcgag   108540
tgatcgcgtc gcccgctact ggaacagggt gtgtacaggt cgctgaggta ttcgtggtgc   108600
ggatgagcta gcaactgcgt aaagtgtgat agctcggcca atgaacagag gcccgtttct   108660
acgatgaaga tttcgcgtct ctccgtcgta tgtaccaaca tggagtggac gaggctgccc   108720
atgaggtaga gttcttggcg cgcgaaggct gaaagaaaag aggccaggtg cgttttgtgt   108780
aattgtaggg caaagtcggc gatctgtcgt agtgcccact ggggaatgag atgttgctga   108840
ttctgtttag aaagtatgta gaccaggcgt acgaggctgg tgatgtcggt gatctggtcc   108900
ggcgtccaga gggctcgttt ggccaggtcc acggctgtgg gatatagcag caatgtggtg   108960
cgtggtggtg tttgtgagag gcaggtgatc ataaattctt gtatttgtaa gagtgcggcc   109020
tggcggtcta gggctcgtgg gatggagatt tcggtgccgg cctcttcttg tcgggctgcc   109080 gcaacagtg ctaatgcgta ggcgaaggcc atttctaccg tgcggcggtc aacatttga    109140 catcgaccgc ttttgagtac gtctacagcg taacggtgaa agctgttacg taacagtgcg   109200
ctgaggtcca ggtagttgaa gtcgagtgcg gcgtcgagaa agtccgagtc tttgagatag   109260
gagtgacggt ttagttgagc tttcttaact agtaccagga gctcgtgttt ttcagtttgt   109320
cgtagtataa agttgtcgcg ttgataggc gctttgaaga gtacgcgtgg aagatgaccg   109380
aagataagca gcatgggtgt gtcgtcgtct atagataccg taactacgaa gaagtcctcg   109440
gtcagtgtga ttttaacgta acgtagttcg tccatgaggt aaaagccctg gtgcagacag   109500
ggcgtaacgg tgctgaaaag cagatcgtgt ccatcaaaga ggatacaggt ctggttaaag   109560
tgtggccgat gtagtcccga ggtggtgtgc gatcccttcc agtcgtgtgg agtggtttgg   109620
ggtggcatcc aaacgtgagg tattgacaga tcaatgggcg gtggcacggt ggtgggctgc   109680
tgacccaggc tgtcttgtgc cttcagctgc tgcgaaaaag atcggtagct ggccaggtct   109740
ttggatacca atgcgtaggt gttaagtctc tgttggtatc tttctagggt ttcggtcaga   109800
tctacctggt tcagaaactg ctccgccaga ggacccgcaa aaagacatcg aggcatatgg   109860
aatacatagt attgattata gctttggaaa agttgaaac tgatggcgtt ttccctgacg    109920
accgtgctgt tacggaggct gctgttgtag gtgcactggg tggtgttttc acgcaggaag   109980
cggatgggtc tcccgtaggt gttgagtagt aggtgaaatg cgtgagggtc cagcgcttcg   110040
gatgcggcgt ccgcgccata tcgttgcgaa ggtaggtgac tgaggaggta gacggtgaag   110100
acagtgaggt aggggggggag gccgggccgc atagcgcggc tgcgccgctg ggttcagcgg   110160
cgtgatccag gtggtggttg gcgttacacc cgagagaagg agagaaagga tcccaggaag   110220
gggcacccgg gtgtggcgct acgggttaca aaagtcgcgt ctctgtctat ttaatacgat   110280
gtcattggcc gctgcgaagg aagaagaggg gacacgcggg taagccatgc cgtccgggcg   110340
tggggacgac gctgattcga cggggaacgc tctgcggaga ttgcctcacg tgcgtaagcg   110400
gatcggtaag cgtaagcacc tggacatcta ccgtcgcctg ttgcgggtct ttccctcgtt   110460
tgtggccctc aaccgcctgt tgggaggcct tttcccaccc gagctgcaaa agtaccgtcg   110520
ccgtcttttc atcgaagtac gattaagtcg gcggattccc gactgcgtgt tggtgttttt   110580
accgccggac tctgggtcgc gcggcatcgt gtattgctac gtgattgagt tcaaaactac   110640
gtactcagac gccgacgatc agtccgtgcg gtggcacgcc acccacagcc tgcagtacgc   110700
cgagggcctg cgccagctca agggcgcctt ggtggacttt gattttctgc gtctgccgcg   110760
cggtggcggt caagtctgga gcgtagtgcc cagtctggtt ttttttcagc aaaaggccga   110820
tcgcccatct ttttaccggg ctttttcgttc gggccgtttc gacttgtgta ccgattctgt   110880
```

-continued

```
cctggactat ctgggacggc gtcaggatga gtctgttgca cacctttgg cggctacccg    110940 tcgccgtctt cttcgaaccg cacgaggaaa acgtgctgcg ctgccccgag cgcgtgcttc    111000
ggcggttgct ggaggacgcg gcggtgacaa tgcgcggcgg gggctggcgc gaggacgtgc    111060
tcatggaccg ggtgcgcaaa cggtatctgc gtcaggagct cagggatctg ggtcacaggg    111120
tgcagactta ctgcgaggat ctcgaagggc gcgtgtccga ggcggaggcg ctgttgaacc    111180
agcagtgcga gctcgacgaa ggaccgtcgc cgcggacgct gctacaacca ccgtgtcgtc    111240
cgcgttcttc gtccccaggg accggcgtgg caggagcttc tgccgtccca cacggtctttt   111300 atagtcggca cgatgccatc acgggacccg ccgccgcccc gtctgacgtg gtcgccccgt    111360
ctgacgcggt cgccgcgtca gcggccgcg gtgcttcttc tacctggctg gcgcagtgcg     111420
ccgagcggcc gttgcccggg aacgtaccta gctactttgg aatcacgcag aacgatccct    111480
ttatccgctt tcacaccgat tttcgcggcg aggtggtcaa caccatgttc gagaatgcct    111540
ctacttggac tttctccttt ggtatctggt actatcggct caagcggggg ttgtacacgc    111600
aaccacggtg gaaacgagtg taccatctgg cgcagatgga caacttttcc atttcgcagg    111660
agctgctgct cggcgtggtc aacgctttgg aaaacgtgac ggtgtatccg acgtacgact    111720
gtgtactctc cgatttggaa gccgccgcct gtctgctggc cgcctacgga catgcgcttt    111780
gggagggccg cgatccgccg gactccgtgg cgacggtgtt gggtgagctc cctcagctgt    111840
tgccgcgtct ggccgacgac gtgagtcgtg agattgccgc ttgggaaggc cccgtcgccg    111900
cgggtaacaa ctattacgcg tatcgcgact cgcccgatct acgctactac atgcccctaa    111960
gcggtggtcg tcactatcac ccgggcactt ttgatcgtca cgtgctggtg cggcttttcc    112020
acaaacgcgg cgttattcag catttgccgg gctacgggac gataacggag gagctggtgc    112080
aagagcgtct gtcgggccag gtgcgcgacg acgtgctttc tctctggagt cgacgtctgc    112140
tggtcggcaa gctgggtcgc gacgtgcccg tctttgtgca cgaacagcaa tatctgcgtt    112200
cgggcctgac ctgcctggct ggcctgctgt tgttgtggaa ggtgaccaac gcggatagcg    112260
tcttcgctcc gcgcacgggc aaatttacgt tggccgacct gctgggttcg gatgccgtag    112320
ccggcggcgg gttgcccggg gggcgcgcgg cggcgaaga ggagggctac gggggacggc     112380
acgggcgggt acgtaacttt gagtttctgg tacggtacta catcgggccg tggtacgcgc    112440 gcgacccgc ggtcacgctg tcgcagctct ttcccggcct ggctctgttg gccgtgaccg     112500
agagcgtgcg cagcggctgg gatccctcac gtcgcgagga cagcgccgga ggtggcgacg    112560
gcggcggcgc cgtgctcatg cagctcagca agagcaaccc cgtggccgac tacatgttcg    112620
cgcagagctc caaacagtac ggcgatttac gtcgcttaga ggtacacgat gccctgctct    112680
ttcactacga acacgggcta gggcggctgt tgtcagtgac cctgccgcgt caccgtgtgt    112740
ccactctggg ctcgtccctc tttaacgtca acgatattta cgaactgttg tacttttttag   112800 tgttggggtt tcttccgagc gtggcggtgt tgtaatttcc accacgtgtc gctcgctgca    112860
taaagggcga acgtcctcgg agagggtata ttcgttcggc gagagcgggc ggcggtggtg    112920
ggtatgtccc cttctgtgga ggagactacc tcagtcaccg agtccatcat gttcgctatt    112980
gtgagtttca aacacatggg cccgttcgaa ggctactcta tgtcggccga tcgcgccgcc    113040
tcggatctac tcatcggcat gttcggctcc gttagcctgg tcaacctgct gactatcatc    113100
ggttgcctct gggtgttgcg tgttacgcgg ccgcccgtgt ccgtgatgat ttttacttgg    113160
aatctggtac ttagtcagtt ttttccatc ctggccacca tgttgtccaa gggtatcatg     113220
```

```
ctgcgtggcg ctctaaatct cagcctctgt cgcttagtgc tctttgtcga cgacgtgggc  113280
ctatattcga cggcgttgtt tttcctcttt ctgatactgg atcgtctgtc ggccatatct  113340
tacggccgtg atctctggca tcatgagacg cgcgaaaacg ccggcgtggc gctctacgcg  113400
gtcgcctttg cctgggttct ttccatcgta gccgctgtgc ccaccgccgc tacgggttca  113460
ctggactacc gttggctagg ctgtcagatc cctatacagt atgccgcggt ggacctcacc  113520
atcaagatgt ggttttttgct gggggcgccc atgatcgccg tactggctaa cgtggtagag  113580
ttggcctaca gcgatcggcg cgaccacgtc tggtcctacg tgggtcgtgt ctgcaccttc  113640
tacgtgacgt gtctcatgct gtttgtgccc tactactgct tcagagtcct acgcggtgta  113700
ctgcagcccg ctagcgcggc cggcaccggt ttcggcatta tggattacgt ggaattggct  113760
acgcgtaccc ttctcaccat gcgtcttggc attctgccgc tctttatcat tgcgttcttc  113820
tcccgcgagc ccaccaagga tctggatgac tcctttgatt atctggtcga gagatgtcag  113880
caaagctgcc acggtcattt cgtacgtcgg ttggtgcagg cgttgaagcg ggctatgtat  113940
agcgtggagc tggccgtgtg ttactttttct acgtccgtcc gagacgtcgc cgaggcggtg  114000
aaaaagtcct ccagccgttg ttacgccgac gcgacgtcgg cggccgttgt ggtaacgaca  114060
accacgtcgg agaaagccac gttggtggag cacgcggaag gcatggcttc cgaaatgtgt  114120
cctgggacta cgatcgatgt ttcggccgaa agttcctccg tcctctgcac cgacggcgaa  114180
aacaccgtcg cgtcggacgc gacggtgacg gcattatgag cggcggcgct gtacggcagc  114240
ggggagaaaa gtggcagata aatcacgtca ggttcacacg tcgttagcca gcgtcggcat  114300
atgaagggcg cggggcggcca gtacggcctc tgggctgaga caggacgagg cagggtgaga  114360
aagaggagga tggggggggac cggggtggtg gtgctgctgc tgttgtgggt gcggacggtg  114420
cgggtgccgg gacagcgtgc cggcgaacgt tctgtaatct tccataataa agtaaaaat  114480 gcccgtctcg tgtcgactcc gctggatctc gaaggcgtcg ggggtaatgc gcatcttgcc  114540
ggtgccgatg agataaaagt accacatttt ttgacagatg atgcgaatca agggttcgta  114600
cgcttcggca ccccagtggc gcgtgaagaa ggccgccaga cgaaacaagc ggtgtccgta  114660
gagcgtgcct agggagaaga ggatgttgcc gttgcgcgcc aggtcttcgg ggaaaacgac  114720
cggcaggccg gtgtggcgct gcacaaagcg cgtcagcagt ccgccgctca agcgcgggtg  114780
acacaggcgc tggctgagac gggcggcgcg cgtttcatcg aacacggccg cctcaaagtc  114840
cagccccggg aaggcctggc gcagttcgcg gtacagatga ggccagtagg gttgcggcgt  114900
cttgcgacta agcacggcgt ggtccgagac acccaggttg ttcatggttt cgcgcagtag  114960
cagcgtttcg agaccgcggt gaaagaggag acgcagatg aggcgtacga tcttgagttc  115020
ttccaaacgc agcgagctca gcggctgtcc gcgcgacatc ttctcgctaa tctgtaatat  115080
tagatgattg gcgcaagtaa aggagaattt gcccgtgcgg acccgcggga cggcggggtt  115140
ctcttcgtcg cgggccatca tcgttcgctc ggtgagcggg tagcgacggt gacgacaatg  115200
acgatggacg agcagcagtc gcaggctgtg gcgccggtct acgtgggcgg ctttctcgcc  115260
cgctacgacc agtctccgga cgaggccgaa ttgctgttgc cgcgggacgt agtggagcac  115320
tggttgcacg cgcagggcca gggacagcct tcgttgtcgg tcgcgctccc gctcaacatc  115380
aaccacgacg acacggccgt tgtaggacac gttgcggcga tgcagagcgt ccgcgacggt  115440
cttttttgcc tgggctgcgt cacttcgccc aggtttctgg agattgtacg ccgcgcttcg  115500
gaaaagtccg agctggtttc gcgcgggccc gtcagtccgc tgcagccaga caaggtggtg  115560
gagtttctca gcggcagcta cgccggcctc tcgctctcca gccggcgctg cgacgacgtg  115620
```

```
gaggccgcga cgtcgctttc gggctcggaa accacgccgt tcaaacacgt ggctttgtgc   115680
agcgtgggtc ggcgtcgcgg tacgttggcc gtgtacgggc gcgatcccga gtgggtcaca   115740
cagcggtttc cagacctcac ggcggccgac cgtgacgggc tacgtgcaca gtggcagcgc   115800
tgcggcagca ctgctgtcga cgcgtcgggc gatccctttc gctcagacag ctacggcctg   115860
ttgggcaaca gcgtggacgc gctctacatc cgtgagcgac tgcccaagct gcgctacgac   115920
aagcaactag tcggcgtgac ggagcgcgag tcatacgtca aggcgagcgt ttcgcctgag   115980
gcggcgtgcg atattaaagc ggcgtccgcc gagcgttcgg gcgacagccg cagtcaggcc   116040
gccacgccgg cggctgcggc gcgcgttccc tcttcgtccc cgtcgcctcc agtcgaaccg   116100
ccatctcctg tacagccgcc tgcgcttcca gcgtcgccgt ccgttcttcc cgcggaatca   116160
ccgccgtcgc tttctccctc ggagccggca gaggcggcgt ccatgtcgca ccctctgagt   116220
gctgcggttc ccgccgctac ggctcctcca ggtgctaccg tggcaggtgc gtcgccggct   116280
gtgtcgtctc tagcgtggcc tcacgacgga gtttatttac ccaaagacgc ttttttctcg   116340
ctacttgggg ccagtcgctc ggcagtgccc gtcatgtatc ccggcgccgt agcggcccct   116400
ccttctgctt cgccagcacc gctgcctttg ccgtcttatc ccgcgtccta cggcgccccc   116460
gtcgtgggtt acgaccagtt ggcggcacgt cactttgcgg actacgtgga tccccattat   116520
cccgggtggg gtcggcgtta cgagcccgcg ccgtctttgc atccgtctta tcccgtgccg   116580
ccgccaccat caccggccta ttaccgtcgg cgcgactctc cgggcggtat ggatgaacca   116640
ccgtccggat gggagcgtta cgacggtggt caccgtggtc agtcgcagaa gcagcaccgt   116700
cacgggggca gcggcggaca caacaaacgc cgtaaggaaa ccgcggcggc gtcgtcgtcg   116760
tcctcggacg aagacttgag tttcccaggc gaggccgagc acggccgggc acgaaagcgt   116820
ctaaaaagtc acgtcaatag cgacggtgga agtggcgggc acgcgggttc caatcagcag   116880
cagcaacaac gttacgatga actgcgggat gccattcacg agctgaaacg cgatctgttt   116940
gctgcgcggc agagttctac gttactttcg gcggctcttc cctctgcggc ctcttcctcc   117000
ccaactacta ctaccgtgtg tactcccacc ggcgagctga cgagtggcgg aggagaaaca   117060
cccacggcac ttctatccgg aggtgccaag gtagctgagc gcgctcaggc cggcgtggtg   117120
aacgccagtt gccgcctcgc taccgcgtcg ggttctgagg cggcaacggc cgggccctcg   117180
acggcaggtt cttcttcctg cccggctagt gtcgtgttag ccgccgctgc tgcccaagcc   117240
gccgcagctt cccagagccc gcccaaagac atggtagatc tgaatcggcg gattttgtg    117300 gctgcgctca ataagctcga gtaagagaga cgctatattt agggcttccc tctcttttt    117360 ttctacaccg tgatacccta ataaagcaca ccgcggttat tatcaacgtc tctgtgtttt   117420
tattatttag aaataaatac agggaatggg aaaaacacgc ggggaaaaa caaagaagtc    117480 tctctctaga tgcggggtcg actgcgtggg gtgctggaag tggaagcggt gctgatgggt   117540
gagggtcgtg gcgcgggcac ggaccgcaac gtgctgctga tgtctgccgc ggtacgcacg   117600
tcgccgtcca tgtcgctgcg cagataagag gtaggtcgta gtgcggcgtg ctgcacgctc   117660
accgttaatg gtaccaagtc gtcaaggctc gcaaagacgt gccacgaggg gatgacgagc   117720
gtgagagccc cgttgttacc gcttcgacgt cttgtccgg tcaggatcag tgccgggac     117780 agtccggctt gggtgtccga gtcctcgtcg ccgctggctt cctcgaagcc ggcaaacatg   117840
gcttcggaca gggggtcgg cgtcggtgtg gaggagaggt catcttcgtc gtcctcttcc    117900
tcttcttcct cctcttcctc ggtgggtggt aatccggggg actgcgggag aaactcggag   117960
```

-continued

```
acggcgccgc gcatgacgtt gctccgtgga aagagaccgg cgcgcagctg cacctgggga  118020
cgcttgattt tgtccggttt accgggtgtg agagtccaaa acccacggcg gaaaaagtgg  118080
atgcggccta gcggctgtcg gtgttccaaa tgaacggcct gatcgccggt cagcgtgacg  118140
cggagggtga ttcgcacacg atcgggtagc gggccggctt ctatggagac gcccgggatg  118200
ttttccggga aaaagatggt gtcgtgagtc tgattggtct cgaaagcatt ctggatctgc  118260
acgatgtact cgggatgtat gcgcgtcagc gtaaaacttt tgggaatcaa cagctggaag  118320
ccgttgtccg gcaagcgtcg taggtgcggg tacggattgt gtcgcgccac cacctcggcg  118380
cgatgcgtgt aaaccgaaaa gtgcagaaac acgctggtcg gcgggtgcgg tgagtcgtga  118440
tgcagaaaca gcatgatcca ttggcctcgt tcgtccgtct ccgttttgtg gatgtacgtg  118500
ttagggtccg aacaggccag ctgctccagg gcgtctacca gcgtcagcgg gatggcgccg  118560
gcgcgaaagg cgaactggct gacaaagatc tgccctgcct ccaaactgct gtcggttctg  118620
cggcgccagt tcggcgttac ggtcagtcgc acggcccagt ggtgagccgt gcggcggatg  118680
atggcgcgcg cttccattcg cggccgattt tcttcgccgc cgcgccgctg gctctgaaag  118740
aggtgcagtc cgctaacggg cacgcggtcc agcggcagcg caaaggccag taccgagacc  118800
gtgttgtttt ctgagcctgg cgtcaggcgt cgtgggccaa agttgttgag gtccaccagc  118860
agtcggtcct gttcgcccac cacgcagcgg cccttgatgt ttaagtcggt caggtctacg  118920
gtgtcgtgcg gagatttgtt ctcctgaaaa cagcagagaa ccgagggccg gctcacctct  118980
atgttggtac gcaggtccag gagtcgcaga cgaccggctt ccagcgagcc gccttccacg  119040
ttggtgatga gccgaagcac ctggcagtgc aggcgaccaa agcttccgct ggcggcttcg  119100
gcctcgctga tcgcggccgc ttccgacgag ggtccctcac cgggcgagga cgatgcctga  119160
gacattgcga aggcgggatg gggggagggt caggggatgc gcaaaggtga acgggtcttc  119220
gtgggaggtc gggaagggtt ccggcaactg tcgcaaatat agcagcggtg acaggtgtgg  119280
cggccaaaag ttgcgtgtct gagtggacgt gggttttttat agagtcgtcc taagcgcgtg  119340
cggcgggtgg ctcaacctcg gtgcttttttg ggcgtcgagg cgatgcatgg cccgggcaag  119400
gcgtcttgcc ggtggcggcg acgtttgggt tgcgcagcgg gctgccatac gccttccaat  119460
tcggcgaaga tgcggtagat gtcgttggcg tcccagaaga attcctggta cttcagattc  119520
tgaccctgaa ccgtagccac catgggcacc aggttgcggg ccaggatgcc ggcctgccag  119580
ggcggccagg tgaacacggc cggattgtgg atttcgttgt cggaatcctc gtcggtgtcc  119640
tcttcgggcg cgacggtgga ctcggcctta aggcggccgc gtgtcataac gcccgacgtg  119700
cacgccgtcg ccgaggatgc tgatttgcgt ttgcggcccg cggaagtgga ggcgcccgcc  119760
atggcgccgc cgccggtgac gcggggcgtc ttgcgctcgg tggttacgag ttcttcgtcg  119820
gagtccgatc cgctggtcca gacgtcgtcg tcgccctggg cggcaccctc gtcgtgccgg  119880
tcccaggtgt gtcggtactc aagcttgccc tggatgcgat actggctggt gaaggtgggg  119940
tgctcgctgt actgaggccc gcgctgcagc agcaagtcga tatcgaaaaa gaagagcgca  120000
gccacgggat cgtactgacg cagttccacg gtctcgcgta tggcttgtac ctccaggaag  120060
atctgctgcc cgttcatcaa caggttacct gagatgctca ggcccgggat gctcttggga  120120
cacagcagcc caaaatgctc gtgtgaggta aagccacat ccagcatgat gtgcgagatc  120180
ttgcccggtt tgattatcat attttttggga cacaacaccg taaagccgtt gcgctcgtgg  120240
gggcgcatga agggttgcgg gttgcgggtc atcgtcaggt cctcttccac gtcagagccc  120300
agcgtgacgt gcataaagag cttgccggag ggcacgtcct cgcagaagga ctccaggtac  120360
```

```
accttgacgt actggtcacc tatcacctgc atcttggttg cgcgcgtgtt ctccatggag   120420
caaaccagct cgtgcgcgca caccacgtgc cgcagtgcca cgtccttggt gggaaacacg   120480
aacgctgacg tgtagtagac gtcgggctct ttccactggt tctgctgacg cgtccaggcc   120540
agtcccgaga ccgtgagacg cgcctgccac atctgcttgc ccgacgcgtg aatcacagcg   120600
tcagctacgg gcaggtgtcg gtgtttgcgc tcggccgccg acgggtagtg gtgcacgttg   120660
atgctgggga tgttcagcat cttgagcgga agcgcgtaca catagatcga catgggctcc   120720
tggctggggc agatgcttcg gcccgtgggg ttgtgcacgt tgaccgacac gttctccacc   120780
tcgctgcccg taaagtacgt gtgctgcacc tgcagctgat tgtcgccgcg gtggcatggc   120840
gtcgagtcgg gcgtgtactg cgataccaag atcagcgagg gctggctcac gcgtacgtgg   120900 ataccgtct gcaggagtcg cgtctcgtgc ggcagcaccg gcgtatcgcc gcgactaaac   120960
acggctttca gcacgtgccc cgaaatggga cccagtacgg atatcatttc gggacaacg   121020 cgaccgcgcg actccatgct gcctgcgcgt acgggtgtag gcgactgagc ggcgcgccct   121080
ctgcggccgc cgccttacat aggcaggcga ccaaacgcgg aacccgaaat aaaaacgttc   121140
tacacagaga caaccgcgga ttattgagtg tctttttta ttacaaaaaa agaggcgaa   121200 gccccaccgt caccacaccc catcacacac caccaccgat tttttttgt tttaatcccg   121260 tatggcgcgg acgcctagtg tccgtttccc attatcaggg tcctctgttt agagatcgcc   121320
gcagaccatg gctaaagtga caggactcgt cttctctgtc gtattttccg taagcttaca   121380
gtcttgcggt tccgtctccg gggacgccag tcgcatgggc agcaggtcct ccagcgcgat   121440
ggaagcgccc agcaccgaga gctgctgttg cgacggcgaa tgggatgtgg accgcgagtg   121500
tagcgtggat ttgacttggt gcgtcattgc tgacaggcaa ccccgattca gcgtatgctt   121560
tgacgagata aaatagaggc gccccaggag gcgcgtcccgt gggaacgtgg cgccgttctc   121620
gtcgctcacc agtacggtta attccaacca ggagcgcggg agccagaccg taacgggcat   121680
tttgagtccc tgacgttgt gtggtacaaa acacccaga taaggcccgt aaaagcggcg   121740
gtagatacgt aacgtgtgcg agttcttcag cgtcaattcg taagggacgc gcacctccag   121800
tccctcgtcc gccgcgccgg agcgtggcgg tacaaagtaa ggcagtggcg cgtccgaaaa   121860
gaagggtcgt cgcaccgttt cgcgtcgcag ccgcaggcga aacgccactg gtcggctgg   121920 cgcctcggtg cggtcgcagg tcacgttgaa acgtaatatg ccgtcttggt atagcgtgag   121980
tgacgacagc gtcaggtccg gcggtgattc gttcgggtct agctccaatc gtccaaagac   122040
ggagggtccc aatgtcttgg ccgtggtttc cgagaggcgc gccgagatac ggctggtgag   122100
tccacgcggc cccgagatgc cgccttccac tcgatgccag cacagcgcgt gtcgtacgcg   122160
caccgtcagc gtgggcgtca gatccgcgtc cgttgattcc gcggtatcag cgacggaagc   122220
cgcgttctcc gttacgttgt ttatatccag cgtcggctcg aacgtgagtt ctggcagatg   122280
cagcgccaga cagtcgtgta acgccgtgtg atgcgcggct ttacgtcgta cggtagccg   122340 tttcaacagc ggcgtgatga tacggagcgc gaagagatt agtgataggc gcacgatggc   122400
catgcgcgtc agttgttggt caattaccga gcgcaggata tggcagcctg ggcgtgcggg   122460
aaagagagag aaggccgggc gcacgtcaga atcctcgtta gagaccacgc atagaatgcc   122520
gcgttcacga tcgtcgttgc ggtcatcctc gtcctcttct ttcttctctt gttttccctt   122580 tttttttctcg ggctcgtggg aagccgccgt ttcttcttct tgcaacgtcg cggggcggt   122640 ttgagactcg tcgttcgctt cccccaattg cagcggcgta gagagcagaa tctggaaggg   122700
```

-continued

```
atcccgcaat tcttcgggtc ggaggtcgag gtgcaactgg atcagatggt aggtgccgcg  122760
gtgcacccga ggctgacgga tgtcgtgttt atccgtcagt gtgaggatgg tctgcggcga  122820
gccgctgtac ttgtccagct cgtccggcgt tttcaggagg agactgtcgt cgtcggtact  122880
ggcgacgccc atcatggtcg tggtggtagt ggtggcgagg aaagtgagcg gcggcgccga  122940
cagagctcgg cgttggcggc ggcattttcc gctgtgtcgg ctgctattgc tgccaacgcc  123000
accgccgccg cctcgtctgg ctcgtggccg gcgggcccga ttccgaaggt tggggtcgac  123060
gcgtggcatg cttggtgtct gcgggcgcga gagggccggc tcagccttta aatatgcagg  123120
tcgcggattt gttatcgggt gaaacgtcac acaccgtgaa gacgacctgt tcgcggatga  123180
ggtcatccag ctgtcgcagc atgacgaaaa gcgccgacag ccgcgcgatc tcgtcgtcgg  123240
gcgacacgtg ctgcggccgc gcgggcgtgc gcggctcgcc gacgctgcgc tcgcggtcca  123300
gccgcatcag cagctcctgg cacttgacga gcagcatgga gctgtcctct agcgccaact  123360
tgcgcacgta ggtcatggtc agctccgagg ctaggttggc caccatggac atggagaggc  123420
aggcggtctt catgtcgatc agcaggtgct ggtcgatgac cggatcgggg atggtgaagg  123480
tggcgtcgcg aaaagtaatg gtctgcagct gctgcacggc agcctttacc tcctcgtacg  123540
aacggtcgag cgagaagagg cccatgatga gtagtcgctg gttgatttcc agcgccagtg  123600
gcatgggtac gatccagggc agcaccagct cccactggcc cagcgtcagc aggttctcgc  123660
gcgccagcgg tccgtggaag agcggcggca gcacgcatag cgcgtcgccc ttctcccaag  123720
tcacgggtcc cgtgttgagg acggtgtaga gcagtccgtg cgtgggtacg tgtaggagga  123780
tctggttgcc ttctacgcgc cgcatcaacg tcagcgtcat attgcgcagc aggccgcgca  123840
gtcgtacgta gccgcgggtg tgatctacga actggtgtag gcccagctgg tagtgcttga  123900
tgagatgtag acgttgcgga atgggcacaa cggccgctac tagcttggtc agtttgccta  123960
cgtcggcgat gctgagcttg tggtcgaaag tgcagaagat gttggcctcc atggccgcca  124020
tagcggcggt gaaatcctgg ccgcgacgga ggagaggcag agacgaacaa cgtctgcacc  124080 gggcgcggc tcagagcgag cgtggcgcgt ccgggcccgc gtttgcgtct aggtgactcg  124140
ccgctaacct gcggtcgtcg ccgtcctcct caccggacgg cctcacgagt taaataacat  124200
ggattgctgc agcgggatga tttcgcctac gacgtagtta ccaaagtgcg tttcggacgt  124260
agcaaaagcc ccggcgccac ccttgagttt ggtctccatc agcgccagcg tggtggtgct  124320
gaggatcggt agcgcttcct gcgtcagacg gcacgggttt tcgatgagtt gttccgtgcc  124380
ttcgacgcag acgtactgcg tgtccgtgtc gccgcggatg cagtccttgg cgcgtagcag  124440
gtactcgtcg atggttttga agagcgtttt gttggccgcg ataatctctt ctgtgttaaa  124500
gtactgcgcg caagggctgt agaatttgga gttgtagcct agacgttcgc gatgtcgggt  124560
gttgtagagt acgtcgctca gacagccggc ttgcgaggcc caggggttgt gtgtggccgc  124620
gaaagtctgt gcgtccgctt cgcgatggtc gtagatggcc ttggtggcgg cctccgtgtc  124680
gtacggatcg acgccagca tgcaggaggc acgcccgcgc gggttgttgg ggatcttaaa  124740
gtaattaacg tccatcgtca ccggcgtaag gattagttcg cacgcggcct tttgtccgtg  124800
caccgtggcg gcggcattgc gctcggacat gctgccgaac gtcagcatag agatggtctc  124860
cgtgtctaac agttgcggcc gttctacgcc ggccgcgtgc cggatccagc ggtccacctc  124920
gtcgtgccgg tacacgttca tagggaagac gcgaaagagg tcctgcacgc ggacgcccat  124980
gtcggttcgc acgcggttta cgtaggctac gcaggtattt gacgtgtaac ccagacccat  125040
gtctacggtg ttaatgttct gcgtgacgtg gtacgtagtg ctgatgtcgc gttcctcctt  125100
```

```
ggtcacgata gggttgttga tgataactga cgtgcatgat ttgccgctgt agagcagcat 125160
gtccacctcg aaggtgtcgg tgcgtacggc cgtgagtgcg aatcccgggt ggatgtgcgc 125220
cttggtctgc agcaccagtg aaactggtga gattttgtat aacatggcgg ccagcgtcat 125280
gactgagtgc aacacgttgg gacaggtggc cgagtaacgc gaaaagggcg agcgcagcca 125340
gttgtggtac tcgtgcgcga aggctgtggg tagcgggaaa ccaccgtcgt gacggtgata 125400
gtgcgggaac tcggtcacgt agcgtttaat gtcgtcgctc aacgccgcgc agatggtggg 125460
gtttgagtag aaacggtgga aaggtacggg taggctgtac tcgatcaacg tcttaggcgc 125520
cgtcacgacg cagcagccgt tgtaaagcac gtgctgacgt gagataaagt ccggcaggcc 125580
ctgacgctgc gcgtggtcca gaggcgcgcg cacttcgagc accttgacgt gctcgcccac 125640
gaattgcacg gccaaaaaca gttcacgaca ggcctgcagc agcggcgtat gtgcgtcggt 125700
ggcgacgtcc tccaccagct cggtcagcat ctcgcctacg gcttgacgtt gcgccgctat 125760
cgagtcttcg ggggtgacac cgcttgtgct ctctttcgac gtcgtacctg acgtggagac 125820
cgcggtggcg gccggcatca ggagaaacgc cggtcggtaa aagaggtcta ctagcagcgt 125880
cttgaggttg agtcccaggc cgcaggcccg gttgttggtc atggcgggca tgaggcagag 125940
ataaaagacc ttttgtaacg tccattcgtc gtcggtggca cggtaatcgt ccacaaacag 126000
cggctcgtcg gcatccatgg cgcccaaacg cggtacgtcc gaaacgccgt ggtgtcgcgc 126060
ctcgatgttg gccgggttca acggttgccg gtcggccact acctgtacgc cttccatgtt 126120
acgcggcagg tgcgtaacga agggggggcca cagccggtgg tcgtgcagcg cgttcacgta 126180
agccgatagc ggttcctcag ccagttgacc gttgttaagt cccggcagcg ctgagatgcg 126240
cgttaccaga cgcagcacgg cgaccagatt gcggtagtga aagagcaact gcggtggtag 126300
ggcgccatca gccaggtgtt cggcgatcaa cgtcaccagc gcgtagctgt gcgcaaaaac 126360
cagcagctga cgtgtgtgaa acatgttgac gatacaacgt gctacgaaag tgcggattag 126420
caaaaaagcg tcgacgttgc cgtgtaccag cacgtcgacc aggtagcaaa gctcggggta 126480
attggggctt gtcacggtgg ttttgaaaag tcgcaacgtc tcttcgtagt cgggtggtgg 126540
ccgcagtcgc atgtgttcca tgatctccca ggtgcgcagt tcgtggaagg ggcccggtgc 126600
cagtccatct ggcaaattac cgatgacgat acgcggtgta cacagcgcca ccgtttcgct 126660
gttttcctgg cagtgcgtaa agtcgaagaa ggggtgcagc tcggtgtaga gcgtgatgtt 126720
gcccaccttg tagaagtcgg tgaccacaaa gtcctgcttc atttcgttca ccgtgcgcgg 126780
gacctcgcgt cgtacgcggt aaaaatgcgg tatgcggcgc gccgcaccgc ccatgggttc 126840
ctgctgaaaa cgacactcga gcagtcgttg catggcgggt tccgagggcg gtccgcgttc 126900
cgtgaaggtc tgtagacagg gcgcgggctc gtgcagcacc gggtggcaca gcgtcttgag 126960
cgcgtccaca aagtctattt tttgtacggc acggtcccgg tttagcaggt aggccgtggt 127020
gggcaacgcg ttgcgaacgg tgtcgttaag cttaactttg cttttccaccg tggtgtaacc 127080 gcgatcctcg ggcagataca gccctacggg gaagaaaaac gtcaggtcca cgttacgttc 127140
tagcggatct ttggtatcgg tgttttttgta gacgcgccgc aagttttcca taatcaccgt 127200
tttttcgccc agtcggatca cgtccatgct cagcggcgtt aagctgtgcg ccccggcctg 127260
cgaaagcgag tcgttgggca aatgcggttg gcccgaagtc agatgagcct tgtacgagtt 127320
gaaatcggcc aggatcgagt gataggatat ggcagtgacg gcattttcgg gactgagtac 127380
aaaattgccg taggtggccg gcgccgagac cgtttctttg gtgatgtggc ttgagagcag 127440
```

-continued

```
cgacatgatg atctgcataa cgttggccgt gcttaccatc acgccgctga tcttggcccc  127500
cgagctcgtg gtgtacgtgg tggggttgtc taggatgcta tcggtggccg cttcggccag  127560
acgcgtgagg aacttgagca catagtcgcg atcgcgcgtg cgattcagca aaaagagcgt  127620
ggccagcatt ttggccttga agctctgcaa gatgttgctt cgctggatgc ggttcagtgc  127680
ctgtcgcgcc agtgtggcgt tttctaccag cgtctgcacc acaaagtacg gcggcgcctt  127740
gcgtagcagt gtctgtaaaa agctgtgaat caagccgcgc tccatggcgt cggccgtgtt  127800
tttaagcgcg cgcagcaccg tgtgcatggc ttccacgttg aggatcttgt ccaagatggt  127860
gccctcgaat gtctcgcgca gatacgtgag gcaggctgcg ctgagctcga aggggatggt  127920 gatggggat ttttcactgt atttggtgac cataatggtg gtctgacgac tagtgggcaa  127980
accggcgccg ctggccacac gcggcacctg cacgtggaac agcattttgc ccgtagtcag  128040
tttattgagg tcgtggaact tgatggcgtg cgccgccgcg gccaagccgc tggtcaaaaa  128100
ataaacccat tccaggcgat tgcagaaggt gccgaagatg gcttcgaagt gaatattgta  128160
acgctcgggg tcatcgccgt agtagatgcg taaggcctca aacatctcct cgccggcgct  128220
ggtcttgacg tgcgtcagaa agtcagtggg aatgccatct ttaggcagga gctcgagcgc  128280
cgaccagttc tccatcgcgg cggcggcgtg agcgcgaggc gtcggagctc ggggaaagca  128340
gcgcgacccg gagaatggcc ggcgctgcgc gcgccgcct cggctgtgac gctctaatag  128400
tcgttggcgg ctccgctatg ccgcgccggg ttttacacgt ccccgtgcac gttcgcgcct  128460
gcaacctcac ccaagagcta tcgacgggcg aggacgcccg cttttgtcgt ccgcgacccg  128520
ttaacgtcga acgggtgcgc gctgttttg cggctctcta ccgtgcctgt ccgatacacg  128580
tgaggaccga gcccgagcgt gtcaagctgg tactgggtcg tctgttactg ggacccgtgg  128640
ccgtaccctg tttttgcgac ggtgaagtgg agggccacgg tgaacatctg gtacctacga  128700
cgcagttttg tcgcgggccg ctgctctacg tgcaccgacg ttgttgttgc ggatccgtga  128760
ccgccgggcg cgcgctgtcc taccacgttc tcgaaaacca cgtggccacg catgtgctac  128820
gcggattgct ctcgctgacg gaatggaatc gagaattgcc gagcctcttt tgcgactgtc  128880
ctggcggcgg tggcgcctcg ggaaccgagg aacgctacgc tatggcctgc ctgccgcgcg  128940
acctcagcct gcacctggac gactatcctt acctgatggt ggaaatcgga cgcgtactca  129000
gtgtcagcga ggtagacgac tacgtaaccg ccgtctccgg ctacctgggc gaggccgcgg  129060
cgccgcgcat ccaggttcac tacaagctgc tcttttggact caacgtgcgt ccgcaagcgc  129120
cgtgcgcgtt ggacgctaca cgcgactttt ttctgctgga gctgcaaaag ctttggctgg  129180
gcgttgaata tcaccacgaa gtcacgtcgg agttttttcgg tcgcgtactg gctcagctgc  129240
atcgcgaccg cgcccgcgtc atgatggcgc ttcgcttgcc cgagcagacg gtgtgccacc  129300
tgagcacctt cgttctcagt cgcttcaagc gacaggtact gtacttcaag ctacaggtga  129360
gctacggcaa gtgccggact ggtcacgctg acagaagtgg gggaggggg aacggtggaa  129420 atcagggaca ccacaaccta ctgtgttatc gacgccttag cgtcacattt gccgacacag  129480
acacggtgtg gagaaacctt ttctacgtttt attacgaact agctcgggat ctgggtccc  129540 atgggacgga ggaccgaccc gtaagccgcg gttacggtgt ttcttgcgct tcgaggacgt  129600
cgcgactgtc accgtcagaa tcgacggtgg tttcggcgaa cggacacgcg ctgtcttcca  129660
ccgcgctccc gacgacgagc gcgggtcaca agctgtcact gccgcgcgac ccggccgcag  129720
atcgcgttcg acgttacgta tgcattatct cgcgtctcat gtacgctcgg tacggggaga  129780
gatggcgtaa acactgtcaa cggcggtcgg agacgggaga agaggaggag gaagagacgc  129840
```

-continued

```
tggaatcggg ggagactgac gccacgccgc catttgactt tacggggcag cagctgcgcc    129900
gggcctatca ggaacaccga cgtcgtaaac atctagccgt gcagcgttac gcgccgtgcc    129960
gtcgtaagct catcggcggg atggagtttg ccgaggtgac gggcgtgagt ctagaccgca    130020
tcgccgtcaa cgctttcaac accaaccgcg ttatcaatat gaaggctgcg ctctcgtcca    130080
tcgccgcgtc gggtctcggc gtacgcgcgc gcggcttcc caagaacatg acccacagtt    130140
ttgtgatgta caagcacacc tttaaggagc ccgcttgcac cgtcagcact tttgtttcca    130200
acgacgccgt ctacatcaac tcgctcaacg tcaatattcg cggttcctac cccgagtttc    130260
tgtactcgct gggcgtgtac cggctgcacg ttaatatcga tcactttttt ctgccggccg    130320
tggtgtgcaa cagcaactcc tcgctggacg tgcatgggct ggaggaccag gcggtgattc    130380
gctcggagcg cagcaaggtg tactggacca ccaactttcc gtgcatgatc tcgcatacta    130440
acaacgtcaa cgtgggctgg ttcaaagcgg ctacggccat tgtgccgcgc gtctcgggcg    130500
ccgacctgga agccattctg ctcaaagaac tctcgtgcat caagaacatg cgcgacgtgt    130560
gcatcgatta cggtctgcac cgtgttttca cgcaactaga gctgcgcaat tcgtaccaga    130620
tccccttcct ggccaagcag ttagtgctgt ttctgcgtgc ttgcctgctc aagctgcacg    130680
gtcgagagaa gcggctgcag ttggaccgcc tagtatttga ggcggacag cggggtctct    130740 ttgactacag caagaacctc acggcgcaca ccaagatcaa gcacacttgt gcgctcatcg    130800
gcagtcgtct agccaacaac gtgcccaaga tcctggcccg gaacaaaaaa gtcaaattgg    130860
atcacctggg ccggaacgcc aacgtgctga cggtgtgtcg gcacgtggaa gcccacaaga    130920
tccctcgcac gcgcctcaaa gtgttagtcg aggtgctggg cgcgttgcag agtatcagcg    130980
gtacgccgca cacgcgcgaa gtgatccacc agacgttgtt tcgattgtgc tcggcggccg    131040
cagccacatc gggcctgtgt tcatcccctc ccccattgtg tgtgtcctca tcttcctccg    131100
tcccttctgt cccaacctcc gtcagcgttg acggcagttc tgaacccacg tcgccgcgag    131160
cgcggtttgc atcacgatga tggaagccgc ggccgctgcc gccgcggcgt ttcgtccgga    131220
ggagcgtccg acgccgggtt ggcacgacgc ggcgttgtta atggacgacg gtacggtgcg    131280
cgagcacgcg tttcgcaacg gaccgctgtc gcaactgatt cgccgtgtgt taccgccgcc    131340
gcccgacgcc gaagacgacg tggttttgtc ttccgagctg tgttttatt gcagcggtcg    131400 ttttaaccgc aggtcgtccg tcttctccat ctattggcag aagcatagcg atctggtgta    131460
cgcgcttacg ggcattaccc attgcgccaa gttggtggtg gaatgcggtc agttggggag    131520
tagtaggcta cggtggcgcg acggtgatgc gagtggtgag gagcgccggg gagacgacga    131580
cagcagggac gagctgtacg acgtgccggg catttatatg attcgcgtca acgacggcgg    131640
cagcaccggc cccagacacg ttatttggcc gggtaccagc gtgctttggg cgccggacgt    131700
tgtgatcact acggtgcagc gacgaatctc ggcggcgcgc gccctggtga acacgttccg    131760
ccaatatttt tttttgctgg aacggcgctc gcacgaggag ctggttctttt gtccgcccga    131820 gatggaggag cgtctagcgc cgctgttgca gagtgccacg cgcggtgatt cggacatgtt    131880
tgacggtgtg gtggccagcg cttatcaccg tttgcgaatg agtaatattc cgcgttcatc    131940
cgcccgtctg ctggaacact gcgtgggggct ggcgggtgct aagaagctgc tcttgctcga    132000
cgtgccgcgt ctggagaact attttctttg tcaagtctgt ctttacgagc tggacgagga    132060
cgagatgggc gaggagatgc tgggcatgtt ggccggaaag cccgaggatg ccgccgtctc    132120
gggcgcaagc ggcggttttc tgctacatcg caagacgatg aagctggccg cctgtctgtg    132180
```

```
tttgttgctc aattcgctgc atttgcacca ggaggcgctg gaggccttgg atcctccgcc    132240
gccgcgcgtc gaggagaacg accttgtcaa cgtggtgctg cgccgttatt atcgcagtca    132300
cggcggcgtg caggcgcgga cgctggcggc ggcccgggct tgttagccg actacgccga     132360 aacgttttcg cccttgggga gttttacgcg cctgggttac gatcgtctcg tttctgccga    132420
tgccggcgtc agtcgccggc acctggtggc tctgctgcgt gcctagctga ccctgaaacg    132480
gatggcgtgt atatcgtcac acaggtaggt ggccatgatg acggcgatga taagatcgtc   132540
cgagatacga ttctggcgct tggccgagta acgcgccgtc gtgccttcgg ccagcgtgac    132600
gcggtgcagg ttctgaatct gctccagaag atactcgatg gggtcgtggc tcagcttgat    132660
ggtgtaggag acgagctctt gcgaggcttt gatgtagccc gagttgaaac gcagagtaaa    132720
ctgttccacg gccagcgcct tgtcgcggcc catgaggtag aagggctgtt cgatgtggtt    132780
ctggtcgggc gtgtggtaga agagcacgcg gatgagcgtg ctgctctgca cgctctgtcg    132840
gatgaggcag gcgatgcgca cggccgccgc ctggttggtg ttgccctcca cggcgatgcg    132900
cagttcgtcc aggtaagggt gcaggctcag caccgagatg atcatgtgcg ccgcgcactc    132960
ggcgatggct acctcagaac tctcggagag gtcgcgcaaa agaaatgct ctaggccgta     133020 aatgagaaac tggtgtcggt aggcgcctac ggccgccacg cccgtgcccg aggccttgcg    133080
gttggtggtg aaggccgggt ccagatacac gtaaagcgtc ttgccgaaat aatcgtaggc    133140
gttggtgttg agcgtgctgt aacgcaaaat atcgaactct tcgcggctct ggtccgtgat    133200
gagcacggtg ttctgcgaga ttttattggt accgccgatg atctcgtcca tgaaagcgcc    133260
cggcataaac atgttggccg tcttgcgcac ttgcgagttg aggctgatga aggtgggctt    133320
gtgcagtcgg tagcaaggac acgccgtggc gtcgcccttc tccgtgaagc tgtgcaggtg    133380
ctcttcgcac acgtaagaga ccacgttgag catgtcaaag gcgcattgt taaggcgcgt     133440 caagaaacac gtggagtcac tggtagtgtt ggtggacgat atgaagatga tcttggtggt    133500
attctgggcc aggaacccca gaatggtgtt gaaggcctct tcttgatga agtgcgcctc     133560 gtccaccagc agcaagtgga agttttgtcc tcggatgctc tgtgtagaga ggagacagaa    133620
aagggactct tatgattacg cacgctcgac tggaagccta cagagtcggg gtggggccgg    133680
acaggtgagc caggtgagcc gccaggtgag gcgggatcgc cgtgtgccaa ccgggctgcg    133740
acctgaaaac cggaaccaat ccgccgacac cggcgccgcg tgacgcgcgc ccataaaaac    133800
gaaagtgtcg tcgtcgcgac ccgccacagc cgccatgaac tcgttgctgg cggaactcaa    133860
ccgactaggg gtcgcgcacg ccactacgga ggatgttttt atctttgtcg accgcctctt    133920
tcaacacttt tccttccttt tccaggccga ggagtcaggc ccgcgccgct tggaactggt    133980
cgcgtccgtg ttcgagcacc tgacggtgga gtgcgttaac gacatcctgg acgcctgcag    134040
tcacccggac gtgaacgtcg cggagacaag caacacctgt cgtccctgcc cttctcctgt    134100
tccctccgcc cccaaaactg tcagcggcgc tcagacgtca tgtgcgacgc ctcgggcgcc    134160
tgtgacatga ggcacgtcca gaacgcgttt accgaggaga tccagttaca ctcgctctac    134220
gcgtgcacgc gctgctttcg cacgcacctg tgtgatctgg gcagcggctg cgcgctcgtc    134280
tccacgctcg agggctccgt ctgcgtcaag acgggcctgg tatacgaggc tctctatccg    134340
gtggcgcgta gccacctgtt ggaacccatc gaggaggcca cactggacga cgtcaacatc    134400
atcagcgccg tgctcagcgg cgtgtacagc tacctcatga cgcacgccgg ccgttacgcc    134460
gacgtgatcc aggaggtggt cgagcgcgac cgcctcaaaa agcaggtgga ggacagtatt    134520
tacttcacct ttaataaggt tttccgttct atgcataacg tcaaccgtat ttcggtgccc    134580
```

```
gtcatcagcc aacttttat tcagcttatc atcggtatct actcaaagca gaccaagtac    134640
gacgcgtgtg tcatcaaggt tagtcgtaag aagcgcgagg acgcgcttct gaaacagatg    134700
cgttccgaat atggaaacgc acctgtattc ggatctggcg tttgaagcgc ggttcgctga    134760
cgatgagcaa ttgcctctac acttggtgct cgaccaggag gtgttgagta acgaggaggc    134820
cgagacgctg cgctacgtct actatcgtaa tgtagacagc gctggccgat ccacgggccg    134880
cgctccaggc ggagatgagg acgacgcacc ggcctccgac gacgccgagg acgccgtggg    134940
cggcgatcgc gcttttgacc gcgagcggcg gacttggcag cgggcctgtt ttcgtgtact    135000
accgcgccca ctggagttgc tcgattacct acgtcaaagc ggtctcactg tgacgttaga    135060
gaaagagcag cgcgtgcgca tgttctatgc cgtcttcact acgttgggtc tgcgctgccc    135120
cgataatcgg ctctcaggcg cgcagacgct acacctgaga ctggtctggc ccgacggcag    135180
ctatcgtgac tgggagtttt tagcgcgtga cctgttacga gaagaaatgg aagcgaataa    135240
gcgcgaccgg cagcaccagt tggccacgac cacgaatcac cgtcggcggg gcggactgcg    135300
taataactta gacaatgggt cggatcgccg tttgcccgaa gcggctgtgg cttctctgga    135360
gacggccgtc agtactccat tttttgaaat tccgaacgga gcaggaacct cctccgcgaa    135420
cggcgacggc agattcagta acctggagca gcgggtagcg cgtttgttgc gcggcgacga    135480
ggaattcatc tatcacgcgg gtccattgga gccgccttcc aagatacgcg gtcatgagtt    135540
ggtgcagctg cgcctggacg taaatccaga cctcatgtac gccaccgatc cgcacgaccg    135600
cgacgaggtc gcgcgtacgg acgagtggaa gggtgccggt gtctcgcgtc ttcgcgaggt    135660
ctgggatgtg cagcatcgcg tgcgcctccg tgtgctgtgg tacgtcaatt ccttttggcg    135720
cagtcgcgag ctgagctacg atgaccacga agtcgaacta taccgggcgt tggacgctta    135780
tcgggcgcgc atcgccgtcg agtacgtgct gattcgcgcc gtgcgcgacg agatctacgc    135840
tgtactacga cgggacggcg gcgcgttgcc acagcgtttc gcctgccacg tgtcacggaa    135900
catgtcctgg cgcgttgttt gggaactttg ccgtcatgcc ttggcgctct ggatggattg    135960
ggcggacgtg cgtagctgta ttattaaggc gctaacgcct cgtctgagcc ggggtgccgc    136020
cgctgccgct cagcgagctc gtcgccagcg cgagcgctcg gcgcccaaac cgcaggagct    136080
gcttttcggg ccgcggaacg agagcggtcc gcccgccgaa cagacttggt acgctgacgt    136140
ggtgcgctgc gttcgcgcgc aagtggattt gggcgtggaa gtgcgcgcgg cgcgttgtcc    136200
tcgcaccggg ctttggatcg tccgtgatcg ccgcggacgc ctgcgacgtt ggctctcgca    136260
gcccgaggtg tgcgtgctgt acgtcacgcc agacttggac ttttactggg tgctgccggg    136320
cggctttgcc gtctcttcgc gcgtcactct tcatggcttg gcgcagcggg ctttgcgaga    136380
ccgattccag aactttgaag cagttcttgc aagaggaatg catgtggaag ctggtcggca    136440
agagccggaa acaccgcgag tatcgggccg tcgcttgccg ttcgacgatc tttagtccgg    136500
aggacgacag ctcgtgtatc ttatgccagt tgctgttgct ctaccgcgac ggcgaatgga    136560
tcatctgttt ttgctgcaac ggccgttatc aaggccacta tggcgtgaac cacgtacatc    136620
ggcgtcgtcg acgcatctgt catctaccta ccttgtacca actgagcttc ggaggtcctt    136680
tgggtccagc cagcatcgat ttcttgccaa gctttagcca ggtgaccagc agtatgacgt    136740
gcgatggtat tacgcccgac gtgatttacg aggtctgcat gttggtgccc caggatgaag    136800
ccaagcgtat cctggtcaag ggtcacggtg ccatggacct gacctgtcag aaggcagtga    136860
cgctaggcgg cgccggcgcc tggttgctgc cgcgtcccga aggctacacg cttttctttt    136920
```

```
acattctgtg ttacgacctg tttacctcat gcggcaatcg gtgcgatatc ccttccatga 136980
cgcgcctcat ggcggcggcc acggcctgcg ggcaggcggg ttgcagcttt tgcacggatc 137040
acgagggaca cgtagatccc actggcaatt acgtgggttg cacccccgat atgggccgct 137100
gtctttgtta cgtgccctgt gggcccatga cgcagtcgct catccacaac gaggaacccg 137160 cgacttttt ctgtgagagc gatgacgcca agtacctatg cgccgtaggt tctaagaccg 137220
cggcgcaggt cacactggga gacggcctgg attatcacat cggtgttaag gattctgagg 137280
gccgatggct gcccgtcaag accgatgtgt gggacctggt caaggtagag gaacctgtgt 137340
cacgtatgat agtgtgttcc tgtccggtgc ttaagaacct agtgcactaa cggggtctga 137400
cagttcacgg ggagaagaaa caagaaacaa caaaaaaaag gaggacatgg actcgccacg 137460
gtttgtggca aggcgtatgt tatcatcatg gagctactca cgttggtgtt gtagcaactg 137520
gcaaaaagcg ccgtgctctt ggcgccgcgg tggtcgatgc tgatcacgtt gtccttgttc 137580
tcgaccacgt agtcgcgcgc gaaggtgtgg cggcagcgga actcgacctc tttgagcaca 137640
aactgcgaca cgtgcttttg gtgcgccacg tagccgatgc tgatgccgat catgtgctta 137700
agcagaaacg agataatggg gatgatgaac caagtcttgc cgtgacgtcg cggcaccagg 137760
aacacggtgg ctttctgctt aaagatgtcg atggaggtct gcgagaggaa gtcgatctgg 137820
aaggcgtgga tgaggtactg cagcacgcga ttggccagca cggggatctt ggtcacggct 137880 ataaaaaga tgacgtgtat caataaattc ttttgaaacg gttcgagtcg gatggctttt 137940
gcgtcgccct cgacggcggt actgaagccg ccgtcgagcc acttttaaa gtcggtcatg 138000 aagttgttga tctgctgaaa ctgcggatcg cggtagagct cggtcaacgc gtccagcttc 138060
tggtaggagg cgcgctgctc ctcggagcac gggcgaaacg tcagtttatc gagcgcgctc 138120
ttgaggcgct cgtgaaacag cagctcgcgc tggctttcct cgggcgagtt gtagtcgcgg 138180
tggcggccgc agaaggccat gagcggcagg aaggcctcgt tgcacgagtg ggccagcccg 138240
agttcggggt gcatcatctg gtagcgcttg cggcacagcg tcgccacatt ggtgaaggcc 138300
gtggagatgc aggaggtggg gtggctcttg cgcttctgca gctccgcgta gcgctcctgg 138360
atcttggcgg ccgagtctcc gcgcaacatg atggcggcgg cggtggtgcg agcggaggtt 138420
aggcggcagc ggcgagagga gaggaaaaag atggcggccg cgaggacgac ggaggatcca 138480
cccgaaaacc acgttgttgc ggacgtggct cgtgggacgg gcgccgtcac tcgttcgtct 138540
tcgtcgtccc tagtggtgtc gtcttcctcg gcgtcaggct cggacgaatc ttcctccgcc 138600
tctcctctca gtttccccgt ctcctccccc tcaactgccg tcaggtctcc ggggtccgcc 138660 gggggtttcaa cgtccctgtg ctcggtggaa cggatggtcg agctgtcggc gcagtctccg 138720
gccgccgatt tctcggtctc cgaggcttgg cgcttcgagg aggccgtaaa tatggcgctg 138780
gtggcctgcg aggccgtgtc accttacgat cgctttcgcc taattgaaac gcccgacgag 138840
aatttcttgt tggtcaccaa cgtaattccg cgcgaatcgg ccgaggtgcc ggtgttggat 138900
agcagtagca gcgtggcga tagcgggccg gaggacaaaa agaaaaacgt cgggaataaa 138960
accgcggggg aaaagaacgg cggtgggtct cgggccaaac gccgtcgtag acgacgcgct 139020
ccgaaaaacg acgccgccac gccgtctttt ctacgtcgac acgacgtgct ggagcgtttc 139080
gcggccgcgg ctaagccttt gccgtcgctt tgtgtgcgtg attatgcgtt acgcaatgct 139140
gaccgtgtta cctacgacgg cgaattaatc tacggcagtt acctgttgta tcgcaaggct 139200
cacgtggagc tgtcactctc cagcaacaag gtgcaacacg tggaagccgt gctgcgacag 139260
gtgtacacgc cgggcttgtt agatcatcac aacgtgtgcg acgtggaggc cctgctgtgg 139320
```

-continued

```
ctgctgtact gtggaccgcg cagcttttgc gcgcgtgaca cttgtttcgg tcgcgaaaag  139380
aacggttgtc ctttccccgc gttgttgccc aaactctttt acgaacccgt gcgggactat  139440
atgacctaca tgaatctggc tgagctgtac gtctttgttt ggtatcgcgg ctacgaattc  139500
cctgcgccga cgccgcaggc gacgacggcg ggtggtggtg gtggtagtgg tggcggcggc  139560
ggggccggcg cttgtgcggt cgagacgagc gcgtcagcag gccgggtcga tgacgccggc  139620
gacgaggtgc atttgccttt aaagcccgtc tcgctggacc gtctcagaga ggtgttgcag  139680
gcggtgcgcg gccgcttctc ggggcgcgag gtgcccgcct ggccggcctc gtcgcgcacc  139740
tgtttgttgt gcgcgctcta cagtcagaac cgtctctgtt tagatctcgc gcgtgacgag  139800
gcgcggaccg tgagttatag ccccatcgtt atccaagact cgccgcggc tgtcaccgac  139860 gtcactttga gccacatctt gcccggccag agcaccgtct cgcttttccc cgtctaccac  139920
gtcggcaagt tgctggacgc tctctcgctg aacgacgcgg gtctcatcac gttgaatcta  139980
tgacgtcggt caacaaacag ctcttaaagg acgtgatgcg cgtcgacctt gagcgacagc  140040
agcatcagtt tctgcggcgt acctacggac cgcagcaccg gctcaccacg cagcaggctt  140100
tgacggtgat gcgtgtggcc gctcgggaac agacccgata cagtcagcga acgacgcagt  140160
gcgtggccgc acacctgttg gagcaacggg cggccgtgca gcaagagttg caacgcgccc  140220
gacagctgca atccggtaac gtggacgacg cgctggactc tttaaccgag ctgaaggaca  140280
cggtagacga tgtgagagcc accttggtgg actcggtttc ggcgacgtgc gatttggacc  140340
tggaggtcga cgacgccgtc taacaggtat agcaatctcc gtcacgcctc tgttcagatt  140400
ttattaaaaa aaaaacacaa cataacgaca gtgtcggtgt ggtagctagt gcagccttag  140460
gaacagggaa gactgtcgcc actatgtcct ccgcacttcg gtctcgggct cgctcggcct  140520
cgctcggaac gacgactcag ggctgggatc cgccgccatt gcgtcgtccc agcagggcgc  140580
gccggcgcca gtggatgcgc gaagctgcgc aggccgccgc tcaagccgcg gtgcaggccg  140640
cgcaggccgc cgccgctcag gtcgcccagg ctcacgttga tgaaaacgag gtcgtggatc  140700
tgatggccga cgaggccggc ggcggcgtca ccactttgac caccctgagt tccgtcagca  140760
caaccaccgt gcttggacac gcgactttt ccgcatgcgt tcgaagtgac gtgatgcgtg  140820
acggagaaaa agaggacgcg gcttcggaca aggagaacct gcgtcggccc gtagtgccgt  140880
ccacgtcgtc tcgcggcagc gccgccagcg gcgacggtta ccacggcttg cgctgccgcg  140940
aaacttcggc catgtggtcg ttcgagtacg atcgcgacgg cgacgtgacc agcgtacgcc  141000
gcgctctctt caccggcggc agcgaccct cggacagcgt gagcggcgtc cgcggtggac  141060
gcaaacgccc gttgcgtccg ccgttggtgt cgctggcccg caccccgctg tgccgacgtc  141120
gtgtgggcgg tgtggacgcg gtgctcgaag aaaacgacgt ggagctgcgc gcggaaagtc  141180
aggacagcgc cgtggcatcg ggcccgggcc gcattccgca gccgctcagc ggtagttccg  141240
gggaggaatc cgccacggcg gtggaggccg actccacgtc acacgacgac gtgcattgca  141300
cctgttccaa cgaccagatc atcaccacgt ccatccgcgg ccttacgtgc gacccgcgta  141360
tgttcttgcg ccttacgcat cccgagctct gcgagctctc tatctcctac ctgctggtct  141420
acgtgcccaa agaggacgat ttttgccaca agatttgtta tgccgtggac atgagcgacg  141480
agagctaccg cctgggccag ggctccttcg gcgaggtctg gccgctcgat cgctatcgcg  141540
tggtcaaggt ggcgcgtaag cacagcgaga cggtgctcac ggtctggatg tcgggcctga  141600
tccgcacgcg cgccgctggc gagcaacagc agccgccgtc gctggtgggc acgggcgtgc  141660
```

```
accgcggtct gctcacggcc acgggctgct gtctgctgca caacgtcacg gtacatcgac 141720
gtttccacac agacatgttt catcacgacc agtggaagct ggcgtgcatc gacagctacc 141780
gacgtgcctt ttgcacgttg gccgacgcta tcaaatttct caatcaccag tgtcgtgtat 141840
gccactttga cattacaccc atgaacgtgc tcatcgacgt gaacccgcac aaccccagcg 141900
agatcgtgcg cgccgcgctg tgcgattaca gcctcagcga gccctatccg gattacaacg 141960
agcgctgtgt ggccgtcttt caggagacgg gtacggcgcg ccgcatcccc aactgctcgc 142020
accgtctgcg cgaatgttac caccctgctt tccgacccat gccgctgcag aagctgctca 142080
tctgcgaccc gcacgcgcgt ttccccgtag ccggcctacg gcgttattgc atgtcggagc 142140
tgtcggcgct gggtaacgtg ctgggctttt gcctcatgcg gctgttggac cggcgcggtc 142200
tggacgaggt gcgcatgggc acggaggcgt tgctctttaa gcacgccggc gcggcctgcc 142260
gcgcgttgga gaacggtaag ctcacgcact gctccgacgc ctgtctgctc attctggcgg 142320
cgcgcaaatgag ctacggcgcc tgtctcctgg gcgagcatgg cgccgcgctg gtgtcgcaca 142380
cgctgcgctt tgtggaggcc aagatgtcct cgtgtcgcgt acgcgccttt cgccgcttct 142440
accacgaatg ctcgcagacc atgctgcacg aatacgtcag aaagaacgtg gagcgtctgt 142500
tggccacgag cgacgggctg tatttatata acgcctttcg gcgcaccacc agcataatct 142560
gcgaggagga ccttgacggt gactgccgcc aactgttccc cgagtaaccg ggacgcggaa 142620
cgtgacggtt gctgagggga aggcaacag agaaggtaca aacccaccgg cggggaaaat 142680
accgaggcgc cgccatcatc atgtgggcg tctcgagttt ggactacgac gacgatgagg 142740
agctcacccg gctgctggcg gtttgggacg atgagcccct cagtctgttt ctcatgaaca 142800
ccttttttgct gcaccaggag ggcttccgta atctgcccttt acggtgctg cgtctgtctt 142860
acgcctaccg catcttcgcc aagatgctgc gggcccacgg tacgccagta gccgaggact 142920
ttatgacgcg cgtggccgcg ctggctcgcg acagggtct gcgcgacatt ttgggtcagc 142980
ggcacgccgc cgaagcttcg cgcgccgaga tcgccgaggc cctggagcgc gtggccgagc 143040
ggtgcgacga ccggcacggc ggctcggacg actacgtgtg gctcagccgg ttgctggatt 143100
tagcgcccaa ctatcggcag gtcgagctct tccagttgct ggaaaaggaa tcgcgcggac 143160
agtcgcgcaa ctcggtgtgg catctgttgc gtatggacac ggtctcggcc accaagttct 143220
acgaggcctt cgtcagcggc tgtctgccgg gcgccgcggc ggcggacggt tcgggtggcg 143280
gcggctcgca ctacacgggt tcgcgcgccg cgtctcgcc gggcatccag ttcggtatca 143340
aacacgaggg cttagtcaaa acgctggtgg aatgttacgt gatgcacgga cgcgagccgg 143400
tgcgcgacgg cctcggtctg ctcatcgacc ccacgtcggg gctgctgggc gcttccatgg 143460
acctgtgctt cggcgtgctc aagcagggta gcggtcgcac cttgctggtg gaaccgtgtg 143520
cgcgcgtcta cgagatcaag tgccgctaca aatatttgcg caaaaaggag gaccccttttg 143580
tgcagaacgt gctgcggagg cacgacgcgg cggccgtggc ctcgctgttg cagtcacacc 143640
cggtgccggg cgtggagttt cgcggtgaac gcgagacccc gtcggcacgc gagtttctgc 143700
tttcgcacga cgcggcgctc ttcagggcca cgctcaagcg cgcgcgcccg ctcaagccgc 143760
ccgaaccgct gcgcgagtac ctggccgatc tgctgtatct caataaggcc gagtgttcgg 143820
aagtgatcgt gtttgacgcc aagcacctga gtgacgacaa cagcgacggg gacgccacga 143880
tcactattaa cgcgagtctc ggcctagccg cgggcgacgg cgctggcggc ggcgctgatc 143940
accacctgcg gggcagcccg ggcgattcgc cgccgccgat acctttcgag gacgaaaaca 144000
cgcccgagct gctgggccgg ctcaacgtgt acgaggtagc gcgcttttca ctgccggctt 144060
```

```
ttgtcaatcc gcgtcaccag tattactttc agatgctcat tcagcagtac gtgctcagcc    144120
aatactatat aaagaagcat ccggacccgg agcggatcga tttccgcgac ctgcctaccg    144180
tctacctggt ctcggccatc ttccgcgagc gcgaggaaag cgaactgggc tgcgagttgc    144240
tggccggcgg tcgcgttttc cactgcgacc acatcccgct cctgctcatc gtcacgcccg    144300
tggtctttga ccctcagttt acgcgccatg ccgtctctac cgtgctagac cgttggagtc    144360
gcgacctgtc ccgcaagacg aacctaccga tatgggtgcc gaactctgca acgaatatg    144420
ttgtgagttc ggtaccacgc ccggtgagcc cctgaaagat gctctgggtc gccaggtgtc    144480
tctacgctcc tacgacaaca tccctccgac ttcctcctcg gacgaagggg aggacgatga    144540
cgacggggag gatgacgata acgaggagcg gcaacagaag ctgcggctct gcggtagtgg    144600
ctgcggggga aacgacagta gtagcggcag ccaccgcgag gccacccacg acggctccaa    144660
gaaaaacgcg gtgcgctcga cgtttcgcga ggacaaggct ccgaaaccga gcaagcagtc    144720
aaaaaagaaa aagaaaccct caaaacatca ccaccatcag caaagctcca ttatgcagga    144780
gacggacgac ctagacgaag aggacacctc aatttacctg tccccgcccc cggtcccccc    144840
cgtccaggtg gtggctaagc gactgccgcg gcccgacaca cccaggactc cgcgccaaaa    144900
gaagatttca caacgtccac ccaccccogg gacaaaaaag cccgccgcct ccttgcccttt    144960
ttaactcata aactttcagg tctcgcgtac gattcgcgag tcgggaatgg gacacccgtg    145020
ggtgtttctc cgtgtgtata ttatttttt tttttgtgtg tgtttgcgcc cccgtgtgtc     145080
taatgtgctg tttgaaacac gtaaagtagc tggtggaaga acagataaac ctttaataaa    145140
aaaaaagta tgtgctcccg acccacggtc tgcgtgtctc ttttttatgt ccatgtctcc    145200
aagtctggtg cgggtggcgg cggggttaag cgtcctcgaa gtcttcatca tcgtcgtcgt    145260
cctcttcttc gcggaggcga cggctttcca agctgtcgtg gtgactgagc acagcgactt    145320
cttcgccgga ggctgtggcc agcgcctggt acttgacact gccgctaccg cgtccgcgaa    145380
agtagcggac ggcgcgacac gtcgtaaaca tggcccatat gaaaaagagc atgccgaacg    145440
accagctgat gccggtgcgg tattcgttgc tgaggaaggt atcgtactgc acgatggggt    145500
agatgaggcc gcagagtcca agaaggcgc ccaggtggta gccgaattgc accttgacgt     145560
attgaaaaaa gacggcctcg atcagtaaaa agtagatgat ggagatgata gcgtagacca    145620
cgaagacggc taacaccatg tggcctgtac gcacgaaaaa gttgtttccg aagccgtagc    145680
acagggccat ggctaccacg gtggtgttga aaccaagcgc tacctctacc aggttgacga    145740
tgagcgtgcg gaactgcacc gtacctttga gcttggggtg cagacgcgag aagaaaaaga    145800
gtgagcgttt gtagctgcgg tactgcgtga ccatgctcac gttgaaaatg gtcaggcaga    145860
aaaagtgcac ggcggccatg aaggcgatca tgctgggcag ccgaaatgac atggtcagtg    145920
tgaatagttg gaacgtgtcc atgctgagaa tgaagaggaa ggctgtgagg ctgtcgccca    145980
tgtacgaaat gtcgcgtgtc gactggttta ggctcatgcc tttgtccttg cgcatgctga    146040
tcttgatcca gcataccagg tagtagatgg tcacggctaa aaagacgagc tgcatgaaca    146100
cggcgtagca caccaactgc accgagtcta agaaaagcat aggcgtgtgc aggtgcatta    146160
cgttgtaggc cgacatgttg agcctttcaa agtccacgac gtgatagtag acgcaggggt    146220
agcccaggtg cggaaaattg ctcagcacta gatgcacgct gacgttgaca aaagtcagca    146280
ccatgaaaac gatagaagcg ctccatgtcc gtgtattcac cttatccacg tgcgaggggg    146340
ccatggcgat agcggcggcc cgctcgctcg ggaggcgatg ggggcgcgcc gatgacgaca    146400
```

-continued

```
ggctcgcggg tcgttaaata ctacgatggg agccgccgcg gctcacgacg cggtttgagc    146460
acgtccgggc ggtcggtgaa aaaagacccc gcgggccttc gcgactctct tctgtccgag    146520
gatgaccgct cagccgccgc tgcaccaccg ccaccacccg tacaccctgt tcgggaccag    146580
ctgtcatctc agctggtacg gccttctaga ggcctcggtg cctatcgtac aatgtctgtt    146640
tttggatctg ggtggcggcc gtgccgagcc gcggcttcac acgttcgtgg tgcgcggtga    146700
ccgtctaccg ccggctgagg tgcgtgctgt gcatcgcgcc agctagggtg cgctggcctc    146760
ggccgtgact acgacgccg atgagcgtcg gcgcggccta gagcagcgta gcgccgtgtt    146820
ggcgcgcgtg ttgctagaag gcagcgcgtt aatccgcgtg ttggcgcgca ccttcacgcc    146880
ggtgcagatt cagacggacg ctagtggcgt ggagattttg gaggccgcac cggcactggg    146940
cgtggaaacc gcagcgctgt cgaacgcgct tagtctttc cacgtagcca agctagtggt    147000
catcggctcg tatcccgaag tgcacgagcc gcgtgtggtc acgcataccg cggaacgcgt    147060
ctccgaagag tatggcaccc acgcgcacaa aaaattgcgt cgcggttact acgcctacga    147120
tttggccatg tcgtttcgcg tcggcactca caagtatgtg ctggagcgcg acgacgaggc    147180
cgtcctggca cgcctctttg aggtgcgcga ggtgtgtttt ttgcgcacct gtctgcgtct    147240
ggtcacgcct gtcggtttcg tggccgtggc agtgaccgac gagcagtgtt gtttattgct    147300
gcagtcggcc tggactcacc tttacgacgt gcttttccgt ggtttcgctg ggcagccgcc    147360
gctacgcgac tacctggggc cggacctctt tgagacgggc gccgcccgtt ctttcttttt    147420
tcccggtttc ccgcccgtgc ccgtctacgc ggtccacggt ctgcacacgt taatgcgcga    147480
gacggcgttg gacgcggcgg ctgaggtgct ctcgtggtgc ggcctgcccg acatcgtggg    147540
ctcggccggc aagctggagg tggaaccctg cgcgctctcg ctcggcgtgc ccgaggatga    147600
gtggcaggtc ttcggtaccg aggccggcgg cggcgccgtg cgtctcaatg ccacggcttt    147660
tcgcgagcga ccggccggcg gcgatcgtcg ctggctgttg ccgccgctgc cacgtgacga    147720
cggcgacggt gaaaacaacg tcgtggaagt cagcagcagc accggcggtg cgcacccgcc    147780
gagcgacgac gccactttca ccgtgcacgt tcgcgacgcc acgctacatc gagtgctcat    147840
cgtggatttg gtcgagcgcg tgctggccaa gtgtgtacgc gcgcgcgact tcaatccctc    147900
cgtgcgttat agtcatcgac tccacactta tgcggtttgt gaaaagttta ttgagaatct    147960
gcgttttcgc tcgcgacgcg ctttctggca gatccagagt ctgctgggct acatctccga    148020
gcacgttacg tcagcctgcg cttcggccgg cctttttgtgg gttctgtcgc gcggccaccg    148080
cgagttttat gtctacgacg gctattcggg tcacggaccc gtctcggccg aagtgtgcgt    148140
gcggactgtg gtcgactgtt attggcgcaa acttttttggc ggcgacgatc cgggtcccac    148200
ctgtcgtgtt caagagagcg cgcccggcgt gctgttggtc tggggcgacg agcggttggt    148260
gggtcccttc aacttcttct acggcaacg cggcgccggt ggtagtccgc tccacggggt    148320
ggtgggtggt ttcgcggcgg gacattgcgg tggcgcttgt tgcgcgggct gcgtcgtcac    148380
tcaccgccat tctagcggcg gcggtggtag tggcgtgggc gacgcggacc acgcgagtgg    148440
cggcggtcta gatgccgctg ccgggagtgg tcataacggc ggtagtgatc gggtttctcc    148500
ctccacgccg cccgcggcgt taggtggctg ttgctgcgca gccggtggcg actggctctc    148560
ggccgtgggt catgtcctgg gccggctgcc ggcgctgtta cgggagcgcg tgagcgtgtc    148620
cgagctggaa gccgtgtacc gcgagatcct ctttcgtttc gtggctcgcc gcaacgacgt    148680
ggacttttgg ttactgcgct ccagcccggg tgaaaacgaa gtaaggccgc acgctggggt    148740
gattgactgc gcgcccttcc acggcgtgtg ggccgagcag ggccagatca tcgtacagtc    148800
```

```
acgcgatacg gcgttggcgg ccgatatcgg ctacggcgtc tatgtggaca aggcctttgc 148860
catgctcacg gcttgcgtgg aggtctgggc gcgagagtta ttgtcgtcct ccaccgcttc 148920
caccaccgct tgttcttctt cttccgttct ctcctccgcc ttgccgtccg tcacttcgtc 148980
ctcttcgggc acggcgacgg tgtctcctcc gtcttgttct tcttcgtcgg cgacttggct 149040
cgaggagcgc gacgagtggg tgcgctcgct ggcggttgac gcgcaacacg ctgctaagcg 149100
ggtggcttcc gagggcctgc ggttttttccg gctcaacgct taacgagtca cgtaggggaa 149160
ctacgtgggt aagtgacgtg gatactagta aaaaaagtgc gtcaaagctc ttagcgtgtg 149220
acgtggatac tagtaaaagg gacgtcaaag ctcactacgt gttgcgtgtt tttttttttt 149280
ctatgatatg cgtgtctagt tcgcttctca ctcttcctct cctcgttccc agcgcggcgg 149340
cagcttgggg ggtgagggca aattgggggta gttggcgttg agcacgtcta gcaggcccag 149400
gcccacgggc caaccgtcca cggtcttgcg ctcggtcagc ttgaggctga acgagtgtgc 149460
ctcgtcctga ccggtaaggc ggaaaaagaa gcgtgctacc agctgcaggc aggtatgccg 149520
cgtctgctgg aagagcacga aggtagcggg cacgtactgc acaatgtgcg gctctttttc 149580
ctcaaagagc aggtagagcg cgctgcagat cagccgcctg gcgctgtggt gcagcagccg 149640
gccgaagctt tcgcgcacgt tcaccgcgtc caggtactgg agcaggtcgt gcaggcactt 149700
gcgcgttaag ttgcaatttt ccacgcacga ataacggta cagagcgcga agtgcagcag 149760
gttgtcggct ttgacgatgc cgcagcgtg tttgagccgc agatccgaga gcctcacctg 149820
cgtgacggcg tcttcggtct cgagcaaaaa cacggcggag tagcctagaa aggccgaggt 149880
gcacagcaac tcgctgcggt actcggccat ggagaccagc agcccgtgct ccgtgtgcag 149940
ccacagcttg tcgccgcgca ccgtaaagtc gagcacttgc ggctccatga tcatcacatt 150000
ctgtctagtg aaatccgtat ggacctccag cacgccgcgg atcatcaggg cctccatttc 150060
gaaatcggcc gacacgctct gggccgcgcc gctcctcgtc tgccgtgatc aagcggcgcg 150120
gcgcggacct ttcaagtgtt cctgggccgc cgctcgaggc agttcccctt tctggcactc 150180
cgcccgccgc ttcgcggctc atttggcgcc gacgcgcctt ctcgcggctg caaatcagct 150240
ccacgtatcg gcaaaacttg ctgtcgtcgt aggcggcggc cacgatctcg ccgaaggaga 150300
gctgcaggta ggcctcgggt acggggtcca gcgtgcccag cgccaggatg tgacacagat 150360
agggcagggt cacgcgctct accgtgtaat tggagtagac gatggcctct tcggcccctt 150420
gatgcgtgac cagacgccgt aggcgaaagg tacggaaata ctcgtttttcc cacaactgcg 150480 tgaggaagcg ttccagcgac tcggtgccgg gcacgaactg cgagaagaag ctgttggcca 150540
ccaggcggtt gtcttccacc gccagcggac ggaagggcgc cgcgtcgcgc gccttgcgca 150600
cggcctccaa cacgggcagg tggtagagtt cggcgtcgcg cgcgcccagg ctcatggagt 150660
cctcgcgccg cgaggcgtag cgcgtgagca ggtcgcgcag ttcgcgcacg cgattctccc 150720
aggtctggtt aagcgtgcgc aggtcctgga tctcgtccac ctgcgactgg atctgctcct 150780
ccaggcactt gataacctgc ttcttaaaca ggtcgcggat gtcccgctcg ggcgccgccg 150840
ggccgggtgg cggcggcagc agcccgacgt ggcccgcggg tcctcccacc acggcgccgc 150900
cgggtcccac cacgccgggt ccgcccggac cacgcgcggg tagtagacgg ttttggtcca 150960
ccagcgaggg ggtcaggtcc tgcagaaagg actcgacgct gtcctcgatg ccgatgcgcg 151020
atttgctgtc cgagacgtta agcaaaaact tcataatgga cttttttggcg tcgctgcccc 151080 ggtcgtgctg ctccatcatc tccaccagct tcttgcagtt gagctcgtgg cggctggcgg 151140
```

```
tcaccacttt cacaggaaag gtattgagca actggcagat cttttggtgg cggcagagcc 151200
cgtcgtagcg cagaatctcc tcgtgcaggt gtgccaccgg cgtggtgaac agcagcttgt 151260
cgcgctcata agccagcggt tcggccgcca cgtacaagcg gatgtgcttg ccgcgcagct 151320
gcgcctccag ccgctccgag cgcaccttct tgaagacgcg tacctcgggc gcgttggcta 151380
cgcgcacggc gcccaggcgc tcggccacct gcagcagcag cgccaggtta gcctgcagca 151440
ggtcctgcgc cagcgggtgt gtctcggtgg cccgctgcac ggccgcgcgt acaaattgcg 151500
cccgctcggc cgcctcgctc ggcttggtct tcacgtccag cagcggtacc agtcccaccg 151560
ttacgcacca atccacgtag agaccatagt cgtcgttatc ggcgtactga tataaaatgt 151620
cgcggaggcc gcccagcacg cccgtttgca cgctctggcg caacgaggcg ctccacacca 151680
acagatactg ctccaggtcc tcttcgtcca gcgcgcggta gggaaatagc gccgcgtgca 151740
acttccactc ctcggccacg cgccgcaccg tgatggtgtc aaagagcgtt ttgcacactc 151800
cgtagagcag ctgcttgcgc agcacgcacg ggtcgcgcag cacctggtgc atgctttggc 151860
cgcgacacgt ccccagaaag ccgtgcagca accgcaggaa gctcatcgtc tgccccgtgg 151920
ggaaaatgtc gatgacggcc tcgtcatcca cgccgcggcc cacgcccaag tacgacgacg 151980
ccttgatcct caacctctcg tcggccgcca agatcgaacg gatcgtcgac aaggtcaagt 152040
ccctctcgcg cgagcgcttt gcgcccgagg attttcgtt ccagtggttt cgctccatca 152100
gtcgcgttga acgaacgaca gataacaacc cctctgccgc aactaccgcc gcggcaacga 152160
cgaccgttca ctcctccgcc tcctcttctg ccgccgctgc cgcttcgtcc gaggccggcg 152220
gcacgcgcgt gccctgcgtc gaccgttggc ccttctttcc cttccgcgcg ctgctcgtca 152280
ccggcacggc gggcgccggc aagacttcca gcatccaggt gctggcggcc aatctagatt 152340
gcgtgatcac cggtaccacg gtgatcgccg cgcagaacct cagcgcgatc ctcaaccgca 152400
ctcgctcggc gcaggtcaag accatctacc gcgtcttcgg cttcgtcagc aagcacgtgc 152460
cgctggctga cagcgccgtt agccacgaga cgctggaacg ctaccgcgtg tgcgagccgc 152520
acgaggagac caccatccag cgcctgcaga tcaacgatct gctcgcctac tggccggtca 152580
tcgccgacat cgtggacaaa tgcttaaata tgtgggagcg caaggccgct tcggcctccg 152640
ccgcggccgc agccgccgcc tgcgaggacc tctcggagct gtgcgagagc aatatcatcg 152700
tcatcgacga gtgcggcctt atgctgcgct acatgctgca ggtggtggtg ttttttact 152760 acttttacaa cgccctgggc gacacgcgac tttaccgcga acgccgcgtg ccctgcatca 152820
tctgcgtcgg ttcgcccacg cagaccgagg cgctggagag ccgctacgac cactacacgc 152880
aaaacaagag cgtgcgcaag ggcgttgacg tgctctcggc gctgattcag aacgaggtgc 152940
tcatcaacta ctgcgacatc gccgacaact gggtcatgtt tattcacaac aagcgttgca 153000
ccgacctgga cttggcgac ctgctcaagt acatggagtt cggtatcccg ctcaaggagg 153060
agcacgtggc ctacgtggat cgcttcgtgc ggccgcccag ctccatccgc aacccctcgt 153120
acgccgccga gatgacgcgg cttttctctt cacacgtcga ggtgcaggct tacttcaagc 153180
ggctgcacga gcagatccgc ctgagcgagc gccaccgtct ctttgatctg cccgtctact 153240
gcgtggtcaa caaccgcgcg taccaggagc tctgcgagct ggccgaccg ctgggcgact 153300 cgccgcagcc cgtcgagctc tggttccgcc agaacttggc gcgcatcatt aactactcgc 153360
agtttgtcga ccacaacctc tccagcgaga tcaccaagga ggcgctgcgc cccgcggccg 153420
acgtcgttgc caccaacaac tcctccgtcc aggctcacgg aggggagga tctgtaatcg 153480 ggagcaccgg cggcaacgac gagacggcgt ttttccagga cgatgatacc accactgcgc 153540
```

```
ccgatagccg tgagacgctg ctcaccttgc gcattaccta catcaagggc agttcggtgg    153600
gagtcaactc taaggtgcgg gcctgtgtta tcggatacca gggcacggtc gaacgtttcg    153660
tggacatctt gcaaaaggac acgtttatcg aacgcacgcc ctgcgagcag gcggcctacg    153720
cctactcgtt agtttcgggc ctgctcttct cggccatgta ctacttctac gtgtcgccct    153780
acacgaccga ggagatgttg cgtgagctgg cgcgcgttga gctgcccgac gtgagttcgc    153840
tctgcgccgc tgccgccgcc acggccgccg ctcccgcttg gagcggggga gagaatccga    153900
taaataatca cgtcgacgcg gattcttctc agggcggcca gagcgtgccg gtatctcaac    153960
ggatggaaca tggccaagag gagacccacg acatcccctg cctgtccaac caccatgacg    154020
actcggacgc catcacggac gccgaactca tggatcacac cagtctgtac gcggatccct    154080
tttttctcaa atacgtcaag ccacctagcc tggcgctgct ttctttcgag gagacggtgc    154140
acatgtacac taccttccgc gacattttc tcaagcgcta ccagctcatg cagcgtctca    154200
cgggcggtcg cttcgccacg ttgccgctcg ttacctacaa tcgccgtaac gtggtgttca    154260
aggccaactg tcagatcagc tcgcagaccg gctccttcgt gggcatgctt tcgcatgtgt    154320
cgccggcgca gacgtacacg ctcgagggct acaccagcga caacgtgctc agtctgccca    154380
gtgaccgcca ccgcatccac cccgaggtgg tgcagcgcgg cctttcgcgg ctggtgctac    154440
gcgatgcgct tgggttcctc tttgtgctcg acgttaacgt ttcgcgcttc gtcgagtcgg    154500
cgcagggcaa gagtctgcac gtgtgcacca ccgtggacta cggcctcact tcgcgcacgg    154560
ccatgaccat cgccaagagt cagggcctgt cgctcgagaa ggtggccgtg gactttgggg    154620
accatcccaa gaacctcaag atgagccaca tctacgtggc catgtcgcga gtcacggacc    154680
ccgaacacct catgatgaac gttaacccgt tgcgactgcc ctatgagaag aacaccgcta    154740
tcacccccta tatctgtcgc gcgctcaaag acaaacgcac cacgcttatt ttttgacaca    154800
acaccgtgta aggaaaacgt gactttattg agcagggtaa aaaccacgta caagaaccac    154860
gttgtctatc cccaaaaaaa cacacaccgt cagggaacac atcgcctata gatagcggca    154920
ctttacataa aaccaccgta cctgcatcac ggtggctcga tacactggaa attcaataaa    154980
aaccaccgtg tctccgtgac ggtacttatc gggtcagcgt cttttgagat ttctgttcgt    155040
aaacttatcc gtttccccgg tccgcggtgt ctcctcgcga ggctgacagt cgacgggtgg    155100
tacctgcaag agaagaaacc cgggtgggag cgacgccgtc gctgggtatc aaccccgcgg    155160
ctgaccgtcg tccggtaaag gaacaacccg tcgtcgcaag ccgggttcga ccaagagaaa    155220
aaacccgggt gcgggggggag acgggtcgtc cttggttgt tcgcggacgg cgtacatgcc    155280
gcgtgggtca gtcgacggcg tcgctccgtg cggtcggtca tcattctgct tcacatatat    155340
gggttgtttg tgttttttt tataatgaat acgcactgat cctatccgtg actgcgcgtg    155400
tggcagagag gatgccttat aacatgtatt ttgaaaaatt gccaacagct ataatttctc    155460
tcatgtagca gaatagagac cttttgtcgt cttttgttt gtcattactt gttttccagg    155520
gaattagaga gagggaaccg cgcctccggc ggcggtgccc gcggacccg gccccttctc    155580 gcgtgcgcgg tgtgactggt tgagcgaatg agcagctagg cttggtggtg ctccgcgtgc    155640
gggggagaag acgattaaca acaaaaaata agtggaagtg gccggtgggt ctttgtccgc    155700
gtgcgcgccc atccgtcgcc gggaccgagc agaaagtgat gtggtggtac attgattttt    155760
tccttgacag gaaagaaaaa aaagagtttt gttttcctat gtgagaggag aaaggtatgt    155820
gaggagatgt tcgatgatcg tatgttacag ttatgctgta aggaagcttt tatcgtgcgt    155880
```

```
cctgtttttc atttgatgta tatgacacaa ttgaaaccta tcgataggcg tatatcgagg  155940
attcatcaat tcttagaatc gtcgtctttt tggctaattg gactttgccc atgttggttg  156000
tcattcgtgg cctgaggtca tcgtcgtcca cgacgacgtg tctatagcgt gcggtgtgat  156060
cattgtgtcg agccagagaa agcgcgcctc gcacgacgtt tgcggatcgg ctcgcgggtg  156120
tgtggaattc ctaagaacat aatcagctgg tcgtctttct ttgatgtgtt gttgtcgtcg  156180
aggtcttgct tcgttttctt ttttcttttt agtcgatgga acttttcttc ggtacgggtt  156240
cttgttatgg aagcttgtgt tttcgaacat gaattcgaaa aaataaaaag gcctatcttc  156300
gtttcaaaaa aaggacagat atcaatcttc ttaacttata tcatggtaaa ttcagaatcc  156360
tatggtgtct tattatctct aaagtagtca acattatggt ctaacttgta tttccctgac  156420
gagatatata tgatccttat aacctggcta ctatcatgaa caacaatatc cttacttaca  156480
gtcatcttcg tgagttaatg aagtataata tcggtcatct atcaacttat ctgctatgta  156540
acgtacccct ttaggtattt tgcgtttctt aacgagtgta cccgcctgtg tgaggcgaaa  156600
ctctgagaag tctaccgagt cgagttacaa gtcactaaaa cacttacacg agttatctat  156660
actaaaatca ctatctatgt tgtttgctta cctaattatt atcctacatg acgaagctac  156720
ctcccaacgt aaggtagggg gagaggagac agaacaataa aaagtaacta atgtttctta  156780
gaacttaccc gctaaggact taccaaacta tattcaccaa aaaacaacag ctacgtgttt  156840
catttgtttt aatctaccga agtaaaaaaa aaagatgat tagctatcca gaacctactt  156900
acttcttaat gttttaacta aggatgccta tgggattgga aaaaaaatca cagcaacttg  156960
ctactaatca gttgacagcg aagagactca taacaaagat ttctgggtaa tacggttata  157020
ataatgctta tggactaaag gatacttgga aaaaagaac gggctatgac tatagagatt  157080
cgtcgagata tcaaacttca aataggcggc tatcattcat ggttgtggtg actatatcgt  157140
ggagaaaaaa tgtgatcgtt agttagctag gtgagactta cagctatcca tccgtctagt  157200
ttttcgttgt aatgatgata gtacgtctat ggtggtgatc gattttggtt aacaatttgt  157260
tcgtttaaag gcttaatgta cttatgctac atgatgtatt attctttgat tcatcgttcc  157320
tcctaagggg gtgtatgtat gtatgtacta gtcgtatagt gttcctaaca tcatgactat  157380
tcagactatg gcttcatcta tcgtgtctaa agttcactta ttctactatt actatatata  157440
tgcactacta tgtaactagg atatggtcct ataaggtgtc ttctatcacg gtggcttgtt  157500
tatcgcttgg cggttacgag caagagttca tcacggacca gccgtgaggc agggcacacg  157560
cgggtcggcg gcgatgatgt cccccgcgaa ggggacaacg aaaacaagag gccgccggcc  157620
gcggccacgg atgcgtagcg gttacacaat gtttggttga gcgttttgtt tcatcgtcgt  157680
ggtggttttg ttgttctctg tatatatcgt gtggtggctt tatcgtcatc attattatca  157740
tcattcttgt ttccatcatc acgatgagtt ttctccgttt tcctctcctc cagtggtagt  157800
cgtgtatcat catcaatcat cgtagtgacg tcgttgctgc tgctgctctt gccttcatgg  157860
cggtatttct cttcctcccc cctaacccca tattaactcg tgagtgtgat ggttagagtg  157920
gctgcttgtt ttttttttct tttctctttg gaacaacaaa agaggataaa gatggtcggt  157980
gaatgtatta ttattatcat cattatgata cggtcgcgt cttcttctcc gatgacgaaa  158040
cctgcgcaca tcgaagaaaa gacgagcgcg cgaaccgata gccgtccgtc tgggacgaag  158100
gagaagatga tggggagagg aggagagccc cagaagccag agcagaaagg gagacgacag  158160
acatacgtcg tcaccgtcct ctggaggagg cacggcggcg ctgtttgttg tttggatgct  158220
tgattatatc ctgttctatg gggtagatta ttatcaatag gcttggtttt caaaggtcag  158280
```

```
cctgtgtatt gtcgtgtctt ttttttttcgt tctcatgatc gcggagacca cacagacgtg   158340
cgcgtctccc aatggctagg cgttcttttt aggtagtaat ttttgatct ttttttttc     158400
ttaacaagtc tggcttgatt tcttttatct atgatcgatt cttctttttc tcggggttg    158460
catcttccgt gaaagtaaag tgacactact ctaaatggta accatattat ctgttgatta   158520
ggagaaaaaa taatttttc gcacgaaatc gatcctaagt gaggtgattt acttgctatc    158580
acacgaaatg attatctttt gctgctaacg tactgaattt tttaacagaa ttgcttctcc   158640
gtaactattt ccgcagattc agacagattg tcaaaaaga atacggcaca gaaatagtgg    158700
gtctgtggct tttggttcgt gtacattcgc gtttgcgtgt cgagatttct acggtatgtt   158760
tattcttcct gcgatgatgt agggtccttg gtgtaagtag gatttcgagt atctctctta   158820
gagcgaacaa aataatcaaa aaacaacagc taggaaatcg agggttactc tacgataaag   158880
tgtctctaca aagtgaagaa tgttacgttg tggtggaata ataagactcg cgtgatcgat   158940
gagtgatcga gagcggctcg aaccttcttt aagagctttg tttagtgcaa ctttaaatta   159000
caaggagtag aaagctgaaa tgaatctatg aaggtgctat tctttgaata tcttactttg   159060
tacgcttcac attcgttatt tggatagaga gttgtctaga gaaaatctgt gattctctat   159120
gagtgttatt tttattatcc ttttggggac tacgatttt cttcttgttc tacataccac    159180
tactactcgt aatcacatac atggacgaaa aaaaaattcg tcaggcagta gataccagat   159240
tctccgacgt tacggcgtct ttttttttctt ttgagagagt atctgctgag attgtccgtg   159300
gtgtatctag tcgctatttt tgttgttact agtagttttg cacacagttt attcagtata   159360
gttttttcttc ttgccatgat caattaagcc caccacctt ttttttagag aggaggaatt    159420
tcgtcttgat ctccagccgg agacaacggc ggtggtggtg gtggcgggag agacttcaag   159480
gcaatgaaaa aaaaaattc gttttgccat caagtggtga cgataacccg tcagattgat   159540
aattggttcc tacagaaact attctaaccg cggaagaaag aaattgaaaa aaaaaattga   159600
caaaaacatc ataacataaa ggaccaccta cctgggacgc gcagttgggc ggcggactgg   159660
gacggcatgc tgcggcgatg ctgtcggtga tggtctcttc ctctctggtc ctgatcgtct   159720
tttttctagg cgcttccgag gaggcgaagc cggcgacgac gacgataaag aatacaaagc   159780
cgcagtgtcg tccagaggat tacgcgacca gattgcaaga tctccgcgtc acctttcatc   159840
gagtaaaacc tacgttggta ggtcacgtag gtacggttta ttgcgacggt cttttctttc   159900
cgcgtgtcgg gtgacgtagt tttcctcttg tagcaacgtg aggacgacta ctccgtgtgg   159960
ctcgacggta cggtggtcaa aggctgttgg ggatgcagcg tcatgactg gttgttgagg    160020
cggtatctgg agatcgtgtt tcccgcaggc gaccacgtct atcccggact caagacggaa   160080
ttgcatagta tgcgctcgac gctagaatcc atctacaaag acatgcggca atgtgtaagt   160140
gtctctgtgg cggcgctgtc cgcacagagg taacaacgtg ttcatagcac gctgttttac   160200
ttttgtcggg ctcccagcct ctgttaggtt gcggagataa gtccgtgatt agtcggctgt   160260
ctcaggaggc ggaaaggaaa tcggataacg gcacgcggaa aggtctcagc gagttggaca   160320
cgttgtttag ccgtctcgaa gagtatctgc actcgagaaa gtagcgttgc gatttgcagt   160380
ccgctccggt gtcgttcacc cagttacttt aataaacgta ctgtttaacc acgttgcgtc   160440
gtgacgttgt ttgtgggtgt tgctaggcgg gctggaaaga tgatgtataa atagagtctg   160500
cgacggggtt cggcgctctg ccggctgcgg cggcactcgc tccacggcct ccgacgagcg   160560
ttgcgctcgc gctttgcgcc gccgcgtcat ggatctccct actaccgtcg tgcgaaaata   160620
```

-continued

```
ctggactttt gcgaatccta atcgcatcct gcatcaaagc gtcaatcaga ctttcgacgt  160680
gcgccagttc gtcttcgata ccgcgcgtct ggtcaactgc gtggacggcg atggcaaggt  160740
gctgcacctc aacaagggct ggctctgcgc taccattatg cagcacgcg aggcttcggc  160800
cggcgccaag acgcagcagg gcttcatgtc tattgacatt acgggcgacg gggagctgca  160860
ggagcaccte tttgtacgcg gcggtatcgt cttcaacaaa tccgtctcct cggtggtggg  160920
ctccagcgga cccaatgaga gcgcgctgct caccatgatt tccgagaacg gtaatttgca  160980
agtgacttac gtgcggcatt acctgaaaaa ccacggcgaa tcctccagcg gaggcggtgg  161040
ttgcggcgcc gcgtctaccg cttccgccgt ctgcgtgtcc tcgctgggtg gcagcggcgg  161100
gactcgcgac ggcccttctg cggaggaaca gcaacggcga aggcaggaac agcgtcacga  161160
agaacggcgc aaaaagtcgt cctcgtctgc cggtggtggt ggaggcggcg gcgctggtgg  161220
tggcggtggc ggcggcggga gcggcggtca gcactcctcg gactccgcca acggactgct  161280
gcgggatccc cggttgatga accggcagaa ggagcggcgg ccgcctccct cctccgagaa  161340
cgacggtgag tcccggccct cctcgcgtca cggtgctttc cgagtggact cgtgagcctc  161400
ccgtagcgca cgagcgagca ggcgagcggt gttggtgcgc tggtggttgt gtggatgata  161460
accatgtgct ttttcgtgcg ctatgtgtcg tcccgtctgt aggctctcct cccctccggg  161520
aggcgaagag acaaaagacc accgcacagc acgaaggcca tggcggcggc ggcaagaacg  161580
agacggagca gcagtccggt ggtgctggcg gtggtggtgg cggcggcagc ggccgcatgt  161640
cgctgccgct ggacacgtct gaagcggtgg ccttttctcaa ttactcgtcc tcatcctccg  161700
cggtctcttc ttcctccaac aaccaccacc accatcatca ccaccataac gccgtgacgg  161760
acgtggccgc cggcaccgac ggtgcgttac ttctacccat tgagcgcgga gcggtggttt  161820
cgtcgccgtc gtcgacgtcg ccgtcgtcac ttctttcgct ccctcgaccc agcagcgccc  161880
acagcgcggg cgagacggtg caggagtccg aggcggcggc gacggcggcg gctgcgggt  161940
taatgatgat gaggaggatg aggagggctc cggctgaggc ggcggaggca ccaccgcagt  162000
cggaggagga gaatgattcc accactccag tctctaactg ccgtgttcct ccgaattcgc  162060
aggaatccgc ggcgcctcag cctcctcgca gtccgcgttt tgatgacatt atacagtcat  162120
tgaccaaaat gctcaatgat tgtaaggaga aagattgtg cgatctcccc ctggtttcca  162180
gcagactctt gccagagacg tcgggcggga ctgtcgtcgt caaccacagc agcgtcgcga  162240
ggaccgccgc agctgtctcc gcagccgcg ttggccccccc agcagccgca tgtccgccac  162300
tcgtcaccac cggtgttgta ccctcaggtt ccgtcgccgg tgtcgcgccc gttgccgccg  162360
caatcgaaac accagctgct cctccccggc ccgtgtgtga aatcaagccc tacgtggtaa  162420
accccgttgt cgccaccgcc gcggctgcca gtaactcttc ctcgtcttct tcggctccac  162480
tgccgccgcc gccaccaccg tcgggcggac gtcgggtcg ggcccggaac aatactcgag  162540
gaggcggcgg tggtggcggt ggtagaaaca gccggcggca ggctgcatcg tcgtcgtcct  162600
cctcctctcg gagatcgcga cggagaaaca accgccacga ggacgaggag acaacgacc  162660
ctctgctccg gttgtcgcaa gttgccggca acggccgccg gcgagggccc tcgttcctcg  162720
aggacggact cgaaattatc gatcccagcg aggaggctgc gatcgccgcc gcctcgatcg  162780
cggcgttttt cgacgattaa aaaccgagc cgagaccgga aaaatatga aacaggacgc  162840
gcttggacat ttgggtttcc accccttttg gtgtgtgtct atatatattg gtcactgatt  162900
ttttttacaa taaagagata gacatcacag ttcaccacct tgtctccccg gtgtgtctat  162960
tatcatcaat cacccacaga gtcgccagtc catggtctct cggtaatgcg tgtccagata  163020
```

```
cgcgttggcc agtataaaat ggtcgttgcc cacgaaggcg cgggtggtgt tgcgcggcga    163080
cgggtggcag gacttgagta ccaagtgccg ccgtcggtcg atcaggtact cgcaggtgtg    163140
cgcgtcggcg ccccacagca tgaacaccag atgctcccgg cgctctgaca gcctccggat    163200
cacatggtta ctcagcgtct gccagcctaa gtgacggtga gatccaggct gtccgtgcac    163260
cacggtgaac acggtgttga gcagcagcac gccgcgtcgc gccaggcgt ccaggcaacc     163320 cgaggccgga cgctgaaacc cgtccaccgt acgcgccagt tcgcgaaaca cgttgttgag    163380
ggagggcggc ggcggtcggc ccgccagcgt gccgaaggcc aggccgctgg cgctgccgtc    163440
gcagtacggg tcctggccca cgatcaccac gcgcacctgc tcgggcggac acagatagct    163500
ccagcggtgt acgtgctcgg gtgccgggta caccatctcg agttgccgcg cgccctccac    163560
cgccgccacc gtgtcgcgca gcagcaccgt gtcgtggtcg ggcaagctga ggaagcggat    163620
ccagtcggcg ctcagacaaa acacgcgagc ctgctcgtcg ggggttaaca gagagccttt    163680
attatcagca atgttagcga gcatccactg cttgagggcc atagcgcgag tgagccggca    163740
ggttgacgcg cgtctgcttc agctcgggcg gcagtccggc gtagtattta tctaggtggc    163800
gtagtagcgg cgggtccagc tggtgacgca ggcagaattc cttcactgcg ttgtacaggc    163860
cgtaaaagag tgtgatgccc tcgggcgcgg cagcggtgct cacgggcaga cgcacggcgc    163920
ggttggtacg cgtggcttcg ttgcgtatgg ccaccaccac gttaaagaga gacggtggca    163980
ccagctcgaa gcctaacacg tgttccgtga agatgctgcg cccgtatgac agtcgcgtga    164040
ggtcgtagcc gcggcacagg tcgtccacgc acgtgtacac ggccggcgag ccatcgccgc    164100
actcgctgta gccgcgcatc accgtcatcc agcgcggcgc tgtgtccgag ctcaacagcg    164160
tcagcagggc ccgcaattga tccggattgt tgtacagcag gccagagtg tccaggaaag      164220 catcgtccaa cagcacggag ttggcggcct ccggcgtaac gggacggtaa cgaataagtt    164280
gcgatagcgg gccatcgcgt ctggtaacat tcaccaacgg gcgcagccaa ctttcatact    164340
tgtcaccctg aaacacctca cccaacaggc atcgacgcgt tagttcgggg cactccgcgg    164400
ggactttctc ggcggcggta ggagcgacgc tgacggcgac tgaggaaaca atgggcagca    164460
gaaggcaaca ccacagcagt accaccggtc caggtgagaa agagaagccg caatccgggc    164520
ggcggcacat caagtctgcg gcacgatgag agtgtgacgg taaggagcca gttggcgccg    164580
aaagttggcg ctcaggtctt cgatccctaa aacgttatat attgcatcca gcaggtgagc    164640
caggctaaac ggattcacgt accaggtttg gttacccgcg acgatgacgg ccagaccgtg    164700
ggcgctacag ttggagaggt tcctgggtac gaaggtaact gagtcgatgt cgcgccacgt    164760
ggggaatgag acagacgact ggcgcacgct gtaatcacaa ctgtgattga cgtgtagcgt    164820
gtaatttcgg ttgcactcag cctcgaagta gaggggaac cacagttcgt cgtactcgtc     164880
gtcgtcctcc agttctggct cttcttcatc caccgcaatg tctacgctgc tctgagattc    164940
ctcttcgtac aggatgattg acaggttatg gctacacagg tcctgggcgg gaggacgcgt    165000
gggagcgcgg gtggtggtaa tgttttccag atcgtcaaaa gtcggagtgt agtctgacgc    165060
cgtgacgaca ccgtcgacgg agatggtaga agttcggcc ggtgtcacgg tggtaagtat     165120
ggatacagaa ggggagggg aagtagcgtt cgtaccgatg gttgtggtat tattattccc      165180
tgtgtttctt gttccagaaa ccgttgacgt tgagatggga atcgacgtgg tgctggacgt    165240
cagattgctg accgaggaaa ccgtggtggg agtggtgacg gtgttactcg tggtttgaagt   165300 gacgttaggg gaggtagtag tggtaccggt ggtggcgacg gtagtgtttg tcgtggcggc    165360
```

```
ggcagcggtg gtactggtaa cggtggtcgc gttggtttcc accgcttcac acagtaagca   165420
aaagcacagg gccgggaaaa gcaaccagcc ccgccatcgc cgccgccgct tcatgaggtg   165480
ggcaggcgaa agctggtgaa ttcgttgtac agcggcaagt ggggcgccgc gatcgaaggg   165540
tacgtcaaca agctgacgtt gatattaaat acgtctggct gcttttctac gatggaagcg   165600
cacagggtta cggcgtcaaa caggtctttc ttggtggcgc ccgagaccca catctggtat   165660
acacccgtct cgtggtacga agtagagcgc ggcaccaccg gacggatgca gtccagaacg   165720
cggttgggat cctggtgaaa gaatttgaac gtggctacgg cctgtggcgt gtgcggcatc   165780
gtctgcgtga tgagctgctg gcccgctaac acggtgacgt tgtgcaactt gagcagggca   165840
ctcttgaggg cctggaaagc gttgccgcac gaggcgctga tctgcagctg cacggccgtg   165900
gagtcgtgca gccgcatgag acgtgatacc tcttcgaaga cgtacttgta tttgctggca   165960
aaaagtggcg cgtaccgaca gtcggccggc aaaatgtagg tggcgttacc gccgttggtg   166020
gccacggcgg gcgcagcggc cgcggaggcc ggcgtaaaca gcgtcagcgg ccggtggtgg   166080
ctggtaaggt cgatcatggg cggcgtggtg accgtggcgg tggcgggcat gacggggttt   166140
gcggcgacgg gcactccggc cacagcggcg gccgcggcgg ccacggcggc acttgccgag   166200
cccacacccg ccggcagtcc tccgccaccc atgacgccgc cgggcagagc gtcgcccaga   166260
cagacttccg cagtggcggg cgcgctctca gcggtcagta cggtttgccg atcgacctcg   166320
cgacgaaagc tggtgaggaa ctcactgtga tccatggccg cagggcccga gatcccggga   166380
ttctgcgggt gctgaccgag tgcggggcga gttatatgga agacgattag cttggagcgg   166440
agttttgcgt ccctagctga cctgcggatc agcgacgtgc cataggggata gactgtgagc   166500 ggcggccgca acgcgggggt cggccgccgc tcgtcgtcac ggggcggcgc gagggaggag   166560
gaggtggtgg gtacgatctt gacgtggttg acgtcctgcc cgtccggggg aatacgcaaa   166620
aaaccccgtc gcggcgctac cacgatggtg cgatgggtct ttctcttgtt ggccggggcc   166680
agggacttgc agatgcgtgt ggagccgtag acgatctgga cgtggtcctg ggagaacatg   166740
accatcgccg ccaacgctca gcgggggggac gtgttgggaa cacagaggct gagggaaaac   166800
tccgtagaag tcagcgaaat aaagacaaca cagcagccac tcctctcgtc tcgggcccta   166860
ccactgcttg aagtagggca ccgggtgttt cttttcctca acgggctcct ccagtctctt   166920
ataggaccag tcccgccggc gcgccagcat gtaggtcacg tacaaaagaa taatcaccat   166980
gaacaccagg aaagccagca cgccgtaggc cagcagccgg tcctcgaaca gcgggtcgct   167040
cttgataaac acgtaggtgg tggtaaaact tcggcccgca atctgaacgt ggagacgcac   167100
gacagtatac gtgccgttga ggtagaagac aaactcgcgt aaccgttgtc cgttatacgt   167160
cacgttacta atattccacg gcggaatgag ctggttgccc tgatgcagat gcacggtgct   167220
gttggggtga tagaggctgc taccgttgag caagcagtgt tcgtgttcct gaagcagcac   167280
gcggacccgc atcgtggtgg cgttcaggcg agtcccgtac acggcgtaga tgggataggt   167340
gaaaaggtcc caagtggcgt tgtgatggcg gccccagctg aagaaagagc acgtgtactc   167400
agtggtctcc tgcggcctga gtcccgagat aagcagctct tgagcagtag cgttgtagga   167460
gagatgtagt tttcctgtgg ataaaattca taagttgttt attttgttgg caggttggcg   167520
ggggaggaaa agggggttgaa cagaaaggta ggtgctactt accttcatta tcgggggggga   167580 aggcgctaag atacccccacc tgagtgaagg gaccccttgca gtctgtccgt gcataacaag   167640
taactgataa aatgtctgga ttttttggtgt tattcaacag gataactttg caggtggcgt   167700
ttagagacac ttggtcgtgg ctgtagctgg cttcgcaatt cacagtatac aggtgcccct   167760
```

```
ctttctgcgt cgtggctatc acggaagtgg aggcggacga ggtagaggtt tgtaccgtgg   167820
tggtgacagc agaagtgacg ttgttagagg tacttattga cgtagtagac gtgacggtgg   167880
tattactagg ggaagtgacg gcgcttgtgg tgctactttt cacccccggg tgcatgtcgc   167940
ccaagagcgc aactacgagc gcgatcgcca gtacggaaca catgttgccg tgtgacgaga   168000
cggcgtgtgg acgagctata tgtggcagga ggtcgcgtca cctcttgtga cgcctaaacg   168060
tccagctcca gataaaagag gcgttaataa tgaagaccac aaaaaccact tgcgtcagta   168120
tgacaatcat aaaggctcgg tgattgctac gcctaaagta cgcgggatta ccaccagtt   168180
catcctgctg aacaaagtgg atgattgacg tattggtgtt actatccgtg ttgttgacca   168240
tggatttgac taagaaagtc ttggcgccaa agtcccgtt agagcccag caggtgacgc   168300
tgctattcac ataagttccc ggtgccccg ctagcatgta tttcagttgg tgggtataat   168360
tttttctgtc gttatccatg tcattgctgt agttgacctt gctggtgaga aagcgtgttt   168420
tcaacggggc acttatcatc atccctgagg ccaaaaggg cgaattgcaa gctgtagtgt   168480
tacaaaaat agtcaagtta gtgtcattgt attgataaat gtaagccatg cttacttcag   168540
gctcatacca cccgattcca atcgcggccg ccatcgttac cacgtcccat cttcccagac   168600
ttaccaccgc caccactaac agcgtcaccc ccgcacggta catagttacc ctctcgacgt   168660
cgccggctgt caatgacgtg cctgcgtcag tggctatgat ttatagcttt tgggcccaac   168720
cgcaacggat ctgtcgtaat ctaccttcca cagggccgcc gcgacgatgc tgaacgacag   168780
gatcagacag acggcgtaca aaagtcctag gtcggcgtcg acgcggcagg tgcggatgtc   168840
tgcagggtg ggtagatggg cgatgcacaa ctctttctcc ccccgcccgt acatcccatc   168900
ttgtatcagc agccgtagcg tggcattgat ggtcagcggg gtaaccaaag aaatcacata   168960
gggatgtgta caggaagtgc agtgacgggt atccgtgaga tgtaagtcac caccctcctc   169020
accgtcatca tgaaagacca ggactcgggt gagacgaccc gatgaatact ggatctccca   169080
ccacagtctt tggtccaaca ccgagagggc gcaagagatt ctaagtctcc ctgggttggg   169140
ggagcagatg taagtcccgt atgtgcctct cgccatcagg gccatacaca tgaggggag   169200
aaggacaatt atccgggacc acccgcaccc ccacatcacg agaccagaga cggagatgta   169260
taaaaaagc tacttttatt aaacagcatt ctcaccacac gttaatactg tcacgggaa   169320
tcactatgta caagagtcca tgtctctctt tccagttttt cacttactga gacttgttcc   169380
tcaggtcctg gatggctgcc tcgatggcca ggctcagggt gtccaggtct cgggagggg   169440
tctcggtggg ctgctcaaac tgccccacgg cgtaggcctt cgcggccgtc tcgtagatag   169500
gcagcatgaa cccaccctgg ttggtggaga agatgcgcac catgacctgt ttgggaaact   169560
tttgcatcag gggcaggcac aggttgagag cgcccaacag gtccacgggg gtggcagcgt   169620
ggatgatcat gttgcggtaa tcggaggaac ggggcataa ttggtgggtg tgcaattctt   169680
tgaggctcca cgcggccttg acgccttcgt tacaagcatc ggctgtgcgc tgcgccactt   169740
cgggtggatg tgtcacgggc atggtgtgct ccatgaggaa gggagtggag agggccaggt   169800
tgcacatggt gcccaggcga caccgcaccg catccacctc actcttcacc tcatgattgc   169860
gggtgtagat aatctggatg cccttgttgt tcacctgcat ggttttgcag gcttgatgg   169920
cctcatctaa cacctggtgc atactgggaa tcgtgaaggg caggttcttg tactcaagag   169980
agcgattggt gttgcggaac atgcggctca cctcgtcaat cttgacgcga ccccgccgag   170040
tctgcacgtt gggtgtgcag aagggggtgt tcttatcttt catgatattg cgcaccttct   170100
```

-continued

```
cgttgtccaa ctcggagatg cgtttgctct tcttcttgcg gggtccggtg ctcgccccgc   170160
cgctgctctg atggccgcag ctcagcagag aggaggaggc cgcgccacca aaaccgccgc   170220
gcccatggtg gctcgaggtc acggatgctc ctccgccact gctgcatttc atctcctcgg   170280
actcactctc cgagtccgaa gccgaactgc aggaggagga agacgaagag gaactatctt   170340
catcgggccg gcccaaggga tcgggaagag gagggtggtt catctgggag agcgggtgcg   170400
tgggagaggt cactcgcggc gtgccgctgc cggtggaagg ggaagacgcg gtagcaccgc   170460
gggtttcgac ttcttcaccc tgttcttcct cgctatcaga gatcacgata cagccggcgg   170520
tatcgataat cttgttgcgg tactggatgg taaagtcggg ctcgggcttg atgtcttcct   170580
gtttgatgag gggcagcatg ataggcgcgg gaggcacggg cggtttaata atcaccttga   170640
aaggacgcgt ggttttgcgc ggtttcttac gcgggctgag ctcgggagta gcggatgccc   170700
cggggagagg agtgttagta accgcgacgc tggtgggggt cggcttgtta agaggggcgc   170760
tgctaacgct gcaagagtgg gttgtcagcg tggggccggt gctactggaa tcgataccgg   170820
catgattgac agcctgggcg aggatgtcac ctgatggtga taagaagaca cgggagactt   170880
agtacggttt cacaggcgtg acacgtttat tgagtaggat tacagagtat aacatagagt   170940
ataatataga gtatacaata gtgacgtggg atccataaca gtaactgata tatatataca   171000
atagtttact ggtcagcctt gcttctagtc accataggat gggtgctctt gcctccagag   171060
gcggtgggtt cctcagcacc atcctcctct tcctctgggg caacttcctc tatctcagac   171120
actggctcag acttgacaga cacagtgtcc tcccgctcct cctgagcacc ctcctcctct   171180
tcctcatcac tctgctcact ttcttcctga tcactgttct cagccacaat tactgaggac   171240
agagggatag tcgcgggtac aggggactct ggggtgaca ccagagaatc agaggagctg   171300
acaccagcgg tggccaaagt gtaggctaca atagcctctt cctcatctga ctcctcggcg   171360 atgcccgta gtcatccac actaggagag cagactctca gaggatcggc cccagaatg   171420 tactgggcaa agaccttcat gcagatctcc tcaatgcggc gcttcattac actgataacc   171480
tcaggcttgg ttatcagagg ccgcttggcc agcatcacac tagtctcctc taagacatag   171540
cagcacagca cccgacagaa ctcacttaag agagagatgc ccccgtacat ggtcatcata   171600
caagcgtcac tagtgacctt gtactcatta cacattgttt ccacacatgt agtgaggata   171660
tccataaata tgtgatcaat gtgcgtgagc accttgtctc tctcctcatc caaaatctta   171720 aatatttct gggcataagc cataatctca tcaggggagc actgaggcaa gttctgcagt   171780
gccgccatgg cctgactgca gccattggtg gtcttaggga aggctgagtt cttggtaaag   171840
aactctatat tcctgtagca catatacatc atctttctcc taagttcatc ctttttagca   171900
cgggccttag cctgcagtgc acccccaac ttgttagcgg cgcccttgct cacatcatgc   171960
agctccttaa tacaagccat ccacatctcc cgcttatcct caggtacaat gtagttctca   172020
tacatgctct gcatagttag cccaatacac ttcatctcct cgaaaggctc atgaaccttc   172080
tctaagatat ctaaggcatt ctgcaaacat cctcccatca tattaaaggc gccagtgaat   172140
ttctcttccg tctgggtata ttttttcagc atgtgctcct tgattctatg ccgcaccatg   172200
tccactcgaa ccttaatctg tttgactgta gaggaggata acaacacata taagtatccg   172260
tcctcctgac tcatttatcg ctatctcgat gccccgctca catgcaagag ttaatcttta   172320
ctctatctga catacacaag taaatccacg tcccatgcag gttagtatac atcacataca   172380
tgtcaacaga cttaccgagt tctgccagga catctttctc ggggttctcg ttgcaatcct   172440
cggtcacttg ttcaaaagtt ttgagggatt cttcggccaa ctctggaaac agcgggtctc   172500
```

```
ccagactcag ctgactgtta acctccttcc tcaacatagt ctgcaggaac gtcgtggcct 172560
tggtcacggg tgtctcgggc ctaaacacat gagaaataga gtcataagca catgggtcac 172620
atacaggaga tatgtatata acattaatac aattttatta aaaaaaaagg gggggcacaa 172680
accccgacac gtaccgtggc accttggagg aagggccctc gtcaggatta tcagggtcca 172740
tctttctctt ggcagaggac tccatcgtgt caaggacggt gactgcagaa aagacccatg 172800
gaaaggaaca gtctgttagt ctgtcagcta ttatgtctgg tggcgcgcgc ggcagcaacg 172860
agtactgctc agactacact gccctccacc gttaacagca ccgcaacggg agttacctct 172920
gactcttatc agaacacaac aactcagctg cctgcatctt cttctgccgc tgccttaagt 172980
cttccaaatg cgtcagcggt gcaagcccgc tccccgagct cattttcaga cacataccct 173040
accgccacgg ccttgtgcgg cacactggtg gtggtgggca tcgtgctgtg cctaagtctg 173100
gcctccactg ttaggagcaa ggagctgccg agcgaccatg agtcgctgga ggcatgggag 173160
cagggctcgg atgtagaagc tccgccgcta ccggagaaga gcccatgtcc ggaacacgta 173220
cccgagattc gcgtggagat cccacgttat gtttaataaa actgcgggc actggggacg 173280 gtggtgttgt atatgtgaat ttgtaaataa taaatgagac cccatcctgt aaaaatacag 173340
agtccgtgtc agtctctgaa ggacagtgta ttggcatata gccaataaag agagttgtgg 173400
caaagagcca tgttatggat tagtaatgga aagtatcgtc accaataggg gagtggtcaa 173460
taatggtcaa taacccacac ctataggcta agctatacca tcacctataa catgaggaag 173520
cgggggtgta tagaccccaa gccaaaaaca gtatagcatg cataagaagc caaggggtg 173580 ggcctataga ctctataggc ggtacttacg tcactcttgg cacggggaat ccgcgttcca 173640
atgcaccgtt cccggccgcg gaggctggat cggtcccggt gtcttctatg gaggtcaaaa 173700
cagcgtggat ggcgtctcca ggcgatctga cggttcacta aacgagctct gcttatatag 173760
acctcccacc gtacacgcct accgcccatt tgcgtcaatg gggcggagtt gttacgacat 173820
tttggaaagt cccgttgatt ttggtgccaa aacaaactcc cattgacgtc aatgggtgg 173880 agacttggaa atccccgtga gtcaaaccgc tatccacgcc cattgatgta ctgccaaaac 173940
cgcatcacca tggtaatagc gatgactaat acgtagatgt actgccaagt aggaaagtcc 174000
cataaggtca tgtactgggc ataatgccag gcgggccatt taccgtcatt gacgtcaata 174060
gggggcgtac ttggcatatg atacacttga tgtactgcca agtgggcagt ttaccgtaaa 174120
tactccaccc attgacgtca atggaaagtc cctattggcg ttactatggg aacatacgtc 174180
attattgacg tcaatgggcg gggtcgttg ggcggtcagc caggcgggcc atttaccgta 174240
agttatgtaa cgcggaactc catatatggg ctatgaacta atgaccccgt aattgattac 174300
tattaataac tagtcaataa tcaatgtcaa catggcggta atgttggaca tgagccaata 174360
taaatgtaca tattatgata tggatacaac gtatgcaatg ccaatagcc aatattgatt 174420 tatgctatat aaccaatgaa taatatggct aatgccaat attgattcaa tgtatagatc 174480
gatatgcatt ggccatgtgc cagcttgatg tcgcctctat cggcgatata gcctcatatc 174540
gtctgtcacc tatatcgaaa ctgcgatatt tgcgacacac agaatcgccc aagtcaccaa 174600
agtcgtctat cgccatcccc cgtaaacgat ataagcgcta tcgccagata tcgcgtatgc 174660
ccaaaaatca cttttggaaa aatggcgata tcagttacac agaaactcac atcggcgaca 174720
ttttcaatat gccatatttt caaatatcga tttttccaat atcgccatct ctatcggcga 174780
taaacaccac tatcgcgcga catgaattta gtcggcgaca gaaatctcaa aacgcgtatt 174840
```

```
tcggacaaac acacatttta ttattcactg cagcatatag cccatttag cgcggcacac  174900
atccagccgt tgtgttttt taacgctctc caggtactga tccaggccca cgatccgggt  174960
tatcttgtcg tattccaggt tgatccatcg atagggaacg ctgccagcgg cgcccagcag  175020
gtactgcgcc ttgtcgttca ctttgccgca gcgtattcgc ccgtcagctt cgaggtataa  175080
cctacaacac ggaggggaag gggggtaca aaacgtgaaa ttagactttt tttttaatga  175140
tgttttgtcc ctctgtctta ctttcccata ggctgtaagg ccctcgagga agagacttac  175200
ggattgtagt tgcagctcgt cagtttgttg tgtacgacct ggcgtgtcaa tgaatgggtc  175260
atggtggtga cgatcccgcg aatctcagcc gttttctcgg gactgtagca gacttcgccg  175320
tccggacacc gcagcctgtg gattcatgaa aatctactct ggcattcccg aggatcgtcg  175380
atggaacatg gctatcagaa acgtcgagag acaaatccag acgcaccaca gaacgcagac  175440
aatcataaaa atacgtacgc gacggtgaag cgattgcaca ttttgaaatc gtaacagcgt  175500
tccggcgggt ggttgacgtt tatgaattcg caacattctt ctgcgcgcac ccgcggcacg  175560
cggctgtgac ccaatagcag ccacaacgtc gtcaagaacg gcgtcaggtc tttgggactc  175620
atgacgcgcg gttttcaaaa ttccctgcgc gcgcgacggg ctcaaacgat gagattggga  175680
tgggtacaga aggtgtaagt ctggttattg gcctcggtga acgtcaatcg cacctgaaaa  175740
gacacgctgt agtcccggaa gacgtgggcc cagctctcca gcttcatcac acacatctga  175800
taacgcgtgc catcgttgac gacgaagcgt agcagcttgg tctgcttggg caccatgtgc  175860
gctccaaaaa tcttggcgtc ttccacgctg atctgcacgt ttccgtcgct cggtttcgaa  175920
gccgtttggg gcatccgttg gaggatggtc tggttgcgac cgctcagata ccagatcacc  175980
tttttcaccc aggtggagct tctctccacc aaggtctggc cttccggtt gtacagcaga  176040
tacagggtct cgttgcgaca ctcgggaccc gttgatacct gctggaaccc cgagaattgc  176100
aagggggacc gtggggcga gggatagaga aaaggacagt aaaacgtcgc cgcgtcatgc  176160
ggtttggaat acgtcagttt agaccatggc ggggacggat tctggtttgc cgttagcgtc  176220
gaccacggag acgccagaca gggcgttgcc caaaccgcgc acagaagcag gcagtgaaag  176280
tggtgacgaa gcagaagccg cagcatatta tttcccgtga cgcaggctag ttggcaaaga  176340
gccgcacgct gaactcgagg ctccgggcgt gtggcgccag cgaaccggcg gcgttgaacg  176400
tggtcctttt gttggtgccg ccgcgacggt tctgacgtct aaagtcgctg atgagcaacg  176460
acacctcggt cacgttgatt ctgcaagcac aggttccaaa cgtcatttca taccccatgc  176520
ggttacttag ccgttacccg ttcgcccta ccttcccgtt gtcatgcacc tttagcgcgt  176580
accctcacct cttgagcacg tcaaagttgt ccaagccgtg gctcgcatcg tagtggtagt  176640
tcaacgtgag gtccacgagc tgttccacat acttgtaacg ggtttggtcg ggcagcgcgc  176700
gagagcacgc gtcccagtaa tgcggtactc ggtaataatc gttttttttc cgcggtttcc  176760
cgctggcact gacccagcac cacggcgcac agacaaacag acagccacac ccgacacagc  176820
cgcatgttgc agactgagaa agaaagcttt attatgagac atcatacaca tagtataggc  176880
gaggtgatgg ggcggggaaa gagttggaac cgaaagacaa aaaaaaaagc ctagtcgtac  176940
tcgggatctc tgagcgagac gggttgcatg gcaactttca ttagtttggg aatctgccag  177000
ctggtgctgt tcgaaggttc ttccattcc gaggcggtca gttcatcgta caccgaaacg  177060
tagtacctga tggggtcctc ctcattgtcc gagaggtgag attcgatggt caaaggcgag  177120
cctctcccat aattgggatt cacgaacgac gtgtccaagt tgccatcctt tctgaaatag  177180
atgacgttct caggatcatg tttcatgcgc tcgcgggccg cggacgcctc ctcctcctcg  177240
```

-continued

```
tcccagtccc gagtttccaa ccgctgataa gggctcgagg aacaaaatcc ggcggggatc  177300
tgagaacctc gtcgggaacc gctgccaaac gggctgctgc cgccactgtc gtccgtgtcg  177360
tccaacaggt tgacggcctc ttcgtcggcg aaacgaaagc ggcccgggtg cttgcaacac  177420
gaggagtaaa ctaccgcgat cagtaccgct atgaagctga aaatggaggt gcctgtcacg  177480
atgtagaaga ggatagccag cactttcatg atttcgtcat tgcgcgcgtc gtgaacggaa  177540
gattcgcggg cagtggtcat gttggtttcg gttgtaggtt cgctactcgt ggtgctctcg  177600
acggtatttc tgctgctggt gctagtaggg acgtttgtgc tgctggtcat atttgtagcg  177660
tcgctgaagt cgatgtgaag cagcaacccg aacgcgacca ggaccaggaa tgttgcgcga  177720
aggagacccc gcggggccgg cattcttgag acgtggcgac gtggatttct tgttatgtcc  177780
gcgaacgacg tgtaacgagg acgtggtttc cgcaagcctc taccgacgcc gcgacaccag  177840
gtaggttatc aaaacgcgag cccatatcgc cgccatcatt gtaatcagca atgtgttgag  177900
gtactgcacg atgaatctgt ctagtgacac cagccaaccc tctgcttttg cgggcaagcg  177960
cgctttcggt gacagggtgt atcgtacgta gccgcgggtc aggcgcgcgt tgtagcggta  178020
cacgcagaaa tctatccaca ggccaacgcc cggctgtagc ttcggatggt ggataatagc  178080
gcggtgacgt acgccgcgtg gctttagaat ctccacctgt aaggccatct cctccaggta  178140
gtgggtctga ctgcgacgca gcgtccagtt catgtaaaag tcggtctcgc cgtgtccggc  178200
cacgaagagg ctgcttacta atccagtcta cattgtgcca tttctcagtc tgattgcatt  178260
ttttagagtt atgttgccac caacgtatcc tgttacgttg attacctcgt aactgcggtc  178320
gcatctttta tggactgtat aattgaaacc atcacaagta acggtcgtgg tggtgttggt  178380
acatgtggta gtctcaacgt ttgtatttgt cgttgtggat atctgtgtgg ttgttttcga  178440
cggttttgta gaaacggtgg ttgctggtgc agttgcagta gagcaattta tagattctga  178500
agtgctttta ttgctgataa ctgttgtact gtatgttgat gtggctgtct cagtactagt  178560
ggaatagtta acggtagtac tacagggaca ttgacaggaa caggtttgat tgcagctttc  178620
tgataacgcg gatattagta tcgtccacat aaccgtaaat cgccagtcca ttgcaatatt  178680
agttctcgct caatgggcat taatattcct ttgaacgctg agccttacag aatgtttag   178740 tttattgttc agcttcataa gatgtctgcc cggaaacgta gctcaatctt catgttctgt  178800
gtgatatcga acaatgaatt ctgattcact gacggtgtct tgcaacatat ggtactttt   178860 gttaaaggct cgtcgtgcaa aaaacagaac tatgcaggcc atacaaacca acacgatggt  178920
ccatacggtg cggcttcttt gcgagctatg atagagatta cgtttgtggt gatgtgtatt  178980
gttagtatgt tgacttcctt tctctctatc ttcattttcg atatcggtgt tgtatctagg  179040
gcaaacgaaa gtagcattaa tagcttcagt atgattttt ggtgttacta ataggtagaa  179100
attttcatct tcgtgatgtc ctgtgaagta atttcttta aaacaacgtc tgctgtacct  179160
gccggaattg gtgatattta gatcgtacag atgtagttct gtgttgttgc acgaacgaca  179220
taagtcatgg tacagtgaag gtctttcatg ttgagaatga catacagtat gagaggtaag  179280
gatgcgtaac caataccaag attgggtatg tgcgttctta cgatgaccta gatgatgtcc  179340
gtgtgtggat cgattgtaat gtcgtatcca ggcgactgaa agacaatccc acgtagaatt  179400 acctttatg gtgacattac tcccttctat tcctgttgta ttagtttctt tgaaacgtat    179460
gattgttgtc tctgtgtgac aagcgttgga agagttagta cggttgtacg tggtgtacgt  179520
tgtggcgctg caatttgtaa gccatggcgt gcttataagt gcagtattag tggatacgtt  179580
```

```
gtgcgaagtt tcatctgacg tgatagttac ggtgattgtt gtgttataag atgatgtagc    179640
gtttgctgtt acgttggtaa aagataatat agtgttggta tttgttgaaa tcaattctgt    179700
agtggcagcc gtattggata tattagcata tgatgtattg aatgtagaat atacggttgt    179760
gaaagtactc aagtcggagg taacgttggt gatgttgcca atggttgacg cttgtgaggt    179820
gacagatgtg tgtggcgtcg ttgatgtgtt gttattcgga gtagaaaata cgctggtcac    179880
aaaggtggta gaagcagtgt tgggtgatgt gatggatgca gtattggtag tagtactgtt    179940
gcatgtaact ctatgcagaa tatagaatat tatgattgta tacgccgtat gcctgtacgt    180000
gagatggtga ggtcttcggc aggcgacacg catcttttac tgtaaatccc cgtccaccgt    180060
caacaacaaa ggttccgtat ctaggtccgt ccgcagatgt tcagcgtcct gttccccgat    180120
tcgttgcgat cgcaggaagc agatgaccag cgcgccaaca aagatcatca ttcccgaaac    180180
ccaggcgcaa tggagtgaga ggccggacca ctggcgtttt aaatccgaga taattgcccg    180240
gtctgcctct tgggaatccg taaccacaac tctccctggt cccggataaa agcatcgacg    180300
cgtttccaag gctcggcaga agctacgtgg gtggatgatg aggtagaaag cctcgacatc    180360
gccggtatac tgatcctgca ggaggtagac tcccgtatct ttaaccgtga gattgtacag    180420
cgtcagattt tggcgcgtgc acgcgaacgc cgcaccgccc tgacgcgtgg tttctttata    180480
ggcgtctgta atgatacaaa gtggcggcat acgacgcatg tatctgctgt agatatcata    180540
acgctgccag actacgctgt gatggctagt gttaagcctg gtaaccagcg tgcgtgtacg    180600
gtcctcgcag gtggcacggt agttggcgag ctttaggggg ttttttggttg gttcgacggc    180660 gttcgatgaa cttccctgag ttgtgaacaa aaacagcgac gtgactatga caagcgtgag    180720
gggggtgctg taggtctgca tggtgcaaaa cacgttctcg ccttccttat cagacgttgt    180780
cgtcctcgtc ctcttcgtcg tctgtgcccg tcggttcgat caacggggag ttatctttct    180840
gtctggaggg tcggtatgga atccgttcgt agatgttctg cttttttagcc gcgtgttgtt    180900 ccagcttttt gcgtgtcagg ctccgatagg ccagacattg atctacctcg gtgcccgtgt    180960
tgtttttctc ctcctcgcgc gcgtaaatta caaagaagac caccagcagg actatcagcg    181020
tagccacgaa cgagcccgcg ccccaggccg agtatgcgcc tagcatggta atgggttctg    181080
tgatccggca tttgcacatc gcgtggcact tgctgccatt gccggtatta gatgatgtgt    181140
tattcggact gcacttgcac gtcaaatggg tattttctga tttcacgaga cagttggtgg    181200
cgactttggt ttcggcgcag acggccacat agcttaccaa gctgagtgcc agaaagcaca    181260
ccgcgtgcat tacacgcgga tacatattaa acaccgtgt tccacaagca ccgcacacgt    181320
caatcctccc cgcacggtct tcagcccgcc catgacatga tctccctcac gttacccttc    181380
aacaccctgt agtactctgt ctcggcttcc ggtccccatg tcctaattat aacaaaacac    181440
cgtgacactg tccatctccc tgtctttttg cgccgccggt ccccccaaa tcatgtctct    181500 agatgccgcc ggccaccaac cggaggcacg gcggctattg gattcggcat tggtgcgccg    181560
cgtcttggcc tgcatgatca tcgtcatcat gattgccatt agcatctgga tcctgaccta    181620
cgtgctgttt ctctaataag aaccccggcc cctgacggta atttttccttt cttctccgtt    181680 tctcctcagc tgccgtacgt gatgcctcac ggccatctcc acaggccct ctccccgacc    181740 tcctggacat gtgagggctt gttgctcctc ctgggattgc tggtgctctt ctttcaccac    181800
cacaaccagt cggccgtgga gaggcgtcgc cgcgtctcgt tcgtcgaggc cgatcgactg    181860
ccgcatgaga gcgggtggta ttcttccgat gacgacggaa accgggacgg tgatgaggaa    181920
actggagaga gccacaacag aaacagcgtg ggactgtccg ctgttttttag ctgactggcg    181980
```

```
tgcgacctgt aaaccgttac tcgggtctca agatggtttg gaagttgtga ctcatcttcc    182040
tgtgggtgat acccaaccgg acgcgagtgt tccataaaag ccgggcgctc cggcgagacc    182100
atgccatcct cgccttcgga cgccccgctc ctcttctctc tcctctcctc cccgctgccg    182160
cggccattgc cgccgccgcc cataccatcg gcatgtcggc cgacaaatcg cagctgtctt    182220
cgccgccgca gctgtagcag ttaacgtcgc cggcctccag gaggagatgg cgctgtgcgt    182280
cgtctcttcg tcccgtctcc ctctgtggtc gtgggtggtg cgagagtaca cgatgggtgg    182340
ctctcgtctc gggggaccac aggggagggg gggtaattta ttattcgtat tactgtaatt    182400
ttgtatcgct taatttgttt agagccgcac gcttgacaac gccttgtata gccttattta    182460
tcccgatgac tttttctcc gtacaagaaa tggacgtcac ttgagcagac acagtttcat    182520
cgaccacgac agtctcatga tctgactacc tctgacccgc aacgagaaa accgaaaagt    182580 aaaagatgac cgcgccctcg gagtcctttt ttccttttca atcatgaaag caagaggcag    182640
ccgagagaat gccagtaaga gacgaccatc gcagacacag tacgatactc atcttagaac    182700
gaaccagcga ataaccatca cacgtacagc agaatctcat gaactagtca accaacgtca    182760
taaaatcttc acacaatcgt ttttgcgaac ttttaggaac cagcaagtca acaaaagact    182820
aacaaagaaa aaccatcttg gaattaaaaa agtagcatc gttaccttat gaaccagcag    182880
cattcagtat atacaccaga tataatatat ttattaatgt atcctctctt tctcctgatg    182940
taattttgtt tttgtaaatt caattgttga aagtctctcc ctgggggaat tgcatatctt    183000
attgatgaag aagaaatccc tgccatatgt gttgtcaaac tatcattatt tctctatatg    183060 ggtattttt ttctaagaag caaaagacta gcagcagcca aataaaacct gatgaaatct    183120
ttaactgaac tcccagtggt ctgtgtgtat atttctgttg gtggtcggtt gtctgaaccc    183180
gggtgggttg ttcggaaacg gcgggacggg gaaacggatg gaaacagcgt cgctatatac    183240
gtgacttttg atctaaacgg acgtcgctag gctgacagtt tacgaattgc taaacaagat    183300
aggaacaaaa caagcggggc tttgcctggt aggatttcct gtggaaacaa taaccggatg    183360
tgattgtggc tggtacataa gctggttctg gctgcaagcg cttttcactg cattaggttt    183420
ggcgtttgct tttgcctggg aacgctatgg ctataacggg aaagaaccgg tttggcaaca    183480
ttccattgtg gggggggggt acttatagcg tgcctagcta tgacgttgat atatgtggat    183540
gcggataata ctcgtaatga gctaaaagcg acgactggta gtaattttac cattacgcat    183600
aggaaagatc cgttgacaac taagtggaaa accgttttg gtaacaatgg tgatcagtgg    183660
ttgtgcaacg ttacgggtat aggtaatgct actgtgaata gtaacgcaac tatttgtgtg    183720
tcgagctgtg gtcataatac gttggattta tgtaatttaa agtcgggaga ttctggcttc    183780
ttcgatctgt ctcgttggtt cggtgaaaac atggatgaat acagtggtga tgtgtggcac    183840
ttggaagtca gctaaatgtt gtatcgctta gtgaattggt gttcttacag ttttcatgta    183900
ataaactacg tgtaattcgt taaatttgtg tgtttttttg ttagtattct gcgtaacggt    183960
ggaataaaat tgcgttgacc tagttagatt tcctgtgtag aacaatgacc ggacgtgctt    184020
ggactggtac atacgcaggg gctggacgtg gttaccggtc actggactcg gtttcgctgt    184080
agctgtggtt caacctgaac atggctccca gagctgctag gaaccggtcc agtcacattt    184140
tttggtgggt gggggggtact aaaaaagtgt ttaatatttg ggtttaatga taaaatccag    184200
gttatggata tgaggaaact gaataccctcg cagggtcgaa atcttaccac agttgatgat    184260
agaagacggt tttccatcgg gtgggaaaca tgggataacg gtggtgacta ataatggtac    184320
```

```
aacggtcgtc aatacaacag cctgtgtttc aagttgttcg catacgtcgc ttgtgctttg 184380
caatatgacg cagcagactg attcgttgta cggagtgggt catcggttga atgacgaaga 184440
agatggtgaa ctgtggagag tttcggtttc ttaataatcc catacgacat gtgttcattt 184500
atatctgaat tttaggatga tgactatagt ataactctgg ggaacaaata tcatacgtta 184560
atcactttaa gttacgccgt taggaaaaga aaatcagtcc gaatgaagca tagtcagccg 184620
aatgatacag caatagcttg tttacaacgt gttcttttt acattatgaa cgtgccttgc 184680
tttttataca cacatggaga cagaggtccc tcagcccttg tcacgacaac tccctttttc 184740
taaaccgtat gtgctccaaa ccgtatctcc tcatcgtcac gtgaaatacc atgggacccc 184800
ttttcgtcac acacgtcttt ccgcttaccc aacgcgtcag cccgcgctcg gcagagctac 184860
catataaaaa cgcaggggtt tagcagcttc cccagatcgc tgctgccccg gcgttctcca 184920
gaagccccgg cgggcgaatc ggccggctgg tcggtcggcg ctcggacgga tggggagaac 184980
ggcggtgact tagccgcccg tggccgggag aagacggagg agccgagatg acaacagcag 185040
tcgtggaagg gtcgccaagc cccggtcctt ctcttctgtc tggtcgaatc ttgtttttctt 185100
ttttcaaccg ctctttttgt cacctttta tgtgagtttc tcttccgcgt ctcccggccg 185160
taccatccac ccatgcagca tgcacgcgtg tatgtatgca tcgcctctcc tccgtcccga 185220
ctaccatcag cagtaccact gccgccaccc ccagcgccac caccgctgcc gtcgccaccg 185280
cgttatccgt tcctcgtagg ctggtcctgg ggaacgggtc ggcggccggt cggcttctgt 185340
tttattattt ttttttattt tttatcttct cctttcctta atctcggatt atcatttccc 185400
tctcctacct accacgaatc gcagatgata aacaagaggg taaaagaaa aaagctacag 185460
acatttgggt acctcagctt tccgataact cgaagaattc aaagtcgacg attcccaaca 185520
agagaaaaca gaacaaaaac aaggtcattt ttatttatcc tcatcgtcaa caacaactac 185580
cgacaacaac gaaacaccac caagaatgtc aatccgcaag ggtgttcctg cccctcgac 185640
gcgcctgtcg cgatcctcat ggcgaggacc gcgatctccg tataggtaga tgaaattatc 185700
ccgtgtccga tcctgattcc ccgcatgccc tgcacatcct gacgcgtcgg tcagcagcca 185760
aacaatcata ggaaatgaac cagaagaaca aaagatcat ctctctcggt gtatagcaac 185820
accaacaaca accgcatcgc aacatcttca tccgcaagac ggaaagaaaa caacaataat 185880
gagaatgaaa tcaccacaac caagccagat ttcacgtcca tgagttttta ttatattatt 185940
atcaaaacga aaaacagaaa aactgtcata gataaatata aaaaaaaata gaaaccacaa 186000
acgactacta gtactccaat cttagatgta tatgctccta gataagattt agtattacca 186060
taatcatcga agaatgaaag acgacgatga ttccttaccg ctcctgccac ccggtctgta 186120
tgtagagaga gaagagagaa aacggtgaat ccaagatccc cgggtcggcg tcggcatgcc 186180
gctgatcgca gtggcccac ctcggcatgc cggcgcgggg cgaggaattg ctcatgaaaa 186240
aaagtatctt tctgtaaaaa agaaaacaa tacatgatta accgaaaaga aaccaacaaa 186300
aagaacccga gatcagtcga tttcgatcac tacgataaac acatggaaga tttcttgaaa 186360
aaagaaaaga gaaagagacc accttcccgg cggcggacac gctcctctcc gtcgccgttc 186420
tgcaccatga ttcgatcaat aacaacatca tcatcggaga ccatctttta atcaatcagc 186480
gttgcagtag tcgactccct ggacacgaag gagtcatcca ttttatcct cgcacttctt 186540
cgctctcaaa gccgccttta aagttgaaat gaaaggatgg aaacatgaa tacagtttta 186600
attgcacgta tcaccatttt actacaaaaa gaaaaaaaaa caacttacac atagtattac 186660
cttaggttta cggataagta gagtgtaggc gttttttgaaa cagttcagcc aatgcaatct 186720
```

```
tgtctcggca taatcactct ttctgcatat aatagtagta gtagatttat tcacatcaac   186780
acagcgaaaa actccagcat caaagtacac ctagagacag cccttaaaat atagtttgca   186840
gcttttagat gtacttacac caaagaagat taccgtcctt acgagaaaac agatactcgg   186900
atataggaat caagacagct ctgcactgaa acacactct cctgtcacga caccgcgcca   186960
caccagaggc gtacgcgtga cttcatcgca acgatccatc gtgatgtccc tcgcagaacc   187020
taaaaagacc aaaaaaaaat cttggaccac agttgtcgat acttgaagac aatattctcg   187080
tgagaacttt gagattcgca cttgaaacct cttaggatcc acaaaaacaa caacctctgt   187140
atggaaaatg cgctatttta tctcagcttt tctcccaaac ctcggtttct tcctattctt   187200
atgttttccc tagtatattt gcctccttat aagaaaagaa gcacaagctc ggtcgcacgg   187260
attattcctt ctgctaatct attattttgt tccttttttt tttctttgcc ttcaccctct   187320
tcactccctg tagcaacaca gagtagtaga cacaataaat gagaagtttg catgcatttg   187380
tcgtgtccgt ggtttgttat ggcgtgtgga gtgctcggga tgggtggacg tggggacgga   187440
ttcttgaggc tacaaagata cgcggagacg tcgtggcgag gggatgggtt tattggatat   187500
cggtgaagca gcgtggcggc gaaagacgcg atccctgggc tggtagatcc ccctacccg   187560 tctaccaggt acgtttatcc tttggacacg taaatgtctc ggccggcatc cacgcgccac   187620
gttcaccgcg ttgtgcccag cgccatgtgc gggtcgtttc ggcgtgaagt tggacggcgt   187680
agtttcgggg attgtgaacc gtggctgagg gtgtagatgg gacaggaaaa agcgtgtgat   187740
ctgaccgagg cgaagcatgt gggtggtgcg atgcggtgga tgtggcgggg tgcggcggtt   187800
tccgacgtgg agatgtggag atgggggtga tccggatgcg tggcaagagg cctcgagctt   187860
gggcttctcc cgcggatgga cgttctaact gtacacggcg gccgtggcct ccgagtaaaa   187920
aaaccaggtg ctgacgccag acagagacgc cgtcctcgga atcgtgtgcg cgaaagcctg   187980
tgccgcggca gcgtacgacg ttccagtcag cgaggccgtc gcgttggcgc gccaacagta   188040
aggtgacgac aggttggcgg cccatggttc cgaagcgtcc ccacatgcac cagcagtcgg   188100
cgtcaaagtc gcttgcgctg tcggcccagt cgccaccgcc gcggcggatt tccgcgcggg   188160
ggacggggta gccgagtgct gcgccctcgc caatgttgtg aagtggatgc gtgagttgat   188220
gttgattctc tgtgggaaaa tgagcgctgt cctgtgggtt ggtgttgggg tatgcgagta   188280 gtagggggttg tgtttgatcg tagaggtgtt ggcgggcctg tgcgcaagca gcgtagtctg   188340
cggcgtcgag ctccatctgt gtgcggtgtt cttcgtcggc gtgtttgtcc gaggtttgga   188400
catgcggttg tgtgttgctg tggtgtaagg gtaacgtgtg ttgggcgtct gggtgaagcg   188460
gcgtggtgtg ggtgctgttt gtgtctgtgg ctggcatgat tgtgcggcat gtgtgtgttg   188520
tagtgggtgg aggttaaata ggtgaggtgg gttccctggt ccgcgccgca aactgtcccc   188580
gtccccaacg taacctcccc tacgcggcgc gaacagcccc ggcccagcg caaccccgt   188640 ccccggcccc aacaccgtcc cgcacacccc ccgtctccgc aacacccgg catcgccggc   188700 ggccagaacg ctcgaaaacc cccgacaagc gcagcgccga aacgacacag gcaaggaccg   188760
tggaacgcac cggcagcgcg ccgaaacacc gtcccgaagc ccggtgccga caacaaatac   188820
cgtgggacga cacgcaccgg cagtgcgcag gcagcgtcgg acacaacacg cttacggccc   188880
tcaacactcc ctcgaggacc caccacgcgg ccccgcaccg gcggtgtttt gggtgtgtcg   188940
gggcgcggcc gggtgggtgt gtgccgggtg tgtcgcgggc gtgtgttggg tgtgtcgggg   189000
gtgtgttggc agggtgtgtc aggtgtgtc gcgggcgtgt gccgggtgtg tcgtgccggg   189060
```

-continued

```
tgtgtcgcgg gcgtgtggcg ggtgtgccgg cggggtgtgg tggcggggtg tgtcggcggt    189120
gtgcgcggcc tcggggtgtg cggcttcgca ggaacgagtg tgtggcctcg cggccgttat    189180
ttccccgcg  gtcccagg  ccgtcgtccc tcgccccgg  gcgttgcttt tcgtgtgtcc    189240
ccagggaccc atgctgccgt cccccgggaa cttcctcttt tccccgggga atcacacaga    189300
cacagacacg cgtcttcttt tcgccgtgcg cgccgcacgt cgcttttatt cgccgtcgcc    189360
gtcctccgca ccacacgcaa ctagtcgccg tccacacacg caactccaag tttcaccccc    189420
ccgctaaaaa caccccccg  ccctcgagg  acccaccacg cggcccggaa tggatgtcgg    189480
gcgtccacct agatgggtgc gcgcccggga ggcggctgtg cgctccagtg gtacgcgcct    189540
gccgcgcgtc ttccttcggg tagctgcctt tcccagtcca cggccttcca gactgcgtgg    189600
cgccaaggcg gcgccagcac gcgccgtgca cgtcgctgcc tataaagcc  agctgcgtgt    189660
cgcccgcggc acacgggcga cgaaggcgtc cgcgtgtcta aaccgcgtgc tcgctgacgg    189720
gggtttgctt cctatatagt ggacgtcgga ggtgtccggc gcccatggcc cagcgcaacg    189780
gcatgtcgcc gcgcccccg  cccttggtc  gcggccgcgg ggccggaggg ccttcggggg    189840
ttggttcctc tcctccttct tcttgtgtgc cgatgggagc gccgtcaaca gcgggcactg    189900
gtgcgagtgc tgcggctacg acgacgccgg gccacggcgt ccaccgggta gaaccccgcg    189960
ggccgccggg cgcccctccg agtagcggca acaatagcaa cttttggcac ggcccggagc    190020
gcctgttgct gtctcagatt ccggtggagc gccaggcgct gacggagctg gaataccagg    190080
ccatgggcgc cgtgtggcgc gcggcgtttt tggccaacag cacgggccgc gccatgcgca    190140
agtggtcgca gcgcgacgcg ggcacgctgc tgccgctcgg acggccgtac ggattctacg    190200
cgcgggtgac gccgcgcagc cagatgaacg gcgtgggcgc gacggacctg cgtcaactgt    190260
cgccgcggga cgcgtggatc gtactggtgg ctaccgtggt gcacgaggtg gaccccgcag    190320
ccgacccgac ggtgggcgac aaggccggcc atcccgaggg tctgtgcgcg caggacggac    190380
tgtacctggc gctgggcgcc gggttccgcg tgttcgtgta cgacctggca acaacacgc     190440
tgatcctagc ggcgcgcgac gcggacgagt ggtttcggca cggcgcgggc gaggtggtgc    190500
ggctgtaccg ctgcaaccgg ctgggcgtgg gcaccccgcg cgcgacgctg ctgcctcagc    190560
cggcgctcca acagacgttg ctgcgcgccg aggaggcgac ggcgctcgga cgggagctgc    190620
gccggcggtg ggccggcacg acggtggcgc tgcagacgcc gggcaggcga ctgcagccga    190680
tggtactgct gggcgcgtgg caggagctgg cgcagtacga gccgttcgcg tcggcgccgc    190740
accccgcgtc gctgctgacg gccgtgcgtc ggcacctgaa ccagcgtctg tgctgcggct    190800
ggctggcgct gggcgcggtg ctgccgcgcg ggtggctggg ctgcgcggcg gggccggcga    190860
cggggacggc ggcggggacg acgtcgccgc cagcggcgag cggcacggag acggaggccg    190920
ccggcgggga cgcgccgtgc gcgatagcgg gagccgtggg gtccgctgta cctgtgcctc    190980
cgcagccgta cggcgccgcc ggcggggcg  cgatttgcgt gcctaacgcg gacgcgcacg    191040
cggtggtcgg ggcggacgcg gcagcagcag cggcgccgac ggtgatggtg ggttcgacag    191100
cgatggcggg tccggcggcg tcggggaccg tgccgcgcgc catgctggtg gtgctgctgg    191160
acagctgggg cgccgtgttc gggtactgcc cgctggacgg gcacgtgtac ccgctggcgg    191220
cggagctgtc gcactttctg cgcgcgggcg tgctgggcgc gctggcgctg gacgcgagt     191280
cggcgcccgc cgccgaggcc gcggcggcg  tgctgcccga gctggaccgc gagcagtggg    191340
agcggccgcg ctgggacgcg ctgcacctgc acccgcgcgc cgcgctgtgg gcgcgcgagc    191400
cgcacgggca gtgggagttc atgtttcgcg aacaacgcgg tgaccccata aatgatcccc    191460
```

```
tcgcatttcg tctttcggac gctcgaactc tcggtctcga cctcaccacc gtcatgacag  191520
agcgtcaaag tcaattgccc gaaaagtata tcggtttcta tcagattagg aaacctcctt  191580
ggctcatgga acaacctcca cccccatctc gccaaaccaa accggacgct gcaacgatgc  191640
ccccaccgct cagtgctcag gcaagcgtca gctacgcgct ccgatacgat gacgagtcct  191700
ggcgcccgct cagcacagtt gacgaccaca aagcctggtt ggatctcgac gaatcacatt  191760
gggtcctcgg ggacagccga cccgacgata taaaacaacg cagactgctg aaggccactc  191820
aacgacgagg cgccgaaatc gacagaccca tgcctgtcgt gcctgaagaa tgttacgacc  191880
aacgcttcac taccgaaggc caccaggtca tcccgttgtg cgcgtccgaa cccgaggatg  191940
acgacgaaga tcctacctac gacgaattgc cgtcgcgccc accccagaaa cataagccgc  192000
cagacaaacc tccgcgctta tgcaaaacgg gccccggccc acctccgctg ccgccaaagc  192060
aacggcacgg ttccaccgac ggaaaagttt ctgcgcccg acagtcggag catcataaaa  192120
gacagacccg accgccaagg ccgccaccgc ccaaattcgg ggatagaacc gcggcccatc  192180
tctcgcaaaa tatgcgggac atgtacctcg atatgtgtac atcttcgggc cacaggccac  192240
ggccgccagc acctccgcgg ccgaaaaaat gtcaaacaca cgcccctcac cacgttcatc  192300
attgaaagtc tctccagtcc atatgttgtc aggacgtgct gtcgttctcc gcttgctgcg  192360
aagcccgttc ttccgagtcg tgtcgctgcg tccagcgtcg cgcccaagat gggaatttgg  192420
gtcttttcac gcgtagcctc ctccaccacg gctgctgatc gccgtcacta aggaccgaca  192480
cggaggatga cgaggagctt ctccccgact ccgcggtccg cgaccggcta cgtagcgcgt  192540
gtccctgcca gtccgcag ttacaccaca cgtcgtgagc agcgtgcacc tgctgccgcc  192600
actgggcctc ggcgtgctca ggccaccgc cggagcccgg tctgagctcc gacgcaggat  192660
gcgcgtactc aacgtgcgcc ttccagtcca tacagcaaca ccataggtcg tgcgagtcgt  192720
cggctacccg ccgccaggcc agttcccgca tgggaaggct ggacacgccg accgagaggt  192780
caccgagccc ggacgccatc tcttcttcct ctccgtcgct gtcattaagc agccaggtca  192840
cctcctccgc tccgcgtccg ccggtctcga cggaccgcgc cgccgtcggc aacacggaaa  192900
acagcacgcc agcccgagcc gctaaggccg catgcccctg ccgccaaact gaacacgcat  192960
accccgctca actgcgtttt gccacccctg tcagtgctct cgctcgagca ccaccccgca  193020
tctcccaacc ttttccaat aaacgaaacc gacatgacac acgtaatggg tactcgtggc  193080
tagatttatt gaaataaacc gcgatcccgg gcgtctcagc acacgaaaaa ccgcatccac  193140
atcatagaca agttacagtc cacagtcaca tacacgataa acaataccaa cagggtaatg  193200
tttatggagt aaaacactat tgtccaggcc acatgcgtgt atgacttccg caccatcccg  193260
tactgcatgt tccacatgta cgcgctagac gtgtaatcca ctcgcagttc ggggacgcaa  193320
cgcagccaga tcacatcccc ttgcagtacc agacgcaggg ctagcgtctc gaagatcggc  193380
atcacatcta agttccgcac gttccacttt aacgactccc cgggaacgaa ctccacgtcg  193440
tcggcgtgta cgtacaggtt ctctcccacg ccgccataat cggccttcgg atcgaagacg  193500
aaccgactca tgttgcccac gatgctcccc cgagcaaaca acttgccgtt gtcaatgtag  193560
caccggttgt cctcgatttg aaaccaggga tgcttggccg tggacttcca gggccggagc  193620
gcgtcttccc cggctttagt gattccatcg ggcaggcgga tcaagggacc catggaggtc  193680
caaagaccca cccaggcttt ccagagattg ttcatggtga aacagcgtgt ggactgtacg  193740 ctcttttccca atttatatcc cagagtagtg acgtgagccc agccacctcc cagattcctg  193800
```

```
acgttttggt tgtctttcct gccaattcct cccgtaaact tatgattatc ctagcccatt   193860
cccgataaaa atacacggag acagtagata gagttacgaa taaaccggtt tatttattca   193920
agtgtctcag gagattattg aacgagcgtg gataccacgc cgtcgtcagt tcatggtggc   193980
attgagcagc catagcacca gagtcccggc gcccggtatc agacacgctg acctaccggg   194040
cgccttcgag tccgtacccc gcggcctggg tgttagagtc cgtaccttgc agcccaggta   194100
ggtttcaggt accagctggt tcgtacctgt taaataaatc gcagacgggc gctcacccct   194160
acggtcagga gcacaagaac aaccagagag aacagatata cgagcagggt tctgaacagc   194220
agaccccaat tgtcgtctct catgcttcgc tgaaggtacc agttgatggt ctgagagcta   194280
tagtccatcc tcacctgagg aacacacgcg gcatatttct tggggtctcc ccacctcgta   194340
gacaacgtga tgtccaccat atccacggtg tgcgtcaccg ggtgcccacc gatgttccac   194400
tcgaaatagg ctccgcgctc atcatggtgg tactgctcac cggacacctg cagtctgtcc   194460
atgtaagatt gagagacgat acccacgttc acaaagtgtt tctcggtgaa gttgcccgac   194520
atcctcccct tgaagtacag catgcccata tggaaccagc attggttctc ctccactcga   194580
aagtgggccg atctgatctc cgataccacc acatccaggg gccggggcac cgagtccgcg   194640
agtctcagga acaagacggc caggatcgcg agcaccaaca ccggcttcat ggctccgaag   194700
gtccgctgct cggctccgct caccgctccg gtctggctgc agcagtgctt cgctgagaag   194760
tagcgtgtgg actgaacggt gtttttgaat atatagcgtt tcttggtgac gttgtttccc   194820
ctacgtagta ggcaactacg tgccaaaaga ggcgttacgg tactttccgt actgggcttt   194880
ccaaaccggg actttccaca cggcggtttc aacaccggga cttttcacac ggtgatttcg   194940
gcaccgggac tttccgcacg gcggtttcgc caccgctgac gttctcatcg ccgcccacgt   195000
caacggtggc gacaccgtac tttcccatgc ggtttataaa cgtcaagagt cacgtcagtc   195060
gcccacccct attacacggc gatatcccga tagggcatga ggggacccgg gtgtcgcgac   195120
atgtcgacga caggtgcgga ttagtggtcg tgtcgcgaca tggacgtgca gggggatgtc   195180
tgtcgcgata gagttgatgt gacagcccgc tacacctctc tgtcgcgaca tgcatacaca   195240
acgggccggc ttgtcggcga ttgtcgcgac atatcgttat cagttagcga ccggagttgt   195300
ctatcgcgac atatcgtcga ctatcgcgac agaaaaaata ccgttcgtag agaatgccgt   195360
gttgaaggaa cgcgctttta ttgagacgat aaaacagcat caggagccac aacgtcgaat   195420
cccacgtcca gtcgattcgt atgttatgct gcacagcaat gctagaataa caaccagcag   195480
ggtaatcccg caacataaat acaaagtcac agcgaagaat ccgtgtcgtt ctatcaagcg   195540
aaacgcgttc caaacggccc cgtcacagac gcagttattc ataagcgtta acaaccggtg   195600
gctaggatga atatccaaat cacagggcag tagccgacgg actcgttgac aggtcagcct   195660
accctcaagg ttcctatcgt tcggacggga ttttgtgcgt ttaggcctct ttttcgccgc   195720
ctgcaagcat tggtgcgcaa agtcctcacc cagctgtttc cagctatcat ctgcatctgt   195780
gcagtcccct gtatcgttgt aacaaacggg tctgtgcgac ttcgttctcg aacacaagc    195840 ttgttgtcgc ggagacagag agagaagggt tttcgggtca cgcgaagacc gctcaccggg   195900
ggtcggcaac gcacacatca acagaaaacc gagacgaatc aagagatcca tagtgaagga   195960
gtgatatcga cgtgcttacg aaacggcgat tatatatgtt ctcaacaata ccgccctacg   196020
ttgtatgatg taacgtgtga cgtgagtctg atccaacact gaacgctttc gtcgtgtttt   196080
tcatgcagct tttacagacc atgacaagcc tgacgagagc gttcatcggg gcatgaagta   196140
cgcattacac aaactccata tatttgttac gatagaatac ggaacggagg aggctttcgc   196200
```

```
cacacctatc ctgaaagcgt tgcattcttt atgataggtg tgacgatgtc tttaccattc   196260
ccacggctgc tttgcgtgat gatgacattc atcatgtatt tccattcaca cataccttt    196320 gtgcatacgg tttatatatg accatccacg cttataacga acctaacagt ttattagccc   196380
ttgacaggat aggtcaaaag attatatgta ggttttccgg taaaccgaat tgtgatattt   196440
ctctgcagga aatagaacag cctggtacct ataaaacgga caatgcagta ctgtagcagc   196500
gtaaccaagt aggtccacat gaacacgtac aaaattatgg taagccatcg tttttcatac   196560
cacagcctgt agctgtcgta catgaatgag gacggtcgag gaacccaggg tagttgtaat   196620
tgggggcgac attcgtactg tccagaagac aattgcacgg gtttcagtga gatgagtact   196680
ttagcgatgt cggcgggggc gctacgtttc accgtgacgg tgagaacttg accgtcgttt   196740
tgtatttcat gaggcacgtt atacaagcca ctggtatcat gaaggatgac ctctgatgcg   196800
atgtgaggat taaattgtcc ctcaaaccgc aaacgctgg tcatgtttcc accgtcaatt   196860
acgcagctga cggtgtgaga taccacgatg ttggacttag gtttgggggc taattgcctt   196920
tttacaaatt cccttctgta ttgcaggtcc tgctgccact gcttttccgt gcggaaagtc   196980
gccatgtctt ccacacgtgt ggcgacgata gacgccacca aggtagctac cagaagcagc   197040
tggatccgca tggcattacc gtatgtcaat tagaaagttg agcggacacg gttatcgttc   197100
ctggcggata taagtatata aacgcgagtt agcctttccc gtccgttttg tacaccgtt    197160 ccccacacaa atgacgaata cgacctttt tttatataaa ataaaccacg tgtattatat    197220
aaaaacattt acatagaaaa gagacacacg gatcaacata aggacttttc acacttttgg   197280
ggtacacagg cgtgccaccg cagatagtaa gcgctggata cacggtacac agtcctggcc   197340
agcacgtatc ccaacagcag caccatcgcc atacagatgg cgatcacgac cccgagctct   197400
aagtgtctgt attcatagtg tagtcgccgc aggttatcca ctgaattccc gtaactgaaa   197460
taacgtatat ggtaccgagg ctggcaccac atgggtttgc atttggtgca cggcaccaaa   197520
tgcagagtga gatggtccaa gtccgtgggc acccactggc gcaaacggaa tacggcttcg   197580
gtggtctcca cgaggcactc cggggcgtgc agacggcccc actttcgtcc gcgacggccc   197640
gaccagccga cccgagccac tatccctttc tcgggataga acgtaccctg tacacgccac   197700
acagcgtcca acacgccgtc cttgacgacg cagctggcct gatagctgga cacgttgtta   197760
agcggcggaa agcgaaactg acgtgccggc ggagccacat agttcggttc accgtgttgt   197820
cgcggttcgt cctccctata gtaatagtag tcgtcgtcct cataggggtt gccggcgtga   197880
gccagcgtta cccaacagca gcccaggcca acgaggaggc gcagccaccg cctcatggcg   197940
gcttcgccag tcaatcgtct ttagcctctt cttcccgtga ggtccttccg gtggcgcggt   198000
gccgacctcg gacccaggga cgtatccacc tcaggtacac acagcaggct acctggacac   198060
cgaagctgaa caaggctacg tgtttcacaa actgcaccag taccacatag ggaatgtca   198120 ggtagcgtct ctccgcaaac agccgttcca agtctgaggg cgttacccgc agcggcaacc   198180
agggcagcct ggacgccggc cggcaatgga gcacgctccg gttacaggca ctgcagggt    198240 aaacggttaa catcacgtaa gagagtcgtg cgtccacctg tgggagctca gtttcgtaac   198300
gtagagcccc gtcattttcc agctgggtg cgccgacctt gaaatgggtc gcgctccgct    198360
cgttacccca ggtgccgtag gctctcgggg ccgtatcgga gaagttgcca cgcacaagcc   198420
aggcggccac gagtaccccg tgctggacgt aacattcgga cacggaactg gagacacggt   198480
agccggacac gtccccaaac ccgcgagggt actggggcag acggacggac ttgctatttg   198540
```

```
acaacggaca gatacgagac gacgaggacg cagacgactc gtcgctggac cacgacaacc  198600
ggagcgactc cttggagcgg ctcgagagta cacttactgc gatcagacac cagtgccaga  198660
agaaggaaca ggtggacggg gaccacagga tcatagccgc cggcaccgcg gccggccgca  198720
ggaagccgcc cggcgcgtcg tctgtgtgcg ggagccgaaa caccgtgcct ctttatatcg  198780
tcccgacgtg acgcgagtat tacgtgtcag gggaaacccc cgtcacgacg aacgtgattt  198840
gtaagtgacg cggggtgctg acggggttcg gcccgagagg tgacggagcg cctcacgtca  198900
gtatgatgtc cgatccgcgt cagccccgac gtggttgtgg tcaccgaaac ccacgtttat  198960
atggacgttg agagcagcgc ctgaccacat gattcatcat accatttctc ggaatcgggc  199020
ccatgccggg aaagcacatt ccttttcagt aaacaacaat gacatcataa caaatcattt  199080
tattcgcgag gtggataata accgcatatc aggaggaggg atcgggtgat gacgcaggcc  199140
ccgcagaaca gtccgaaata aattttagt attgccccat agtcgcctag ataccagagg  199200
tacgttaagt tcatcaaaac gcccatcggc gtcccggaat cgtataccgg gcacacgaag  199260
cgttcataac aatcccggga ggcgagtgtt agggtagcag agtagtttcg gggtcggttt  199320
ccttccggcg acgacagttc cgtgggcagc agaatgtaca gcgcctcggt agctgtcgcg  199380
gtgccttcca cgaggatggg ctgccggtgc ctttcgtgat tttccccgtc gtgtagccaa  199440
gccgaggccc gcaaagtctt aggcgagggg aattgtccat agagtttcac cgcacccttc  199500
agtacatggt tctgaataac acagccgcac gtgaagtagg taggttctct cgtctcctcc  199560
gtggctgccg ccaccactcc cagccaccac aacaggcaga tcgccagagg gttccggagg  199620
cttccccggc gtagcatggt tttgggttaa agcaaaaagt ctggtgagtc gtttccgagc  199680
gactcgagat gcactccgct tcagtctata tatcaccact ggtccgaaaa catccaggga  199740
aaatgtcggt gcagccaacc tttcacatac agcccccaaa acacttgaat cactgccacc  199800
atcatcagcg tatactgcgc cgacttaatc gtgagcgcgt agtacgccat tagacggcga  199860
tcttcgaaca atagtcgttc gatgtcctct aacgagctcc acagggaaac ccaaggcacg  199920
aggcaccggg gttcgcactc tacataataa gtttggcatt ggtggcaggg ggaaaagtag  199980
aacaacacga gttttgtgcg ttggggaaca cgatagtccc ggagccagta gcgttttgcg  200040
acgaggcttt cggagacgtc ctccaccggc gtcggcactc gatccgcgta gcctccagc  200100
gtctggtagt acacccgggg tgtcggcgtg ggcacggaca ggttcccgcg cagggtccac  200160
agagcctcca gtcgaccgcc cgatcggagc acgcagcgcg cctcggaata tctctactcgg  200220
tactccgaaa catcggacag aggcggtaac ggctccgtct ccaccaaggg cggaggttca  200280
tcgaaaagag tcaaggataa ttcaggcata ctacccgcga ccggggccca gagggctaga  200340
ataagcatta caaggttcat tctgtcttac aagggaaggc tgttaccctg tctagactca  200400
aaagctgtaa ggctgtctta tagcatgtag tcttgcacgt cacggggaac agggtggtga  200460
tctagtgacg tcgggagaac acggtgtttt agggtgcggg ggacaaagga cagtacgaca  200520
gattaggtga tagaaacgtt ttttttatt tatgaaaaag ccagtgtgcc gtgcggccta  200580
gggcccggc gtagtttgga taccagatgg gggccgtcag gggtactacc acgagcagaa  200640
acataatgac ttggtccatg tatagcagca tagcggtgcg cagcaggtcg ccgtccgtgt  200700
agcaatttga cggtgagcga taaagcaccg ttaatgtgtc gcggataagc acgatcttga  200760
ggccgtagat gaagctcaca gtcagtgcta aaatgatgcg ttggtatggt tcccaggact  200820
gcacggcgat gaagagccag agtatgggaa gcatgaagct tagcaaacag aggatggcta  200880
accgtcgttg catgttccag gccatgagcc aggctaggcc cgtacaccag acgcagagca  200940
```

```
tggatgacag gacataggcc tggattacca cggtgcgatc gaaacacagc ccgatggtgg 201000
acacggatat cgtagtgagg gtggtatata ccatgaccag catcagggtc ccgggtcggc 201060
gccgacgttc cagccagtac gcgtggcaac gcagagcgca gggtagcagt gtgctccaga 201120
agggcaatgt atcgcgcagg tagggggccg tcacgcgcca cggtatgagc atgaaaagga 201180
tggtagtggc tatggtggcg ctggtctgga acacgacagt gccgtagaga cgtaccatcc 201240
agagaaagtg ttgaacgctc cgcagggtgt cttcatcttt ggtgattacg gtgactcgac 201300
ggatcggcgg tggtgacggc ggcgacacgg gtgggggttt ctctttctta tggccgagtg 201360
gctcgccttg gtgaaactgg atctgtacca tgacgggtgc tcgacgaaca gtcgtggggg 201420
ctttaggtac ccggcaagtt ttatagagaa agggggacga tgggtggtgg ctacgagcca 201480
ccgccacctt cgcaatacga ggatctgaag gcggcaaaga cggtcgtcca gggcaggcgc 201540
cagaggttgg gactgagcac gatcagcgtg attttaaaca tggtcaccag tcctacgtag 201600
atcagcagcg agccgcgtaa cgtctgagca gccggcagtt cgtcgcggat gtaacgcgtg 201660
ccgtagaaag tcacggtcat cataaggaag acgatggcgc cgtagccgta gagtagaata 201720
cgctgatgat ggaacacggt ctggtcgccg ataacccaga gcgtgatgaa aaaacgctg 201780
gtgagtaccc gtgagcatat gagctcccaa cgcttagcgc gaaagctgtc cccaaccatg 201840
acagcgccgg tgcaagctat ccacagcgtg aggaccagtg tgtagtcgat gaggatggcg 201900
ggcaggtcgg agcaccaggt gtagaaaacc gtggtaacgg agaggaggcc tacgtagccc 201960
atggtcaata ccacgtcgtc ggggtgcctt cgccctgta tcaagaccaa acaccagaga 202020
agggaggggg caaaaaccag cagcagaggg gaagattcat gttgacatat gttgtgggaa 202080
tcggggatac ccagccaaat cattccgcag aaagccgtac tgatggcgat gtgaaagacc 202140
actagggcgt agacccggac gaggacagca aaacggcgca gccacataag gccgtggtgc 202200
agctgcagga gggaagccca ttgcggcgaa tgtagcgacg gtagcggcgg gtccatgagg 202260
cgggtgatgc gcccgagtga acgggtgagc gtctcggtgg agtcttctta taaaccagcg 202320
gagctcaggc agccttgctc tggaacgtcg cagtggtggt gttgaggatg acgctgagcg 202380
tgccgttgtc aatcaggtaa tgatgatagg tgccgagctt ggccaggtag ctgaacattt 202440
ggtcccagcg tgccgaccac accacggggcg tgagcatcag gagtgtggtg tgatagatta 202500
gtgtttcggt ggcgtaaagt atcagcgagc tgcggatgac gtggctcacg ggcattttgg 202560
tggcgatgta gcgcacgtct tggaaaagga cggccaggat gcagcccacg aacacggtgt 202620
agagacacag caaagtctta tgtaaccagg tgtaagtaga agccaggacg ctgaccatca 202680
ccgtcaaaag tgtggaggta aaaagcgcgt cacgccacac ggagctgaga cggtgctccc 202740
aagccacgcc gttgcaggcc acgaacaacg tccacgttag gatgaggcta gaaatgccga 202800
tgggcgctgt ggcgcacagg ttgagcccgg cggtggtgaa cgagagaagc gccacataca 202860
gcgcaaacac caggccgttg ctgggtgtc tgtgatcggt gagctccagc gcgcccagaa 202920
ccaatactgg tgtgcagcta agcaatagcg gcgagggatc gtcgctgcac ttgtagccca 202980
gcgagggta acccagccaa accagcgcgc taatgagtac gctgaaagcg gtttccagcg 203040
tcagcaatcc gtagacacgc atgacaatcg cggtccgccg tagccaacac acggcatctt 203100
cggaaactgt ggacgctgtt ccgaataccc gggaggagat cgtgcttccc tcttccaagg 203160
atcggaaagt agcgtccgtc gtttccgcgg acgcggcttc cctggtacgc tccgtttccg 203220
acgacgcggt ttcccgctgc gtggaaactg tctccatgtc gggaccgcag cgcccggcgg 203280
```

```
cgtatccgca aggtctcgaa gctacagctt gtcagaggaa aagtaggttt gcaaaaaggt   203340
gcgcagggtc atgattctca gcaccatcag cagagtgaaa accagactga gaaacacctt   203400
gacggccgcc aaaagcgcgc gttccagcgg cgtctcgtag cgtacagcca gggccgcttc   203460
gtggaaatgc gagacggcta gacaggtaat gagcacgctg aaggacaaga cgatcttaaa   203520
gcaccaggac caaccacgcc tcaagatgac caccacgatt gccgtgaagg tcaacgtgat   203580
caaagcatgg acgaccacga tctgacggcg gacggtacgt tcgggagcca caacgctac    203640 gccggtgcag ctgagaaagg ccagtaaggt gaacaacgcg gccgagatga ccaacgtacc   203700
gtccaggcag agacatatca cgatcaacgg cggcacgtga agcagcgtgt aaaagagcag   203760
aacgccgata ttgctgggat gcgatgtttc gtaacagtga atgaagatca ctgacgtgac   203820
gggtatgaca aagacgaggc tgggcgagga ctccgtgaga cacagacgag aatggtgaaa   203880
ccacgtcgcg ggcgccgcgt agcagaaggc gctcaacaac gcggtcaagc cggccagctg   203940
ccaacccacg gcgccatagg tgtgcagcgc cacgcggcaa cagtcgaccc aagccagact   204000
gcgggtcgcc agccgggtct cttggatccc gggggcacg tagatgaccg tgccatcggt    204060
gggtacttga aacccttttt ctcttctcat ggtgcgctgc gttctctgga aacggctgct   204120
ctgtccgaaa accagttccg aacgaaaatc tagggcgaga gggtggacaa cggcgtcgac   204180
gacgaagcat gggacaggtc gttcggcgtt aacgtcatcg cgtcggacga cggtagttct   204240
aagagacgta gatcgctcag caggtcctga cagttgcgga ttcgcaagat cagaaaaaaa   204300
agggaaatga acgtaataaa gagctgtagc gacgtatgcg ccacatcgcg tggcataaga   204360
acgtgacgga cgaaaaggac ctgctgcgaa aagtgaccgg cgaagataag gcccaccgtg   204420
ctgtagaagc ccaaaagcag ccgcaggggc caagtccagg gccgcgtgaa gacgatgaga   204480
acgttgacca gaaagaccac gacccagacg ccgttgatga gggtaaattg atcggacagg   204540
gtgcagttgt cgcgacagat gaagactact tccgcgcaga gcaaggtgat gaccaacgtg   204600
agcacaaacg acgtcaacac ctcgcggggc tcctggcagg cacacgtgac acctagcgcc   204660
gggatgtgcg ccaggaggcc ggcgagtaat agcaccagct gtcggaacgg acgacggcag   204720
cgcgggtgcc ggtttcgctg agcgagaacc ggtcgctcat agcggaaata cacgaagagc   204780
gcggaggcca caggcaccag gaggagcacc tcgggcgccc agacaacgtg acaaggaaag   204840
cccggacgcg acttgagagt cgctgtaggg aagaccagag agaagctacc caagacggcc   204900
accgccgcgg agatttggaa gaggagcaag ccggcgattc ggacgacaac ctcgaagcga   204960
tgcacccagc ccagcacggc caccacggcc gcttcatcat agtcgtcgtt gttgccgctg   205020
tcgaacagcc gccgaaacac gatctgtcgc tgggtcgcgg tgggaaagcg cagacccatg   205080
acagccggag gctatatgac cgcgcgtcta agacgcgaga tccgtggggg gacttttaga   205140
tgtttgggcg gcccgcggtt ctaacaggct tgattggtgg agacgccgg cgcggcgggt    205200 gggggaaacg acgagttttt ccgttacgcc atggttcgcg tgaggtttct ctgtacctcc   205260
cgcaaaaggt cacagcccga aatggaggcc gcgttggtgg cccggtggc gcgtgacgat    205320 aaccaggtca tccaagcgat gagtttgtct aatgagtcct cggtggtgaa gaggatgaga   205380
atgagcaggt acaggtacac caggttctca tagagacaca aggtgagcag gtcagcctcg   205440
gaccacgcga tctcaaacag gcgcgtggtg tcaaagaccg tgacgaccag catgaagctg   205500
agcgccatgg cgtaatagcc caaaaaaagt ttgtgcccca acggtacggg ctgcaggtaa   205560
agtgcgatca agaacgcgat aacgccgatc acaaacagct tgacgatgac ctgccatcga   205620
cggtgattat ggccggctag acccgtgacg cagctgcaga ggctaaaaag cacgcaagcc   205680
```

-continued

```
aagaggcccg agaaggtcac tagcgtagag gaggagcagg cgctggccac gatcaccgaa 205740
agcgtcgtga gcacgctata aatggtgagc aggccagggc tcggtggcga cgtgaacgat 205800
ccttcatcgc gtttgccgtg cagcagggcc aaacagatgt gggcaccat caaacttaag 205860
ggcggcataa agccggtgca acagagaaag acggtgcctt taagatgcgg aaaagccagc 205920
accaggccca gacagagcaa gaaggtgcag gtgccctgca cggccacggt gctgtagacc 205980
cgcatacaaa gtaaaaagcg acgtacgtcg ttcgtcgaca cggaggaaat cataatgact 206040
ccgcgcgagg gtcgcggggg tggggcgcc caggccgtcc cggtggcctc tgagttcgga 206100
gacatgacgg cggtggcgat caaaaggcgc gtatgagaaa ccgtttatag agtgtaatag 206160
aatcaccgtc attcccacac ggcgttcccc cataaagtca cgtaacactc gagtaagcgt 206220
gaaaaagctt tattgttgaa taaaaacac gagtacaaca ccgagttgcg gtgtcctgtc 206280
tgtctactgg gtgggaagg ttcatcgtct gtctctagag ggaaggtggg gaatgtctaa 206340
gcgagcggga gcgtgtcatc tcccccatct ttttacaaca agctgaggag actcacgccg 206400
tcgatgcgtc cgccgtgttt ctcggcgtac tgctgcaccc agacgtggcc gctaaatatg 206460
gcgacgctca tgtttaggag actcatgacg atggtgtaca acacgacgct gacacagacg 206520
ctgttttag acaacgttcc acgctggtag atgagatcca gggtctcgta aataagcacg 206580
gccgaagcgg cggtcaccac caggacgtag agtccgctgt agatcttgct gacccacagc 206640
acgggcgaaa agtaaagcaa taggtaaaag acgatgacgg accagccgta gccaatcccg 206700
atgactttcc agcgcgtggg attgttgccg gccaggtagg tgagaccgct gcagagaacg 206760
aaaaagacca tcaccagggc aaacgacaga ccgatgacgc gcctttctcc gcaaaagccc 206820
gtgcacacgg tgatgccggt gttgatcagc aagcacgcca ccgtgagatg agcaaaattg 206880
gtggtgtgtg ggcgaaactc ggcgaaaccg cgtagcatag ccagcgtgga cacgggtacg 206940
atggaggata gggctggcac tatgccgttg gcgcactgtc cctgcacatc ggggaaggcg 207000
agccaagcca gcaagcagac cgtgagggta caagccagct gccacacgag cccgtgatag 207060
acctccatga gcagcttaaa gcgtttcaac cattggaaga gctgctgttc ggccaccagc 207120
gcgtggctgc gatggagcgg cacgatggtg accgtcggcg actcatggtg ttcggaaacc 207180
gaggcggtgt cgcccatgct gccgcttacg accgctgtcg gtctaaggta ggcgtcgatg 207240
aaacagtccg tcttatcagc acccggttac cgcggatttg attgacgtca cgagtgtggt 207300
caaaccgtgg cggcaccctg tatccgaccc gtcgtcatgg gctccacaac cagagcctca 207360
gaagatggta catgccgatg aataaagcca cattttcgac atagaggcgt agcgagggct 207420
gaaaactctc cgggaaagaa ctctgacagg tgatcaggga cagatcgtga attagcatca 207480
gcgtcaccgt caacagcgtc gtcgcgtgta accgagaaa gaacggggcc gcggcccgca 207540
gcagccaaag tcccagcgcc gtagcgcaga gcagagacag gaccgacggt agccacagcc 207600
gccggagaga cgcgccagga tcgcaaccca aaagcgaggc ccccaggcag ctgagatcta 207660
ccgcagggc gagaagagcc gcgccgacaa aggcctgcgg cgacggctgg cacatcagca 207720
aggtcagaaa ggctagcgcg tgcggcaggc agtaagccaa caggagtggg agtttgcggg 207780
gacaacggtc gatcgacgga ccgcgtagca gcaggaacag gcagccgacg ggcacgacga 207840
ggctgagatg agaaagcggc ggtgggtcgt cgtcccgtcc ccgctcgcat agctcggcca 207900
ccggtggcgg catgagccac cagctgagca cgctgagggc gacggtggcg gtaagctgga 207960
aggcgacgag gacggaggcg cgcagccata ccgccagcct ctctaggtag gggactacct 208020
```

-continued

```
cctcgacggt ccattctagc gggacgacat gaagcatggc gacaagcgcg gctgctgtga 208080
aaacgggcac ggttttatag gcattaggac ttccccgtcg tactggcggc tgtcaaagtc 208140
ccgttgtcca aaggcgcgcc gtccgaaaga ctaatccaac ggggacccga gagcatgagc 208200
aacaacgtga gaaagatggc catgctgtcc aggtagagac agacggcgtg acggatgcat 208260
tggttaggtg ggcagaaaaa gatgaccata agactgtcgt aggccagaat acccaaaaag 208320
aagctgatag agaaggcgca caacgtcacc actatcttct gcagccaatc ggcgtcgctt 208380
agcagagcga gcgtgaggaa cgaaagcagc attaccacgt agacgcagct gatgcatttc 208440
cagcgacgtc ggtcacggcc acctagaaac gccagccccg taaaggagat aaacaacgcc 208500
agggtcatca cgtaggaacc tactagtacg cggctttcag agcacatttg gaagatggcc 208560
gccgtcaggc tgttggccaa cagatagatg aaaagcaccg tggcgttact agggtgttcg 208620
ttgcccaacg tgtacgtgat gaacatgcag acgatgggca cgagcacggt gagaaagaag 208680
ctgtagttct cgacgcaaaa gttgcggttt tgtgggaacc ccaaccaaaa aacgcttccc 208740
aagccgaagc tgaaagccag ctgaaagatg aagatggcgt acacgcgcag ccatacggtg 208800
aactttttga accactcgag agcctccatg cgggagagca gcagcgcgtt agcctcctgc 208860
gcctgcatgg tggcgacggt ctcggcacaa agccgctgcg gcgcacctac ccttctctta 208920
tacacaagcg agcgagtggg gcacggtgac gtggtcacgc gcgacacg tcgattagga 208980 gacgaactgg ggcgacgccg ctgctgtggc agcgaccgtc gtctgagcag tgtgggcgct 209040
gccgggctcg gagggcatga agtagagcac ggagacaaag aggtacatga ggtccatgta 209100
caagcagagc gcgcccggga tataactctc atactcgatg tcgtgcagga tgtcctgcgt 209160
atcgcacacc accgaggtca cgatgacggc caaaccggct atcatcacca ggatctcact 209220
taccgcctcg ggaaaaagag aaaatacggc gaacagtaag agaatcagcg tggatgcgcc 209280
cgtcaatagg gaacgctgta attccacgtc gcgggcaaac agatacgtag cgagcgtgag 209340
gaaacaaaat agcgtcactg tggccaccat ggcataaatg actgaacgat gactaaagtg 209400
gaagcctgac gccgtgacag ccacgctggt aagcaacgtg tacgtcagta agatccatac 209460 gttttttggga aagttgggct cggcccaacg caacagacct aggcacacga tggagatcat 209520
taagcaagac agcgtcagac gcacgctgga aaagagctgc tccaaccggt gcggcaacac 209580
cagccagcaa aaggcgcaga cgctcataag gatgaggcat tgcacccaga taaggatgta 209640
gatgcgcagc aggaagaccg accgggctat ctggacctga ccgcggagcg acatggcggc 209700
aacgccggcg gttatcgccg agattcgtct aaatacacga agcgaactag aaaacgcaca 209760
cacgtgattt gcaaaaagaa agcagctgcc ggcttattat tttattaaaa atttatctgt 209820
gcagaatcat aagtttatga tgaataaaaa cggggaaagg gaatctgctt ttagggaccc 209880
gggtctggtc cgtcgtctcc catctggtcg ggttcgggga tggggacctg tttcagcgtg 209940
tgtccgcggg cgtgcatggc ttttgctcgc cggccgcgct gtaaccaggc ctctttctct 210000
gtggtcggca agtcttccga cgggtaggga gcctgggagt ccatcgcttc aggcccaccg 210060
ctcgttccct cgaccgtcgt gtcgtcctcg ttttcgctat tacacgggt ttctggagta 210120 tcgcctatac ggttggcgat tctccggggg cggccgctct cgtcctcgtc gctgctatcg 210180
ccgcccggta attcgacgcc gcattcgttg tacggaacgc ggcacatggg cggcggaaag 210240
aacttgggca tgcgaaagca gcgttgtcca tccacggtct gcgtggtttc atcgttatcc 210300
tcccataatc ccccctgtag cgccggcagc gtttcgacgc tgtgagaggg gaaggcccag 210360
ttctggttgt cttgcagcgc gcccgtgggc agtaggtccg tgcggcccca tgcgctgctg 210420
```

-continued

```
ttgttgggta ccttgtcagt gccgcgagta ggtcgcagaa accagtccag agcgctctct 210480
agctgcgagc gtgtgatggt gcccagtgcg ccgtgccagc gcagcacgtc tcttttcagc 210540
gtgtggtgac agacgggcag ctcctccaac cgacactcgc cgcgcaatcc gcggtcgaag 210600
cggcagagac cacgcagttt aagcagaccg cacttgagaa acatgtgaaa attatcggca 210660
atgcgatata ggtccgagtc ctcgatcttg tgtaggtaga ccacgccaaa cttgtcgagc 210720
agcaccaggc cgctgggcac aaaaggcccg taggccaggt aatagcccac gaggccgacg 210780
acgtaccact cgcagcacaa gcgttgacga ataaagttca gaagatcgcg aaagtccgcg 210840
gccggcatgt ggtcaaaagg ccggcaggcg cgcaggccct cgatggagcc cagcatgagc 210900
aacggctcca cctcggtgcg acccggcgtg cggatgacca ggttgagacc gctcatttcg 210960
cgggccgtct tggccacggc cgcagcgtca gtgggtcgg tgcagaggaa tttttgcaca 211020
tgatagcgcg gttcggtggt ggcgaacggc gtttgtgggt gccgatacac atattcgcac 211080
cagagtaggc cgttcttgga aaaggctttg atatcactgg ccacctcgta gagcccgtcg 211140
gtctcccagt cgtagacgta gacggtgccg taatgactta gcatgagcac gcagggcagt 211200
tcctgcgcct gcttggtgtt tcgtgttaga tcgctgtcgg gtggacgcac ggctagtaca 211260
ccgacggctt ccagggtgtc atcgcagcag agatagtcgg cggccagaga acgtgcgtaa 211320
atctgcggga tggcggcctg ttcgcgcatc actaggaacc agttggcggg gttgcgcagt 211380
gctacggtgg ttccttggtg gcgttgcacg taggttctca gcgccggagg atcgtactgg 211440
cgcagataga ggccttgcag catcgataac gtcttttgaa agacggtgtt tctaaattga 211500
aaaacgccgt agtcgcagcg gatagcatct tcgcacgctc gtcgcgctgt cggagatagg 211560
tgccccaggc ttcggcggcg gctttggtga gtagggacat gccggcggag ccgtctcgac 211620
agcgagtcgg ataaagcgcg ctgcgcgaaa gcttaatata ggagcagcgt cagacgaatc 211680
gcggctggtg gcccggggggg tgggacgcgc cgcctacaca aagtgctccc gaaaatcgaa 211740
actcttgacc cactccggag acaaatccgt attcagattg atgcgtcgag cttccacttc 211800
ggcttccgaa acctcggcct ccgtccggta ggcgttaaca atacgctgac ccaggtgcca 211860
acgtctcttc tctgccaaac gccgttgctc aaaccattcg tctacgtcct tgaggtcaaa 211920
gacagtgtcc tcctcaaggt caaagcctag gtcttcccac tcgtcgtcat cgctctcgtg 211980
gccggcggcc atacgcgcgg caaccgcgtc ttcccctcct cttctttcaa cgttgggtac 212040
cacgttgttt tcttcgggtt ccataggttc tgcgccgctg tcgtcatcat cctctccctg 212100
ctcctcatcg tccgccaagg cgtcgtggat tacctccagg ttctgattgt cgggtacgac 212160
gtggttatct tcgtcgtcgt cgcgtggcat gggcggcggc cgacgcggga cgaccggcat 212220
ggcgcggccg tcgtttcctt cgtcttcctc ttcaccgtct cccaaggaac gcggtcgacg 212280
acgttccgcg aagtcgccgc ggaccacgcg cgcctgccaa atggtaaacg cgtcccaacc 212340
gtcccagtta ttgagcattt cggcgcgaaa acggtcgcct cgacagagcc agcgaaactg 212400
ccgcgcgtag tcgcggtcta cgccgctgtc gaacatggta aagtgcagac gcgccgcctc 212460
gcccatgtgt acgcagcctc cgttgcgttc cagcctggcc gcgcgccgta gaccgtgttc 212520
gtagcggcga cgcacgtaca ccttcatgag gccggcgcga aaaagttcct ctaggctgtc 212580
ggccagccgg tagatttcac cggctagacg ctgcaggggc ggcgagcggt ccagatgcga 212640
cttgacaatc accacgtaaa aacgacagaa acggtcgaag atgatgagga aggacgtgtc 212700
aaaaaaacca ccggcgcggt aagagcccac ggcacccagc aggtaccagc ggcaacgcag 212760
```

```
ttgcagcgtg acgtacattt cgcactcggc caagcgggcg gctggcgcta cctcgaaggg  212820
ccagcagtcc gtcaagcagc cgaaactggt caggagtttc aacgttttgg catggcgtcc  212880
aggtgtatga aagttcacgt cgcgtccgtg gtgttcgcca acgcaggcgg ccaacgcgtc  212940
ggcgtcatga ccgtgacgca gcagcatcgc taccacgtcg tgcggtaccc gcgtagcaaa  213000
tggcgtctgt ggctgacggt atacggcttc ggtgtacatc ataccgtaac gcgccagctc  213060
gtccagatga cgcgcgcaca gcagcagaat ctcttgcgag ggttcgtaga tgtagaggcg  213120
cgtaccgcca cccatgcaga gcaccagctc cgtctcttcg tagtgatctt ccaccatgat  213180
cacgcacttg cctagcacga taaggcgttc ggggcaacaa atcacgtcgt ccagcagctg  213240
gtcgcgtagc tccggcatgg tgctgccggg ccgtacctgc aggaaccagt tgtgcggaat  213300
gccgagcgac agcacctggt cgacgtggtt acggacccag tcgcgaagca cgtcggcgct  213360
gtactggcac tcgaagatgc cctgaaagtc gcccatgacc cgcagaaaag tttcgtagcg  213420
cgtgtggcaa tagaggaatt catcgtttcg cgtaaacgtg ggagctccgt cttcccaacg  213480
tgtacgccac atgtcaaaag aggccgccag ctagacaccc cagaaaagaa gcagagaaag  213540
agacttcttt gtgcgacacg tttttattctg cgtcctccgc tcgacgttca aatctggatg  213600
tactcgcgca cacccgtcag gctctttaag ggaaaagggt ccgagtacgt cactaaccgc  213660
gactgatgca ccagggcggt aatcacccgc tccgcgccct cgcgcgtcga cgaacgcgtc  213720
gtcaccaggc aatgcagccg cgggcccgta tcgtcctgat gaccagcggc ctcgcgctcg  213780
gctgcttcca caccgacaat gtcgggatcc aacacgtagc tctgcgagtt ggtgtcgtag  213840
cggtgtagca ccaacgtgtt ggggtccaga cgctcccacg cgccctcgtg cgggtcaaaa  213900
cgctccgtta aacagagcca gtcatactgc tgctgcagaa tacgccgctc gcgctcgcgt  213960
cgctcatcgg gcaacgcggc gtcttcgttg aagagaatgt cccgcttgtg gtctacggca  214020
cgctcgtggt ggtgcgggca caggtgacgg tgttccatac gcgtctgacg ttgacgctcg  214080
cgctcaaaac gccggtgtcg aaagaccatt ttcagcaacc ccatgcggaa aaactccgtg  214140
atggtgttgg caacgcgccg cacatagtgg ttggggtcgt ccatctggat ggcgtacacg  214200
gcaccgaacc agtccagcag taccagcact tcggccacaa aactgcgtcc cggtcgcgga  214260
cgtcccgtca cgcctagcac ataccacggc gtggccagat tagcacggac agcccaccac  214320
caacgacggc tctccacctc ggtgagcgca caaaagggcc aaatgcggtg taactgctgt  214380
accgttttca tcaaccgcat aatcaccgta ccgtaacccg gtgtatgcaa ctttacgtcg  214440
caacccagga ttcgttcggc cgtggcgtac gagccctcgg gcgtggtgtc attgagaaac  214500
aaaacatgca tggtacgcgc gcccttagga tatcgtcgcg gaacgggtac cgtcattctc  214560
cgcagagtgg tgtgaatcac gtcgcgatac gcaatctccg aacgtgacac accgtaacgt  214620
gccagttcgt ccaggttgtg cgataccaac accatgtact tttcacgagt gtcgtaggcg  214680
tagacgcgag aaaagcgacc cataaaaacc acgtacgagg tagccaccat gccatcatgg  214740
tgatcgcgac gtggctcggg caacaaaata acagcgtatc ccaacggcgt caacggctcg  214800
cggcaacaga tgagctttga cgccgcctgt ttggcggcgg taatgatccc gtcctccgta  214860
cgtaacatca catgccagcc cttggggga cccaaggaca dacagcgtcc ctcgttacga  214920
tgaacgtaac gcgtgatttc cattggctcc aggcaaaaga acagttcctt aaaatcccgc  214980
aacacttgtc ggtataacgc catgggatcc tcggccgcca caggcagcgc ggggagctcc  215040
ggcggcataa ctgcagcgcc gtcagggcca gaacccgcag ccggatccat cattgagcga  215100
cactctcagc cggacaaccg gcgtcactga cagaagccga gccaaataca gagaaagcaa  215160
```

```
cgctacaccg tcaccccgct cccaagcgcc gcggaaagtg ctccgatttt tcaccgtcgt    215220
tcgcgacgtt gatttgcctc ggtctgagaa ccgacctagc gttcggaccg gtgcgcagaa    215280
acagccggcg gtccgagcca ctgagcggtt cacagccccg gccgccgata gttaccggag    215340
agacgttcga gctgcaggta catcagcgct tcccgcttcg ccaccccgcg cccgcccag     215400 tttatactct ccgacgcccc gtccaacgcg cctgtggagg gccaatcgga ccgcgggagc    215460
tctccaagtg gatgacaggc acagccgagt gcccgaccgt gaagagccct catccacctg    215520
aacagaccgc taaccgaagg accccgagtc gcgtccgtcg gtcccgacgt ccgtcgccat    215580
ctggctccct gctgttggct acctctcgga tttcaaaaaa gagcacgtgc cgatgacggt    215640
gcacaggaaa gagccaaagt gtcacggcgt cttttttat ttgtattcct ttcctgtttt     215700
gtactcgtaa actgttgatg ttgtttttac atccaaaagg gcaagtaaga aacaggatga    215760
ggcatggtag gtttgggcgt ggggcggccc tccagcacgg cggcccggc cgcccggcgg     215820 gtgagcaccc ggcgttgcgc cgtgtctatc ttgtgtttct tctgtgtctt tttcctatct    215880
tgttccgcga cggcctcttt catcacgttc agcatgcgtt cctcgacgcc ctccaggat    215940 cctggggagg agggagtcct agtgaggctt ccaatgttgt tttgtggatt ttcggtttcc    216000
ttttcttggt cgtcatcgtc ggacgtgtcg tcttcctctt gatcctcttc ttcgtccgag    216060
tagtagacgc atagtccttg gttcatcagg ctgggattca tcaggttctg acggggaatc    216120
cgctgttgta gacgtttaac cgcccgttcc aggcgagagc tcatgccgca ccagacgctg    216180
taacgccgca cgggcccgta gcgggctgtt tgttcgcgta catgatcgtt gagctcttgc    216240
caatattgtt tggcacactc cagatcggag gtttgtggat agtcgggtcg gatccgcgga    216300
tcccaactga catcggcggt gccggagact tcgtccagac tgttacgcat agagcaccag    216360
tcgggtcgga cgataaacct gtccttgcgg attaaccatt tataacgtag ttcgtgatgg    216420
cgtgtagagg cccgtacacg ctccacggtc ccaaagcggt cccagaaggg aaagttttcg    216480
tgggggcagc gacccggcac ttccagacgt tcggcgtcgt ccacggcgta gtgaaaacgc    216540
cggccggcct ggtaaatttt gagcagaccc actgttaaca acatatccac gctgtcagcc    216600
aaccgccaga tctcgcggcg agacacgtca aaatagaaaa attcgcaggc tcggtcgacc    216660
aggatcacga aatcggcgtg aaagacgccg gagggtagcg attcgcccac cacacccatt    216720
atcatggttt cacagcataa gcggtccaca aagaacttca acaggtcgtt gaattgctcc    216780
gtctccatac agatgaaggg ccagacgcct ttgaggttct cggcctggcc gcagagcagt    216840
agcggacgtg tcatctcgcc cggagtgcgc agaggcacgc attcgccgcg ataacgacag    216900
gtcacacgct gtagttcgct gatgctgttg tcgtgcaggc gaaggtcgca gataatatga    216960
tccggttgcg tggttagcag cggcgtgcgc atttgctcgc cgtagatggc ctcgcagtgc    217020
aacagcccgt gtcgcgcaaa atcgtccaaa ctgtgcgcca ggtagtaaag caccccgcga    217080
tcgcggtcta gacaccacac ggtttcgtaa cgtcctaaca ggagcaccag acgggcctgg    217140
ctaggtggct caatttcctc tacatacacg aaaaagtcgt catcgtccga gtcctcgtcc    217200
tcagaagagg accgcggccc gtgtactctg gcaacacgg tggtagagaa ctgcaggacg     217260
cccagagact cgagcgattc ttcgcagcag atgagctgac cccagggcgt ttcgggcccg    217320
tcggtgacag ccgcgctgcc aaagatgtcc tcaaactcta caaaatctag acgccatccg    217380
ggtggcgctg aaatgggaag gctaatgttc atatcagcat agctacgaac taagtggcgg    217440
atgtcctgcc gcaagtcttg gcagagaatg agctttcgta aacccttgag ggtcctccga    217500
```

```
acaacggccc cagacgcgta gcgataggac tggcgcatgg tgccgcggcg tggagcggca 217560
cttggcagcc tattttatgg agtttcttca gtgacgtggc ttgttcacgt cgttcgtggg 217620
ctgcggttgg cagctccggt ctgtaaacca cccgaaaaga ctgacatcga cgtcaaagac 217680
tcacgtaatt tggaacatgt gcgaccgcaa agtgcgtcag aatagcacgt ggctttagga 217740
cataaaaagt accgtgaggt ctagacgtgg gttttgtgat tgacacttac accaggtaag 217800
ccaagggacg gtgaaactgt atgtgaggaa tctgggtgct tagacgacta acgtgtaatg 217860
cttttttacag gactgttcga caggtgatag tacctgtaag gtgatgacca cctctacaaa 217920
taatcaaacc ttaacgcagg tgagcaacat gacaaaccac accttaaaca gcaccgaaat 217980
ttatcagttg ttcgagtaca ctcggttggg ggtatggttg atgtgcatcg tgggcacgtt 218040
tctgaacgtg ctggtgatta ccaccatcct gtactaccgt cgtaagaaaa aatctccgag 218100
cgatacctac atctgcaacc tggctgtagc cgatctgttg attgtcgtcg gcctgccgtt 218160
ttttctagaa tatgccaagc atcaccctaa actcagccga gaggtggttt gttcgggact 218220
caacgcttgt ttctacatct gtcttttttgc cggcgtttgt tttctcatca acctgtcgat 218280
ggatcgctac tgcgtcatcg tttggggtgt agaattgaac cgcgtgcgaa ataacaagcg 218340
ggccacctgt tgggtggtga ttttttggat actagccgtg ctcatgggga tgccacatta 218400
cctgatgtac agccatacca acaacgagtg tgttggtgaa ttcgctaacg agacgtcggg 218460
ttggttcccc gtgttttttga acaccaaagt taacatttgc ggctacctgg cgcccatcgc 218520
gctgatggcg tacacgtaca accgtatggt gcggtttatc attaactacg ttggtaaatg 218580
gcacatgcag acgctccacg ttcttttggt tgtggttgtg tcttttgcca gcttttggtt 218640
tcctttcaac ctggcgctat ttttagaatc catccgtctt ctggcgggag tgtacaatga 218700
cacacttcaa aacgttatta tcttctgtct atacgtcggt cagttttttgg cctacgttcg 218760
cgcttgtctg aatcctggga tctacatcct agtaggcact caaatgagga aggacatgtg 218820
gacaaaccta agggtattcg cctgttgctg cgtgaagcag gagataccctt accaggacat 218880
tgatattgag ctacaaaagg acatacaaag aagggccaaa cacaccaaac gtacccatta 218940
tgacagaaaa aatgcaccta tggagtccgg ggaggaggaa tttctgttgt aattcgatcc 219000
tctctcacgc gtccgccgca catctatttt tgctaattgc acgtttcttc gtggtcacgt 219060
cggctcgaag aggttggtgt gaaaacgtca tctcgccgac gtggtgaacc gctcatatag 219120
accaaaccgg acgctgcctc agtctctcgg tgcgtggacc agacggcgtc catgcaccga 219180
gggcagaact ggtgctatca tgacaccgac gacgacgacc gcggaactca cgacggagtt 219240
tgactacgat gaagacgcga ctccttgtgt tttcaccgac gtgcttaatc agtcaaagcc 219300
agttacgttg tttctgtacg gcgttgtctt tctcttcggt tccatcggca acttcttggt 219360
gatcttcacc atcaccctggc gacgtcggat tcaatgctcc ggcgatgttt actttatcaa 219420
cctcgcggcc gccgatttgc ttttcgtttg tacactacct ctgtggatgc aatacctcct 219480
agatcacaac tccctagcca gcgtgccgta tacgttactc actgcctgtt tctacgtggc 219540
tatgtttgcc agtttgtgtt ttatcacgga gattgcactc gatcgctact acgctattgt 219600
ttacatgaga tatcggcctg taaaacaggc ctgccttttc agtatttttt ggtggatctt 219660
tgccgtgatc atcgccattc cacactttat ggtggtgacc aaaaaagaca atcaatgtat 219720
gaccgactac gactacttag aggtcagtta cccgatcatc ctcaacgtag aactcatgct 219780
tggtgctttc gtgatcccgc tcagtgttat cagctactgc tactaccgca tttccagaat 219840
cgttgcggtg tctcagtcgc gccacaaagg tcgcattgta cgggtactta tagcggtcgt 219900
```

```
gcttgtcttt atcatctttt ggctgccgta ccacctaacg ctgtttgtgg acacgttaaa  219960
actcctcaaa tggatctcca gcagctgcga gttcgaaaga tcgctcaaac gtgcgctcat  220020
cttgaccgag tcgctcgcct tttgtcactg ttgtctcaat ccgctgctgt acgtcttcgt  220080
gggcaccaag tttcgcaaga actacactgt ctgctggccg agtttcgcca gcgactcttt  220140
tcccgcgatg tatcctggta ccacagcatg agcttttcgc gtcggagctc gccgagtcga  220200
agagagacat cttccgacac gctgtccgac gaggtgtgtc gcgtctcaca aattataccg  220260
taataaaaaa gcgctacctc ggccttttca tacaaacccc gtgtccgccc ctcttttccc  220320
cgtgcccgat atacacgata ttaaacccac gaccatttcc gtgcgattag cgaaccggaa  220380
aagtttatgg ggaaaaagac gtaggaaagg atcatgtaga aaaacatgcg gtgtttccga  220440
tggtggctct acagtgggtg gtggtggctc acgtttggat gtgctcggac cgtgacggtg  220500
ggtttcgtcg cgcccacggt ccgggcacaa tcaaccgtgg tccgctctga gccggctccg  220560
ccgtcggaaa cccgacgaga caacaatgac acgtcttact tcagcagcac ctctttccat  220620
tcttccgtgt cccctgccac ctcagtggac cgtcaatttc gacggaccac gtacgaccgt  220680
tgggacggtc gacgttggct gcgcacccgc tacgggaacg ccagcgcctg cgtgacgggc  220740
acccaatgga gcaccaactt ttttttctct cagtgtgagc actaccctag tttcgtgaaa  220800
ctcaacgggg tgcagcgctg gacacctgtt cggagaccta tgggcgaggt tgcctactac  220860
gggggttgtt gtatggtggg cggggtaat cgtgcgtacg tgatactcgt gagcggttac  220920
gggaccgcca gctacggcaa cgctttacgc gtgaattttg ggcgcggcaa ctgcacggcg  220980
ccgaaacgca cctaccctcg gcgcttggaa ctgcacgatg gccgcacaga ccctagccgt  221040
tgcgatccct accaagtgta tttctacggt ctgcagtgtc ctgagcaact ggttatcacc  221100
gcccacggcg gcgtgggtat gcgccgctgt cctaccggct ctcgtcccac ccgtcccgg   221160 ccccaccggc atgacttgga gaacgagcta catggtctgt gtgtggatct tctggtgtgc  221220
gtccttttat tagctctgct gctgttggag ctcgttccca tggaagccgt gcgtcacccg  221280
ctgcttttct ggcgacgcgt ggcgttatcg ccgtccactt ccaaggtgga tcgcgccgtc  221340
aagctgtgtc ttcggcgcat gtttggtctg ccgccgccac cgtcagtcgc accacctggg  221400
gaaaagaagg agctaccggc tcaggcggcc ttgtcgccgc cactgaccac ctggtcacta  221460
ccgccgtttc cgtccacgcg gatacctgac agtccgccgc caccgtacca gcttcgtcac  221520
gccacgtcac tagtgacggt acccacgctg ctgttatata cgtcatccga catcggtgac  221580
acagcttcag aaacaacgtg tgtggcgcac gctacttatg gggaaccccc ggagcccgct  221640
cgatcgacgg ctacggttca ggaatgtacc gttcttaccg ccccgaattg cggcatcgtc  221700
aacaacgacg gcgcggtctc tgaaggccaa gaccatggag atgcggttca ccatagcctg  221760
gatgtggttt cccagtgtgc tgctgatact ggggttgttg acacctccga gtaacgggtg  221820
caccgtcgat gttggacgaa acgtatccat tggagaacag tgccgccttc gaaacggtgc  221880
gacgttctcc aagggagaca tcgaaggtaa cttcagtggg cccgtcgtcg tggagttgga  221940
ctacgaagat atcgatatta ctggcgaacg gcagcgactt cggttccatc tcagcggact  222000
cgggtgtcct acaaaggaaa atataagaaa agacaatgaa agcgacgtca acggtggaat  222060
tcgctgggct ctatatatac aaaccggcga cgccaagtac ggtattcgta accagcattt  222120
gagtatacgg ttaatgtatc ctggggaaaa aaatacacaa cagctgttgg attctgattt  222180
cagttgcgaa cgtcaccgga gaccgtccac gccgttggga aagaacgccg aagtgcctcc  222240
```

-continued

```
cgcgacccgc acgtcttcta catacagcgt cctcagcgct tttgtagtgt ggatcggatc   222300
cggcctcaat atcatctggt ggaccggcat cgtgcttctg gcggtggacg ctctcggact   222360
tggcgagcgt tggctgaggt tagcactgtc tcaccgggac aaacatcacg catcgcgaac   222420
cgcggcgctc cagtgtcaac gcgacatgtt acttcggcaa cgtcgacggg ctcggcggct   222480
gcacgccgtt tctgaaggca aactgcagga agagaagaaa cgacagtctg ctctggtctg   222540
gaacgttgag gcgcgaccct ttccgtccac acatcagctg attgtgctgc ccctcctgt    222600
agcgtcagct cctcctgcgg ttccctcgca gccccccgag tattcgtctg tgtttccgcc   222660
tgtataaaaa taaagagacg ggaggctgat cgcggccttc agcgtctcat ttgtctttac   222720
tctcgagtgc ggtcggtgtc tcgtcggtga gacgaggccg ccgcccgaca agttcgatct   222780
catgtcgctc ttggagcgcg aagagagttg gcgtcgcgta gtcgactact cgcacaacct   222840
gtggtgtacg tgcggtaact ggcagagcca cgttgagatt caggacgagg agccaaactg   222900
cgagcagccg gagcccgcac actggctgga atacgtggcg gtccagtggc aggcccgggt   222960
tcgcgattct cacgatcgct ggtgtctctg caacgcctgg cgtgatcacg ccttgcgcgg   223020
ccgttggggt acggcgtatt cctcgggttc ctcggcctct tcctccggtt tcgtcgcgga   223080
gagcaagttc acctggtgga aacgactgcg ccacagtacc cggcgctggt tgtttcgccg   223140
ccggcgagct cgatacactc cgtctaactg tggggaaagt agcactagca gcggccgaga   223200
tagcggtgac gagagtaact gcagtctacg cacccacggc gtgtacacac ggggtgaaca   223260
acactaatcg ataagtcgcg tgtaggcgac tggctacatc aaccggatat ctgcggggat   223320
ttaaaaagac gacccgttgt catccggctt agaccaaacc gtccttttat catcttccgt   223380
cgccatggct atgtacacat ccgaatccga acgcgactgg cgtcgtgtaa tccacgactc   223440
gcacggcctg tggtgcgact gcggcgactg gcgagagcac ctctattgtg tgtacgacag   223500
ccattttcag cgacgaccca cgacccgagc cgaacgagg gccgccaatt ggcggcgaca    223560
gatgcggcgg ttacaccgtt tgtggtgttt ttgtcaggac tggaagtgtc acgcgttata   223620
cgccgagtgg gacggcaaag aatccgacga cgagtcgtcg gcgtcttcct cgggcgaagc   223680
gccagagcaa caggtccccg cttggaagac cgtgcgggcc ttctcgcggg cctaccacca   223740
ccgcattaac cggggtctgc ggggcacgcc cccaccgcgc aacttgccgg gatacgagca   223800
cgcctccgag ggctggcggt tttgcagtcg acgggaacgg cgagaggacg atcttcgcac   223860
gcgggctgag ccggaccgcg tggtgttcca gttaggggga gtaccccctc gccgtcaccg   223920
ggaaacttac gtgtaagaac acggcgtgac aataaacaac atagcgtaaa tccccgtgtg   223980
atgtgtgtga ttgacgttcg ggaaacatgt ccccatcatc agcgtcacaa ttgacgtggg   224040
ttggtcactg acgtgcagga tgttacgcga gtcagagaat cgcataagaa cggagtggtg   224100
agcgggttcc cacaggagtc tctggcgcaa aagcaccatg agcctcaggt tccccgagag   224160
ggtgggttac gagaaactgg gataccgccc gcatgccaaa cgcgtgcggg tgcatgactc   224220
gttgggattg acgcggttta tcatgaggca actcatgatg tacccgctgg tgttgccgtt   224280
cacttttccg ttttacgtgc cgcggtccta gcacgtcagt ggtgacgctg ataattgcaa   224340
catgcccat gacgaacccg cttgggacga acgtcaatac cacgtcaaac caccgtgact    224400
tggctgaacg ttgaaacata aagccaaagc gccgtcggca cttggcttca gagcagcgcc   224460
tcggggcgat gcgacggcga tgaacttaga gcaactcatc aacgtccttg gtctgctcgt   224520
ctggattgcc gctcgtgctg tcagccgcgt tggtccgcat ggctccggac tcgtttatcg   224580
tgagcttcat gatttctacg ggtatctgca gctggacctt ctgggaccag tggtggcggg   224640
```

```
gaatcgctca gtccggacct ggagagagca ggcggaccga gccagaggga ccttcgcttg 224700
gcgttcaggc cttaatacta gccgcatctt acctgtcggc agcatgtatc ggggctccga 224760
cgccttaccc gccggcctgt atcgtcccga agaagaggtg ttcctcctct tgaatcgctg 224820
ccatgggcca ctgtcaacgc cgaaaaatgc ttgtctggct gaggttggtg tcgctaatgc 224880 cactttttg tctcgcttca atgtcggtga ttttcacgga gcgtcatggg aaaacggtac 224940
cgctcccgat ggagagcccg gggtatgctg aaattcctct taaaatttcg taaacgacgt 225000
cgtccagtcg ttgtgccgcg attcgtacgg ttcatcgtct acgtcgtttt gttcaccgtc 225060
gctgtgcaac gcgtgaaaca agagcgtgat gcgcaccttc ggcggtatga agaacgatta 225120
cggaaaaacc gcgcacggcg tcggcagtct tttccgtgac ttggggcgat gggtccgagc 225180
tgcggtatgg gtcacggcgg cgtgtgtttt attgacgaag atgccgatgt gtgactaaaa 225240
acgtcccagc cccagagcga tatgtttcaa taaaaaaaat atgtagtatc atattatgcg 225300
tgtcctggtt tttcattttt ggatgtatgt atcgcataaa gggtggcgag gtgtgaggat 225360
gaaacatatg cagatacgca gtgttgttat ccgaacgaaa cccgtgtaat gcgtacaacg 225420
gtacttcagt atgaaagtcc cgtgtgtggg ggggggggc aaatagttgc gtttgccgtt 225480
gggcgtacgc tacgtttgta tttctggcta taatatgtgc ggtcatgtgt cgatgttcct 225540
attgggaagg gtgtgactgt agggtgtata aagtacggtg ggacgcagag ggacattgat 225600
agaaacaggt tgagcgctgt acgagtttca cacgctgaat cggcgccaag aataaaacag 225660
tggttattcg taaaagtatg ggggggggg ggatgttgtc gacggttgtt agatgcattg 225720
cgtatctgta ttagtagttt tgcaagccgt ggtgcgtgtt attgtgacgt agcaattatc 225780
gtattgtgca tgtgtcgttc atcacagagt ttagtatact aatatgaagc gtcgcgagta 225840
ttaaagcaat tggtgtctct gtgctagtct aacaacacct gtgtaatgcg tacaacgaga 225900
aaaaagacgc gaaagcaacg tgtatggggg gggggggaa taatattgct aatcatgcgt 225960
cttgcagtac agatagccgc tgtatcttac gcgtattgtc gcaacagttc cacatcggtg 226020
taattggatg tctggtactt atcactggcg tcgttataac attgtaaaac aagttttcga 226080
aacataacga cagctgcaaa agaaaaccag tttattgagc attgtaatgg tagtgtgtgg 226140
ctatattaga aaacgtgacg cgtcgcatgt cgcggcacaa tctggcagcg gggtcggggt 226200
agggtacggt gggaggcatg tacacagatg gaacaaaagc agaagtaacg tgagaaggag 226260
catacagtcc agtatccagc ggttcctgag tagcaccacc catcaactga atgccctcat 226320
gagtaaaagt ctgcgggcga cagcccttgg ggaccgttgg catgggacga tcaatctcca 226380
aaccacagcg taacaccgtt ttcttccaac gtcgttgata gacgtcgttt ttacggttac 226440
tcccaagaac ccagaaagtc tcgtccaagt cgtaccagga atcttctccg gggagacgcg 226500
acggttccca atcctcgtcg tctcgtctca aagcacgtcc caaactggct tgaggagtca 226560
acggtggttc tgtgggtcgg gtgtagcgcg agtgttttcc cttcatgagc gattcatcct 226620
ccttgccttt aggcttttg gtctttttgt gtatcatctg gccgccggcc tccataacca 226680
ccgtggccaa gtccagtccc agagcttgag cgtcggcgcg cgtcgggcg tcttgcaggt 226740 agtcttccac atttgcacag atggccgggt gtttggtggc tagggtgagg acctcagcct 226800
cgccgcgacc cggacgtagc aaaaaagcca actgcccgtg cggctcgcgc gcccacagcg 226860
cggcgcgcgg gtgcaggtgc agcgcgtccc agcgcggccg ctcccactgc tcgcggtcca 226920
gctcgggcag cagccgccgc gcggcctcgg cggcgggcgc cgactcgcgt cccagcgcca 226980
```

```
gcgcgcccag cacgcccgcg cgcagaaagt gcgacagctc cgccgccagc gggtacacgt 227040
gcccgtccag cgggcagtac ccgaacacgg cgcccagctc gtccagcagc accaccagca 227100
tggcgcgcgg cacggtcccc gacgccgccg gacccgccat cgctgtcgaa cccaccatca 227160
ccgtcggcgc cgctgctgct gccgcgtccg ccccgaccac cgcgtgcgcg tccgcgttag 227220
gcacgcaaat cgcgccccg ccggcggcgc cgtacggctg cggaggcaca ggtacagcgg 227280
accccacggc tcccgctatc gcgcacgcg cgtccccgcc ggcggcctcc gtctccgtgc 227340
cgctcgccgc tggcggcgac gtcgtccccg ccgccgtccc cgtcgccggc cccgccgcgc 227400
agcccagcca ccgcgcgggc agcaccgcgc ccagcgccag ccagccgcag cacagacgct 227460
ggttcaggtg ccgacgcacg gccgtcagca gcgacgcggg gtgcggcgcc gacgcgaacg 227520
gctcgtactg cgccagctcc tgccacgcgc ccagcagtac catcggctgc agtcgcctgc 227580
ccggcgtctg cagcgccacc gtcgtgccgg cccaccgccg gcgcagctcc cgtccgagcg 227640
ccgtcgcctc ctcggcgcgc agcaacgtct gtcggagcgc cggctgaggc agcagcgtcg 227700
cgcgcggggt gcccacgccc agccggttgc agcggtacag ccgcaccacc tcgcccgcgc 227760
cgtgccgaaa ccactcgtcc gcgtcgcgcg ccgctaggat cagcgtgttg tttgccaggt 227820
cgtacacgaa cacgcggaac ccggcgccca gcgccaggta cagtccgtcc tgcgcgcaca 227880
gaccctcggg atggccggcc ttgtcgccca acgtcgggtc ggctgcgggg tccacctcgt 227940
gcaccacggt agccaccagt acgatccacg cgtcccgcgg cgacagttga cgcaggtccg 228000
tcgcgcccac gccgttcatc tggctgcgcg gcgtcacccg cgcgtagaat ccgtacggcc 228060
gtccgagcgg cagcagcgtg cccgcgtcgc gctgcgacca cttgcgcatg gcgcggcccg 228120
tgctgttggc caaaaacgcc gcgcgccaca cggcgcccat ggcctggtat tccagctccg 228180
tcagcgcctg gcgctccacc ggaatctgag acagcaacag gcgctccggg ccgtgccaaa 228240
agttgctatt gttgccgcta ctcggagggg cgcccgcgg cccgcggggt tctaccggtt 228300
ggacgccgtg gcccggcgtc gtcgtagccg cagcactcgc accagtgccc gctgtggacg 228360
gcgctcccat cggcacacaa gaagaaggag gagaggaacc aacccccgaa ggccctccgg 228420
ccccgcggcc gcgaccaagg ggcgggggc gcggcgacat gccgttgcgc tgggccatgg 228480
gcgccggaca cctccgacgt ccactatata ggaagcaaac ccgcgtcagc gagcacgcgg 228540
tttagacacg cggacgcctt cgtcgcccgt gtgccgcggg cgacacgcag ctggcttta 228600 taggcagcga cgtgcacggc gcgtgctggc gccgccttgg cgccacgcag tctggaaggc 228660
cgtggactgg gaaaggcagc tacccgaagg aagacgcgcg gcaggcgcgt accactggag 228720
cgcacagccg cctccggc gcgcacccat ctaggtggac gcccgacatc cattccgggc 228780
cgcgtggtgg gtcctcgagg ggcgggggg tgtttttagc gggggggtga aacttggagt 228840
tgcgtgtgtg gacggcgact agttgcgtgt ggtgcgagg acggcgacgg cgaataaaag 228900
cgacgtgcgg cgcgcacggc gaaagaaga cgcgtgtctg tgtctgtgtg attccccggg 228960 gaaagagga agttcccggg ggacggcagc atgggtccct ggggacacac gaaaagcaac 229020 gccggggc gagggacgac ggccctgggg accgcggggg aaataacggc cgcgaggcca 229080
cacactcgtt cctgcgaagc cgcacacccc gaggccgcgc acaccgccga cacacccgc 229140 caccacaccc cgccggcaca cccgccacac gcccgcgaca cacccggcac gacacacccg 229200
```

-continued

```
gcacacgccc gcgacacacc ctgacacacc ctgccaacac accccgaca cacccaacac 229260 acgcccgcga cacacccggc acacacccac ccggccgcgc cccgacacac ccaaaacacc 229320
gccggtgcgg ggccgcgtgg tgggtcctcg aggg                     229354
```

GENERATION OF HUMAN CYTOMEGALOVIRUS YEAST ARTIFICIAL CHROMOSOME RECOMBINANTS

GOVERNMENTAL RIGHTS

This invention was made with government support under Contract No. AI30627 by the National Institutes of Health. The government has certain rights in the invention.

BACKGROUND OF THE INVENTION

Human cytomegalovirus (HCMV) is the leading cause of viral congenital infections worldwide, involving about 1% of newborns. In children, the consequences may be severe, especially in case of maternal primary infection during pregnancy. In the United States, about 30,000 to 40,000 newborns are affected each year; more than 9,000 of these children are left with permanent neurological sequelae. Demmler, G. J., 1994, Congenital cytomegalovirus infection, Semin. Pediatr. Neurol. 1(1):36–42. The annual cost of treating cytomegalovirus infection complications in the United States is about two billion dollars. Daniel Y. et al., 1995, Congenital cytomegalovirus infection, Eur. J. Obstet. Gynecol. Reprod. Biol., 63(1):7–16.

HCMV is a species-specific member of the herpes virus family. Other well-known members of the herpes virus family include herpes simplex virus, types I and II, Epstein-Barr virus and Varicella Zoster virus. Although these viruses are related to each other taxonomically as double-stranded DNA viruses, infections due to these viruses manifest in a clinically distinct manner. In the case of HCMV, medical conditions arising from congenital infection include jaundice, respiratory distress, and convulsive seizures which may result in mental retardation, neurologic disability or death. As noted above, congenital HCMV infection produces significant problems from both personal and public health perspectives.

Infection in adults is frequently asymptomatic, but may manifest as mononucleosis, hepatitis, pneumonitis, or retinitis. HCMV infection is particularly significant in immuno-compromised patients such as AIDS sufferers, chemotherapy patients, and organ transplant patients undergoing tissue rejection therapy.

The mechanisms of HCMV pathogenesis are not fully understood. It is believed that host factors, such as cellular and/or humoral immune responses might be involved. See, Alford and Britt, "The Human Herpesviruses", Eds. Roizman, B., R. J. Whitley and C. Lopez, Raven Press, N.Y., 1993, pp 227–55. It has also been speculated that genetic variability (either structural or antigenic or both) among different strains of HCMV could be responsible for the variability in clinical manifestations observed. See, Pritchett, R. F., 1980, DNA nucleotide sequence heterogeneity between the Towne and AD169 strains of cytomegalovirus, J. Virol. 36(1):152–61; Lehner, R. et al., 1991, Comparative sequence analysis of human cytomegalovirus strains, J. Clin. Microbiol. 29(11):2494–502; Fries, B. C., 1994, Frequency distribution of cytomegalovirus envelope glycoprotein genotypes in bone marrow transplant recipients, J. Infect. Dis. 169(4):769–74.

Classical drug therapies have generally focused upon interactions with proteins in efforts to modulate their disease causing or disease potentiating functions. Such therapeutic approaches have failed for cytomegalovirus infections.

Effective therapy for HCMV has not yet been developed despite studies on a number of antiviral agents. Interferon, transfer factor, adenine arabinoside (Ara-A), acycloguanosine (Acyclovir, ACV), and certain combinations of these drugs have been ineffective in controlling HCMV infections. Based on preclinical and clinical data, foscarnet (PFA) and ganciclovir (DHPG) show limited potential as antiviral agents. PFA treatment has resulted in the resolution of HCMV retinitis in five AIDS patients to date. DHPG studies have shown efficacy against HCMV retinitis and colitis. DHPG seems to be well tolerated by most treated individuals, but the ppearance of a reversible neutropenia, the emergence of resistant strains of HCMV upon long-term administration, and the lack of efficacy against HCMV pneumonitis limit the long term applications of this compound.

Immunoglobulin has also been utilized for treating HCMV infections. See, Condie, R. M. et al., 1984, Prevention of cytomegalovirus infection in bone marrow transplant recipients by prophylaxis with an intravenous, hyperimmune cytomegalovirus globulin, Birth Defects, 20:327–344; Perrillo, R. P. et al., 1987, Immune globulin and hepatitis B immune globulin, Arch. Intern Med., 144:81–85; Snydman, D. R., et al. 1987, Use of cytomegalovirus immune globulin to prevent cytomegalovirus disease in renal-transplant recipients, N. Engl. J. Med., 317:1049–1054. The development of more effective and less-toxic therapeutic compounds and methods is needed for both acute and chronic use.

Several HCMV vaccines have been developed or are in the process of development. Vaccines based on live attenuated strains of HCMV have been described. See, Plotkin, S. A. et al., 1984, Lancet, 1:528–30; Plotkin, S. A. et al., 1976, J. Infect. Dis., 134:470–75; Glazer, J. P. et al., 1979, Ann. Intern. Med., 91:676–83; and U.S. Pat. No. 3,959,466. A proposed HCMV vaccine using a recombinant vaccinia virus expressing HCMV glycoprotein B has also been described. Cranage, M. P. et al., 1968 EMBO J., 5:3057–3063. However, vaccinia models for vaccine delivery are believed to cause local reactions. Additionally, vaccinia vaccines are considered possible causes of encephalitis.

Adenoviruses have been developed previously as efficient heterologous gene expression vectors. For example, an adenovirus vector has been employed to express herpes simplex virus glycoprotein gB (Johnson, D. C. et al., 1988, Virol., 164:1–14), human immunodeficiency virus type 1 envelope protein (Dewar, R. L. et al., 1988, J. Virol., 63:129–136), and hepatitis B surface antigen (Davis, A. R. et al, 1985, Proc. Natl. Acad. Sci., U.S.A., 82:7560–7564; Morin, J. E. et al., 1987, Proc. Natl. Acad. Sci., U.S.A., 84:4626–4630). Adenoviruses have also been found to be non-toxic as vaccine components in humans (Takajuji, E. T. et al., 1970, J. Infect. Dis., 140:48–53; Collis, P. B. et al., 1973, J. Inf. Dis., 128:74–750; and Couch, R. B. et al., 1963, Am. Rev. Respir. Dis., 88:394–403). U.S. Pat. Nos. 5,591,439 and 5,552,143 provide novel vaccine components for HCMV which comprise an adenovirus expression system capable of expressing a selected HCMV subunit gene in vivo.

Human CMV is a large, enveloped herpesvirus whose genome consists of a double-stranded DNA molecule approximately 240,000 nucleotides in length. This genome is the most complex of all DNA viruses and is approximately 50% larger than the genome of herpes simplex virus (HSV). Intact viral DNA is composed of contiguous long (L) and short (S) segments, each of which contains regions of unique DNA sequence flanked by homologous regions of repetitive sequence. As a group, human CMV isolates share at least 80% sequence homology, making it nearly impossible to classify cytomegaloviruses into subgroups or subtypes, although variations in the restriction endonuclease patterns of various CMV DNA preparations are identifiable in epidemiologically unrelated strains. The DNA of the prototypic strain of CMV (AD 169) has been sequenced and reported to contain a conservative estimate of 175 unique translational open reading frames (ORFs). A number of the predicted CMV gene products show homology to other human herpesvirus gene products.

The large genome of CMV is difficult to manipulate. Cloning and mutagenesis of murine CMV (MCMV) has been accomplished using a bacterial artificial chromosome ("BAC"). See, Messerle, et al. 1997, Cloning and mutagenesis of a herpesvirus genome as an infectious bacterial artificial chromosome. *Proc. Natl. Acad. Sci. U.S.A.*, 94: 14759–14763. Cloning of MCMV in a BAC allows for manipulation of the CMV genome within the bacterial system. Another useful vector, the yeast artificial chromosome ("YAC") has been utilized to clone an infectious adenovirus (Ketner et al., 1994, *Proc. Natl. Acad. Sci. U.S.A.* 91:6180–6190). However, it has not yet been demonstrated that the CMV genome could be successfully cloned into and manipulated within a yeast artificial chromosome ("YAC").

Yeast artificial chromosomes (YACs) allow the propagation of very large segments of exogenous DNA in a microbial organism that is easy to work with and grow (Schlessinger, D. 1990, Yeast artificial chromosomes: tools for mapping and analysis of complex genomes, *Trends In Genetics* 6:248–253). The great promise that YAC technology holds for studies of gene function and regulation has been strengthened by the development of methods for transferring YACs into mammalian cells and animals (Choi, T. K. et al., 1993, Transgenic mice containing a human heavy chain immunoglobulin gene fragment cloned in a yeast artificial chromosome. *Nature Gen.* 4:117–123).

YAC transgenic approaches are very powerful and are greatly enhanced by the ability to efficiently manipulate the cloned DNA. A major technical advantage of yeast is the ease with which specific genome modifications can be made via DNA-mediated transformation and homologous recombination. In particular, an alternative recombinant cloning method of YAC construction has recently been described (Ramsay, M. 1994, Yeast artificial chromosome cloning. *Mol. Biotech.* 1:181–201. The method involves co-transformation of a target DNA, such as the HCMV viral genome, with YAC vector arms containing appropriate DNA segments homologous to the target DNA. Recombination in the yeast cell then generates the desired YAC. A schematic of this procedure is shown in FIG. 1.

The present invention provides a YAC vector that includes the full-length DNA sequence of the CMV virus. This vector provides a solution to the long-felt need for a CMV vaccine, and provides a tool for studying the replication of CMV using cell-line models.

SUMMARY OF THE INVENTION

The present invention provides a YAC vector that includes portions of and full-length DNA sequence of the CMV virus. This vector provides a solution to the long-felt need for a CMV vaccine, and provides a tool for studying the replication of CMV using cell-line models.

The present invention provides recombinant DNA constructs and YAC vectors comprising, in certain embodiments, overlapping segments of the HCMV genome. In other embodiments, the present invention provides a recombinant DNA constructs and YAC vectors comprising the entire CMV genome. This invention provides stable partial and full length YAC-HCMV clones useful for studying CMV replication, generating CMV virus and constructing CMV vaccines.

In general, the present invention provides an isolated recombinant DNA molecule comprising a yeast artificial chromosome, including at least a portion of HCMV genome. In preferred embodiments the DNA molecule further comprises at least one a sequence. Preferably the HCMV genome is derived from the Towne strain or from the AD169 strain. In preferred embodiments, the recombinant DNA molecule comprises a DNA molecule selected from the group consisting of Y1-2, Y3-2, Y2-4, Y4-7 and Y5-26, described in Table 2, below. In another embodiment, the invention provides a composition suitable for use as a vaccine comprising the isolated recombinant DNA molecule and a pharmaceutically acceptable excipient.

DETAILED DESCRIPTION OF THE PREFERRED EMBODIMENTS

Polynucleotides of the Invention

The present invention provides a vector comprising at least a portion and up to substantially all of a full-length CMV genome on a single nucleic acid molecule that is capable of replicating in a host cell such as a yeast cell. Preferably, the CMV genome is a human CMV (HCMV), murine CMV (MCMV), or guinea pig CMV (gpCMV) genome. In a preferred embodiment, the CMV genome is incorporated into a yeast artificial chromosome ("YAC"). The YAC supplies cis-genetic elements that permit maintenance of the YAC in yeast cells (telomeres, a centromere, and origins of replication). The YAC can also supply genetic markers used to select yeast cells containing a YAC. In one embodiment, a YAC-CMV vector is provided that incorporates portions of the pRML1 and pRML2 targeting vectors including conditional centromere and the herpes simplex virus thymidine kinase gene under the control of the yeast DED1 promoter and derived from pCGS966, permitting amplification of the YAC by growth in selective medium as described previously (Spencer, F. et al., 1993, Targeted recombination-based cloning and manipulation of large DNA segments in yeast, *Methods in Enzymology.* 5:161–175; Hieter, P. et al., 1990, Yeast artificial chromosomes: Promises kept and pending, *Genome Analysis* 1:83–119; Smith, D. R. et al., 1990, Amplification of large artificial chromosomes, *Proc. Natl. Acad. Sci. U.S.A.* 87:8242–8246).

Figure 1:
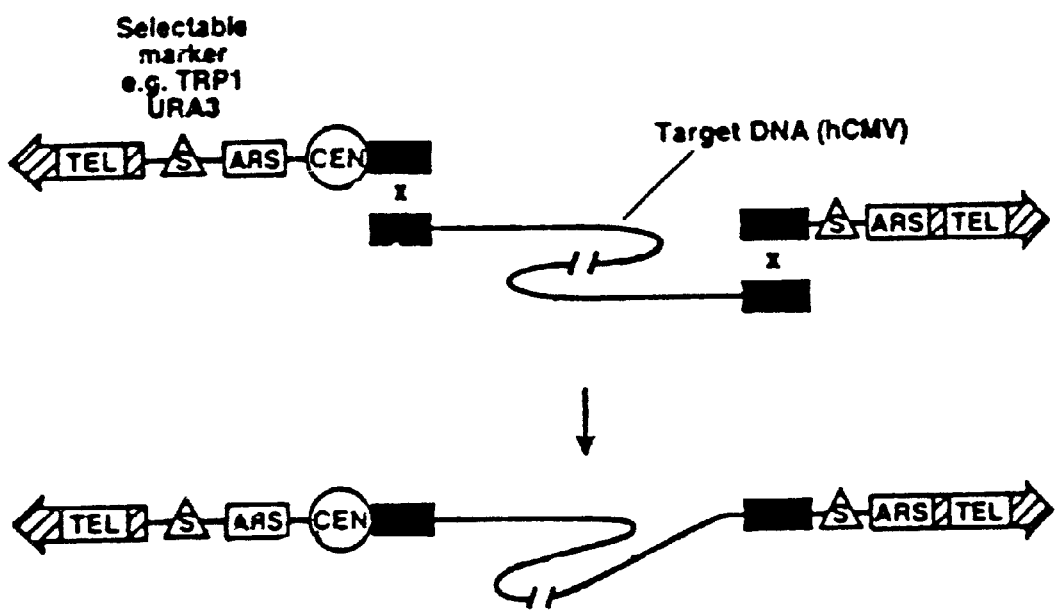
FIG. 1 shows recombinant targeted cloning. A mixture of the two YAC vector arms (derived from linearized plasmids that carry targeting segments represented by black boxes) and the HCMV genome (the target DNA) are simultaneously introduced into transformation competent yeast. Homologous recombination in the yeast cell amongst these DNAs results in the formation of a specific YAC clone.
Figure 2:
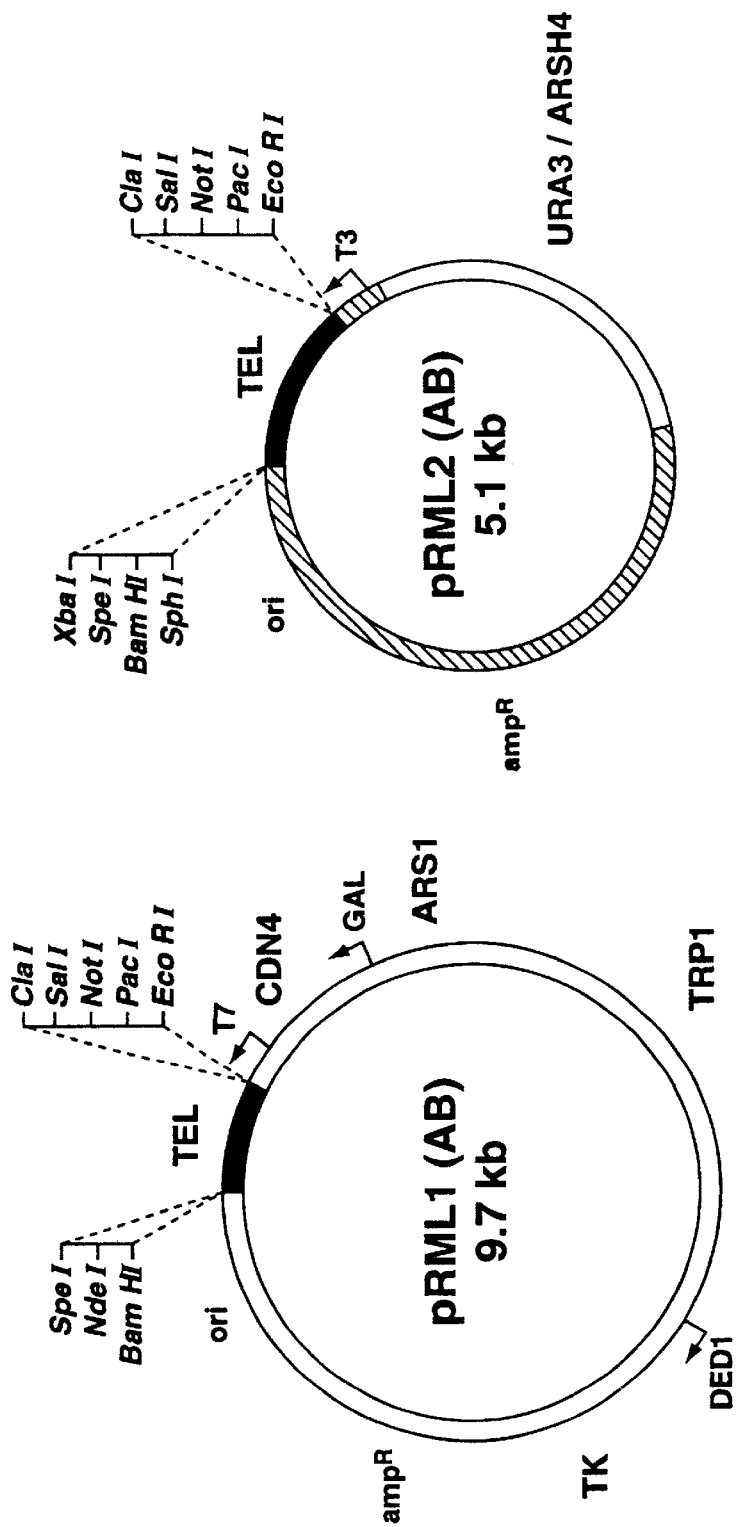
FIG. 2 shows plasmid maps of pRML1(AB) and pRML2 (AB) derived from pRML1 and pRML2 targeting vectors.
Figure 3:
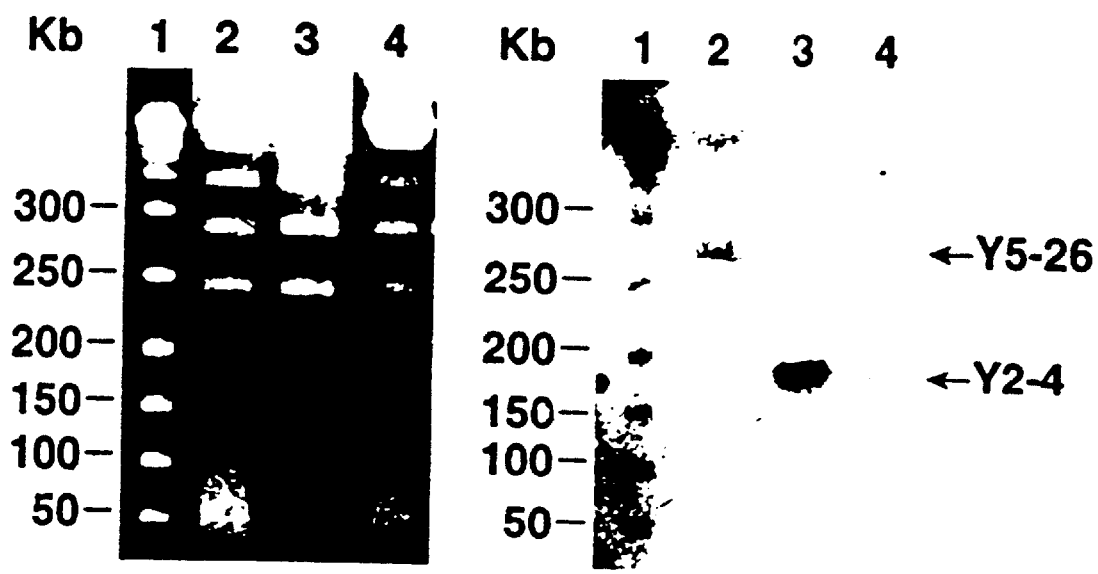
FIG. 3 shows an example of a pulse-field gel analysis of two yeast strains carrying different YAC-HCMV recombinants; Y5-26, lane 2; Y2-4, lane 3; and control yeast without YAC, lane 4. Left panel: the ethidium bromide-stained gel. Right panel: a Southern blot probed with STS5. The positions of the 50 kb marker (lane 1) are shown, and the YAC-HCMV DNAs are marked. Note, Y5-26 co-migrates with the yeast chromosome (VI) of ~290 kb.
Figure 4:
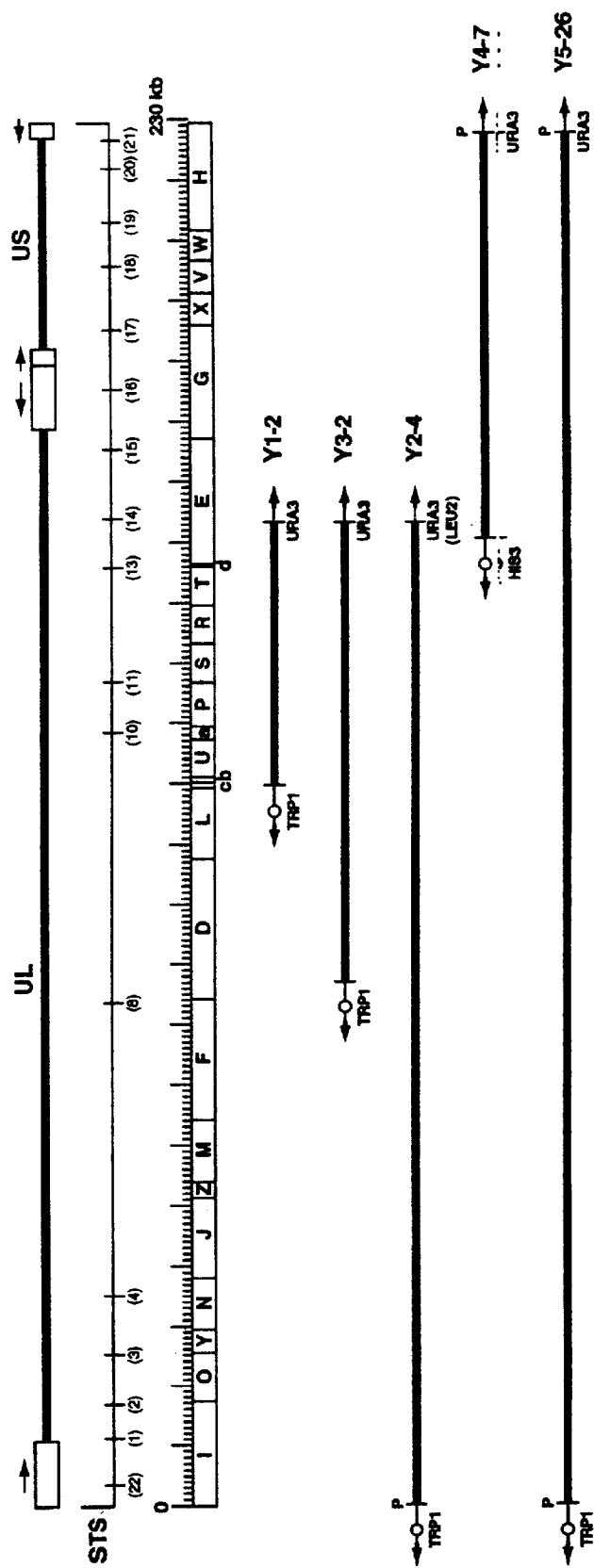
FIG. 4 shows a schematic diagram of YAC-HCMV clones spanning the entire viral genome.
Figure 5:
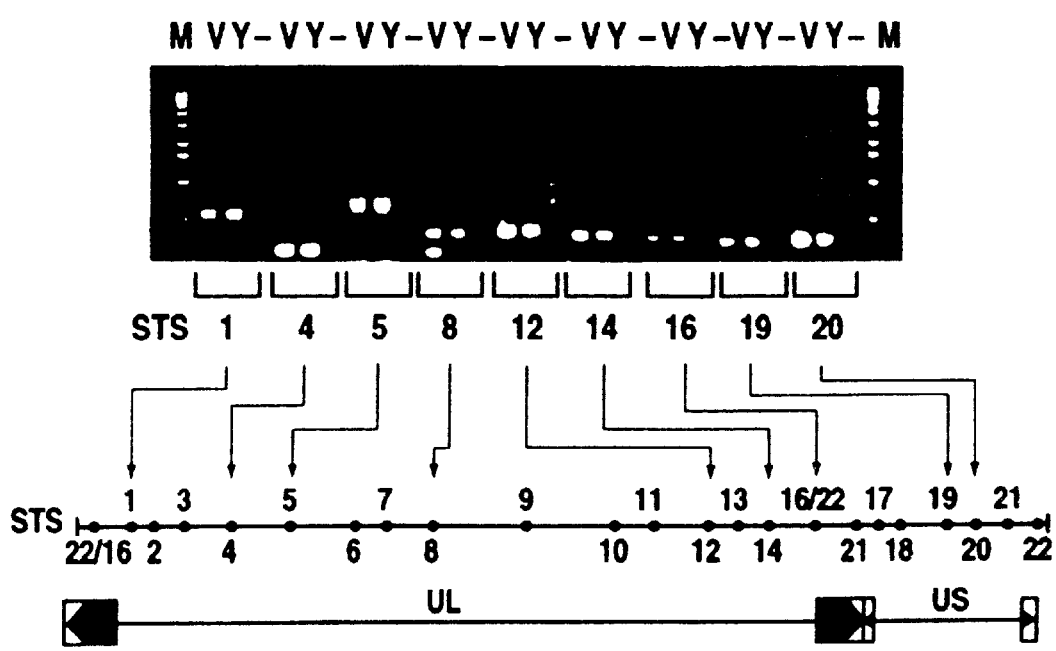
FIG. 5 shows the transfer of Y5-26 to human foreskin fibroblast (HFF) cells, including Sequence Tagged Site (STS) analysis for the integrity of the transferred genome. M stands for the marker lane. Lane V shows viral (HCMV, Towne) injected HFF cells. Lane Y shows YAC 5-26 transferred cells. Lane (..) shows mock transferred cells. Representive STSs (1, 4, 5, 8, 12, 14, 16, 19, and 20) are shown.

The vector may also comprise restriction enzyme sites. Digestion by the appropriate restriction enzyme allows for liberation of virus from YAC vector DNA by restriction enzyme cleavage. It is preferred that the restriction enzyme sites are absent from the CMV genome. CMV DNA replication can be initiated by circularization of the linear virion DNA by ligation of complementary 3' base overhangs following infection (Tamashiro, J. C. and Spector, D. H. 1986, Terminal Structure and Heterogeneity in Human Cytomegalovirus Strain AD 169. *J. Virol.* 59:591–604; Spaete, R. R. and Mocarski, E. S. 1985, The a Sequence of the Cytomegalovirus Genome Functions as a Cleavage/Packaging Signal for Herpes Simplex Virus Defective Genomes. *J. Virol.* 54:817–824; Kemble, G. W. and Mocarski, E. S. 1989, A Host Cell Protein Binds to a Highly Conserved Sequence Element (pac-2) within the Cytomegalovirus a Sequence. *J. Virol.* 63:4715–4728; McVoy, M. A. and Adler, S. P. 1994, Human Cytomegalovirus DNA Replicates after Early Circularization by Concatamer Formation, and Inversion Occurs within the Concatemer. *J. Virol.* 68:1040–1051). In a preferred embodiment, the pRML vectors comprise a Pac I site at one end of the YAC-encoded virus (FIG. 2).

The targeting segments for cloning CMV virion DNA may be derived either from natural restriction products or PCR products. The CMV DNA can comprise at least a portion of a CMV genome. Preferably, the CMV comprises about at least 50, 100, 500, 1,000, 5,000, 10,000, 100,000, 150,000, or 200,000 base pairs of CMV DNA. Preferably, the CMV DNA comprises an entire CMV genome. It has been shown that infectious virion DNA contains a variable number (at least two) of a sequence copies at the long-arm terminus and a single or no a sequence at the short-arm terminus (Tamashiro, J. C. and Spector, D. H. 1986, *J. Virol.* 59:591–604; Spaete, R. R. and Mocarski, E. S. 1985, *J. Virol.* 54:817–824; Kemble, G. W. and Mocarski, E. S. 1989, *J. Virol.* 63:4715–4728; McVoy, M. A. and Adler, S. P. 1994, *J. Virol.* 68:1040–1051). In the instant invention, the targeting vectors for the long-arm terminus preferably comprise an a-a fragment while the short arm terminus fragment preferably contains a single a sequence immediately flanked by a restriction enzyme site, preferably that of PacI.

An a sequence for use in the instant invention may be obtained by cloning the genomic termini of CMV such as that of the Towne CMV strain. It is possible to utilize a sequences obtained from other CMV strains, although the Towne strain is a preferred source. CMV DNA may be isolated from purified virions and blunt ended using T4 DNA polymerase. The DNA may then be cut with XmaI restriction endonuclease and ligated to the pBS-Sk (Stratagene) vector digested by XmaI and HincII. The resultant library of ligated fragments are then subjected to PCR using a nested set of primers. The products of the final PCR step are directly cloned into a vector such as pGEM-T (Promega).

To construct CMV YACs, target DNA is isolated from purified virions. The linearized targeting YAC vector clones may then be introduced, along with CMV virion DNA, into yeast spheroplasts. After transformation, transformants are selected, colony purified, and examined to identify YAC-containing cells. Transformants may be analyzed by, for example, polymerase chain reaction (PCR) using a battery of Sequence-Tagged Sites (STSs). An STS is typically defined by those skilled in the art as a short tract of DNA that can be specifically detected by a corresponding PCR assay and are used as the landmarks on which to base the physical maps of the YAC clones (Nemani, M. et al., 1994, A YAC Contig in 6p23 Based on Sequence Tagged Sites. *Genomics* 22:388–396). STS screening has been found to be a rapid method for identifying candidate YAC clones because direct colony PCR assays can be performed. Clones demonstrating the correct STS-content are then examined by pulsed-field gel electrophoresis and Southern blot hybridization to confirm the presence of a YAC of the expected size carrying CMV virion DNA.

Full length YAC-CMV clones are transferred to a permissive mammalian cell line or fresh tissue sample following isolation and fractionation of yeast chromosomal DNA by, for example, pulsed-field electrophoresis. A preferred permissive cell is a human foreskin fibroblast. Other preferred permissive cell lines include human glioblastoma, U373 MG (available from American Type Culture Collection (ATCC), 10801 University Boulevard, Manassas, Va. 20110-2209 as ATCC No. HTB-17); human embryonic lung fibroblast, HEL 299 (available as ATCC No. CCL-137), and human glioblastoma, U-138 MG (available as ATCC No. HTB-16).

CMV-YAC DNA can be isolated and fractioned by extracting the DNA from agarose gels using GELase-based procedures to avoid shearing of the DNA. CMV virions can be embedded in agarose plugs and the viral membranes and proteins removed. The plugs containing virion DNA can be inserted into loading wells for separation by PFGE. Following PFGE, virion DNA bands can be located by size and extracted by, for example, GELase digestion (Epicenter, Inc). A second separation by PFGE can be done to detect any DNA degradation. Following extraction of HCMV-YAC DNA, the DNA can be introduced into the permissive cells by any of several well-known techniques for transfecting cells, including but not limited to calcium phosphate precipitation, direct micro-injection, liposome-mediated transfection, or spheroplast fusion, for example. Such methodologies are described in *YAC Protocols* (1996), *Methods in Molecular Biology*, (The Humana Press Inc., Clifton, N.J.).

The vectors .described herein are also useful for studying the function of essential cis acting genes or nucleic acid sequences. For example, the vectors may be utilized to study the regulation of genes essential to viral replication, the function of the origin of replication, to generate multiple mutations in a single large DNA molecule, or generate cell-based reporter systems for monitoring the infectious program of a virus.

A major advantage of the vectors described herein is the ease and rapidity with which single or multiple mutations may be introduced into a CMV DNA sequence. The capacity of the vectors described herein to generate multiple mutations exceed the capacity of other vectors such as the bacterial artificial chromosome (BAC).

Compositions Comprising YAC-CMV Polynucleotides

The invention also provides compositions comprising YAC-CMV polynucleotides. Compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, animo acid copolymers, peptoids, lipitoids, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, malodextrin, ethanol, or the like, singly or in combination, as well as substances such as wetting agents, emulsifying agents, or pH buffering agents. Liposomes can also be used as a carrier for a composition of the invention.

If desired, co-stimulatory molecules, which improve immunogen presentation to lymphocytes, such as B7-1 or B7-2, or cytokines such as MIP1, GM-CSF, IL-2, and IL-12, can be included in a composition of the invention. Optionally, adjuvants can also be included in a composition. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsionOptionally, the efficiency of delivery of E1E2 or E2 polynucleotides may be improved by injection of cardiotoxin, purified from the venom of *Naja nigricollis*, about one week prior to an E1E2 or E2 polynucleotide injection. A muscle is injected with from about 0.1 to 20 M of cardiotoxin dissolved in a pharmacologically acceptable vehicle, such as 0.9% NaCl.

Methods of Eliciting an Immune Response

This invention also relates to methods of eliciting an immune response and/or protective immunity in a vertebrate by introducing into the vertebrate a DNA vaccine which comprises a YAC comprising DNA encoding an antigen or antigens, e.g., capsid proteins or polypeptides, of CMV. The uptake of the DNA vaccine by a host vertebrate results in the expression of structural and non-structural proteins, thereby eliciting humoral or cell-mediated inmmune responses, or both, which can provide protection against infection and/or prevent clinically significant cytomegalovirus-caused disease. A CMV deletion mutant may also be synthesized and incorporated into the CMV-YAC construct as a vaccine. One may also utilize a CMV-YAC vector carrying an attenuated or non-replicative CMV genome for direct injection into animal tissue as a vaccine.

YAC-CMV constructs of the invention can be used to elicit an immune response in a vertebrate. Elicitation of an immune response can be used, inter alia, to provide model systems to optimize immune responses to CMV and to provide prophylactic or therapeutic-treatment against CMV infection. YAC-CMV constructs can be used to produce CMV-specific polyclonal and monoclonal antibodies. HCV-specific polyclonal and monoclonal antibodies specifically bind to CMV antigens or epitopes. Preferably, HCMV epitopes are found within the envelope glycoprotein B (gB), for example, the AD-1 epitope (codons 552–635), or the amino terminal 513 amino acids of gB. Preferably, HCMV epitopes are found in the Immediate Early protein (IE), such as the 1E1 epitope. Additional HCMV epitopes are described in Lindenmaier et al., *Arch. Virol.* 113:1–16 (1990). CMV-specific T cells activated by CMV proteins preferably recognize an epitope of a CMV polypeptide. CMV-specific T cells can be CD8+ or CD4+.

Detection and/or quantification of an immune response, such as antibody titer, after delivery of construct of the invention can be used to identify CMV epitopes that are particularly effective at eliciting a CMV immune response. Antibodies elicited by a particular CMV epitope can then be tested using, for example, an ELISA assay to determine which polypeptides contain epitopes that are most effective at generating a strong response. CMV polypeptides or fusion proteins which contain these epitopes or polynucleotides encoding the epitopes can then be constructed and used to elicit a strong CMV immune response.

A YAC-CMV construct of the invention can be administered to a vertebrate, such as a fish, bird, mouse, rabbit, guinea pig, piglet, macaque, baboon, chimpanzee, or human, to elicit an immune response in vivo. Injection of a YAC-CMV construct is preferred. Injection of a construct results in the synthesis of a CMV polypeptide or polypeptides in the host. Thus, the CMV polypeptide is presented to the host immune system with native post-translational modifications, structure, and conformation. A YAC-CMV construct is preferably delivered as "naked DNA." Administration of a YAC-CMV construct can be by any means known in the art, including intramuscular, intradermal, intraperitoneal, or subcutaneous injection, including injection using a biological ballistic gun ("gene gun"). Administration may also be intranasal or oral. Preferably, a YAC-CMV construct is accompanied by a protein carrier for oral administration. A combination of administration methods may also be used to elicit a CMV immune response.

Administration of a YAC-CMV construct can elicit an anti-CMV immune response in the vertebrate that lasts for at least 1 week, 2 weeks, 1 month, 2 months, 3 months, 4 months, 6 months, 1 year, or longer. Optionally, an anti-CMV immune response can be prolonged by providing one or more booster injections of the construct at 1 month, 2 months, 3 months, 4 months, 5 months, 6 months, 1 year, or more after the primary injection.

A composition of the invention comprising a YAC-CMV construct is administered in a manner compatible with the particular composition used and in an amount which is effective to elicit an anti-CMV immune response, as detected by, for example, an ELISA. A YAC-CMV construct is preferably injected intramuscularly to a large mammal, such as a baboon, chimpanzee, or human, at a dose of 1 ng/kg, 10 ng/kg, 100 ng/kg, 1000 ng/kg, 0.001 mg/kg, 0.1 mg/kg, or 0.5 mg/kg. A YAC-CMV construct can be administered either to a vertebrate that is not infected with an CMV or can be administered to an CMV-infected vertebrate. The particular dosages of YAC-CMV constructs in a composition will depend on many factors including, but not limited to the species, age, and general condition of the vertebrate to which the composition is administered, and the mode of administration of the composition. An effective amount of the composition of the invention can be readily determined using only routine experimentation. In vitro and in vivo models can be employed to identify appropriate doses. If desired, co-stimulatory molecules or adjuvants can also be provided before, after, or together with the YAC-CMV compositions.

Immune responses of the vertebrate generated by the delivery of a composition of the invention, can be enhanced by varying the dosage, route of administration, or boosting regimens. Compositions of the invention may be given in a single dose schedule, or preferably in a multiple dose schedule in which a primary course of vaccination includes 1–10 separate doses, followed by other doses given at subsequent time intervals required to maintain and/or reinforce an immune response, for example, at 1–3 months for a second dose, and optionally at 3–6 months for a third dose, and if needed, a subsequent dose or doses after several months.

In accordance with another aspect of the present invention there are provided isolated recombinant DNA molecules contained in ATCC Deposit No. PTA-2186 and ATCC Deposit No. PTA-2187 deposited with the American Type Culture Collection, 10801 University Boulevard, Manassas, Va. 20110-2209, USA, on Jul. 3, 2000. The deposited materials are yeast cell strains that contain, respectively, the y5-26 and y2-4 recombinant DNA molecules. The deposits have been made under the terms of the Budapest Treaty on the International Deposit of Micro-organisms for purposes of Patent Procedure. The strain will be irrevocably and without restriction or condition released to the public upon the issuance of a patent.

These deposits are provided merely as convenience to those of skill in the art and are not an admission that a deposit is required under 35 U.S.C.§112. The present invention is not to be limited in scope by the constructs deposited, since the deposited embodiment is intended as a single illustration of one aspect of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

The sequence of the polynucleotides contained in the deposited materials, as well as the amino acid sequence of the polypeptides encoded thereby, are controlling in the event of any conflict with any description of sequences herein. A license may be required to make, use or sell the deposited materials, and no such license is hereby granted. References to "polynucleotides," "clones," "YAC" and "yeast artificial chromosome" throughout this specification includes the DNA of the deposit referred to above.

Within this application, unless otherwise stated, the techniques utilized may be found in any of several well-known references such as: *Molecular Cloning: A Laboratory*

Manual (Sambrook et al., 1989, Cold Spring Harbor Laboratory Press, Cold Spring Harbor, N.Y.); *Gene Expression Technology* (Methods in Enzymology, Vol. 185, edited by D. Goeddel, 1991, Academic Press, San Diego, Calif.); *PCR Protocols: A Guide to Methods and Applications* (Innis et al., 1990, Academic Press, San Diego, Calif.); *Culture of Animal Cells: A Manual of Basic Technique, 2$^{nd}$ Ed.* (R. I. Freshney, 1987, Liss, Inc. New York, N.Y.); *Methods in Molecular Biology* (Vol. 7), *Gene Transfer and Expression Protocols*, (Ed. E. J. Murray, The Humana Press Inc., Clifton, N.J.); Ramsay, M., 1994, Yeast artificial cloning, *Molec. Biotech.* 1:181–201; Smith, et al., 1990, Amplification of large artificial chromosomes, *Proc. Natl. Acad. Sci. U.S.A.* 87: 8242–8246; and, *YAC Protocols, Methods in Molecular Biology*, (Markie, D., 1996, The Humana Press, Inc., Clifton, N.J.).

The following are provided for exemplification purposes only and are not intended to limit the scope of the invention described in broad terms above. All references cited in this disclosure are incorporated herein by reference.

EXAMPLES

Example 1

Generation of a HCMV-YAC Vector pRML vectors were engineered (FIG. 2) to possess a Pac I site at the end of the YAC-encoded virus to allow liberation of virus from YAC vector DNA by restriction enzyme cleavage. Pac I cleavage sites are not present within the HCMV genome and produce the appropriate overhang for recircularization of the genome after transfection of permissive host cells. The pRML vectors form the backbone of the linearized targeting YAC vector clones.

The targeting segments for cloning CMV virion DNA were derived either from natural restriction products or PCR products. To ensure the production of infectious DNA, the correct structure of the termini was maintained. The targeting vectors for the long-arm terminus were designed to include an a-a fragment while the short arm terminus fragment contains a single a sequence immediately flanked by a PacI site.

The a sequence used in the construction of the targeting vectors was obtained by cloning the genomic termini of HCMV Towne virion DNA. HCMV Towne DNA isolated from purified virions was blunt ended using T4 DNA polymerase, subsequently cut with XmaI restriction endonuclease and ligated to the pBS-SK (Stratagene) vector resected by XmaI and HincII. This library of ligated fragments was then subjected to PCR using a nested set of primers. The outside primer set used the M13 primer and an HH4 primer, 5'-ACGTCGCTTTTATTCGCCGTCG (SEQ ID NO:1) designating a terminal sequence (position 109 to 130). The inside primer set used the T7 primer and HH3 primer 5'-ACACACGCAACTCCAAGTTTCAC (SEQ ID NO:2) (position 51 to 73). The products of the final PCR step were directly cloned into the pGEM-T vector (Promega). An analysis of these clones confirms characterizations of the ends of the HCMV genome (Tamashiro, J. C. and Spector, D. H. 1986. Terminal structure and heterogeneity in human cytomegalovirus strain AD169, *J Virol.* 59(3): 591–604).

The target DNA was prepared from purified virions. The linearized targeting YAC vector clones were then introduced, along with HCMV virion DNA, into yeast spheroplasts. After transformation, TRP1 URA3 transformants were selected, colony purified, and examined to identify YAC-containing cells. Transformants were first analyzed by polymerase chain reaction (PCR) using a battery of Sequence-Tagged Sites (STSs). An STS is defined as a short tract of DNA that can be specifically detected by a corresponding PCR assay and are used as the landmarks on which to base the physical maps of the YAC clones (Nemani, M., et al., 1994. A YAC Contig in 6p23 Based on Sequence Tagged Sites. *Genomics* 22:388–396). STS screening has been found to be a rapid method for identifying candidate YAC clones as direct colony PCR assays can be performed. The STS markers utilized in generating the vectors of the present invention are illustrated in Table 1. Each STS. produces a specific size fragment containing a diagnostic restriction enzyme cleavage site.

TABLE 1

HCMV STS markers developed for mapping HCMV-YAC vectors

| SETS | LOCUS | LEFT PRIMER (SEQ ID NO:) | RIGHT PRIMER (SEQ ID NO:) | SIZE | TEST CUT | SIZES (bp) |
|---|---|---|---|---|---|---|
| Set 22 | 3807–4186 | ATCAGGATCGCGACAG (3) | CGTTATCCGTTCCTCG (4) | 379 | EcoR I | 160, 219 |
| Set 1 | 11157–11706 | ACGAGGTAATCAACGT (5) | ATGTTAAGCCTTAGTC (6) | 549 | EcoR I | 407, 142 |
| Set 2 | 16978–17400 | GACACCTCTATGTTAC (7) | CGTATATGTACGTCAT (8) | 423 (?) | Hind III | 266, 157 |
| Set 3 | 25799–26218 | TAGACAGTATACCCTC (9) | AGTACCACATTTTGC (10) | 419 | EcoR I | 295, 124 |
| Set 4 | 36489–36714 | ACATGGATTCGTGCAC (11) | ATCGATCTGGAGCACT (12) | 225 | EcoR I | 184, 41 |
| Set 5 | 53844–54093 | GTGAAGCCGATACGAG (13) | AGGAGACCACGGTTTG (14) | 249 | EcoR I | 79, 170 |
| Set 6 | 66701–67183 | GGTCCGCAACTTCTGATCCA (15) | CAGATCAGTCCACAGGTTCT (16) | 482 | Bam HI | 233, 249 |
| Set 7 | 73910–74261 | GCTACCTTGTGCAGTC (17) | GTCCTACGTTGCTACT (18) | 351 | EcoR | 207, 144 |
| Set 8 | 84721–85094 | ACGCAGGTGAATATCC (19) | AGGTTATCGTCAAGCG (20) | 373 | Hind III | 143, 230 |
| Set 9 | 107480–107920 | CACCATCTTAGGGACGTCTC (21) | GCATGCTCMGACATGCTGA (22) | 440 | Hind III | 197, 243 |
| Set 10 | 128975–129337 | GATGGTGGMATCGGA (23) | ACCTGTCGGTTGAAGC (24) | 362 | Hind III | 193, 169 |
| Set 11 | 136625–136969 | TCGTCGACGCATCTGT (25) | ATATCGCACCGATTGC (26) | 344 | Hind III | 80, 264 |
| Set 12 | 149371–149770 | GTTGGCGTTGAGCACGTCTA (27) | AGCCGACAACCTGCTGCACT (28) | 399 | Hind III | 274, 125 |
| Set 13 | 155668–156028 | TAAGTGGMGTGGCCG (29) | GACGACGATGACCTCA (30) | 360 (?) | Hind III | 195, 155 |
| Set 14 | 163686–164040 | CAGCAATGTTAGCGAG (31) | TCACGCGACTGTCATA (32) | 354 | EcoR I | 149, 205 |
| Set 15 | 175465–175737 | GTGAAGCGATTGCACA (33) | TCAGGTGCGATTGACG (34) | 272 | EcoR I | 59, 213 |
| Set 16 | 185281–185620 | CGTTATCCGTTCCTCG (35) | CTTGCGGAATTGACAT (36) | 339 | EcoR I | 214, 125 |
| Set 17 | 195675–196056 | TATCGTTCGGACGGGA (37) | TTGGATCAGACTCACG (38) | 381 | Hind III | 162, 219 |
| Set 18 | 206161–206390 | AATCACCGTCATTCCC (39) | CTCCTCAGCTTGTTGT (40) | 229 | Hind III | 64, 165 |
| Set 19 | 213192–213496 | CTAGCACGATGGGCG (41) | TGACATGTGGCGTACA (42) | 304 | EcoR I | 244, 60 |
| Set 20 | 221934–222268 | AGTTGGACTACGMGA (43) | CTGTATGTAGAAGACG (44) | 334 | EcoR I | 123, 211 |
| Set 21 | 226671–227018 | TCCATMCCACCGTGG (45) | GCTGTCGCACTTTCTG (46) | 347 | Not I | 224, 123 |

Those clones that were positive for the correct STS-content (listed in Table 2, below) were then examined by pulsed-field gel electrophoresis and Southern blot hybridization to confirm the presence of a YAC of the expected size carrying HCMV virion DNA.

TABLE 2

SUMMARY OF HCMV STS-POSITIVE CLONES

| CLONE | PLASMID 5' | PLASMID 3' | SEQUENCE (Ref: GenBank No: X17403) (SEQ ID NO:64) |
|---|---|---|---|
| Y 1-2 | pRML1 (H+) | pRML2 (ura) + Ea | 119901–178816 |
| Y 3-2 | pRML1 (+V) | pRML2 (ura) + Ea | 88024–178816 |
| Y 2-4 | pRML1 (I2) | pRML2 (ura) + Ea | 1–178816(*) |
| Y 4-7 | pRML1 (+d) | pRML2 (ura) + Enx | 162053–222057 |
| Y 5-26 | pRML1 (I2) | pRML2 (ura) + Enx | 1–222057(*) |

(*)The insert in plasmid pRML1(I2) goes from nucleotide 228426 (NotI) to the 3' end of the genome (nucleotide 229075), conjoined to nucleotides 1 through 3967 of the 5' end of the genome.

Example 2

Infectious HCMV DNA

HCMV DNA was transferred to permissive human foreskin fibroblasts by first isolating and fractionating chromosomal DNA by pulsed-field electrophoresis. In general, HCMV-YAC DNA was extracted from agarose gels using GELase-based procedures to avoid shearing of the DNA. HCMV virions were embedded in agarose plugs, viral membranes and proteins were removed, and then the plugs containing virion DNA were inserted into loading wells for separation by PFGE. Following PFGE, virion DNA bands were located by size (~240 kb) and extracted by GELase digestion as indicated by the manufacturer (Epicenter, Inc.). Free DNA Irecovered by GELase digestion did not undergo any observable change in band mobility during a second separation by PFGE, indicating that the GELase procedure did not cause any detectable DNA degradation. To avoid shear-induced degradation of the DNA as much as possible, the GELase enzyme was not removed following digestion.

In general, an aliquot of the GELase-purified HCMV DNA was introduced into mammalian cells by either calcium phosphate precipitation methods or by direct microinjection. Preferably, standard methodologies or modifications thereof for calcium phosphate precipitation methods were used.

In general, transfections were performed by the calcium phosphate precipitation method using standard protocols with a slight modification. Yeast DNA (in 1 ml) was mixed with 100 µl of 2.5 M $CaCl_2$ in 1 ml of BSE 1x, incubated for 10 minutes at room temperature and added to the cell cultures seeded in 100 mm dishes containing 20 ml of medium.

Preferably, the mammalian cells used were human foreskin fibroblast (HFF) cells. After three weeks of incubation, the HFF cells were harvested and examined for infectious virus. In three independent experiments, infectious particles were recovered at a level of $\sim 1-10 \times 10^5$ FFU/ug of virion DNA. Thus, recovery of infectious virus has been demonstrated for full length HCMV DNA following PFGE.

Example 3

Full-length HCMV-YAC Clones

The full-length recombinant clone Y5-26 was isolated and shown to be replication-competent in HFF cells. Fourteen independent transfers were performed, of which 50% of the cells in four of the cultures developed cytopathic effects (CPE) between days 30 to 40 post-transfer.

Cultures were harvested on day 45 post transfer. All of the CPE positive cultures, but not the CPE negative cultures, tested positive for the presence of viral DNA. One of these cultures showed extremely high levels of viral DNA, comparable to a fully permissive infection with wild-type virus. The high expressor appears to have an intact genome based on an STS analysis, suggesting that Y5-26 DNA is replication competent.

Example 4

The HCMV-YAC Vector as a Tool for Basic Research: Demonstration of Virus over Host Factors in Cross-species Activation of HCMV Early Gene Expression CMV is a pathogen with a highly restricted spectrum of hosts, and HCMV has a very strong species specificity. HCMV can only replicate in human cells. In other species cells, HCMV can efficiently enter cells, indicating that the species restriction is not at the level of viral binding or penetration. Nowlin et al., *J. Virol.* 65:3114–21(1991). Recent studies have provided direct evidence to show that major IE expression determined by viral immediate-early regulatory sequences is also not species restricted. Angulo et al. *J. Virol.* 72:8502–9 (1998); Grzimek et al. *J. Virol.* 73:5043–55 (1999).

This Example demonstrates that an essential early gene activation pathway governed by HCMV major IE proteins is conserved between host species. However, a marked divergence in the mechanism for this activation between viral species is observed.

Plasmid based analysis of HCMV UL54 promoter activity in NIH 3T3 cells, using transient expression assays and stable cell lines.

The activation of the HCMV UL54 promoter by HCMV in murine cells using a plasmid based transient expression assay was investigated. For these experiments, a 445 bp DNA fragment containing the UL54 promoter (nucleotide positions 80996 through 81441, numbered with respect to SEQ ID NO:64) was cloned in the plasmid pLHN, to produce pLHN.UL54wt. A 432 bp DNA fragment, corresponding to the UL86 promoter (nucleotide positions 128318 through 128750, numbered with respect to SEQ ID NO:64) was cloned into pLHN, deriving pLHN.UL86.

Briefly, yeast strain YPH857 (Matα ura3-52 lys2-801 ade2-101 his320 0 trp163 leu2 1 $cyh2^R$) and derivates were grown in standard media. See Guthrie, C. and G. R. Fink. 1991, Guide to yeast genetics and molecular biology. Methods Enzymol. 194:1–863. Murine NIH 3T3 fibroblasts (ATCC CRL 1658) were propagated in Dulbecco's modified essential medium supplemented with 2 mM glutamine, 100 U penicillin per ml, 100 µg gentamicin per ml, and 10% calf serum. The AD169 and Towne strains of HCMV (ATCC VR-538 and VR-977 respectively) and the Smith strain of MCMV (ATCC VR-1399) were used.

pRML1 and pRML2 were used to create a series of right and left arm plasmids of the YACs, respectively. See Spencer, C. Connelly and P. Hieter. 1993, Targeted recombination-based cloning and manipulation of large DNA segments in yeast. *Methods* 5:161–175. pRML1+$I_2$, the right arm plasmid, was constructed in three steps: first, an EcoR I fragment from the cosmid pCM1035 (Pari, G. S. and D. G. Anders. 1993, Eleven loci encoding trans-acting factors are required for transient complementation of human cytomegalovirus oriLyt-dependent DNA replication. *J. Virol.* 67:6979–88) containing the last 7297 bp of the 3' end of HCMV, plus the 3967 first bp of the 5' end, was cloned into pBluescript-SK (Stratagene, US), deriving pBS-SK-$I_1$. This plasmid was digested with Not I and self-ligated, creating pBS-SK+I and $I_2$. The fragment Not I-Cla I from pBS-SK+$I_2$ was purified and ligated to pRML1 (Spencer, C. Connelly and P. Hieter. (1993), supra) to construct pRML1+$I_2$. This plasmid has 4895 bp of the 5' end of HCMV. pRML2(ura)+Ea, the left arm plasmid, was constructed by cloning a 3292 bp EcoR I fragment (175524 to 178816) (SEQ ID NO:64) from the cosmid pCM1050 into pRML2 (Pari, G. S. and D. G. Anders. (1993), supra; Spencer, C. Connelly and P. Hieter. (1993), supra). YPH857 has the appropriate auxotrophies to select for both YAC arm plasmids. For the construction of pRML2-Leu2-PUR the Pvu II-BamH I 1.4 kb DNA fragment from pPUR was inserted into the blunt-ended BamH I of pRML2-LEU2 (LEU2 is a yeast protein involved in the synthesis of leucine, which complements the leu2 mutation of YPH857), to produce pRML2/D. Then, the LEU2 yeast gene was cloned in the place of URA3, as a Hind III DNA fragment. In order to develop a mutagenesis shuttle plasmid, in which to clone the different promoters, we generated pLHN. This plasmid has the yeast HIS3 gene as a selectable marker in yeast, the neomycin resistance gene for selection in mammalian cells, and the luciferase gene as a reporter. The promoter sequence and the 3' end of the targeted gene are both cloned, flanking the unique Sma I restriction site. pLHN.UL54wt was constructed as follows: a 445 bp DNA fragment from the UL54 promoter (nucleotide positions 80996 through 81441 of HCMV genome, Genbank accession number X17403 (SEQ ID NO:64)), present in the plasmid pPolCAT (Stenberg, R. M. et al. 1990, Promoter-specific trans activation and repression by human cytomegalovirus immediate-early proteins involves common and unique protein domains. *J. Virol.* 64:1556–65), along with an additional viral DNA fragment from the 3' region of UL54 (nucleotide positions 77291 through 77516), were cloned into the multicloning site of pLHN, leaving a unique Sma I site in between them. Digestion with Sma I directs the recombination to the UL54 locus.

pLHN.UL54IRM was constructed by cloning the mutated EcoR I-Sma I DNA fragment, into EcoR I-Sma I digested pLHN.UL54wt, replacing the wt fragment with the mutant one. IRM mutagenesis was used for this step. Briefly, the mutagenesis of the inverted repeat IR1 in the UL54 promoter was done as previously described. See Kerry, J. A. et al. 1996, Multiple regulatory events influence human cytomegalovirus DNA polymerase (UL54) expression during viral infection. *J. Virol.* 70:373–82. The QuickChange site-directed mutagenesis kit (Stratagene, USA) was used, following the instructions of the manufacturer. Briefly, 50 ng of pLHN.UL54wt DNA was mixed with the oligos IRM-A (GACACGTCGTTACAGATATCGCCTTCCTACGAGG) (SEQ ID NO:47) and IRM-B (CCTCGTAGGAAGGCGATATCTGTAACGACGTGTC) (SEQ ID NO:48), 125 ng each, and then incubated for 1 minute at 95° C., followed by 16 PCR cycles (30 seconds at 95° C., 1 minute 55° C., 15 minutes 68° C.). The reactions were digested with Dpn I, and the digested DNA was transformed into *E. coli*. Several clones were analyzed with EcoRV, a unique restriction site introduced with the IRM mutation. Positive clones of the new pLHN.UL54IRM plasmid were confirmed by sequencing.

PCR was used to test the correct integration of pLHN.UL54wt into the viral sequences of Y24P. Two oligonucleotides were used, YAC54.2 (TCGCCCTGGATATCGACCCGCT) (SEQ ID NO:49), complementary to a region of the UL54 promoter outside of the one included in the plasmid pLHN.UL54wt, and GLprimer2 (CTTTATGTTTTTGGCGTCTTCCA)(SEQ ID NO:50), complementary to the 5' region of the luciferase gene.

pLHN.UL86 was constructed as follows: a 432 bp DNA fragment, encompassing the UL86 promoter (nucleotide positions 128318 through 128750 of HCMV genome (SEQ ID NO:64), was cloned along with a 522 bp DNA fragment from the 3' end fragment of the UL86 gene (nucleotide positions 124981 through 125503), with a Sma I site in between them (FIG. 6A). PCR was used to test the correct integration of pLHN.UL86 into the viral sequences of Y24P. Two oligonucleotides were used, YAC86.2 (GTAGCCGGAGACGGCGGTT) (SEQ ID NO:51), complementary to a region of the UL86 outside of the one included in the plasmid pLHN.UL86, and GLprimer2 (SEQ ID NO:50).

In these recombinants the UL54 and UL86 promoters drive the expression of the luciferase reporter gene. In a first attempt to test if the species restriction for HCMV in murine cells occurs at early times, each plasmid was transiently transfected into NIH 3T3 cells, which were then infected with HCMV, and luciferase activity measured at different times post infection.

Briefly, NIH 3T3 cells were grown in Dulbecco's modified Eagle's medium, supplemented with 10% calf serum. Transfections were done in 6-well plates, unless otherwise noted, using the calcium phosphate precipitation method. See Galang, C. K., C. J. Der, and C. A. Hauser. 1994, Oncogenic Ras can induce transcriptional activation through a variety of promoter elements, including tandem c-Ets-2 binding sites. *Oncogene* 9:2913–21. For transient transfections, cells were washed with PBS 16–18 hours after the addition of the precipitate, then incubated 24 hours with 10% calf serum supplemented medium and finally infected with either the Towne strain of HCMV or the Smith strain of MCMV, in 3% calf serum. Stable trans fections were done the same way, except that after the 24 hours recovery in 10% calf serum medium, cells were selected on 400 µg/ml G418 (GIBCO BRL, USA). Clones appeared 10 days after selection. Virus was adsorbed for 2 hours prior to the addition of fresh overlay medium.

To measure the luciferase activity, the Luciferase Assay System (Promega) was used, following the directions recommended by the manufacturer. Cells were washed twice with PBS, and 200 µl Lysis Buffer (provided by the manufacturer) were added to each well. Cells were to scraped and transferred to an Eppendorf tube, frozen and thawed and centrifliged for 2 minutes. The luciferase assays were done in a Micro plate Luminometer LB 96V (EG&G Berthold), using 100 µl extract and injecting 100 µl of Luciferase Substrate, using 2 seconds delay and 20 seconds reading time. The luciferase activity is shown either as the absolute value in relative light units (rlu), as an average of at least two experiments done in triplicate, or as fold activation, in which the absolute value is divided by the corresponding mock-infected sample.

As shown in FIG. 6A, the infection caused a general activation of transcription, reflected by a 5-fold activation of the promoter-less pGL3-basic plamid 24 hours post infection when compared to the mock infected sample, followed by a 2.5-fold activation at 48 hours post infection. The overall activation of UL54 promoter was slightly higher (6-fold), but the fold activation was at a similar level as the negative control (FIG. 6A). UL86 promoter driven luciferase activity responded in a similar manner (FIG. 6A). Thus, transient expression from isolated HCMV promoters is apparently not specifically. responsive to HCMV infection in murine cells.

To test if the non-responsiveness of the HCMV promoters was due to the nature of the transient assay or to the inherent non-responsiveness of the HCMV promoters in murine cells, we generated neomycin resistant stable clones using the same plasmids. A total of 12 neomycin resistant UL54 promoter clones were isolated, four out of which showed some luciferase activity when infected with HCMV. The results for three representative clones are shown in FIG. 6B (2A clones); the luciferase activity values were variable, ranging from 3 to 10-fold peak activation at 24 hours post infection, decreasing by 48 hours. The non-infected samples had some residual activity in the absence of infection, most likely influenced by the site of integration. In order to examine whether the effect of HCMV infection is specific to the expression from UL86 (late promoter), stable cell lines containing the pLHN.UL86 plasmid were investigated. Since HCMV is unable to replicate in murine cells it was expected that the UL86 promoter would not be activated if regulation is specific, while a non-specific enhancement would cause some expression upon infection. In these experiments the UL86 neomycin resistant clones (6A clones in FIG. 6B) showed no significant activation of transcription either in the absence or presence of HCMV. Overall, we conclude that the UL54 promoter, when isolated from its natural surrounding sequences, is poorly activated by HCMV infection in murine cells.

Cloning and Mutagenesis of a HCMV Yeast Artificial Chromosome

Figure 7:
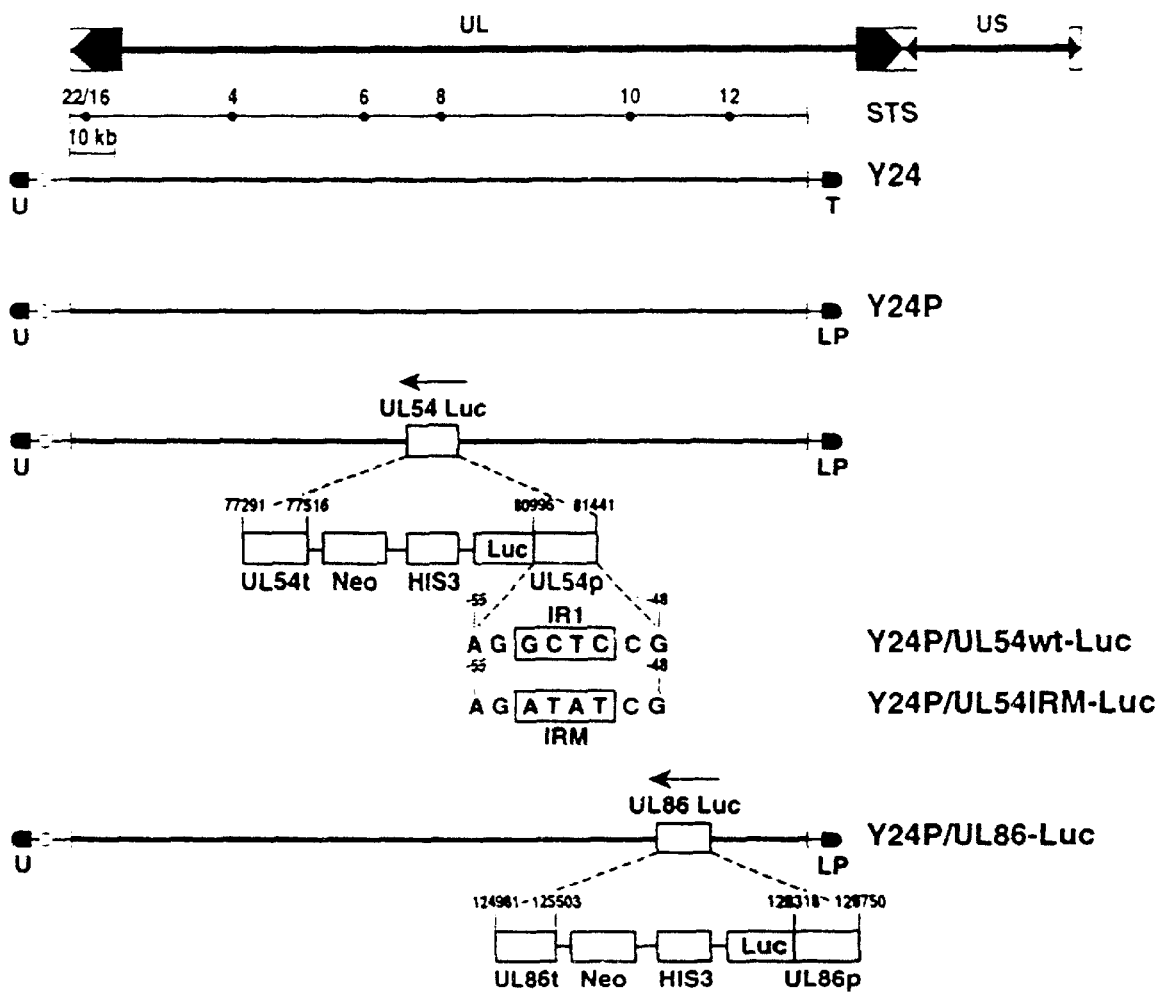
FIG. 7 shows structure of an HCMV's genome, with the Unique Long Region (UL), Unique Short Region (US), and the inverted and direct repetitive sequences. The STS panel shows the relative positions of the pairs of oligonucleotides used to check the integrity of HCMV. Five YACs are shown, with their corresponding mutations outlined. The selectable markers are shown (U, URA3; T, TRP1; L, LEU2; P, puromycin resistance; Neo, neomycin resistance), as well as the positions of the HCMV sequences where the mutations were performed.

It is possible that the lack of a robust activation of UL54 may be due to integration in host chromatin and/or perhaps the lack of its natural sequence context. To investigate the influence of cis-acting sequences on the activity of the UL54 promoter in the context of its natural genomic location, we constructed a YAC with a 178 kb HCMV DNA fragment, encompassing most of the UL region of the viral genome (FIG. 7). This part of the HCMV genome lacks the major immediate-early gene region, and is expected to be defective for viral growth. Briefly, the centromeric plasmid, pRML1+ $I_2$, contains a 4895 bp DNA fragment from the 5' end of HCMV genome. The non-centromeric plasmid, pRML2 (ura)+Ea, has a 3292 bp fragment from the 3' end of the UL region. Both plasmids were co-transformed into the yeast strain YPH857 with HCMV DNA (strain Towne). Different clones were obtained, and the integrity of the selected YAC (Y24) was verified by several methods. If recombination between the two plasmids and the viral DNA is as expected, a new chromosome of around 178 kb should be generated, encompassing the HCMV genome from the 5' end to position 178816.

For the separation of yeast chromosomes a Biometra Rotaphor R 23 was used. The yeast DNA samples, agarose gels, and electrophoresis conditions were done following the directions provided by the manufacturer. To separate Y24, an artificial chromosome of approximately 180 kb, a 20 hour run was done at 180 volts, with 15 seconds intervals and a rotation angle of 120°.

Figure 8:
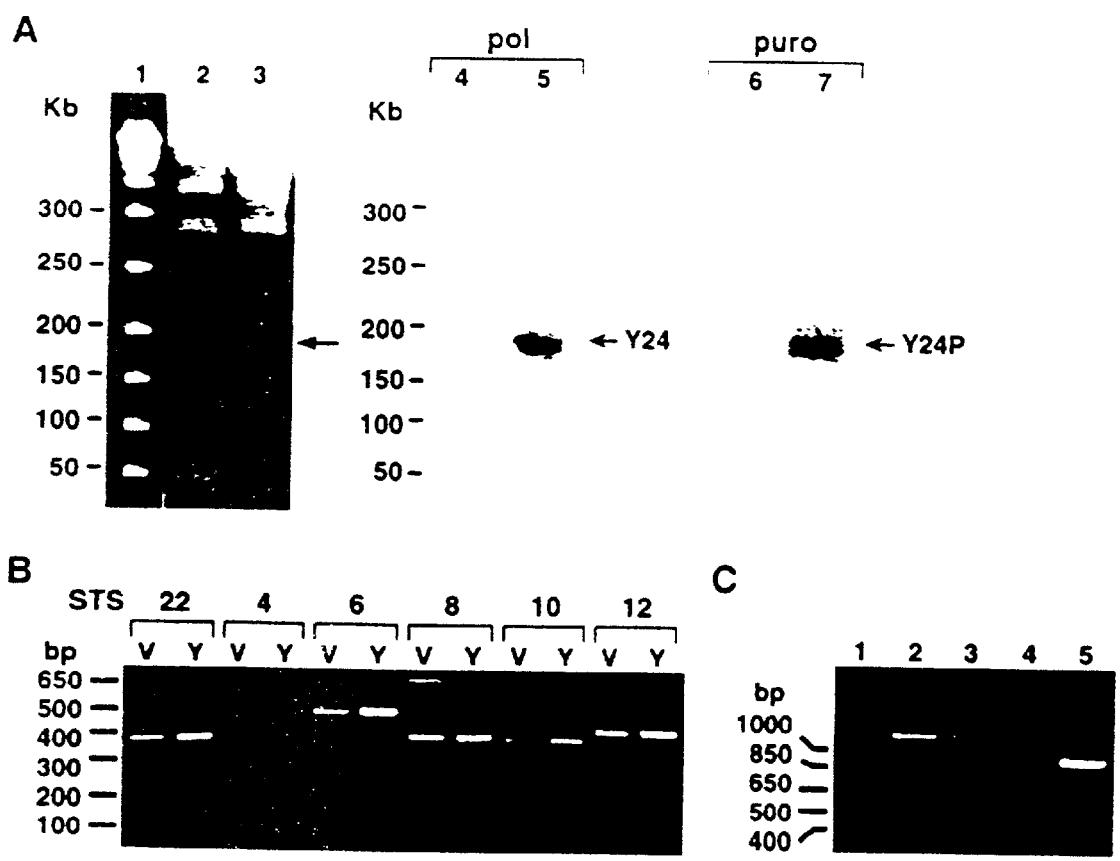
FIG. 8A shows Pulse Field Gel Electrophoresis in which different DNA samples were resolved: size markers (lane 1), YPH857 (lanes 2 and 4), Y24 (lanes 3, 5 and 6) and Y24P (lane 7). The gels were either stained with ethidium bromide (lanes 1 to 3), or hybridized to a UL54 specific probe (lanes 4 and 5, named pol) or to a puromycin specific probe (lanes 6 and 7, named puro). The sizes of the marker DNA fragments are shown in kilobases. The arrows indicate the band corresponding to either Y24 or Y24P.
FIG. 8B shows an agarose gel in which an aliquot of the STS PCR reaction was loaded. The lanes are named V for AD169 DNA or Y for YAC DNA. The set number for the corresponding STS is indicated, as well as the location of the size markers.
FIG. 8C shows PCR reactions to test the UL54-Luc and UL86-Luc mutations, and their integration in the correct position in Y24P. Specific primers were used, YAC54.2 and GLprimer2 (lanes 1 to 3) YAC86.2 and GLprimer2 (lanes 4 and 5). The DNA samples are Y24P (lanes 1 and 4), Y24P/UL54wt-Luc (lane 2), Y24P/UL54IRM-Luc (lane 3), and Y24P/UL86-Luc (lane 5).

FIG. 8A (left panel) shows a PFGE of Y24, along with the parental strain YPH857. Y24 migrates as an approximately 180 kb extra chromosome in the stained gel. When the separated chromosomes were hybridized to a HCMV UL54 specific probe, only Y24 showed specific hybridization (FIG. 8A, second panel).

To further test the overall integrity of the viral DNA, a sequence tagged site (STS) analysis was performed with specific primer sets along the HCMV genome. DNA was prepared from a yeast strain harboring Y24, and PCR was performed using 6 different pairs of STS oligos specific to consecutive regions of HCMV (the locations of the STS are shown in FIG. 7).

Figure 6:
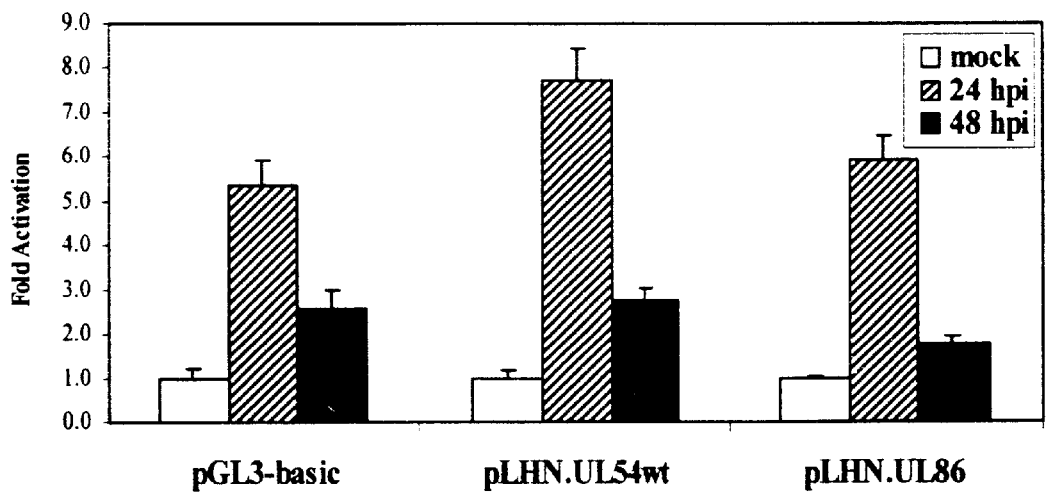
FIG. 6A shows transient transfection assays using 1 µg DNA of the plasmids described, followed by infection with HCMV at a multiplicity of infection (M.O.I.) of 10. NIH 3T3 cells were lysed at different times post infection, or at the moment of infection (mock), and the luciferase activity of the extracts was measured. The relative luciferase activity of a typical experiment is shown, where triplicate measurements were taken. The relative light units (rlu) at each time post infection are normalized to the activity in the corresponding mock-infected cells.
FIG. 6B shows stably transfected clones were infected with HCMV at an M.O.I. of 10, and samples were taken at different times post infection. The average rlu values from at least two experiments in triplicate are shown. Clones 2A-1, 2A-3 and 2A-5 are three representative clones stably transfected with pLHN.UL54wt. Clones 6A-1, 6A-2 and 6A-4 are representative clones stably transfected with pLHN.UL86.
Figure 6:
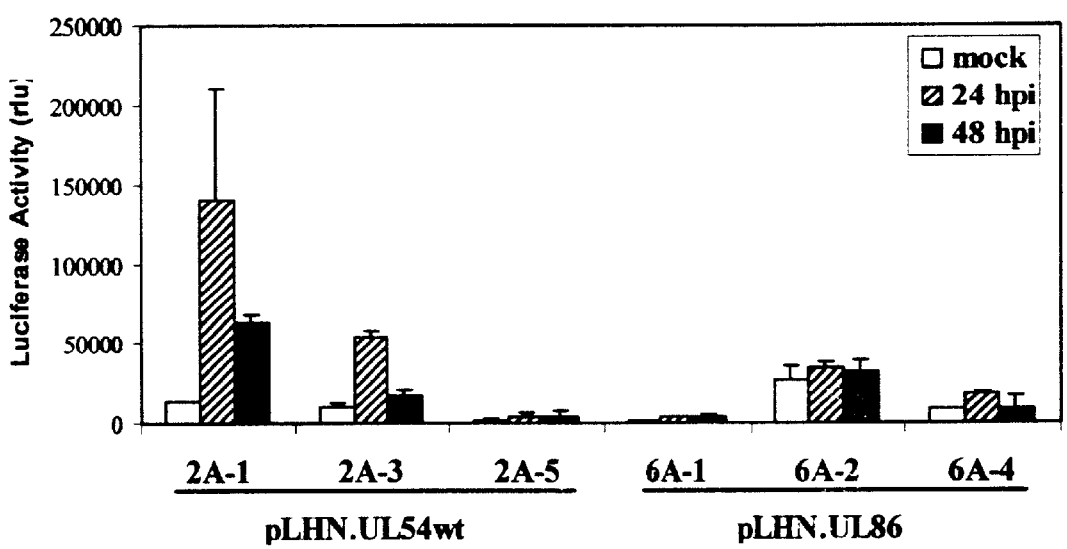

For the STS, analysis specific pairs of primers were designed along the HCMV sequence, with an approximate spacing between them of 20 kilobases, to be able to check for intactness of the viral genome. A subset of those STS pairs was used in this study, as shown in FIG. 6. PCR was performed using either yeast total DNA of a strain containing Y24 or DNA extracted from HCMV AD169 DNA as positive controls. Each PCR reaction contained 100 ng of template DNA, and 25 pmol of each oligonucleotide of the STS pair in a total volume of 25 µl, using standard PCR conditions. The reactions were incubated-one cycle at 94° C. for 3 minutes, followed by 30 cycles of amplification of 30 seconds at 94° C., 1 minute at 50° C., and 1 minute 72° C. An aliquot of the reaction was loaded in a 1% agarose gel, to check for the presence of the expected DNA fragment size. The pair S22 (oligonucleotides S225, ATGAGGATCGCGACAG (SEQ ID NO:52), and S223, CGTTATCCGTTCCTCG (SEQ ID NO:53), positions 3809 and 4186 in the HCMV genome respectively) amplifies a DNA fragment of 378 bp; the pair S04 (oligonucleotides S045, AGATGGATTCGTGCAC (SEQ ID NO:54), and S043, ATCGATCTGGAGCACT (SEQ ID NO:55), positions 36489 and 36714 respectively) amplifies a DNA fragment of 226 bp; the pair S06 (oligonucleotides S065, GGTCCGCAACTTCTGATCCA (SEQ ID NO:56) and S063, CAGATCAGTCCACAGGTTCT (SEQ ID NO:57), positions 66701 and 67183 respectively) amplifies a fragment of 483 bp; the pair S08 (oligonucleotides S085, ACGCAGGTGAATATCC (SEQ ID NO:58), and S083, AGGTTATCGTCAAGCG (SEQ ID NO:59), positions 84721 and 85094 respectively) amplifies a DNA fragment of 374 bp; the pair S10 (oligonucleotides S105, GATGGTGGAAATCGGA (SEQ ID NO:60), and S103, ATATCGCACCGATTGC (SEQ ID NO:61), positions 128975 and 129337 respectively) amplifies a DNA fragment of 363 bp; the pair S12 (oligonucleotides S125, GTTGGCGTTGAGCACGTCTA (SEQ ID NO:62), and S123, AGCCGACAACCTGCTGCACT, (SEQ ID NO:63) positions 149371 and 149770 respectively) amplifies a DNA fragment of 400 bp.

The results from the experiment are shown in FIG. 8B, in which all the specific primer sets amplified DNA fragments of the expected sizes, when compared to the viral DNA. This result demonstrates the overall integrity of the 178816 bp of viral sequence.

The YAC was retrofitted for selection in mammalian cells so that the HCMV YAC could be used for the analysis of essential cis acting sequences in a transgenesis system. The first mutagenesis was targeted to the right arm of the YAC, to introduce the puromycin resistance gene, a mammalian selectable marker. The URA3 gene was substituted by LEU2 plus the puromycin resistance gene, using the plasmid pRML2-Leu2-PUR digested with Not I (see FIG. 7). This replacement is expected to provide a YAC with the same basic features on the non-centromeric arm, but which now includes the mammalian selectable marker puromycin. Recombinant yeast clones were selected in the corresponding medium (yeast synthetic medium, SD, lacking tryptophan and leucine), and analyzed by PFGE and Southern blot analysis. The expected 180 kb specific band appears in the stained PFGE gel and when the puromycin resistance gene was used as a probe in a Southern blot analysis, only the newly made Y24P YAC gave a specific signal of around 180 kb, indicating that the integration had successfully occurred (FIG. 8A, right panel).

To investigate cis-acting sequences and their activity on the UL54 promoter in the context of the UL region, a YAC, Y24P/UL54wt-Luc was constructed, in which a luciferase reporter gene was inserted at position +20 of the UL54 promoter (FIG. 7). The strategy was as follows: SmaI-digested pLHN.UL54wt DNA, which contains the HIS3 gene for selection in yeast, was retrofitted into a strain containing Y24P. The integration of the plasmid in the YAC sequence would produce histidine prototrophs, in which the correct integration can then be tested by PCR. Using specific primers, directed to the region adjacent to the UL54 promoter but not included in the pLHN.UL54wt plasmid, and to the luciferase gene, a specific DNA fragment of the expected size (1.1 kb) was amplified (FIG. 8C, lane 2, compare to Y24P, lane 1). This new YAC has, besides the UL54 promoter fused to luciferase and integrated in its natural position in the HCMV genome, the neomycin resistance gene, which confers an additional marker for positive selection in mammalian cells (see FIG. 7).

In addition, in order to have a control for HCMV late gene expression, another YAC was construced in which the luciferase gene was inserted downstream of the UL86 promoter. The strategy was very similar to the one used to generate the UL54-luciferase fusion, but in this case the plasmid pLHN.UL86 was retrofitted, digested with SmaI, in a yeast strain harboring Y24P (FIG. 7). The recombinant clones were selected on medium lacking histidine, and as previously described, the correct integration was confirmed by PCR, using specific primers directed to the region neighboring the UL86 promoter and the luciferase gene (FIG. 8C, compare lanes 4 and 5).

Analysis of UL54 promoter activity by stable transfer (transgenesis) of HCMV-YAC to NIH 3T3 cells Next, the influence of the surrounding UL region on UL54 transcription activity by direct transfer of Y24P/UL54wt-Luc into NIH 3T3 fibroblasts was examined. In these experiments, $10^8$ yeast spheroplasts were fused to $2\times10^6$ mouse fibroblasts. Polyethylene glycol (PEG) spheroplast fusion was performed as described by Julicher et al. *Genomics*, 43:95–98 (1997). A yeast strain containing the YAC plasmid of interest was grown until it reached log phase ($OD_{600}$ 0.6–0.8). The cells were washed twice with water, and resuspended in SCE (1M Sorbitol, 0.1M Sodium Citrate, 60 mM EDTA, pH7.0), 9 mM DTT and 100 U/ml lyticase. When the protoplasts were formed, they were washed twice with SCE. $10^8$ yeast spheroplasts were fused to $2\times10^6$ NIH 3T3 cells in 0.5 ml 50% PEG 1500, 10 mM $CaCl_2$ for 2 minutes, then washed with serum-free medium and plated. After 48 hours, neomycin was added at a concentration of 400 µg/ml. Colonies appeared two weeks after applying the selection and resistant clones were isolated.

Figure 9:
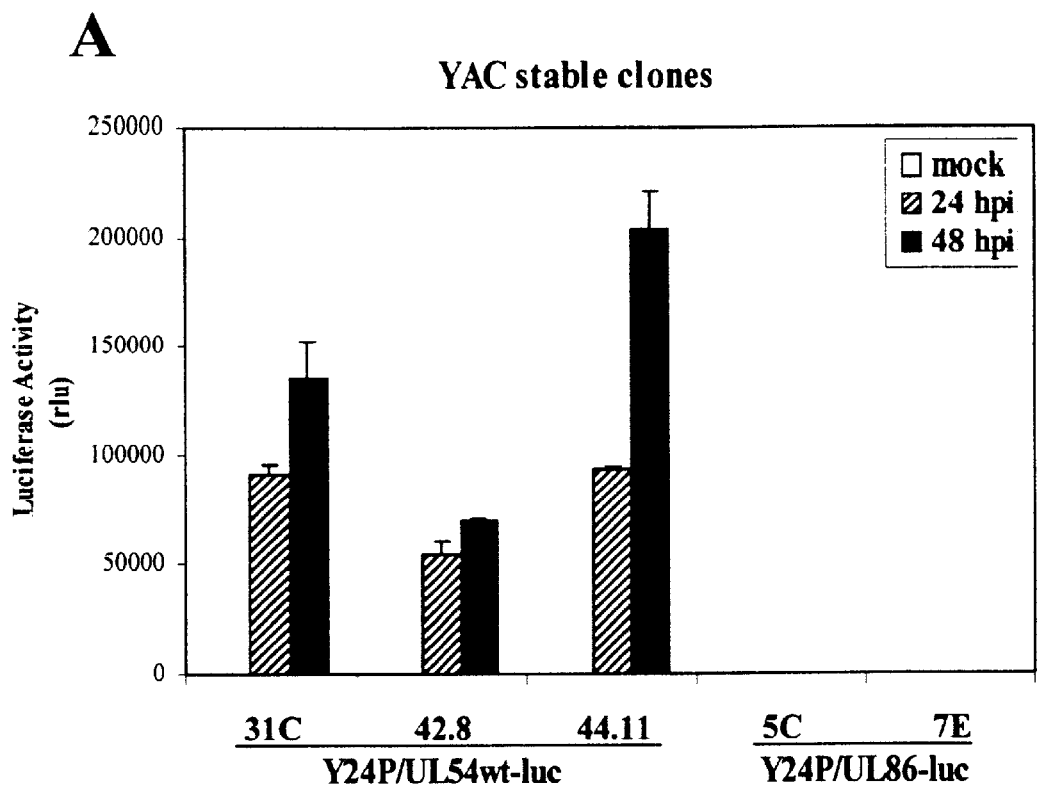
FIG. 9A shows Y24P/UL54wt-Luc transgenic lines were infected with HCMV at an M.O.I. of 10. Samples were harvested at the indicated times post infection. Averages of at least two experiments in triplicate are shown. As a negative control, Y24P/UL86-Luc clones (5C and 7E) were used.
FIG. 9B shows fold activation in luciferase activity in transgenic plasmid H) pLHN.UL54wt lines (2A-1, 2A-3 and 2A-5) and Y24P/UL54wt-Luc lines (31C, 42.8 44.11).
Figure 9:
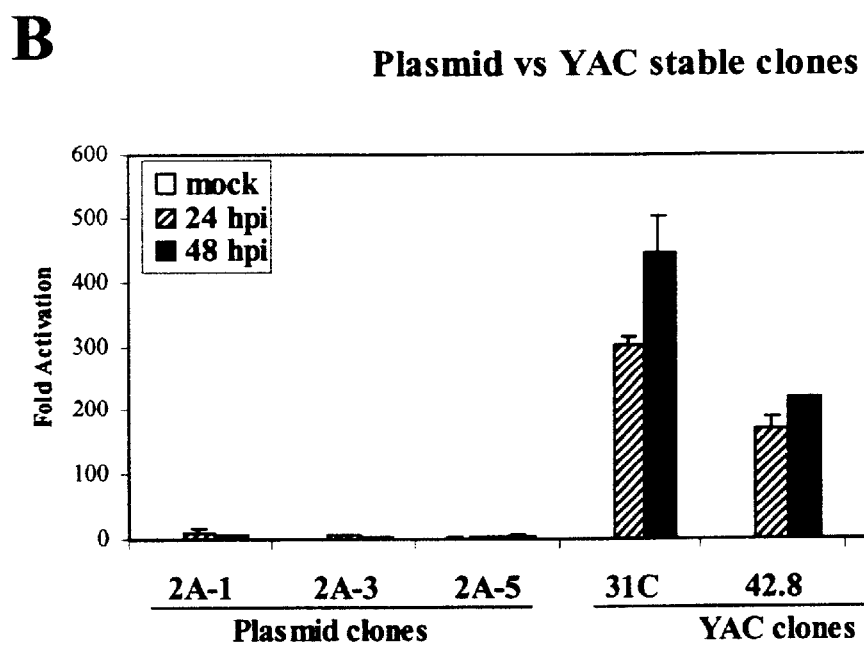
Figure 10:
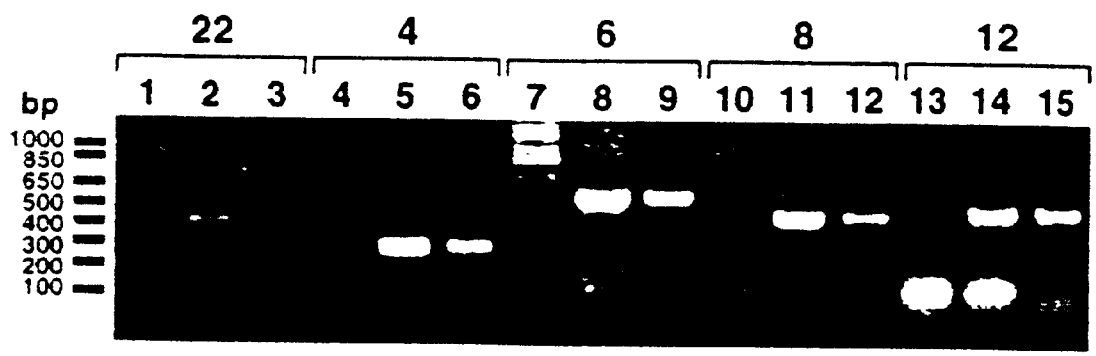
FIG. 10 shows STS analysis of the YAC transgenic NIH 3T3 clones. PCR rections were performed using specific primer sets designed along the HCMV genome. DNA from either NIN 3T3 cells (lanes 1, 4, 7, 10, 13), yeast Y24P positive control (lanes 2, 5, 8, 11, 14) or NIH 3T3/Y24P/UL54wt-luc 44.11 clone (lanes 3, 6, 9, 12, 15) was used, along with different sets of oligos (STS), indicated in the top part of the figure.
Figure 11:
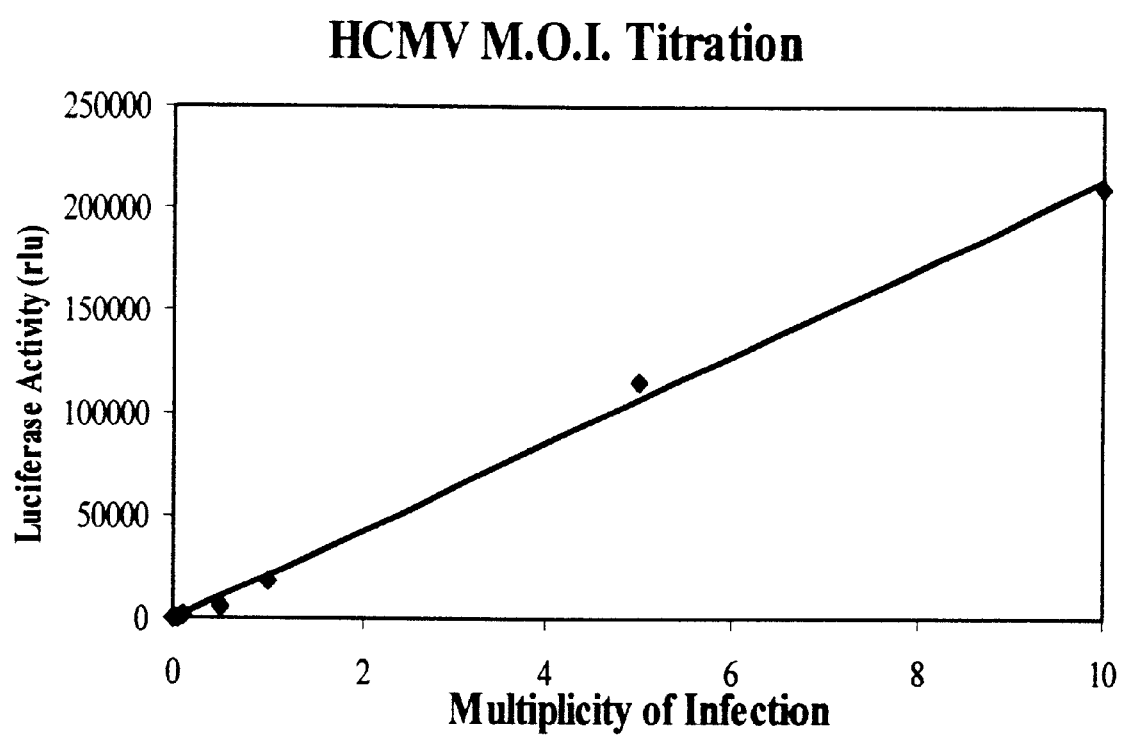
FIG. 11 shows the stable NIH 3T3 clone Y24P/UL54wt-Luc 44.11 was infected with HCMV, at different M.O.I. from 0.005 to 10. Cells were harvested at 48 hours post-infection, and the luciferase activity was measured. Each point represents the average of two independent infections.

A total of 9 neomycin resistant clones were selected and first tested for luciferase activity after infection with HCMV at a M.O.I. of 10. Six of these clones showed some activity in the luciferase assays; three are shown in FIG. 9 (clones 31C, 42.8 and 44.11). UV inactivated virus failed to elicit a response (data not shown) and the response of the UL54 promoter to infection in the YAC transgenic lines is proportional to the multiplicity of infection (FIG. 10). To check the integrity of transferred YACs we performed a STS analysis, using some of the specific pairs of oligos along the HCMV genome. As shown in FIG. 11, PCR reactions using DNA extracted from NIH 3T3 did not amplify any DNA fragment of the expected size. However, DNA from both the yeast strain Y24P and from the transgenesis YAC clones showed amplified DNA fragments of the expected size, indicating that intact YACs had been successfully transferred to NIH 3T3 cells (FIG. 11). In marked contrast to the plasmid transgenic lines, as shown in FIG. 9A, the YAC containing NIH 3T3 cells showed very low luciferase activity when mock-infected; 24 hours post infection with HCMV they exhibited a very strong up regulation, which continued to increase up to 48 hours (FIG. 9A). Furthermore, the absolute values of luciferase activity in the stable YAC clones were less variable and consistently higher than the stable plasmid-containing cell lines. The basal reporter gene levels in mock-infected YAC transgenic cells are subject to a highly specific and very tight regulation.

A comparison between the plasmid and the transgenesis cell lines showed a very strong activation of the-UL54 promoter upon HCMV infection ranging from 170 at 24 hours to 470-fold at 48 hours post infection in the YAC cell lines (FIG. 9B). This activation is very high compared to the stable plasmid clones, suggesting positive influence of remote viral DNA sequences in addition to more stringent regulation prior to activation. It is noteworthy that the second peak of activation at 48 hrs is not observed with the plasmid transgenic lines.

Transgenesis experiments were also carried out with the Y24P/UL86 to murine cells. The UL86 promoter is a true L promoter (Chambers et al. *J. Virol.* 73:5757–66 (1999), which is activated only after the onset of DNA replication. The transfer yielded three neomycin resistant clones, and the presence of the YAC sequences was tested by Southern blot and STS analysis (data not shown). None of these clones showed any luciferase activity before or after infection with HCMV (FIG. 9A, clones 5C and 7E). The lack of activation of UL86 transcription in the transgenesis experiments indicates the expected restriction in replication of HCMV in murine cells. Altogether, these results underscore the importance of sequence context in providing optimal level of gene expression.

Analysis of the UL54 promoter activation pathway by HCMV in murine cells

The primary pathway for early activation of the UL54 promoter is dependent on IE86 mediated activation via the IR1 element that binds the cellular transcription factor Sp1. In order to investigate the early activation pathway of HCMV UL54 in murine cells, we accordingly mutated the IR1 element present in the UL54 promoter. Kerry et al. *J. Virol.* 70:373–82 (1996). FIG. 7 shows the point mutations introduced in the IR1 site, which has been previously shown to completely eliminate IE86 transactivation of the UL54 promoter. Kerry et al. *J. Virol.* 68:4167–76 (1994).

Figure 12:
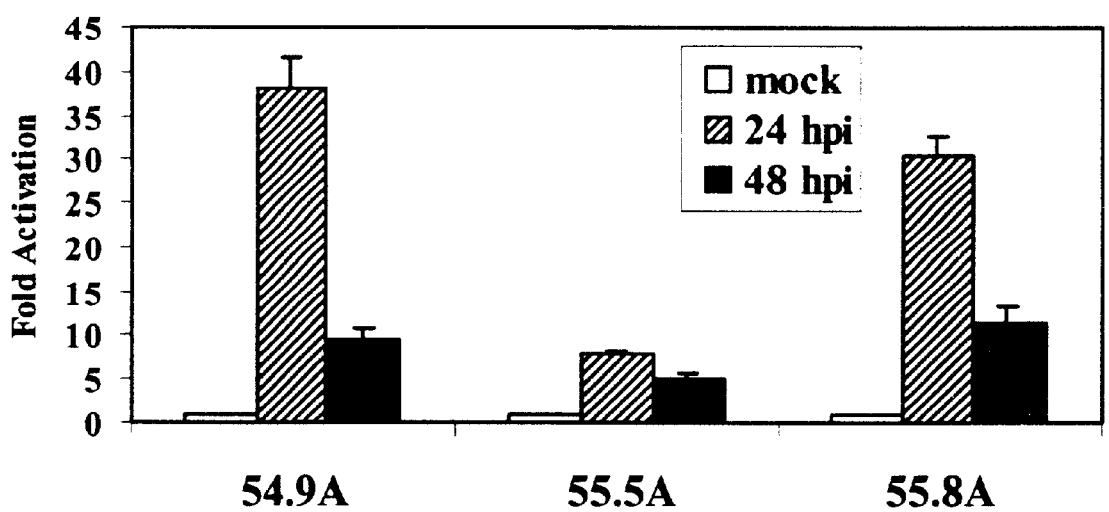
FIG. 12 shows stable Y24P/UL54IRM-Luc NIH 3T3 clones were infected with HCMV at a M.O.I. of 10. Samples were harvested at the indicated times and the luciferase activity determined. Each point represents the average of at least two independent experiments in triplicate. The fold activation was calculated dividing the absolute value by the mock-infected value. Three representative clones are shown.

In agreement with previous studies, the mutant plasmid (pLHN.UL54IRM) showed a much lower activation after transfection in HFF human cells and infection with HCMV (around 17-fold reduction), when compared to the wild type counterpart (data not shown). Kerry et al. *J. Virol.* 70:373–82 (1996). On the basis of this result the plasmid pLHN.UL54IRM was retrofitted into Y24P, to study the effect of the IRM mutation in the UL54 promoter, in the context of the UL region. FIG. 7 shows a schematic of the recombinant generated in yeast (Y24P/UL54IRM-Luc) and its integrity was confirmed by PFGE, STS analysis and Southern blot hybridization (not shown). Transgenesis studies were performed next by spheroplast fulsion of the Y24P/UL54IRM-Luc to NIH 3T3. The PEG fuision produced 8 neomycin resistant clones, three of which showed luciferase activity after infection with HCMV (FIG. 12). The profile of activation, with a peak at 24 hours, was different to the UL54 wild type promoter (compare FIGS. 9B and 12), but most significantly, both the absolute values (not shown) and the extent of the activation (10 to 30-fold, FIG. 12), were significantly diminished. These results suggest that the pathway used for HCMV early activation of the UL54 promoter is conserved in murine cells, and that the same or functionally similar cellular factors bind to the UL54 promoter. From these experiments we conclude that HCMV E activation of the UL54 promoter by IE transactivators is not restricted by host species encoded cellular factors.

Analysis of the MCMV activation of the HCMV UL54 promoter in YAC transgenic clones In the experiments described above, a homologous promoter-virus relationship was maintained in a heterologous host cell background, and the pathway of activation of E gene expression uses the same cellular pathway in both human and murine cells was demonstrated. Knowing that the cellular pathway is conserved between human and murine cells, the effect of changing the species origin of the virus was next tested. For these experiments the YAC transgenic clones Y24P/UL54wt-Luc 31C and 44.11 were infected with MCMV, and their levels of activation of the UL54 promoter were examined. In this scenario the cell-virus relationship is homologous (both are murine), while the promoter-virus relationship is heterologous.

Figure 13:
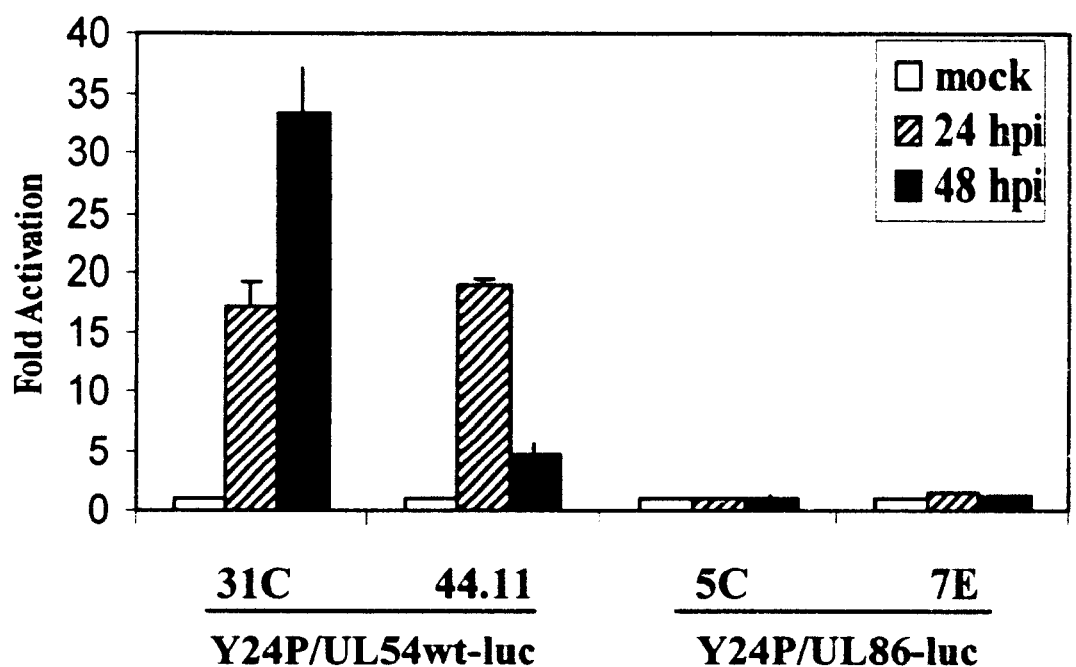
FIG. 13 shows Y24P/UL54wt-Luc NIH 3T3 clones were infected with MCMV at a M.O.I. of 10. Samples were harvested at the indicated times and the luciferase activity measured. Each point represents the average of at least two independent experiments in triplicate. The fold activation was calculated dividing the absolute value by the mock-infected value. Two representative clones are shown.

Two of the Y24P/UL54wt-Luc stable clones were infected with MCMV, at an M.O.I. of 10, and the luciferase activity at 24 and 48 hours post infection was analyzed. The maximum transcriptional activity was ten-fold lower in the MCMV infection, in comparison with the activation by HCMV (FIGS. 9B and 13, clones 31C and 44.11). This lower activation points towards a restriction at a viral trans-acting factor level, making necessary the concordance of species origin of both promoter and viral trans-activators to recapitulate the activation profile of the UL54 promoter. As anticipated, the Y24P/UL86-Luc 5C and 7C clones were not activated by MCMV infection (FIG. 13). Taken together, these results suggest that there is a dominance of virus over host factors in determining species specificity of E gene expression.

In this Example a YAC transgenesis approach was used to examine the species restriction checkpoint of an essential early gene activation pathway of HCMV in murine cells. Toward this end a YAC vector was designed, encompassing most of the UL region of HCMV. This vector is replication defective, lacks the major IE region, thus permitting the analysis of essential cis-acting sequences within the UL region when complemented in trans. For the purpose of this study we chose to study essential cis-acting sequences of the viral DNA polymerase (UL54) promoter complemented by HCMV infection in murine cells. The isolated UL54 promoter, both in transient and stable transfections, showed a profile of activation not in accordance with an early gene. Only when in the context of the UL region, the UL54 promoter was able to recapitulate the early (48 hr post infection) gene activation described in human cells. Kerry et al. *J. Virol.* 70:373–82 (1996). The same plasmids were used for the transfection assays and for the YAC mutagenesis, to avoid variability. In the UL54wt plasmid stable clones, the basal activity in mock-infected cells was not as tightly regulated as in the YAC clones, and the extent and profile of activation was more random. This suggests the need for tight regulation of early events, and perhaps the involvement of long-range cis acting sequences (sequence context) for optimal UL54 gene regulation. Indeed, the results of this study strongly support the suggestion that remote regulatory sequences participate in the control of expression of this essential early gene.

Members of the CMV family have evolved by co-speciation with their host and as a consequence have had sufficient time for acquiring a significant degree of genetic drift. McGeoch et al., *J. Mol. Biol.* 247:443–58 (1995). In particular, the genetics of HCMV speciation has lead to the non-viable replication in other host species. In this case we can assume that genetic changes that have been beneficial or neutral to its natural host background may well be deleterious to another host genetic background because of negative or inappropriate gene interactions that had not been screened by natural selection. For this reason species-specific strains of CMV must have accumulated genetic changes that may be advantageous or neutral with its host species but that produce non-viability in different host species. The results of this study suggest that the virus-host gene interaction pathway for E gene activation is viable between different host species but has significantly diverged between virus species. This strongly argues for co-evolution of viral transacting factors and their viral target promoters. In agreement, the mutation of the IR1 element of the HCMV UL54 promoter showed that the pathway of E activation is equivalent in human and murine cells. Thus, IE86 mediated activation of UL54 via the IR1 element is conserved in murine cells. In support, the primary host factor known to bind the IR1 element is Sp1, in which sequence homology between human and murine Sp1 is over 95%. In contrast, the MCMV transactivator (IE3) not only exhibits more sequence differences (<40% identity) from its related HCMV (IE86) counterpart but also is extremely inefficient at activating the HCMV UL54 promoter via the IR1 element, indicating a divergence of mechanism of action. A prediction from these observations is that it would not be informative to study HCMV IE proteins in the context of MCMV infection. Consistent with this notion, we find that IE3 mutant of MCMV is poorly complemented by HCMV infection in murine cells (AA & PG, unpublished results).

In summary, Example 4 shows the use of a YAC transgenesis system to explore critical host-viral gene interaction pathways in the cross species activation of a key early gene promoter of HCMV, UL54. Example 4 shows a clear dominance of virus factors (major immediate early proteins) for the transactivation of the UL54 early promoter, and point for a species specificity checkpoint at later times of infection.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

We claim:

1. An isolated recombinant DNA molecule selected from the group consisting of the yeast artificial chromosome of ATCC Deposit No. PTA-2186 and the yeast artificial chromosome of ATCC Deposit No. PTA-2187.

2. A composition comprising the isolated recombinant DNA molecule of claim 1 and a pharmaceutically acceptable carrier.

3. The composition according to claim 2 further comprising at least one pharmaceutically acceptable salt.

4. The composition according to claim 2 further comprising a protein substrate selected from the group consisting of serum albumins, keyhole limpet hemocyanin, immunoglobulin molecules, thyroglobulin, ovalbumin, tetanus toxoid and mixtures thereof.

5. The composition according to claim 2 further comprising an excipient selected from the group consisting of water, saline, glycerol, dextrose, malodextrin, ethanol and mixtures thereof.

6. The composition according to claim 2 further comprising a wetting agent.

7. The composition according to claim 2 further comprising an emulsifying agent.

8. The composition according to claim 2 further comprising a pH buffering agent.

9. The composition according to claim 2 further comprising liposomes.

10. The composition according to claim 2 further comprising a co-stimulatory molecule selected from the group consisting of B7-1, B7-2, MIP1α, GM-CSF, IL-2, IL-12 and mixtures thereof.

11. The composition according to claim 2 further comprising an adjuvant.

* * * * *